US012590273B2

(12) United States Patent
Giger et al.

(10) Patent No.: US 12,590,273 B2
(45) Date of Patent: Mar. 31, 2026

(54) STABILIZED GLYCOSIDE HYDROLASE VARIANTS

(71) Applicant: Novozymes A/S, Bagsvaerd (DK)

(72) Inventors: Lars Giger, Valby (DK); Frank Winther Rasmussen, Roskilde (DK); Svend Gunnar Kaasgaard, Skovlunde (DK); Lars Anderson, Malmoe (SE); Kenneth Jensen, Oelsted (DK); Roland Alexander Pache, Valby (DK); Dorte Marie Koefoed Klitgaard, Birkerød (DK); Mette Louise Dissing Overgaard, Copenhagen (DK); Christian I. Joergensen, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 969 days.

(21) Appl. No.: 17/603,259

(22) PCT Filed: Apr. 8, 2020

(86) PCT No.: PCT/EP2020/059965
§ 371 (c)(1),
(2) Date: Oct. 12, 2021

(87) PCT Pub. No.: WO2020/208056
PCT Pub. Date: Oct. 15, 2020

(65) Prior Publication Data

US 2022/0186151 A1 Jun. 16, 2022

(30) Foreign Application Priority Data

Apr. 12, 2019 (EP) .................................... 19168931
Nov. 14, 2019 (EP) .................................... 19209169

(51) Int. Cl.
*C11D 3/386* (2006.01)
*C12N 1/21* (2006.01)
*C12N 9/42* (2006.01)

(52) U.S. Cl.
CPC ........ *C11D 3/38636* (2013.01); *C12N 9/2437* (2013.01); *C07K 2319/00* (2013.01)

(58) Field of Classification Search
None
See application file for complete search history.

(56) References Cited

U.S. PATENT DOCUMENTS 9,506,050 B2* 11/2016 Liu ................ C12Y 302/01004
2009/0162916 A1 6/2009 Adney et al.
2013/0052694 A1* 2/2013 Montalibet ............ C12N 15/80 435/252.35
2014/0017734 A1* 1/2014 Xu .......................... C12P 19/14 435/320.1
2014/0080182 A1* 3/2014 Jones ...................... C12P 19/14 800/298
2018/0362946 A1* 12/2018 Pandey .......... C12Y 302/01004
2019/0106690 A1* 4/2019 Lai ...................... D06M 16/003

FOREIGN PATENT DOCUMENTS

CN 108463552 A 8/2018
CN 108699543 A 10/2018
WO 9407998 A1 4/1994
WO 1994007998 A1 4/1994
WO 1996029397 A1 9/1996
WO 2010096931 A1 9/2010
WO 2015110504 A1 7/2015
WO WO-2017084560 A1 * 5/2017 ......... C11D 3/38645
WO WO-2017106676 A1 * 6/2017 ..... C12Y 302/01004
WO 2019020849 A1 1/2019
WO 2019201783 A1 10/2019
WO WO-2019201785 A1 * 10/2019 ......... C11D 3/38636

OTHER PUBLICATIONS

Chen et al., Fusion protein linkers, Adv. Drug Delivery Rev. 65, 2013, 1357-69. (Year: 2013).*
Uniprot, Accession No. G2QVH7, 2018, www.uniprot.org. (Year: 2018).*
Gao et al., Characterization and crystal structure of a thermostable glycoside hydrolase family 45 1,4-beta-endoglucanase from Thielavia terrestris, Enz. Microb. Technol. 99, 2017, 32-37. (Year: 2017).*
Sammond et at., Cellulase Linkers Are Optimized Based on Domain Type and Function, PLOS One, Jul. 2012, e48615. (Year: 2012).*
Gao et al., Linker length and flexibility induces new cellobiohydrolase activity of PoCel6A from Penicillium oxalicum, Biotechnol. J., Oct. 2015, 899-904. (Year: 2015).*
Guerriero et al, 2018, International journal of molecular sciences 19(6), 1782.
Kavoosi et al, 2007, Biotechnol Bioeng 98(3), 599-610.
Poon et al, 2007, J Biol Chem 282(3), 2091-2100.
Sauer et al, 2001, Biochemistry 40(31), 9336-9346.
Shibuya et al, 2000, Biochem J 349(2), 651-656.
Woo et al, 2014, Protein journal 33, 110-117.
Wyk et al, 2010, Enzyme Microb Technol 46(5), 378-383.

* cited by examiner

*Primary Examiner* — Todd M Epstein
(74) *Attorney, Agent, or Firm* — Elias Lambiris

(57) ABSTRACT

Disclosed are variants of a glycoside hydrolase having improved stability, e.g., in the presence of a protease, and the use of such variants in detergent applications, such as laundry or dish wash.

27 Claims, No Drawings

Specification includes a Sequence Listing.

SEQUENCE LISTING

```
<160> NUMBER OF SEQ ID NOS: 210

<210> SEQ ID NO 1
<211> LENGTH: 278
<212> TYPE: PRT
<213> ORGANISM: Thielavia terrestris

<400> SEQUENCE: 1

Ala Ser Gly Ser Gly Gln Ser Thr Arg Tyr Trp Asp Cys Cys Lys Pro
1               5                   10                  15

Ser Cys Ala Trp Pro Gly Lys Ala Ala Val Ser Gln Pro Val Tyr Ala
            20                  25                  30

Cys Asp Ala Asn Phe Gln Arg Leu Ser Asp Phe Asn Val Gln Ser Gly
        35                  40                  45

Cys Asn Gly Gly Ser Ala Tyr Ser Cys Ala Asp Gln Thr Pro Trp Ala
    50                  55                  60

Val Asn Asp Asn Leu Ala Tyr Gly Phe Ala Ala Thr Ser Ile Ala Gly
65                  70                  75                  80

Gly Ser Glu Ser Ser Trp Cys Cys Ala Cys Tyr Ala Leu Thr Phe Thr
                85                  90                  95

Ser Gly Pro Val Ala Gly Lys Thr Met Val Val Gln Ser Thr Ser Thr
            100                 105                 110

Gly Gly Asp Leu Gly Ser Asn His Phe Asp Ile Ala Met Pro Gly Gly
        115                 120                 125

Gly Val Gly Ile Phe Asn Gly Cys Ser Ser Gln Phe Gly Gly Leu Pro
    130                 135                 140

Gly Ala Gln Tyr Gly Gly Ile Ser Ser Arg Asp Gln Cys Asp Ser Phe
145                 150                 155                 160

Pro Ala Pro Leu Lys Pro Gly Cys Gln Trp Arg Phe Asp Trp Phe Gln
                165                 170                 175

Asn Ala Asp Asn Pro Thr Phe Thr Phe Gln Gln Val Gln Cys Pro Ala
            180                 185                 190
```

-continued

```
Glu Ile Val Ala Arg Ser Gly Cys Lys Arg Asn Asp Asp Ser Ser Phe
        195                 200                 205

Pro Val Phe Thr Pro Pro Ser Gly Gly Asn Gly Gly Thr Gly Thr Pro
    210                 215                 220

Thr Ser Thr Ala Pro Gly Ser Gly Gln Thr Ser Pro Gly Gly Gly Ser
225                 230                 235                 240

Gly Cys Thr Ser Gln Lys Trp Ala Gln Cys Gly Gly Ile Gly Phe Ser
                245                 250                 255

Gly Cys Thr Thr Cys Val Ser Gly Thr Thr Cys Gln Lys Leu Asn Asp
            260                 265                 270

Tyr Tyr Ser Gln Cys Leu
        275


<210> SEQ ID NO 2
<211> LENGTH: 283
<212> TYPE: PRT
<213> ORGANISM: Humicola insolens

<400> SEQUENCE: 2

Ala Asp Gly Arg Ser Thr Arg Tyr Trp Asp Cys Cys Lys Pro Ser Cys
1               5                   10                  15

Gly Trp Ala Lys Lys Ala Pro Val Asn Gln Pro Val Phe Ser Cys Asn
            20                  25                  30

Ala Asn Phe Gln Arg Ile Thr Asp Phe Asp Ala Lys Ser Gly Cys Glu
        35                  40                  45

Pro Gly Gly Val Ala Tyr Ser Cys Ala Asp Gln Thr Pro Trp Ala Val
    50                  55                  60

Asn Asp Asp Phe Ala Leu Gly Phe Ala Ala Thr Ser Ile Ala Gly Ser
65                  70                  75                  80

Asn Glu Ala Gly Trp Cys Cys Ala Cys Tyr Glu Leu Thr Phe Thr Ser
                85                  90                  95

Gly Pro Val Ala Gly Lys Lys Met Val Val Gln Ser Thr Ser Thr Gly
            100                 105                 110

Gly Asp Leu Gly Ser Asn His Phe Asp Leu Asn Ile Pro Gly Gly Gly
        115                 120                 125

Val Gly Ile Phe Asp Gly Cys Thr Pro Gln Phe Gly Gly Leu Pro Gly
    130                 135                 140

Gln Arg Tyr Gly Gly Ile Ser Ser Arg Asn Glu Cys Asp Arg Phe Pro
145                 150                 155                 160

Asp Ala Leu Lys Pro Gly Cys Tyr Trp Arg Phe Asp Trp Phe Lys Asn
                165                 170                 175

Ala Asp Asn Pro Ser Phe Ser Phe Arg Gln Val Gln Cys Pro Ala Glu
            180                 185                 190

Leu Val Ala Arg Thr Gly Cys Arg Arg Asn Asp Asp Gly Asn Phe Pro
        195                 200                 205

Ala Val Gln Ile Ser Ser Ser Thr Ser Ser Pro Val Asn Gln Pro Thr
    210                 215                 220

Ser Thr Ser Thr Thr Ser Thr Ser Thr Thr Ser Ser Pro Pro Val Gln
225                 230                 235                 240

Pro Thr Thr Pro Ser Gly Cys Thr Ala Glu Arg Trp Ala Gln Cys Gly
                245                 250                 255

Gly Asn Gly Trp Ser Gly Cys Thr Thr Cys Val Ala Gly Ser Thr Cys
            260                 265                 270

Thr Lys Ile Asn Asp Trp Tyr His Gln Cys Leu
```

275 280

<210> SEQ ID NO 3
<211> LENGTH: 295
<212> TYPE: PRT
<213> ORGANISM: Staphylotrichum coccosporum

<400> SEQUENCE: 3

Ala Asp Gly Lys Ser Thr Arg Tyr Trp Asp Cys Cys Lys Pro Ser Cys
1 5 10 15

Ser Trp Pro Gly Lys Ala Ser Val Asn Gln Pro Val Phe Ala Cys Ser
20 25 30

Ala Asn Phe Gln Arg Ile Ser Asp Pro Asn Val Lys Ser Gly Cys Asp
35 40 45

Gly Gly Ser Ala Tyr Ala Cys Ala Asp Gln Thr Pro Trp Ala Val Asn
50 55 60

Asp Asn Phe Ser Tyr Gly Phe Ala Ala Thr Ser Ile Ser Gly Gly Asn
65 70 75 80

Glu Ala Ser Trp Cys Cys Gly Cys Tyr Glu Leu Thr Phe Thr Ser Gly
85 90 95

Pro Val Ala Gly Lys Thr Met Val Val Gln Ser Thr Ser Thr Gly Gly
100 105 110

Asp Leu Gly Thr Asn His Phe Asp Leu Ala Met Pro Gly Gly Gly Val
115 120 125

Gly Ile Phe Asp Gly Cys Ser Pro Gln Phe Gly Gly Leu Ala Gly Asp
130 135 140

Arg Tyr Gly Gly Val Ser Ser Arg Ser Gln Cys Asp Ser Phe Pro Ala
145 150 155 160

Ala Leu Lys Pro Gly Cys Tyr Trp Arg Phe Asp Trp Phe Lys Asn Ala
165 170 175

Asp Asn Pro Thr Phe Thr Phe Arg Gln Val Gln Cys Pro Ser Glu Leu
180 185 190

Val Ala Arg Thr Gly Cys Arg Arg Asn Asp Asp Gly Asn Phe Pro Val
195 200 205

Phe Thr Pro Pro Ser Gly Gly Gln Ser Ser Ser Ser Ser Ser Ser Ser
210 215 220

Ser Ala Lys Pro Thr Ser Thr Ser Thr Ser Thr Thr Ser Thr Lys Ala
225 230 235 240

Thr Ser Thr Thr Ser Thr Ala Ser Ser Gln Thr Ser Ser Ser Thr Gly
245 250 255

Gly Gly Cys Ala Ala Gln Arg Trp Ala Gln Cys Gly Gly Ile Gly Phe
260 265 270

Ser Gly Cys Thr Thr Cys Val Ser Gly Thr Thr Cys Asn Lys Gln Asn
275 280 285

Asp Trp Tyr Ser Gln Cys Leu
290 295

<210> SEQ ID NO 4
<211> LENGTH: 277
<212> TYPE: PRT
<213> ORGANISM: Acremonium thermophilum

<400> SEQUENCE: 4

Ala Leu Asp Gly Lys Ser Thr Arg Tyr Trp Asp Cys Cys Lys Pro Ser
1 5 10 15

Cys Gly Trp Pro Gly Lys Ala Ser Val Asn Gln Pro Val Phe Ser Cys

```
            20                  25                  30

Ser Ala Asp Trp Gln Arg Ile Ser Asp Phe Asn Ala Lys Ser Gly Cys
        35                  40                  45

Asp Gly Gly Ser Ala Tyr Ser Cys Ala Asp Gln Thr Pro Trp Ala Val
    50                  55                  60

Asn Asp Asn Phe Ser Tyr Gly Phe Ala Ala Thr Ala Ile Ala Gly Gly
65                  70                  75                  80

Ser Glu Ser Ser Trp Cys Cys Ala Cys Tyr Ala Leu Thr Phe Asn Ser
                85                  90                  95

Gly Pro Val Ala Gly Lys Thr Met Val Val Gln Ser Thr Ser Thr Gly
            100                 105                 110

Gly Asp Leu Gly Ser Asn Gln Phe Asp Leu Ala Ile Pro Gly Gly Gly
        115                 120                 125

Val Gly Ile Phe Asn Gly Cys Ala Ser Gln Phe Gly Gly Leu Pro Gly
    130                 135                 140

Ala Gln Tyr Gly Gly Ile Ser Asp Arg Ser Gln Cys Ser Ser Phe Pro
145                 150                 155                 160

Ala Pro Leu Gln Pro Gly Cys Gln Trp Arg Phe Asp Trp Phe Gln Asn
                165                 170                 175

Ala Asp Asn Pro Thr Phe Thr Phe Gln Arg Val Gln Cys Pro Ser Glu
            180                 185                 190

Leu Thr Ser Arg Thr Gly Cys Lys Arg Asp Asp Asp Ala Ser Tyr Pro
        195                 200                 205

Val Phe Asn Pro Pro Ser Gly Gly Ser Pro Ser Thr Thr Ser Thr Thr
    210                 215                 220

Thr Ser Ser Pro Ser Gly Pro Thr Gly Asn Pro Pro Gly Gly Gly Gly
225                 230                 235                 240

Cys Thr Ala Gln Lys Trp Ala Gln Cys Gly Gly Thr Gly Phe Thr Gly
                245                 250                 255

Cys Thr Thr Cys Val Ser Gly Thr Thr Cys Gln Val Gln Asn Gln Trp
            260                 265                 270

Tyr Ser Gln Cys Leu
        275


<210> SEQ ID NO 5
<211> LENGTH: 212
<212> TYPE: PRT
<213> ORGANISM: Artificial sequence
<220> FEATURE:
<223> OTHER INFORMATION: Catalytic domain of SEQ ID NO: 1

<400> SEQUENCE: 5

Ala Ser Gly Ser Gly Gln Ser Thr Arg Tyr Trp Asp Cys Cys Lys Pro
1               5                   10                  15

Ser Cys Ala Trp Pro Gly Lys Ala Ala Val Ser Gln Pro Val Tyr Ala
            20                  25                  30

Cys Asp Ala Asn Phe Gln Arg Leu Ser Asp Phe Asn Val Gln Ser Gly
        35                  40                  45

Cys Asn Gly Gly Ser Ala Tyr Ser Cys Ala Asp Gln Thr Pro Trp Ala
    50                  55                  60

Val Asn Asp Asn Leu Ala Tyr Gly Phe Ala Ala Thr Ser Ile Ala Gly
65                  70                  75                  80

Gly Ser Glu Ser Ser Trp Cys Cys Ala Cys Tyr Ala Leu Thr Phe Thr
                85                  90                  95

Ser Gly Pro Val Ala Gly Lys Thr Met Val Val Gln Ser Thr Ser Thr
```

-continued

```
            100                 105                 110

Gly Gly Asp Leu Gly Ser Asn His Phe Asp Ile Ala Met Pro Gly Gly
        115                 120                 125

Gly Val Gly Ile Phe Asn Gly Cys Ser Ser Gln Phe Gly Gly Leu Pro
    130                 135                 140

Gly Ala Gln Tyr Gly Gly Ile Ser Ser Arg Asp Gln Cys Asp Ser Phe
145                 150                 155                 160

Pro Ala Pro Leu Lys Pro Gly Cys Gln Trp Arg Phe Asp Trp Phe Gln
                165                 170                 175

Asn Ala Asp Asn Pro Thr Phe Thr Phe Gln Gln Val Gln Cys Pro Ala
            180                 185                 190

Glu Ile Val Ala Arg Ser Gly Cys Lys Arg Asn Asp Asp Ser Ser Phe
        195                 200                 205

Pro Val Phe Thr
    210


<210> SEQ ID NO 6
<211> LENGTH: 37
<212> TYPE: PRT
<213> ORGANISM: Artificial sequence
<220> FEATURE:
<223> OTHER INFORMATION: carbohydrate binding module of SEQ ID NO: 1

<400> SEQUENCE: 6

Cys Thr Ser Gln Lys Trp Ala Gln Cys Gly Gly Ile Gly Phe Ser Gly
1               5                   10                  15

Cys Thr Thr Cys Val Ser Gly Thr Thr Cys Gln Lys Leu Asn Asp Tyr
            20                  25                  30

Tyr Ser Gln Cys Leu
        35


<210> SEQ ID NO 7
<211> LENGTH: 37
<212> TYPE: PRT
<213> ORGANISM: Artificial Sequence
<220> FEATURE:
<223> OTHER INFORMATION: carbohydrate binding module of SEQ ID NO: 2

<400> SEQUENCE: 7

Cys Thr Ala Glu Arg Trp Ala Gln Cys Gly Gly Asn Gly Trp Ser Gly
1               5                   10                  15

Cys Thr Thr Cys Val Ala Gly Ser Thr Cys Thr Lys Ile Asn Asp Trp
            20                  25                  30

Tyr His Gln Cys Leu
        35


<210> SEQ ID NO 8
<211> LENGTH: 37
<212> TYPE: PRT
<213> ORGANISM: Artificial sequence
<220> FEATURE:
<223> OTHER INFORMATION: Carbohydrate binding module of SEQ ID NO: 3

<400> SEQUENCE: 8

Cys Ala Ala Gln Arg Trp Ala Gln Cys Gly Gly Ile Gly Phe Ser Gly
1               5                   10                  15

Cys Thr Thr Cys Val Ser Gly Thr Thr Cys Asn Lys Gln Asn Asp Trp
            20                  25                  30

Tyr Ser Gln Cys Leu
        35
```

<210> SEQ ID NO 9
<211> LENGTH: 37
<212> TYPE: PRT
<213> ORGANISM: Artificial sequence
<220> FEATURE:
<223> OTHER INFORMATION: Carbohydrate binding module of SEQ ID NO: 4

<400> SEQUENCE: 9

```
Cys Thr Ala Gln Lys Trp Ala Gln Cys Gly Gly Thr Gly Phe Thr Gly
1               5                   10                  15

Cys Thr Thr Cys Val Ser Gly Thr Thr Cys Gln Val Gln Asn Gln Trp
            20                  25                  30

Tyr Ser Gln Cys Leu
        35
```

<210> SEQ ID NO 10
<211> LENGTH: 311
<212> TYPE: PRT
<213> ORGANISM: Artificial sequence
<220> FEATURE:
<223> OTHER INFORMATION: Synthetic Construct

<400> SEQUENCE: 10

```
Ala Val Pro Ser Thr Gln Thr Pro Trp Gly Ile Lys Ser Ile Tyr Asn
1               5                   10                  15

Asp Gln Ser Ile Thr Lys Thr Thr Gly Gly Lys Gly Ile Lys Val Ala
            20                  25                  30

Val Leu Asp Thr Gly Val Tyr Thr Ser His Leu Asp Leu Ala Gly Ser
        35                  40                  45

Ala Glu Gln Cys Lys Asp Phe Thr Gln Ser Asn Pro Leu Val Asp Gly
    50                  55                  60

Ser Cys Thr Asp Arg Gln Gly His Gly Thr His Val Ala Gly Thr Val
65                  70                  75                  80

Leu Ala His Gly Gly Ser Asn Gly Gln Gly Val Tyr Gly Val Ala Pro
                85                  90                  95

Gln Ala Lys Leu Trp Ala Tyr Lys Val Leu Gly Asp Lys Gly Glu Gly
            100                 105                 110

Tyr Ser Asp Asp Ile Ala Ala Ala Ile Arg His Val Ala Asp Glu Ala
        115                 120                 125

Ser Arg Thr Gly Ser Lys Val Val Ile Asn Met Ser Leu Gly Ser Ser
    130                 135                 140

Ala Lys Asp Ser Leu Ile Ala Ser Ala Val Asp Tyr Ala Tyr Gly Lys
145                 150                 155                 160

Gly Val Leu Ile Val Ala Ala Ala Gly Asn Glu Gly Pro Lys Pro Asn
                165                 170                 175

Thr Ile Gly Tyr Pro Ala Gly Phe Val Asn Ala Val Ala Val Ala Ala
            180                 185                 190

Leu Glu Asn Val Gln Glu Lys Gly Thr Tyr Arg Val Ala Asp Phe Ser
        195                 200                 205

Ser Arg Gly Asn Pro Ala Thr Ala Gly Asp Tyr Ile Ile Gln Glu Arg
    210                 215                 220

Asp Ile Glu Val Ser Ala Pro Gly Ala Ser Val Glu Ser Thr Trp Tyr
225                 230                 235                 240

Thr Gly Gly Tyr Asn Thr Ile Ser Gly Thr Ser Met Ala Thr Pro His
                245                 250                 255

Val Ala Gly Leu Ala Ala Lys Ile Trp Ser Ala Asn Thr Ser Leu Ser
```

-continued

```
            260                 265                 270

His Ser Gln Leu Arg Thr Glu Leu Gln Asn Arg Ala Lys Val Tyr Asp
        275                 280                 285

Ile Lys Gly Gly Ile Gly Ala Gly Pro Gly Asp Asp Tyr Ala Ser Gly
    290                 295                 300

Phe Gly Tyr Pro Arg Val Lys
305                 310


<210> SEQ ID NO 11
<211> LENGTH: 269
<212> TYPE: PRT
<213> ORGANISM: Bacillus lentus

<400> SEQUENCE: 11

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 12
<211> LENGTH: 13
<212> TYPE: PRT
<213> ORGANISM: Artificial sequence
<220> FEATURE:
<223> OTHER INFORMATION: Linker

<400> SEQUENCE: 12
```

-continued

Thr Thr Pro Pro Thr Pro Thr Pro Thr Pro Thr Pro Gly
1 5 10

<210> SEQ ID NO 13
<211> LENGTH: 15
<212> TYPE: PRT
<213> ORGANISM: Artificial sequence
<220> FEATURE:
<223> OTHER INFORMATION: Linker

<400> SEQUENCE: 13

Thr Thr Pro Thr Pro Pro Thr Pro Thr Pro Thr Pro Thr Pro Gly
1 5 10 15

<210> SEQ ID NO 14
<211> LENGTH: 17
<212> TYPE: PRT
<213> ORGANISM: Artificial Sequence
<220> FEATURE:
<223> OTHER INFORMATION: Linker

<400> SEQUENCE: 14

Thr Thr Pro Thr Pro Thr Pro Pro Thr Pro Thr Pro Thr Pro Thr Pro
1 5 10 15

Gly

<210> SEQ ID NO 15
<211> LENGTH: 19
<212> TYPE: PRT
<213> ORGANISM: Artificial sequence
<220> FEATURE:
<223> OTHER INFORMATION: Linker

<400> SEQUENCE: 15

Thr Thr Pro Thr Pro Thr Pro Thr Pro Pro Thr Pro Thr Pro Thr Pro
1 5 10 15

Thr Pro Gly

<210> SEQ ID NO 16
<211> LENGTH: 34
<212> TYPE: PRT
<213> ORGANISM: Artificial sequence
<220> FEATURE:
<223> OTHER INFORMATION: Synthetic Construct

<400> SEQUENCE: 16

Thr Pro Pro Thr Pro Pro Thr Pro Pro Thr Pro Pro Thr Pro Pro Thr
1 5 10 15

Pro Pro Thr Pro Pro Thr Pro Pro Thr Pro Pro Thr Pro Pro Thr Pro
20 25 30

Pro Gly

<210> SEQ ID NO 17
<211> LENGTH: 13
<212> TYPE: PRT
<213> ORGANISM: Artificial sequence
<220> FEATURE:
<223> OTHER INFORMATION: Linker

<400> SEQUENCE: 17

Thr Pro Thr Thr Pro Thr Thr Pro Thr Thr Pro Thr Gly
1 5 10

```
<210> SEQ ID NO 18
<211> LENGTH: 19
<212> TYPE: PRT
<213> ORGANISM: Artificial sequence
<220> FEATURE:
<223> OTHER INFORMATION: Linker

<400> SEQUENCE: 18

Thr Pro Thr Thr Pro Thr Thr Pro Thr Thr Pro Thr Thr Pro Thr Thr
1               5                   10                  15

Pro Thr Gly


<210> SEQ ID NO 19
<211> LENGTH: 13
<212> TYPE: PRT
<213> ORGANISM: Artificial sequence
<220> FEATURE:
<223> OTHER INFORMATION: Linker

<400> SEQUENCE: 19

Ser Pro Ser Ser Pro Ser Ser Pro Ser Ser Pro Ser Gly
1               5                   10


<210> SEQ ID NO 20
<211> LENGTH: 16
<212> TYPE: PRT
<213> ORGANISM: Artificial sequence
<220> FEATURE:
<223> OTHER INFORMATION: Linker

<400> SEQUENCE: 20

Ser Pro Ser Ser Pro Ser Ser Pro Ser Ser Pro Ser Ser Pro Ser Gly
1               5                   10                  15


<210> SEQ ID NO 21
<211> LENGTH: 16
<212> TYPE: PRT
<213> ORGANISM: Artificial sequence
<220> FEATURE:
<223> OTHER INFORMATION: Linker

<400> SEQUENCE: 21

Ser Pro Pro Ser Pro Pro Ser Pro Pro Ser Pro Pro Ser Pro Pro Gly
1               5                   10                  15


<210> SEQ ID NO 22
<211> LENGTH: 31
<212> TYPE: PRT
<213> ORGANISM: Artificial Sequence
<220> FEATURE:
<223> OTHER INFORMATION: Linker

<400> SEQUENCE: 22

Ser Pro Pro Ser Pro Pro Ser Pro Pro Ser Pro Pro Ser Pro Pro Ser
1               5                   10                  15

Pro Pro Ser Pro Pro Ser Pro Pro Ser Pro Pro Ser Pro Pro Gly
            20                  25                  30


<210> SEQ ID NO 23
<211> LENGTH: 22
<212> TYPE: PRT
<213> ORGANISM: Artificial Sequence
<220> FEATURE:
<223> OTHER INFORMATION: Linker

<400> SEQUENCE: 23
```

```
Pro Pro Ser Ser Pro Ser Ser Pro Ser Ser Pro Ser Ser Pro Ser Ser
1               5                   10                  15

Pro Ser Ser Pro Ser Gly
            20


<210> SEQ ID NO 24
<211> LENGTH: 5
<212> TYPE: PRT
<213> ORGANISM: Artificial Sequence
<220> FEATURE:
<223> OTHER INFORMATION: Linker

<400> SEQUENCE: 24

Ser Pro Ser Pro Gly
1               5


<210> SEQ ID NO 25
<211> LENGTH: 11
<212> TYPE: PRT
<213> ORGANISM: Artificial Sequence
<220> FEATURE:
<223> OTHER INFORMATION: Linker

<400> SEQUENCE: 25

Ser Pro Ser Pro Ser Pro Ser Pro Ser Pro Gly
1               5                   10


<210> SEQ ID NO 26
<211> LENGTH: 11
<212> TYPE: PRT
<213> ORGANISM: Artificial sequence
<220> FEATURE:
<223> OTHER INFORMATION: Linker

<400> SEQUENCE: 26

Thr Pro Thr Pro Thr Pro Thr Pro Thr Pro Gly
1               5                   10


<210> SEQ ID NO 27
<211> LENGTH: 4
<212> TYPE: PRT
<213> ORGANISM: Artificial sequence
<220> FEATURE:
<223> OTHER INFORMATION: Linker

<400> SEQUENCE: 27

Pro Pro Pro Pro
1


<210> SEQ ID NO 28
<211> LENGTH: 5
<212> TYPE: PRT
<213> ORGANISM: Artificial sequence
<220> FEATURE:
<223> OTHER INFORMATION: Linker

<400> SEQUENCE: 28

Pro Pro Pro Pro Pro
1               5


<210> SEQ ID NO 29
<211> LENGTH: 6
<212> TYPE: PRT
<213> ORGANISM: Artificial sequence
<220> FEATURE:
<223> OTHER INFORMATION: Linker
```

<400> SEQUENCE: 29

Pro Pro Pro Pro Pro Pro
1               5

<210> SEQ ID NO 30
<211> LENGTH: 8
<212> TYPE: PRT
<213> ORGANISM: Artificial sequence
<220> FEATURE:
<223> OTHER INFORMATION: Linker

<400> SEQUENCE: 30

Pro Pro Pro Pro Pro Pro Pro Gly
1               5

<210> SEQ ID NO 31
<211> LENGTH: 7
<212> TYPE: PRT
<213> ORGANISM: Artificial sequence
<220> FEATURE:
<223> OTHER INFORMATION: Linker

<400> SEQUENCE: 31

Pro Pro Pro Pro Pro Pro Pro
1               5

<210> SEQ ID NO 32
<211> LENGTH: 9
<212> TYPE: PRT
<213> ORGANISM: Artificial sequence
<220> FEATURE:
<223> OTHER INFORMATION: Linker

<400> SEQUENCE: 32

Pro Pro Pro Pro Pro Pro Pro Pro Gly
1               5

<210> SEQ ID NO 33
<211> LENGTH: 10
<212> TYPE: PRT
<213> ORGANISM: Artificial sequence
<220> FEATURE:
<223> OTHER INFORMATION: Linker

<400> SEQUENCE: 33

Pro Pro Pro Pro Pro Pro Pro Pro Pro Gly
1               5                   10

<210> SEQ ID NO 34
<211> LENGTH: 11
<212> TYPE: PRT
<213> ORGANISM: Artificial sequence
<220> FEATURE:
<223> OTHER INFORMATION: Linker

<400> SEQUENCE: 34

Pro Pro Pro Pro Pro Pro Pro Pro Pro Pro Gly
1               5                   10

<210> SEQ ID NO 35
<211> LENGTH: 12
<212> TYPE: PRT
<213> ORGANISM: Artificial sequence
<220> FEATURE:
<223> OTHER INFORMATION: Linker

<400> SEQUENCE: 35

Pro Pro Pro Pro Pro Pro Pro Pro Pro Pro Pro Gly
1 5 10

<210> SEQ ID NO 36
<211> LENGTH: 14
<212> TYPE: PRT
<213> ORGANISM: Artificial sequence
<220> FEATURE:
<223> OTHER INFORMATION: Linker

<400> SEQUENCE: 36

Pro Pro Pro Pro Pro Pro Pro Pro Pro Pro Pro Pro Pro Gly
1 5 10

<210> SEQ ID NO 37
<211> LENGTH: 9
<212> TYPE: PRT
<213> ORGANISM: Artificial sequence
<220> FEATURE:
<223> OTHER INFORMATION: Linker

<400> SEQUENCE: 37

Pro Glu Pro Thr Pro Glu Pro Thr Gly
1 5

<210> SEQ ID NO 38
<211> LENGTH: 13
<212> TYPE: PRT
<213> ORGANISM: Artificial sequence
<220> FEATURE:
<223> OTHER INFORMATION: Linker

<400> SEQUENCE: 38

Pro Glu Pro Thr Pro Glu Pro Thr Pro Glu Pro Thr Gly
1 5 10

<210> SEQ ID NO 39
<211> LENGTH: 17
<212> TYPE: PRT
<213> ORGANISM: Artificial sequence
<220> FEATURE:
<223> OTHER INFORMATION: Linker

<400> SEQUENCE: 39

Pro Glu Pro Thr Pro Glu Pro Thr Pro Glu Pro Thr Pro Glu Pro Thr
1 5 10 15

Gly

<210> SEQ ID NO 40
<211> LENGTH: 21
<212> TYPE: PRT
<213> ORGANISM: Artificial sequence
<220> FEATURE:
<223> OTHER INFORMATION: Linker

<400> SEQUENCE: 40

Pro Glu Pro Thr Pro Glu Pro Thr Pro Glu Pro Thr Pro Glu Pro Thr
1 5 10 15

Pro Glu Pro Thr Gly
20

<210> SEQ ID NO 41
<211> LENGTH: 17
<212> TYPE: PRT
<213> ORGANISM: Artificial sequence
<220> FEATURE:
<223> OTHER INFORMATION: Linker

<400> SEQUENCE: 41

Pro Ser Pro Thr Pro Ser Pro Thr Pro Ser Pro Thr Pro Ser Pro Thr
1               5                   10                  15

Gly

<210> SEQ ID NO 42
<211> LENGTH: 21
<212> TYPE: PRT
<213> ORGANISM: Artificial sequence
<220> FEATURE:
<223> OTHER INFORMATION: Linker

<400> SEQUENCE: 42

Pro Ser Pro Thr Pro Ser Pro Thr Pro Ser Pro Thr Pro Ser Pro Thr
1               5                   10                  15

Pro Ser Pro Thr Gly
            20

<210> SEQ ID NO 43
<211> LENGTH: 9
<212> TYPE: PRT
<213> ORGANISM: Artificial sequence
<220> FEATURE:
<223> OTHER INFORMATION: Linker

<400> SEQUENCE: 43

Pro Gln Pro Thr Pro Gln Pro Thr Gly
1               5

<210> SEQ ID NO 44
<211> LENGTH: 9
<212> TYPE: PRT
<213> ORGANISM: Artificial sequence
<220> FEATURE:
<223> OTHER INFORMATION: Linker

<400> SEQUENCE: 44

Pro Asp Pro Thr Pro Asp Pro Thr Gly
1               5

<210> SEQ ID NO 45
<211> LENGTH: 9
<212> TYPE: PRT
<213> ORGANISM: Artificial sequence
<220> FEATURE:
<223> OTHER INFORMATION: Linker

<400> SEQUENCE: 45

Pro Arg Pro Thr Pro Glu Pro Thr Gly
1               5

<210> SEQ ID NO 46
<211> LENGTH: 9
<212> TYPE: PRT
<213> ORGANISM: Artificial sequence
<220> FEATURE:
<223> OTHER INFORMATION: Linker

<400> SEQUENCE: 46

Pro Gln Pro Thr Pro Glu Pro Thr Gly
1               5

<210> SEQ ID NO 47
<211> LENGTH: 11
<212> TYPE: PRT
<213> ORGANISM: Artificial sequence
<220> FEATURE:
<223> OTHER INFORMATION: Linker

<400> SEQUENCE: 47

Pro Ser Pro Asn Ser Pro Asn Ser Pro Asn Gly
1               5                   10

<210> SEQ ID NO 48
<211> LENGTH: 9
<212> TYPE: PRT
<213> ORGANISM: Artificial sequence
<220> FEATURE:
<223> OTHER INFORMATION: Linker

<400> SEQUENCE: 48

Pro Glu Pro Thr Pro Arg Pro Thr Gly
1               5

<210> SEQ ID NO 49
<211> LENGTH: 29
<212> TYPE: PRT
<213> ORGANISM: Artificial sequence
<220> FEATURE:
<223> OTHER INFORMATION: Linker

<400> SEQUENCE: 49

Pro Gln Pro Thr Pro Glu Pro Thr Pro Gln Pro Thr Pro Glu Pro Thr
1               5                   10                  15

Pro Gln Pro Thr Pro Glu Pro Thr Pro Gln Pro Thr Gly
            20                  25

<210> SEQ ID NO 50
<211> LENGTH: 13
<212> TYPE: PRT
<213> ORGANISM: Artificial sequence
<220> FEATURE:
<223> OTHER INFORMATION: Linker

<400> SEQUENCE: 50

Pro Asp Pro Thr Pro Asp Pro Thr Pro Asp Pro Thr Gly
1               5                   10

<210> SEQ ID NO 51
<211> LENGTH: 17
<212> TYPE: PRT
<213> ORGANISM: Artificial sequence
<220> FEATURE:
<223> OTHER INFORMATION: Linker

<400> SEQUENCE: 51

Pro Gln Pro Thr Pro Gln Pro Thr Pro Gln Pro Thr Pro Gln Pro Thr
1               5                   10                  15

Gly

<210> SEQ ID NO 52
<211> LENGTH: 17
<212> TYPE: PRT
<213> ORGANISM: Artificial sequence
<220> FEATURE:
<223> OTHER INFORMATION: Linker

<400> SEQUENCE: 52

Pro Gln Pro Thr Pro Glu Pro Thr Pro Gln Pro Thr Pro Glu Pro Thr
1 5 10 15

Gly

<210> SEQ ID NO 53
<211> LENGTH: 11
<212> TYPE: PRT
<213> ORGANISM: Artificial sequence
<220> FEATURE:
<223> OTHER INFORMATION: Linker

<400> SEQUENCE: 53

Ser Pro Ser Pro Ser Pro Ser Pro Pro Pro Gly
1 5 10

<210> SEQ ID NO 54
<211> LENGTH: 11
<212> TYPE: PRT
<213> ORGANISM: Artificial sequence
<220> FEATURE:
<223> OTHER INFORMATION: Linker

<400> SEQUENCE: 54

Ser Pro Ser Pro Ser Pro Ser Pro Asp Pro Gly
1 5 10

<210> SEQ ID NO 55
<211> LENGTH: 11
<212> TYPE: PRT
<213> ORGANISM: Artificial sequence
<220> FEATURE:
<223> OTHER INFORMATION: Linker

<400> SEQUENCE: 55

Ser Pro Ser Pro Ser Pro Ser Pro Lys Pro Gly
1 5 10

<210> SEQ ID NO 56
<211> LENGTH: 11
<212> TYPE: PRT
<213> ORGANISM: Artificial sequence
<220> FEATURE:
<223> OTHER INFORMATION: Linker

<400> SEQUENCE: 56

Ser Pro Ser Pro Ser Pro Ser Pro Ala Pro Gly
1 5 10

<210> SEQ ID NO 57
<211> LENGTH: 12
<212> TYPE: PRT
<213> ORGANISM: Artificial sequence
<220> FEATURE:
<223> OTHER INFORMATION: Linker

<400> SEQUENCE: 57

Ser Pro Ser Pro Ser Pro Ser Pro Ser Pro Ser Gly
1 5 10

<210> SEQ ID NO 58
<211> LENGTH: 10
<212> TYPE: PRT
<213> ORGANISM: Artificial sequence
<220> FEATURE:
<223> OTHER INFORMATION: Linker

<400> SEQUENCE: 58

Ser Pro Ser Pro Ser Pro Ser Pro Ser Pro
1 5 10

<210> SEQ ID NO 59
<211> LENGTH: 11
<212> TYPE: PRT
<213> ORGANISM: Artificial sequence
<220> FEATURE:
<223> OTHER INFORMATION: Linker

<400> SEQUENCE: 59

Ser Pro Ser Pro Ser Pro Ser Pro Ser Pro Ser
1 5 10

<210> SEQ ID NO 60
<211> LENGTH: 11
<212> TYPE: PRT
<213> ORGANISM: Artificial sequence
<220> FEATURE:
<223> OTHER INFORMATION: Linker

<400> SEQUENCE: 60

Ser Pro Ser Pro Ser Pro Ser Pro Ser Pro Pro
1 5 10

<210> SEQ ID NO 61
<211> LENGTH: 11
<212> TYPE: PRT
<213> ORGANISM: Artificial sequence
<220> FEATURE:
<223> OTHER INFORMATION: Linker

<400> SEQUENCE: 61

Ser Pro Ser Pro Ser Pro Ser Pro Ser Pro Glu
1 5 10

<210> SEQ ID NO 62
<211> LENGTH: 11
<212> TYPE: PRT
<213> ORGANISM: Artificial sequence
<220> FEATURE:
<223> OTHER INFORMATION: Linker

<400> SEQUENCE: 62

Ser Pro Ser Pro Ser Pro Ser Pro Ser Pro Asn
1 5 10

<210> SEQ ID NO 63
<211> LENGTH: 12
<212> TYPE: PRT
<213> ORGANISM: Artificial sequence
<220> FEATURE:
<223> OTHER INFORMATION: Linker

<400> SEQUENCE: 63

Ser Pro Ser Pro Ser Pro Ser Pro Ser Pro Gly Gly
1 5 10

<210> SEQ ID NO 64
<211> LENGTH: 11
<212> TYPE: PRT
<213> ORGANISM: Artificial sequence
<220> FEATURE:
<223> OTHER INFORMATION: Linker

<400> SEQUENCE: 64

Ser Pro Ser Pro Ser Pro Ser Pro Ser Pro Lys
1 5 10

<210> SEQ ID NO 65
<211> LENGTH: 9
<212> TYPE: PRT
<213> ORGANISM: Artificial sequence
<220> FEATURE:
<223> OTHER INFORMATION: Linker

<400> SEQUENCE: 65

Pro Glu Pro Thr Pro Glu Pro Thr Pro
1 5

<210> SEQ ID NO 66
<211> LENGTH: 9
<212> TYPE: PRT
<213> ORGANISM: Artificial sequence
<220> FEATURE:
<223> OTHER INFORMATION: Linker

<400> SEQUENCE: 66

Pro Glu Pro Thr Pro Glu Pro Thr Arg
1 5

<210> SEQ ID NO 67
<211> LENGTH: 13
<212> TYPE: PRT
<213> ORGANISM: Artificial sequence
<220> FEATURE:
<223> OTHER INFORMATION: Linker

<400> SEQUENCE: 67

Pro Glu Pro Thr Pro Glu Pro Thr Pro Glu Pro Thr Pro
1 5 10

<210> SEQ ID NO 68
<211> LENGTH: 21
<212> TYPE: PRT
<213> ORGANISM: Artificial sequence
<220> FEATURE:
<223> OTHER INFORMATION: Linker

<400> SEQUENCE: 68

Pro Glu Pro Thr Pro Glu Pro Thr Pro Glu Pro Thr Pro Glu Pro Thr
1 5 10 15

Pro Ser Pro Thr Gly
20

<210> SEQ ID NO 69
<211> LENGTH: 21
<212> TYPE: PRT
<213> ORGANISM: Artificial sequence
<220> FEATURE:
<223> OTHER INFORMATION: Linker

<400> SEQUENCE: 69

Pro Glu Pro Thr Pro Glu Pro Thr Pro Glu Pro Thr Pro Glu Pro Thr
1 5 10 15

Pro Thr Pro Thr Gly
20

<210> SEQ ID NO 70
<211> LENGTH: 21
<212> TYPE: PRT
<213> ORGANISM: Artificial sequence
<220> FEATURE:
<223> OTHER INFORMATION: Linker

<400> SEQUENCE: 70

Pro Glu Pro Thr Pro Glu Pro Thr Pro Glu Pro Thr Pro Glu Pro Thr
1               5                   10                  15

Pro Gly Pro Thr Gly
            20

<210> SEQ ID NO 71
<211> LENGTH: 21
<212> TYPE: PRT
<213> ORGANISM: Artificial sequence
<220> FEATURE:
<223> OTHER INFORMATION: Linker

<400> SEQUENCE: 71

Pro Glu Pro Thr Pro Glu Pro Thr Pro Glu Pro Thr Pro Glu Pro Thr
1               5                   10                  15

Pro Asp Pro Thr Gly
            20

<210> SEQ ID NO 72
<211> LENGTH: 20
<212> TYPE: PRT
<213> ORGANISM: Artificial sequence
<220> FEATURE:
<223> OTHER INFORMATION: Linker

<400> SEQUENCE: 72

Pro Glu Pro Thr Pro Glu Pro Thr Pro Glu Pro Thr Pro Glu Pro Thr
1               5                   10                  15

Pro Glu Thr Gly
            20

<210> SEQ ID NO 73
<211> LENGTH: 21
<212> TYPE: PRT
<213> ORGANISM: Artificial sequence
<220> FEATURE:
<223> OTHER INFORMATION: Linker

<400> SEQUENCE: 73

Pro Glu Pro Thr Pro Glu Pro Thr Pro Glu Pro Thr Pro Glu Pro Thr
1               5                   10                  15

Pro Glu Pro Thr Asp
            20

<210> SEQ ID NO 74
<211> LENGTH: 9
<212> TYPE: PRT
<213> ORGANISM: Artificial sequence
<220> FEATURE:
<223> OTHER INFORMATION: Linker

<400> SEQUENCE: 74

Pro Glu Pro Thr Pro Glu Pro Thr Glu
1               5

<210> SEQ ID NO 75
<211> LENGTH: 19
<212> TYPE: PRT
<213> ORGANISM: Artificial sequence
<220> FEATURE:
<223> OTHER INFORMATION: Linker

<400> SEQUENCE: 75

Pro Glu Pro Thr Pro Glu Pro Thr Pro Glu Pro Thr Pro Glu Pro Thr
1               5                   10                  15

Pro Glu Pro

<210> SEQ ID NO 76
<211> LENGTH: 20
<212> TYPE: PRT
<213> ORGANISM: Artificial sequence
<220> FEATURE:
<223> OTHER INFORMATION: Linker

<400> SEQUENCE: 76

Pro Glu Pro Thr Pro Glu Pro Thr Pro Glu Pro Thr Pro Glu Pro Thr
1               5                   10                  15

Pro Ser Pro Thr
            20

<210> SEQ ID NO 77
<211> LENGTH: 21
<212> TYPE: PRT
<213> ORGANISM: Artificial Sequence
<220> FEATURE:
<223> OTHER INFORMATION: Linker

<400> SEQUENCE: 77

Pro Glu Pro Thr Pro Glu Pro Thr Pro Glu Pro Thr Pro Glu Pro Thr
1               5                   10                  15

Pro Arg Pro Thr Thr
            20

<210> SEQ ID NO 78
<211> LENGTH: 21
<212> TYPE: PRT
<213> ORGANISM: Artificial sequence
<220> FEATURE:
<223> OTHER INFORMATION: Linker

<400> SEQUENCE: 78

Pro Glu Pro Thr Pro Glu Pro Thr Pro Glu Pro Thr Pro Glu Pro Thr
1               5                   10                  15

Pro Glu Pro Thr Thr
            20

<210> SEQ ID NO 79
<211> LENGTH: 20
<212> TYPE: PRT
<213> ORGANISM: Artificial sequence
<220> FEATURE:
<223> OTHER INFORMATION: Linker

<400> SEQUENCE: 79

Pro Glu Pro Thr Pro Glu Pro Thr Pro Glu Pro Thr Pro Glu Pro Thr
1               5                   10                  15

Pro Glu Pro Thr
            20

<210> SEQ ID NO 80
<211> LENGTH: 21
<212> TYPE: PRT
<213> ORGANISM: Artificial sequence
<220> FEATURE:
<223> OTHER INFORMATION: Linker

<400> SEQUENCE: 80

Pro Glu Pro Thr Pro Glu Pro Thr Pro Glu Pro Thr Pro Glu Pro Thr
1 5 10 15

Pro Glu Pro Thr Ser
20

<210> SEQ ID NO 81
<211> LENGTH: 21
<212> TYPE: PRT
<213> ORGANISM: Artificial sequence
<220> FEATURE:
<223> OTHER INFORMATION: Linker

<400> SEQUENCE: 81

Pro Glu Pro Thr Pro Glu Pro Thr Pro Glu Pro Thr Pro Glu Pro Thr
1 5 10 15

Pro Glu Pro Thr Arg
20

<210> SEQ ID NO 82
<211> LENGTH: 29
<212> TYPE: PRT
<213> ORGANISM: Artificial sequence
<220> FEATURE:
<223> OTHER INFORMATION: Linker

<400> SEQUENCE: 82

Pro Pro Pro Gly Gly Pro Gly Gly Pro Gly Thr Pro Thr Ser Thr Ala
1 5 10 15

Pro Gly Ser Gly Pro Thr Ser Pro Gly Gly Gly Ser Gly
20 25

<210> SEQ ID NO 83
<211> LENGTH: 29
<212> TYPE: PRT
<213> ORGANISM: Artificial sequence
<220> FEATURE:
<223> OTHER INFORMATION: Linker

<400> SEQUENCE: 83

Pro Pro Pro Gly Gly Pro Gly Gly Thr Gly Thr Pro Thr Ser Thr Ala
1 5 10 15

Pro Gly Ser Gly Pro Thr Ser Pro Gly Gly Gly Ser Gly
20 25

<210> SEQ ID NO 84
<211> LENGTH: 29
<212> TYPE: PRT
<213> ORGANISM: Artificial sequence
<220> FEATURE:
<223> OTHER INFORMATION: Linker

<400> SEQUENCE: 84

Pro Pro Ser Gly Gly Pro Gly Gly Pro Gly Thr Pro Thr Ser Thr Ala
1 5 10 15

Pro Gly Ser Gly Pro Thr Ser Pro Gly Gly Gly Ser Gly
20 25

<210> SEQ ID NO 85
<211> LENGTH: 17
<212> TYPE: PRT
<213> ORGANISM: Artificial sequence
<220> FEATURE:

<223> OTHER INFORMATION: Linker

<400> SEQUENCE: 85

Pro Glu Pro Thr Pro Arg Pro Thr Pro Glu Pro Thr Pro Arg Pro Thr
1 5 10 15

Gly

<210> SEQ ID NO 86
<211> LENGTH: 17
<212> TYPE: PRT
<213> ORGANISM: Artificial sequence
<220> FEATURE:
<223> OTHER INFORMATION: Linker

<400> SEQUENCE: 86

Pro Lys Pro Thr Pro Glu Pro Thr Pro Lys Pro Thr Pro Glu Pro Thr
1 5 10 15

Gly

<210> SEQ ID NO 87
<211> LENGTH: 17
<212> TYPE: PRT
<213> ORGANISM: Artificial sequence
<220> FEATURE:
<223> OTHER INFORMATION: Linker

<400> SEQUENCE: 87

Pro Glu Pro Thr Pro Lys Pro Thr Pro Glu Pro Thr Pro Lys Pro Thr
1 5 10 15

Gly

<210> SEQ ID NO 88
<211> LENGTH: 17
<212> TYPE: PRT
<213> ORGANISM: Artificial sequence
<220> FEATURE:
<223> OTHER INFORMATION: Linker

<400> SEQUENCE: 88

Pro Glu Pro Thr Pro Gln Pro Thr Pro Glu Pro Thr Pro Gln Pro Thr
1 5 10 15

Gly

<210> SEQ ID NO 89
<211> LENGTH: 13
<212> TYPE: PRT
<213> ORGANISM: Artificial sequence
<220> FEATURE:
<223> OTHER INFORMATION: Linker

<400> SEQUENCE: 89

Pro Arg Pro Thr Pro Glu Pro Thr Pro Arg Pro Thr Gly
1 5 10

<210> SEQ ID NO 90
<211> LENGTH: 13
<212> TYPE: PRT
<213> ORGANISM: Artificial sequence
<220> FEATURE:
<223> OTHER INFORMATION: Linker

<400> SEQUENCE: 90

Pro Lys Pro Thr Pro Glu Pro Thr Pro Lys Pro Thr Gly
1 5 10

<210> SEQ ID NO 91
<211> LENGTH: 9
<212> TYPE: PRT
<213> ORGANISM: Artificial sequence
<220> FEATURE:
<223> OTHER INFORMATION: Linker

<400> SEQUENCE: 91

Pro Glu Pro Thr Pro Gln Pro Thr Gly
1 5

<210> SEQ ID NO 92
<211> LENGTH: 9
<212> TYPE: PRT
<213> ORGANISM: Artificial sequence
<220> FEATURE:
<223> OTHER INFORMATION: Linker

<400> SEQUENCE: 92

Pro Glu Pro Thr Pro Gln Pro Thr Gly
1 5

<210> SEQ ID NO 93
<211> LENGTH: 7
<212> TYPE: PRT
<213> ORGANISM: Artificial sequence
<220> FEATURE:
<223> OTHER INFORMATION: Linker

<400> SEQUENCE: 93

Thr Pro Pro Thr Pro Pro Gly
1 5

<210> SEQ ID NO 94
<211> LENGTH: 7
<212> TYPE: PRT
<213> ORGANISM: Artificial sequence
<220> FEATURE:
<223> OTHER INFORMATION: Linker

<400> SEQUENCE: 94

Ser Pro Ser Ser Pro Ser Gly
1 5

<210> SEQ ID NO 95
<211> LENGTH: 10
<212> TYPE: PRT
<213> ORGANISM: Artificial sequence
<220> FEATURE:
<223> OTHER INFORMATION: Linker

<400> SEQUENCE: 95

Ser Pro Ser Ser Pro Ser Ser Pro Ser Gly
1 5 10

<210> SEQ ID NO 96
<211> LENGTH: 7
<212> TYPE: PRT
<213> ORGANISM: Artificial sequence
<220> FEATURE:
<223> OTHER INFORMATION: Linker

<400> SEQUENCE: 96

Thr Pro Thr Thr Pro Thr Gly
1 5

<210> SEQ ID NO 97
<211> LENGTH: 10
<212> TYPE: PRT
<213> ORGANISM: Artificial sequence
<220> FEATURE:
<223> OTHER INFORMATION: Linker

<400> SEQUENCE: 97

Thr Pro Thr Thr Pro Thr Thr Pro Thr Gly
1 5 10

<210> SEQ ID NO 98
<211> LENGTH: 4
<212> TYPE: PRT
<213> ORGANISM: Artificial sequence
<220> FEATURE:
<223> OTHER INFORMATION: Linker
<220> FEATURE:
<221> NAME/KEY: misc_feature
<222> LOCATION: (2)..(2)
<223> OTHER INFORMATION: Xaa = any amino acid
<220> FEATURE:
<221> NAME/KEY: misc_feature
<222> LOCATION: (4)..(4)
<223> OTHER INFORMATION: Xaa = any amino acid

<400> SEQUENCE: 98

Pro Xaa Pro Xaa
1

<210> SEQ ID NO 99
<211> LENGTH: 4
<212> TYPE: PRT
<213> ORGANISM: Artificial sequence
<220> FEATURE:
<223> OTHER INFORMATION: Linker
<220> FEATURE:
<221> NAME/KEY: misc_feature
<222> LOCATION: (1)..(1)
<223> OTHER INFORMATION: Xaa = any amino acid
<220> FEATURE:
<221> NAME/KEY: misc_feature
<222> LOCATION: (3)..(3)
<223> OTHER INFORMATION: Xaa = any amino acid

<400> SEQUENCE: 99

Xaa Pro Xaa Pro
1

<210> SEQ ID NO 100
<211> LENGTH: 6
<212> TYPE: PRT
<213> ORGANISM: Artificial sequence
<220> FEATURE:
<223> OTHER INFORMATION: Linker
<220> FEATURE:
<221> NAME/KEY: misc_feature
<222> LOCATION: (1)..(1)
<223> OTHER INFORMATION: Xaa = any amino acid
<220> FEATURE:
<221> NAME/KEY: misc_feature
<222> LOCATION: (3)..(3)
<223> OTHER INFORMATION: Xaa = any amino acid
<220> FEATURE:
<221> NAME/KEY: misc_feature
<222> LOCATION: (4)..(4)
<223> OTHER INFORMATION: Xaa = any amino acid
<220> FEATURE:
<221> NAME/KEY: misc_feature
<222> LOCATION: (6)..(6)
<223> OTHER INFORMATION: Xaa = any amino acid

<400> SEQUENCE: 100

Xaa Pro Xaa Xaa Pro Xaa
1 5

<210> SEQ ID NO 101
<211> LENGTH: 6
<212> TYPE: PRT
<213> ORGANISM: Artificial sequence
<220> FEATURE:
<223> OTHER INFORMATION: Linker
<220> FEATURE:
<221> NAME/KEY: misc_feature
<222> LOCATION: (1)..(1)
<223> OTHER INFORMATION: Xaa = any amino acid
<220> FEATURE:
<221> NAME/KEY: misc_feature
<222> LOCATION: (2)..(2)
<223> OTHER INFORMATION: Xaa = any amino acid
<220> FEATURE:
<221> NAME/KEY: misc_feature
<222> LOCATION: (4)..(4)
<223> OTHER INFORMATION: Xaa = any amino acid
<220> FEATURE:
<221> NAME/KEY: misc_feature
<222> LOCATION: (5)..(5)
<223> OTHER INFORMATION: Xaa = any amino acid

<400> SEQUENCE: 101

Xaa Xaa Pro Xaa Xaa Pro
1 5

<210> SEQ ID NO 102
<211> LENGTH: 4
<212> TYPE: PRT
<213> ORGANISM: Artificial sequence
<220> FEATURE:
<223> OTHER INFORMATION: Linker
<220> FEATURE:
<221> NAME/KEY: misc_feature
<222> LOCATION: (2)..(2)
<223> OTHER INFORMATION: Xaa = Ser, Thr, Arg, Lys, Asp, Glu, Asn, Gln
<220> FEATURE:
<221> NAME/KEY: misc_feature
<222> LOCATION: (4)..(4)
<223> OTHER INFORMATION: Xaa = Ser, Thr, Arg, Lys, Asp, Glu

<400> SEQUENCE: 102

Pro Xaa Pro Xaa
1

<210> SEQ ID NO 103
<211> LENGTH: 4
<212> TYPE: PRT
<213> ORGANISM: Artificial sequence
<220> FEATURE:
<223> OTHER INFORMATION: Linker

<400> SEQUENCE: 103

Pro Ser Pro Ser
1

<210> SEQ ID NO 104
<211> LENGTH: 4
<212> TYPE: PRT
<213> ORGANISM: Artificial sequence
<220> FEATURE:
<223> OTHER INFORMATION: Linker

<400> SEQUENCE: 104

Pro Ser Pro Thr

1

<210> SEQ ID NO 105
<211> LENGTH: 4
<212> TYPE: PRT
<213> ORGANISM: Artificial sequence
<220> FEATURE:
<223> OTHER INFORMATION: Linker

<400> SEQUENCE: 105

Pro Ser Pro Arg
1

<210> SEQ ID NO 106
<211> LENGTH: 4
<212> TYPE: PRT
<213> ORGANISM: Artificial sequence
<220> FEATURE:
<223> OTHER INFORMATION: Linker

<400> SEQUENCE: 106

Pro Ser Pro Lys
1

<210> SEQ ID NO 107
<211> LENGTH: 4
<212> TYPE: PRT
<213> ORGANISM: Artificial sequence
<220> FEATURE:
<223> OTHER INFORMATION: Linker

<400> SEQUENCE: 107

Pro Ser Pro Asp
1

<210> SEQ ID NO 108
<211> LENGTH: 4
<212> TYPE: PRT
<213> ORGANISM: Artificial sequence
<220> FEATURE:
<223> OTHER INFORMATION: Linker

<400> SEQUENCE: 108

Pro Ser Pro Glu
1

<210> SEQ ID NO 109
<211> LENGTH: 4
<212> TYPE: PRT
<213> ORGANISM: Artificial sequence
<220> FEATURE:
<223> OTHER INFORMATION: Linker
<220> FEATURE:
<221> NAME/KEY: misc_feature
<222> LOCATION: (2)..(2)
<223> OTHER INFORMATION: Xaa = Ser, Glu

<400> SEQUENCE: 109

Pro Xaa Pro Thr
1

<210> SEQ ID NO 110
<211> LENGTH: 6
<212> TYPE: PRT
<213> ORGANISM: Artificial sequence
<220> FEATURE:
<223> OTHER INFORMATION: Linker -continued

```
<400> SEQUENCE: 110

Pro Pro Ser Pro Thr Pro
1               5


<210> SEQ ID NO 111
<211> LENGTH: 6
<212> TYPE: PRT
<213> ORGANISM: Artificial sequence
<220> FEATURE:
<223> OTHER INFORMATION: Linker

<400> SEQUENCE: 111

Pro Pro Thr Pro Thr Pro
1               5


<210> SEQ ID NO 112
<211> LENGTH: 6
<212> TYPE: PRT
<213> ORGANISM: Artificial sequence
<220> FEATURE:
<223> OTHER INFORMATION: Linker

<400> SEQUENCE: 112

Pro Pro Ser Pro Ser Pro
1               5


<210> SEQ ID NO 113
<211> LENGTH: 6
<212> TYPE: PRT
<213> ORGANISM: Artificial sequence
<220> FEATURE:
<223> OTHER INFORMATION: Linker

<400> SEQUENCE: 113

Ser Pro Pro Pro Thr Pro
1               5


<210> SEQ ID NO 114
<211> LENGTH: 6
<212> TYPE: PRT
<213> ORGANISM: Artificial sequence
<220> FEATURE:
<223> OTHER INFORMATION: Linker

<400> SEQUENCE: 114

Ser Pro Thr Pro Pro Pro
1               5


<210> SEQ ID NO 115
<211> LENGTH: 6
<212> TYPE: PRT
<213> ORGANISM: Artificial sequence
<220> FEATURE:
<223> OTHER INFORMATION: Linker

<400> SEQUENCE: 115

Ser Pro Pro Pro Pro Pro
1               5


<210> SEQ ID NO 116
<211> LENGTH: 6
<212> TYPE: PRT
<213> ORGANISM: Artificial sequence
<220> FEATURE:
<223> OTHER INFORMATION: Linker

<400> SEQUENCE: 116
```

Ser Pro Thr Pro Thr Pro
1 5

<210> SEQ ID NO 117
<211> LENGTH: 6
<212> TYPE: PRT
<213> ORGANISM: Artificial sequence
<220> FEATURE:
<223> OTHER INFORMATION: Linker

<400> SEQUENCE: 117

Thr Pro Pro Pro Ser Pro
1 5

<210> SEQ ID NO 118
<211> LENGTH: 6
<212> TYPE: PRT
<213> ORGANISM: Artificial sequence
<220> FEATURE:
<223> OTHER INFORMATION: Linker

<400> SEQUENCE: 118

Thr Pro Ser Pro Pro Pro
1 5

<210> SEQ ID NO 119
<211> LENGTH: 6
<212> TYPE: PRT
<213> ORGANISM: Artificial sequence
<220> FEATURE:
<223> OTHER INFORMATION: Linker

<400> SEQUENCE: 119

Thr Pro Pro Pro Pro Pro
1 5

<210> SEQ ID NO 120
<211> LENGTH: 6
<212> TYPE: PRT
<213> ORGANISM: Artificial sequence
<220> FEATURE:
<223> OTHER INFORMATION: Linker

<400> SEQUENCE: 120

Thr Pro Ser Pro Ser Pro
1 5

<210> SEQ ID NO 121
<211> LENGTH: 8
<212> TYPE: PRT
<213> ORGANISM: Artificial sequence
<220> FEATURE:
<223> OTHER INFORMATION: Linker

<400> SEQUENCE: 121

Pro Ser Pro Thr Pro Glu Pro Thr
1 5

<210> SEQ ID NO 122
<211> LENGTH: 16
<212> TYPE: PRT
<213> ORGANISM: Artificial sequence
<220> FEATURE:
<223> OTHER INFORMATION: Linker

<400> SEQUENCE: 122

Pro Ser Pro Thr Pro Glu Pro Thr Pro Ser Pro Thr Pro Glu Pro Thr
1 5 10 15

<210> SEQ ID NO 123
<211> LENGTH: 8
<212> TYPE: PRT
<213> ORGANISM: Artificial sequence
<220> FEATURE:
<223> OTHER INFORMATION: Linker

<400> SEQUENCE: 123

Pro Glu Pro Thr Pro Ser Pro Thr
1 5

<210> SEQ ID NO 124
<211> LENGTH: 12
<212> TYPE: PRT
<213> ORGANISM: Artificial sequence
<220> FEATURE:
<223> OTHER INFORMATION: Linker

<400> SEQUENCE: 124

Pro Glu Pro Thr Pro Ser Pro Thr Pro Ser Pro Thr
1 5 10

<210> SEQ ID NO 125
<211> LENGTH: 4
<212> TYPE: PRT
<213> ORGANISM: Artificial sequence
<220> FEATURE:
<223> OTHER INFORMATION: Linker

<400> SEQUENCE: 125

Pro Glu Pro Thr
1

<210> SEQ ID NO 126
<211> LENGTH: 6
<212> TYPE: PRT
<213> ORGANISM: Artificial Sequence
<220> FEATURE:
<223> OTHER INFORMATION: Linker

<400> SEQUENCE: 126

Ser Pro Pro Glu Pro Thr
1 5

<210> SEQ ID NO 127
<211> LENGTH: 6
<212> TYPE: PRT
<213> ORGANISM: Artificial sequence
<220> FEATURE:
<223> OTHER INFORMATION: Linker

<400> SEQUENCE: 127

Ser Pro Pro Ser Pro Thr
1 5

<210> SEQ ID NO 128
<211> LENGTH: 6
<212> TYPE: PRT
<213> ORGANISM: Artificial sequence
<220> FEATURE:
<223> OTHER INFORMATION: Linker

<400> SEQUENCE: 128

Pro Ser Pro Glu Pro Thr

-continued 1 5

<210> SEQ ID NO 129
<211> LENGTH: 6
<212> TYPE: PRT
<213> ORGANISM: Artificial sequence
<220> FEATURE:
<223> OTHER INFORMATION: Linker

<400> SEQUENCE: 129

Pro Ser Pro Ser Pro Thr
1 5

<210> SEQ ID NO 130
<211> LENGTH: 4
<212> TYPE: PRT
<213> ORGANISM: Artificial sequence
<220> FEATURE:
<223> OTHER INFORMATION: Linker

<400> SEQUENCE: 130

Ser Pro Ser Pro
1

<210> SEQ ID NO 131
<211> LENGTH: 6
<212> TYPE: PRT
<213> ORGANISM: Artificial sequence
<220> FEATURE:
<223> OTHER INFORMATION: Linker

<400> SEQUENCE: 131

Ser Pro Ser Pro Ser Pro
1 5

<210> SEQ ID NO 132
<211> LENGTH: 8
<212> TYPE: PRT
<213> ORGANISM: Artificial sequence
<220> FEATURE:
<223> OTHER INFORMATION: Linker

<400> SEQUENCE: 132

Ser Pro Ser Pro Ser Pro Ser Pro
1 5

<210> SEQ ID NO 133
<211> LENGTH: 12
<212> TYPE: PRT
<213> ORGANISM: Artificial sequence
<220> FEATURE:
<223> OTHER INFORMATION: Linker

<400> SEQUENCE: 133

Ser Pro Ser Pro Ser Pro Ser Pro Ser Pro Ser Pro
1 5 10

<210> SEQ ID NO 134
<211> LENGTH: 14
<212> TYPE: PRT
<213> ORGANISM: Artificial sequence
<220> FEATURE:
<223> OTHER INFORMATION: Linker

<400> SEQUENCE: 134

Ser Pro Ser Pro Ser Pro Ser Pro Ser Pro Ser Pro Ser Pro
1 5 10

<210> SEQ ID NO 135
<211> LENGTH: 16
<212> TYPE: PRT
<213> ORGANISM: Artificial sequence
<220> FEATURE:
<223> OTHER INFORMATION: Linker

<400> SEQUENCE: 135

Ser Pro Ser Pro Ser Pro Ser Pro Ser Pro Ser Pro Ser Pro Ser Pro
1 5 10 15

<210> SEQ ID NO 136
<211> LENGTH: 8
<212> TYPE: PRT
<213> ORGANISM: Artificial sequence
<220> FEATURE:
<223> OTHER INFORMATION: Linker

<400> SEQUENCE: 136

Pro Pro Pro Pro Pro Pro Pro Pro
1 5

<210> SEQ ID NO 137
<211> LENGTH: 9
<212> TYPE: PRT
<213> ORGANISM: Artificial sequence
<220> FEATURE:
<223> OTHER INFORMATION: Linker

<400> SEQUENCE: 137

Pro Pro Pro Pro Pro Pro Pro Pro Pro
1 5

<210> SEQ ID NO 138
<211> LENGTH: 10
<212> TYPE: PRT
<213> ORGANISM: Artificial sequence
<220> FEATURE:
<223> OTHER INFORMATION: Linker

<400> SEQUENCE: 138

Pro Pro Pro Pro Pro Pro Pro Pro Pro Pro
1 5 10

<210> SEQ ID NO 139
<211> LENGTH: 11
<212> TYPE: PRT
<213> ORGANISM: Artificial sequence
<220> FEATURE:
<223> OTHER INFORMATION: Linker

<400> SEQUENCE: 139

Pro Pro Pro Pro Pro Pro Pro Pro Pro Pro Pro
1 5 10

<210> SEQ ID NO 140
<211> LENGTH: 12
<212> TYPE: PRT
<213> ORGANISM: Artificial sequence
<220> FEATURE:
<223> OTHER INFORMATION: Linker

<400> SEQUENCE: 140

Pro Pro Pro Pro Pro Pro Pro Pro Pro Pro Pro Pro
1 5 10

<210> SEQ ID NO 141
<211> LENGTH: 13
<212> TYPE: PRT
<213> ORGANISM: Artificial sequence
<220> FEATURE:
<223> OTHER INFORMATION: Linker

<400> SEQUENCE: 141

Pro Pro Pro Pro Pro Pro Pro Pro Pro Pro Pro Pro Pro
1               5                   10

<210> SEQ ID NO 142
<211> LENGTH: 14
<212> TYPE: PRT
<213> ORGANISM: Artificial sequence
<220> FEATURE:
<223> OTHER INFORMATION: Linker

<400> SEQUENCE: 142

Pro Pro Pro Pro Pro Pro Pro Pro Pro Pro Pro Pro Pro Pro
1               5                   10

<210> SEQ ID NO 143
<211> LENGTH: 15
<212> TYPE: PRT
<213> ORGANISM: Artificial sequence
<220> FEATURE:
<223> OTHER INFORMATION: Linker

<400> SEQUENCE: 143

Pro Pro Pro Pro Pro Pro Pro Pro Pro Pro Pro Pro Pro Pro Pro
1               5                   10                  15

<210> SEQ ID NO 144
<211> LENGTH: 8
<212> TYPE: PRT
<213> ORGANISM: Artificial sequence
<220> FEATURE:
<223> OTHER INFORMATION: Linker

<400> SEQUENCE: 144

Pro Glu Pro Thr Pro Glu Pro Thr
1               5

<210> SEQ ID NO 145
<211> LENGTH: 12
<212> TYPE: PRT
<213> ORGANISM: Artificial sequence
<220> FEATURE:
<223> OTHER INFORMATION: Linker

<400> SEQUENCE: 145

Pro Glu Pro Thr Pro Glu Pro Thr Pro Glu Pro Thr
1               5                   10

<210> SEQ ID NO 146
<211> LENGTH: 16
<212> TYPE: PRT
<213> ORGANISM: Artificial sequence
<220> FEATURE:
<223> OTHER INFORMATION: Linker

<400> SEQUENCE: 146

Pro Glu Pro Thr Pro Glu Pro Thr Pro Glu Pro Thr Pro Glu Pro Thr
1               5                   10                  15

<210> SEQ ID NO 147
<211> LENGTH: 8
<212> TYPE: PRT
<213> ORGANISM: Artificial sequence
<220> FEATURE:
<223> OTHER INFORMATION: Linker

<400> SEQUENCE: 147

Pro Ser Pro Thr Pro Ser Pro Thr
1               5

<210> SEQ ID NO 148
<211> LENGTH: 12
<212> TYPE: PRT
<213> ORGANISM: Artificial sequence
<220> FEATURE:
<223> OTHER INFORMATION: Linker

<400> SEQUENCE: 148

Pro Ser Pro Thr Pro Ser Pro Thr Pro Ser Pro Thr
1               5                   10

<210> SEQ ID NO 149
<211> LENGTH: 16
<212> TYPE: PRT
<213> ORGANISM: Artificial sequence
<220> FEATURE:
<223> OTHER INFORMATION: Linker

<400> SEQUENCE: 149

Pro Ser Pro Thr Pro Ser Pro Thr Pro Ser Pro Thr Pro Ser Pro Thr
1               5                   10                  15

<210> SEQ ID NO 150
<211> LENGTH: 20
<212> TYPE: PRT
<213> ORGANISM: Artificial Sequence
<220> FEATURE:
<223> OTHER INFORMATION: Linker

<400> SEQUENCE: 150

Pro Ser Pro Thr Pro Ser Pro Thr Pro Ser Pro Thr Pro Ser Pro Thr
1               5                   10                  15

Pro Ser Pro Thr
            20

<210> SEQ ID NO 151
<211> LENGTH: 6
<212> TYPE: PRT
<213> ORGANISM: Artificial sequence
<220> FEATURE:
<223> OTHER INFORMATION: Linker

<400> SEQUENCE: 151

Ser Pro Ser Ser Pro Ser
1               5

<210> SEQ ID NO 152
<211> LENGTH: 9
<212> TYPE: PRT
<213> ORGANISM: Artificial sequence
<220> FEATURE:
<223> OTHER INFORMATION: Linker

<400> SEQUENCE: 152

Ser Pro Ser Ser Pro Ser Ser Pro Ser
1               5

<210> SEQ ID NO 153
<211> LENGTH: 12
<212> TYPE: PRT
<213> ORGANISM: Artificial sequence
<220> FEATURE:
<223> OTHER INFORMATION: Linker

<400> SEQUENCE: 153

Ser Pro Ser Ser Pro Ser Ser Pro Ser Ser Pro Ser
1 5 10

<210> SEQ ID NO 154
<211> LENGTH: 15
<212> TYPE: PRT
<213> ORGANISM: Artificial sequence
<220> FEATURE:
<223> OTHER INFORMATION: Linker

<400> SEQUENCE: 154

Ser Pro Ser Ser Pro Ser Ser Pro Ser Ser Pro Ser Ser Pro Ser
1 5 10 15

<210> SEQ ID NO 155
<211> LENGTH: 6
<212> TYPE: PRT
<213> ORGANISM: Artificial sequence
<220> FEATURE:
<223> OTHER INFORMATION: Linker

<400> SEQUENCE: 155

Thr Pro Thr Thr Pro Thr
1 5

<210> SEQ ID NO 156
<211> LENGTH: 9
<212> TYPE: PRT
<213> ORGANISM: Artificial sequence
<220> FEATURE:
<223> OTHER INFORMATION: Linker

<400> SEQUENCE: 156

Thr Pro Thr Thr Pro Thr Thr Pro Thr
1 5

<210> SEQ ID NO 157
<211> LENGTH: 12
<212> TYPE: PRT
<213> ORGANISM: Artificial sequence
<220> FEATURE:
<223> OTHER INFORMATION: Linker

<400> SEQUENCE: 157

Thr Pro Thr Thr Pro Thr Thr Pro Thr Thr Pro Thr
1 5 10

<210> SEQ ID NO 158
<211> LENGTH: 15
<212> TYPE: PRT
<213> ORGANISM: Artificial sequence
<220> FEATURE:
<223> OTHER INFORMATION: Linker

<400> SEQUENCE: 158

Thr Pro Thr Thr Pro Thr Thr Pro Thr Thr Pro Thr Thr Pro Thr
1 5 10 15

<210> SEQ ID NO 159
<211> LENGTH: 16
<212> TYPE: PRT
<213> ORGANISM: Artificial sequence
<220> FEATURE:
<223> OTHER INFORMATION: Linker

<400> SEQUENCE: 159

Pro Glu Pro Thr Pro Arg Pro Thr Pro Glu Pro Thr Pro Arg Pro Thr
1               5                   10                  15

<210> SEQ ID NO 160
<211> LENGTH: 16
<212> TYPE: PRT
<213> ORGANISM: Artificial sequence
<220> FEATURE:
<223> OTHER INFORMATION: Linker

<400> SEQUENCE: 160

Pro Glu Pro Thr Pro Lys Pro Thr Pro Glu Pro Thr Pro Lys Pro Thr
1               5                   10                  15

<210> SEQ ID NO 161
<211> LENGTH: 16
<212> TYPE: PRT
<213> ORGANISM: Artificial sequence
<220> FEATURE:
<223> OTHER INFORMATION: Linker

<400> SEQUENCE: 161

Pro Glu Pro Thr Pro Gln Pro Thr Pro Glu Pro Thr Pro Gln Pro Thr
1               5                   10                  15

<210> SEQ ID NO 162
<211> LENGTH: 12
<212> TYPE: PRT
<213> ORGANISM: Artificial sequence
<220> FEATURE:
<223> OTHER INFORMATION: Linker

<400> SEQUENCE: 162

Pro Arg Pro Thr Pro Glu Pro Thr Pro Arg Pro Thr
1               5                   10

<210> SEQ ID NO 163
<211> LENGTH: 12
<212> TYPE: PRT
<213> ORGANISM: Artificial sequence
<220> FEATURE:
<223> OTHER INFORMATION: Linker

<400> SEQUENCE: 163

Pro Lys Pro Thr Pro Glu Pro Thr Pro Lys Pro Thr
1               5                   10

<210> SEQ ID NO 164
<211> LENGTH: 8
<212> TYPE: PRT
<213> ORGANISM: Artificial sequence
<220> FEATURE:
<223> OTHER INFORMATION: Linker

<400> SEQUENCE: 164

Pro Glu Pro Thr Pro Gln Pro Thr
1               5

<210> SEQ ID NO 165
<211> LENGTH: 12
<212> TYPE: PRT
<213> ORGANISM: Artificial sequence
<220> FEATURE:
<223> OTHER INFORMATION: Linker

<400> SEQUENCE: 165

Pro Glu Pro Thr Pro Gln Pro Thr Pro Glu Pro Thr
1 5 10

<210> SEQ ID NO 166
<211> LENGTH: 12
<212> TYPE: PRT
<213> ORGANISM: Artificial sequence
<220> FEATURE:
<223> OTHER INFORMATION: Linker

<400> SEQUENCE: 166

Thr Thr Pro Pro Thr Pro Thr Pro Thr Pro Thr Pro
1 5 10

<210> SEQ ID NO 167
<211> LENGTH: 14
<212> TYPE: PRT
<213> ORGANISM: Artificial sequence
<220> FEATURE:
<223> OTHER INFORMATION: Linker

<400> SEQUENCE: 167

Thr Thr Pro Thr Pro Pro Thr Pro Thr Pro Thr Pro Thr Pro
1 5 10

<210> SEQ ID NO 168
<211> LENGTH: 16
<212> TYPE: PRT
<213> ORGANISM: Artificial sequence
<220> FEATURE:
<223> OTHER INFORMATION: Linker

<400> SEQUENCE: 168

Thr Thr Pro Thr Pro Thr Pro Pro Thr Pro Thr Pro Thr Pro Thr Pro
1 5 10 15

<210> SEQ ID NO 169
<211> LENGTH: 33
<212> TYPE: PRT
<213> ORGANISM: Artificial sequence
<220> FEATURE:
<223> OTHER INFORMATION: Linker

<400> SEQUENCE: 169

Thr Pro Pro Thr Pro Pro Thr Pro Pro Thr Pro Pro Thr Pro Pro Thr
1 5 10 15

Pro Pro Thr Pro Pro Thr Pro Pro Thr Pro Pro Thr Pro Pro Thr Pro
20 25 30

Pro

<210> SEQ ID NO 170
<211> LENGTH: 13
<212> TYPE: PRT
<213> ORGANISM: Artificial sequence
<220> FEATURE:
<223> OTHER INFORMATION: Linker

<400> SEQUENCE: 170

```
Pro Pro Pro Pro Pro Pro Pro Pro Pro Pro Pro Pro Gly
1               5                   10


<210> SEQ ID NO 171
<211> LENGTH: 15
<212> TYPE: PRT
<213> ORGANISM: Artificial sequence
<220> FEATURE:
<223> OTHER INFORMATION: Linker

<400> SEQUENCE: 171

Pro Pro Pro Pro Pro Pro Pro Pro Pro Pro Pro Pro Pro Pro Gly
1               5                   10                  15


<210> SEQ ID NO 172
<211> LENGTH: 16
<212> TYPE: PRT
<213> ORGANISM: Artificial sequence
<220> FEATURE:
<223> OTHER INFORMATION: Linker

<400> SEQUENCE: 172

Pro Pro Pro Pro Pro Pro Pro Pro Pro Pro Pro Pro Pro Pro Pro Gly
1               5                   10                  15


<210> SEQ ID NO 173
<211> LENGTH: 37
<212> TYPE: PRT
<213> ORGANISM: Chaetomium thermophilum

<400> SEQUENCE: 173

Cys Thr Thr Gln Lys Trp Gly Gln Cys Gly Gly Ile Gly Tyr Thr Gly
1               5                   10                  15

Cys Thr Asn Cys Val Ala Gly Thr Thr Cys Thr Gln Leu Asn Pro Trp
            20                  25                  30

Tyr Ser Gln Cys Leu
        35


<210> SEQ ID NO 174
<211> LENGTH: 37
<212> TYPE: PRT
<213> ORGANISM: Chaetomium thermophilum

<400> SEQUENCE: 174

Cys Thr Thr Gln Lys Trp Gly Gln Cys Gly Gly Ile Gly Tyr Thr Gly
1               5                   10                  15

Cys Thr Asn Cys Val Ala Gly Thr Thr Cys Thr Glu Leu Asn Pro Trp
            20                  25                  30

Tyr Ser Gln Cys Leu
        35


<210> SEQ ID NO 175
<211> LENGTH: 36
<212> TYPE: PRT
<213> ORGANISM: Mycothermus thermophilus

<400> SEQUENCE: 175

Cys Ala Ser Lys Trp Gly Gln Cys Gly Gly Gln Gly Trp Ala Gly Pro
1               5                   10                  15

Thr Cys Cys Glu Ala Gly Ser Thr Cys Thr Arg Gln Asn Glu Trp Tyr
            20                  25                  30

Ser Gln Cys Leu
        35
```

<210> SEQ ID NO 176
<211> LENGTH: 37
<212> TYPE: PRT
<213> ORGANISM: Ovatospora medusarum

<400> SEQUENCE: 176

Cys Thr Ala Ala Arg Trp Gln Gln Cys Gly Gly Ile Gly Tyr Ser Gly
1 5 10 15

Cys Lys Ala Cys Ala Ser Pro Trp Thr Cys Gln Lys Leu Asn Asp Trp
20 25 30

Tyr His Gln Cys Leu
35

<210> SEQ ID NO 177
<211> LENGTH: 37
<212> TYPE: PRT
<213> ORGANISM: Thermothelomyces heterothallica

<400> SEQUENCE: 177

Cys Thr Val Ala Lys Trp Gly Gln Cys Gly Gly Gln Gly Tyr Ser Gly
1 5 10 15

Cys Thr Val Cys Ala Ala Gly Ser Thr Cys Gln Lys Thr Asn Asp Tyr
20 25 30

Tyr Ser Gln Cys Leu
35

<210> SEQ ID NO 178
<211> LENGTH: 38
<212> TYPE: PRT
<213> ORGANISM: Ovatospora medusarum

<400> SEQUENCE: 178

Cys Ser Val Gln Ala Phe Gly Gln Cys Gly Gly Thr Gly Tyr Ser Gly
1 5 10 15

Cys Thr Gln Cys Ala Asp Gly Tyr Thr Cys Lys Asp Val Ser Pro Pro
20 25 30

Tyr Tyr Ser Gln Cys Val
35

<210> SEQ ID NO 179
<211> LENGTH: 37
<212> TYPE: PRT
<213> ORGANISM: Thielavia arenaria

<400> SEQUENCE: 179

Cys Thr Val Ala Lys Trp Gly Gln Cys Gly Gly Leu Gly Trp Thr Gly
1 5 10 15

Cys Thr Thr Cys Ala Ala Gly Ser Thr Cys Asn Lys Ala Asn Asp Phe
20 25 30

Tyr Ser Gln Cys Val
35

<210> SEQ ID NO 180
<211> LENGTH: 37
<212> TYPE: PRT
<213> ORGANISM: Ovatospora medusarum

<400> SEQUENCE: 180

Cys Thr Val Ala Lys Tyr Gly Gln Cys Gly Gly Asn Asn Tyr Ser Gly
1 5 10 15

Cys Thr Thr Cys Ala Ala Gly Ser Thr Cys Ser Arg Thr Asn Glu Tyr
20 25 30

Tyr Ser Gln Cys Val
35

<210> SEQ ID NO 181
<211> LENGTH: 37
<212> TYPE: PRT
<213> ORGANISM: Chaetomium thermophile

<400> SEQUENCE: 181

Cys Val Thr Gln Lys Trp Ala Gln Cys Gly Gly Asn Gly Phe Ser Gly
1 5 10 15

Cys Arg Thr Cys Ala Ser Gly Ser Thr Cys Gln Val Leu Asn Glu Trp
20 25 30

Tyr Ser Gln Cys Leu
35

<210> SEQ ID NO 182
<211> LENGTH: 37
<212> TYPE: PRT
<213> ORGANISM: Chaetomium thermophile

<400> SEQUENCE: 182

Cys Thr Val Ala Lys Trp Ala Gln Cys Gly Gly Ile Gly Tyr Ser Gly
1 5 10 15

Cys Thr Thr Cys Glu Ala Gly Ser Thr Cys Arg Arg Thr Asn Asp Tyr
20 25 30

Tyr Ser Gln Cys Val
35

<210> SEQ ID NO 183
<211> LENGTH: 36
<212> TYPE: PRT
<213> ORGANISM: Ovatospora medusarum

<400> SEQUENCE: 183

Cys Thr Ala Ala Gln Trp Gln Gln Cys Gly Gly Thr Asn Phe Asn Gly
1 5 10 15

Cys Thr Thr Cys Ala Ala Gly Tyr Asn Cys Lys Leu Ile Asn Glu Tyr
20 25 30

Tyr Ser Gln Cys
35

<210> SEQ ID NO 184
<211> LENGTH: 38
<212> TYPE: PRT
<213> ORGANISM: Chaetomium thermophile

<400> SEQUENCE: 184

Cys Thr Ala Gln Arg Tyr Gln Gln Cys Gly Gly Asn Gly Tyr Thr Gly
1 5 10 15

Cys Thr Asn Cys Ala Ala Gly Ser Thr Cys Ser Ala Val Ser Pro Pro
20 25 30

Tyr Tyr Ser Gln Cys Leu
35

<210> SEQ ID NO 185
<211> LENGTH: 37
<212> TYPE: PRT

<213> ORGANISM: Thermothelomyces heterothallica

<400> SEQUENCE: 185

Cys Thr Ala Ala Gln Trp Ala Gln Cys Gly Gly Ile Asn Phe Thr Gly
1 5 10 15

Cys Thr Thr Cys Ala Ser Pro Tyr Lys Cys Asn Phe Ile Asn Asp Tyr
20 25 30

Tyr Ser Gln Cys Tyr
35

<210> SEQ ID NO 186
<211> LENGTH: 37
<212> TYPE: PRT
<213> ORGANISM: Thielavia species

<400> SEQUENCE: 186

Cys Val Ala Gln Lys Trp Ala Gln Cys Gly Gly Ser Gly Phe Thr Gly
1 5 10 15

Cys Thr Thr Cys Ala Ser Gly Ser Thr Cys Gln Lys Gln Asn Asp Phe
20 25 30

Tyr Ser Gln Cys Leu
35

<210> SEQ ID NO 187
<211> LENGTH: 38
<212> TYPE: PRT
<213> ORGANISM: Thielavia arenaria

<400> SEQUENCE: 187

Cys Thr Val Gln Arg Tyr Gly Gln Cys Gly Gly Gln Gly Tyr Thr Gly
1 5 10 15

Cys Thr Thr Cys Ala Ser Gly Ser Thr Cys Thr Gly Val Ser Ala Pro
20 25 30

Tyr Tyr Tyr Gln Cys Ile
35

<210> SEQ ID NO 188
<211> LENGTH: 37
<212> TYPE: PRT
<213> ORGANISM: Thielavia arenaria

<400> SEQUENCE: 188

Cys Ala Ala Ala Lys Tyr Gly Gln Cys Asp Gly Lys Asn Trp Asn Gly
1 5 10 15

Cys Lys Ser Cys Val Ala Gly Thr Thr Cys Arg Tyr Gln Asn Asp Tyr
20 25 30

Tyr Ser Gln Cys Leu
35

<210> SEQ ID NO 189
<211> LENGTH: 37
<212> TYPE: PRT
<213> ORGANISM: Ovatospora medusarum

<400> SEQUENCE: 189

Cys Val Ala Gln Lys Trp Ala Gln Cys Gly Gly Lys Gly Phe Thr Gly
1 5 10 15

Cys Lys Asn Cys Val Ser Gly Thr Thr Cys Gln Glu Gln Asn Gln Trp
20 25 30

Tyr Ser Gln Cys Leu

35

<210> SEQ ID NO 190
<211> LENGTH: 37
<212> TYPE: PRT
<213> ORGANISM: Thielavia arenaria

<400> SEQUENCE: 190

Cys Asn Val Ala Gln Trp Gln Gln Cys Gly Gly Ser Thr Tyr Thr Gly
1 5 10 15

Cys Thr Gln Cys Ala Ser Pro Tyr Thr Cys Lys Asn Ile Asn Thr Tyr
20 25 30

Tyr Ser Gln Cys Gln
35

<210> SEQ ID NO 191
<211> LENGTH: 37
<212> TYPE: PRT
<213> ORGANISM: Chaetomium thermophile

<400> SEQUENCE: 191

Cys Thr Ala Ala Arg Trp Gly Gln Cys Gly Gly Ile Gly Tyr Ser Gly
1 5 10 15

Cys Thr Ala Cys Ala Ser Pro Trp Thr Cys Gln Arg Ile Ser Asp Trp
20 25 30

Tyr His Gln Cys Leu
35

<210> SEQ ID NO 192
<211> LENGTH: 36
<212> TYPE: PRT
<213> ORGANISM: Adineta vaga

<400> SEQUENCE: 192

Cys Asn Asn Ile Tyr Asn Gln Cys Gly Gly Asn Gly Trp Asn Gly Thr
1 5 10 15

Thr Asn Cys Cys Ser Gly Leu Ser Cys Val Tyr Lys Asn Ser Ser Tyr
20 25 30

Ser Gln Cys Leu
35

<210> SEQ ID NO 193
<211> LENGTH: 37
<212> TYPE: PRT
<213> ORGANISM: Chaetomium species

<400> SEQUENCE: 193

Cys Val Ala Gln Lys Trp Ala Gln Cys Gly Gly Lys Gly Phe Thr Gly
1 5 10 15

Cys Thr Thr Cys Val Ser Gly Thr Thr Cys Lys Glu His His Glu Trp
20 25 30

Tyr Ser Gln Cys Leu
35

<210> SEQ ID NO 194
<211> LENGTH: 37
<212> TYPE: PRT
<213> ORGANISM: Achaetomium strumarium

<400> SEQUENCE: 194

Cys Thr Ala Gln Arg Trp Ser Gln Cys Gly Gly Asn Gly Phe Thr Gly 1 5 10 15

Cys Thr Thr Cys Val Ser Gly Thr Thr Cys Gln Lys Gln Asn Asp Trp
20 25 30

Tyr Ser Gln Cys Leu
35

<210> SEQ ID NO 195
<211> LENGTH: 36
<212> TYPE: PRT
<213> ORGANISM: Chaetomium thermophile

<400> SEQUENCE: 195

Cys Thr Val Pro Gln Trp Ala Gln Cys Gly Gly Val Asn Tyr Thr Gly
1 5 10 15

Cys Thr Thr Cys Ala Pro Gly Tyr Thr Cys Lys Tyr Thr Asn Asp Tyr
20 25 30

Tyr Ser Gln Cys
35

<210> SEQ ID NO 196
<211> LENGTH: 37
<212> TYPE: PRT
<213> ORGANISM: Ovatospora medusarum

<400> SEQUENCE: 196

Cys Val Ser Gln Lys Trp Ala Gln Cys Gly Gly Asn Gly Tyr Thr Gly
1 5 10 15

Cys Thr Gln Cys Val Ser Gly Thr Thr Cys Asn Lys Leu Asn Asp Trp
20 25 30

Tyr Ser Gln Cys Leu
35

<210> SEQ ID NO 197
<211> LENGTH: 37
<212> TYPE: PRT
<213> ORGANISM: Chaetomium olivicolor

<400> SEQUENCE: 197

Cys Thr Ala Gln Lys Trp Ala Gln Cys Gly Gly Ser Gly Phe Ser Gly
1 5 10 15

Cys Thr Ser Cys Val Ser Gly Thr Thr Cys Gln Lys Gln Asn Asp Trp
20 25 30

Tyr Ser Gln Cys Leu
35

<210> SEQ ID NO 198
<211> LENGTH: 37
<212> TYPE: PRT
<213> ORGANISM: Taifanglania major

<400> SEQUENCE: 198

Cys Val Ala Gln Lys Trp Ala Gln Cys Gly Gly Asn Gly Phe Thr Gly
1 5 10 15

Cys Thr Thr Cys Val Ser Gly Thr Thr Cys Thr Lys Ser Asn Asp Trp
20 25 30

Tyr Ser Gln Cys Leu
35

<210> SEQ ID NO 199
<211> LENGTH: 37

<212> TYPE: PRT
<213> ORGANISM: Trichocladium asperum

<400> SEQUENCE: 199

```
Cys Phe Ala Gln Lys Trp Ala Gln Cys Gly Gly Asn Gly Phe Thr Gly
1               5                   10                  15

Cys Thr Ser Cys Val Ser Gly Thr Thr Cys Gln Lys Gln Asn Asp Trp
            20                  25                  30

Tyr Ser Gln Cys Leu
        35
```

<210> SEQ ID NO 200
<211> LENGTH: 37
<212> TYPE: PRT
<213> ORGANISM: Ovatospora brasiliensis

<400> SEQUENCE: 200

```
Cys Val Ala Gln Lys Trp Ala Gln Cys Gly Gly Asn Gly Phe Ser Gly
1               5                   10                  15

Cys Thr Thr Cys Val Ser Gly Ser Thr Cys Gln Lys Gln Asn Asp Trp
            20                  25                  30

Tyr Ser Gln Cys Leu
        35
```

<210> SEQ ID NO 201
<211> LENGTH: 262
<212> TYPE: PRT
<213> ORGANISM: Artificial sequence
<220> FEATURE:
<223> OTHER INFORMATION: Synthetic Construct

<400> SEQUENCE: 201

```
Ala Ser Gly Ser Gly Gln Ser Thr Arg Tyr Trp Asp Cys Cys Lys Pro
1               5                   10                  15

Ser Cys Ala Trp Pro Gly Lys Ala Ala Val Ser Gln Pro Val Tyr Ala
            20                  25                  30

Cys Asp Ala Asn Phe Gln Arg Leu Ser Asp Phe Asn Val Gln Ser Gly
        35                  40                  45

Cys Asn Gly Gly Ser Ala Tyr Ser Cys Ala Asp Gln Thr Pro Trp Ala
    50                  55                  60

Val Asn Asp Asn Leu Ala Tyr Gly Phe Ala Ala Thr Ser Ile Ala Gly
65                  70                  75                  80

Gly Ser Glu Ser Ser Trp Cys Cys Ala Cys Tyr Ala Leu Thr Phe Thr
                85                  90                  95

Ser Gly Pro Val Ala Gly Lys Thr Met Val Val Gln Ser Thr Ser Thr
            100                 105                 110

Gly Gly Asp Leu Gly Ser Asn His Phe Asp Ile Ala Met Pro Gly Gly
        115                 120                 125

Gly Val Gly Ile Phe Asn Gly Cys Ser Ser Gln Phe Gly Gly Leu Pro
    130                 135                 140

Gly Ala Gln Tyr Gly Gly Ile Ser Ser Arg Asp Gln Cys Asp Ser Phe
145                 150                 155                 160

Pro Ala Pro Leu Lys Pro Gly Cys Gln Trp Arg Phe Asp Trp Phe Gln
                165                 170                 175

Asn Ala Asp Asn Pro Thr Phe Thr Phe Gln Gln Val Gln Cys Pro Ala
            180                 185                 190

Glu Ile Val Ala Arg Ser Gly Cys Lys Arg Asn Asp Asp Ser Ser Phe
        195                 200                 205
```

-continued

```
Pro Val Phe Thr Thr Thr Pro Pro Thr Pro Thr Pro Thr Pro Thr Pro
    210                 215                 220

Gly Cys Thr Ser Gln Lys Trp Ala Gln Cys Gly Gly Ile Gly Phe Ser
225                 230                 235                 240

Gly Cys Thr Thr Cys Val Ser Gly Thr Thr Cys Gln Lys Leu Asn Asp
                245                 250                 255

Tyr Tyr Ser Gln Cys Leu
            260


<210> SEQ ID NO 202
<211> LENGTH: 20
<212> TYPE: PRT
<213> ORGANISM: Artificial sequence
<220> FEATURE:
<223> OTHER INFORMATION: Synthetic construct

<400> SEQUENCE: 202

Ser Pro Ser Pro Ser Pro Ser Pro Ser Pro Ser Pro Ser Pro Ser Pro
1               5                   10                  15

Ser Pro Ser Pro
            20


<210> SEQ ID NO 203
<211> LENGTH: 20
<212> TYPE: PRT
<213> ORGANISM: Artificial sequence
<220> FEATURE:
<223> OTHER INFORMATION: Synthetic construct

<400> SEQUENCE: 203

Pro Ser Pro Ser Pro Ser Pro Ser Pro Ser Pro Ser Pro Ser Pro Ser
1               5                   10                  15

Pro Ser Pro Ser
            20


<210> SEQ ID NO 204
<211> LENGTH: 20
<212> TYPE: PRT
<213> ORGANISM: Artificial sequence
<220> FEATURE:
<223> OTHER INFORMATION: Synthetic construct

<400> SEQUENCE: 204

Pro Pro Pro Pro Pro Pro Pro Pro Pro Pro Pro Pro Pro Pro Pro Pro
1               5                   10                  15

Pro Pro Pro Pro
            20


<210> SEQ ID NO 205
<211> LENGTH: 20
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (2)..(2)
<220> FEATURE:
<221> NAME/KEY: MISC_FEATURE
<222> LOCATION: (4)..(4)
<223> OTHER INFORMATION: X= S, T, R, K, D, or E
<220> FEATURE:
<221> NAME/KEY: MISC_FEATURE
<222> LOCATION: (6)..(6)
<223> OTHER INFORMATION: X= S, T, R, K, D, E, N, or Q
```

<220> FEATURE:
<221> NAME/KEY: MISC_FEATURE
<222> LOCATION: (8)..(8)
<223> OTHER INFORMATION: X= S, T, R, K, D, or E
<220> FEATURE:
<221> NAME/KEY: MISC_FEATURE
<222> LOCATION: (10)..(10)
<223> OTHER INFORMATION: X= S, T, R, K, D, E, N, or Q
<220> FEATURE:
<221> NAME/KEY: MISC_FEATURE
<222> LOCATION: (12)..(12)
<223> OTHER INFORMATION: X= S, T, R, K, D, or E
<220> FEATURE:
<221> NAME/KEY: MISC_FEATURE
<222> LOCATION: (14)..(14)
<223> OTHER INFORMATION: X= S, T, R, K, D, E, N, or Q
<220> FEATURE:
<221> NAME/KEY: MISC_FEATURE
<222> LOCATION: (16)..(16)
<223> OTHER INFORMATION: X= S, T, R, K, D, or E
<220> FEATURE:
<221> NAME/KEY: MISC_FEATURE
<222> LOCATION: (18)..(18)
<223> OTHER INFORMATION: X= S, T, R, K, D, E, N, or Q
<220> FEATURE:
<221> NAME/KEY: MISC_FEATURE
<222> LOCATION: (20)..(20)
<223> OTHER INFORMATION: X= S, T, R, K, D, or E

<400> SEQUENCE: 205

```
Pro Xaa Pro Xaa Pro Xaa Pro Xaa Pro Xaa Pro Xaa Pro Xaa Pro Xaa
1               5                   10                  15

Pro Xaa Pro Xaa
            20
```

<210> SEQ ID NO 206
<211> LENGTH: 20
<212> TYPE: PRT
<213> ORGANISM: Artificial sequence
<220> FEATURE:
<223> OTHER INFORMATION: Syntheitic construct
<220> FEATURE:
<221> NAME/KEY: MISC_FEATURE
<222> LOCATION: (1)..(1)
<223> OTHER INFORMATION: X=S, T, R, K, D, or E
<220> FEATURE:
<221> NAME/KEY: MISC_FEATURE
<222> LOCATION: (3)..(3)
<223> OTHER INFORMATION: X=S, T, R, K, D, or E
<220> FEATURE:
<221> NAME/KEY: MISC_FEATURE
<222> LOCATION: (5)..(5)
<223> OTHER INFORMATION: X=S, T, R, K, D, or E
<220> FEATURE:
<221> NAME/KEY: MISC_FEATURE
<222> LOCATION: (7)..(7)
<223> OTHER INFORMATION: X=S, T, R, K, D, or E
<220> FEATURE:
<221> NAME/KEY: MISC_FEATURE
<222> LOCATION: (9)..(9)
<223> OTHER INFORMATION: X=S, T, R, K, D, or E
<220> FEATURE:
<221> NAME/KEY: MISC_FEATURE
<222> LOCATION: (11)..(11)
<223> OTHER INFORMATION: X=S, T, R, K, D, or E
<220> FEATURE:
<221> NAME/KEY: MISC_FEATURE
<222> LOCATION: (13)..(13)
<223> OTHER INFORMATION: X=S, T, R, K, D, or E
<220> FEATURE:
<221> NAME/KEY: MISC_FEATURE
<222> LOCATION: (15)..(15)
<223> OTHER INFORMATION: X=S, T, R, K, D, or E
<220> FEATURE:
<221> NAME/KEY: MISC_FEATURE
<222> LOCATION: (17)..(17)

<223> OTHER INFORMATION: X=S, T, R, K, D, or E
<220> FEATURE:
<221> NAME/KEY: MISC_FEATURE
<222> LOCATION: (19)..(19)
<223> OTHER INFORMATION: X=S, T, R, K, D, or E

<400> SEQUENCE: 206

Xaa Pro Xaa Pro Xaa Pro Xaa Pro Xaa Pro Xaa Pro Xaa Pro Xaa Pro
1               5                   10                  15

Xaa Pro Xaa Pro
            20

<210> SEQ ID NO 207
<211> LENGTH: 18
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X=S, T, R, K, D, E, N or Q
<220> FEATURE:
<221> NAME/KEY: MISC_FEATURE
<222> LOCATION: (3)..(3)
<223> OTHER INFORMATION: X=S, T, R, K, D or E
<220> FEATURE:
<221> NAME/KEY: MISC_FEATURE
<222> LOCATION: (4)..(4)
<223> OTHER INFORMATION: X=S, T, R, K, D, E, N or Q
<220> FEATURE:
<221> NAME/KEY: MISC_FEATURE
<222> LOCATION: (6)..(6)
<223> OTHER INFORMATION: X=S, T, R, K, D or E
<220> FEATURE:
<221> NAME/KEY: MISC_FEATURE
<222> LOCATION: (7)..(7)
<223> OTHER INFORMATION: X=S, T, R, K, D, E, N or Q
<220> FEATURE:
<221> NAME/KEY: MISC_FEATURE
<222> LOCATION: (9)..(9)
<223> OTHER INFORMATION: X=S, T, R, K, D or E
<220> FEATURE:
<221> NAME/KEY: MISC_FEATURE
<222> LOCATION: (10)..(10)
<223> OTHER INFORMATION: X=S, T, R, K, D, E, N or Q
<220> FEATURE:
<221> NAME/KEY: MISC_FEATURE
<222> LOCATION: (12)..(12)
<223> OTHER INFORMATION: X=S, T, R, K, D or E
<220> FEATURE:
<221> NAME/KEY: MISC_FEATURE
<222> LOCATION: (13)..(13)
<223> OTHER INFORMATION: X=S, T, R, K, D, E, N or Q
<220> FEATURE:
<221> NAME/KEY: MISC_FEATURE
<222> LOCATION: (15)..(15)
<223> OTHER INFORMATION: X=S, T, R, K, D or E
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 207

Xaa Pro Xaa Xaa Pro Xaa Xaa Pro Xaa Xaa Pro Xaa Xaa Pro Xaa Xaa
1               5                   10                  15

Pro Xaa

<210> SEQ ID NO 208

-continued

```
<211> LENGTH: 15
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(2)
<223> OTHER INFORMATION: X=S, T, R, K, D, E, N, or Q
<220> FEATURE:
<221> NAME/KEY: MISC_FEATURE
<222> LOCATION: (4)..(5)
<223> OTHER INFORMATION: X=S, T, R, K, D, E, N, or Q
<220> FEATURE:
<221> NAME/KEY: MISC_FEATURE
<222> LOCATION: (7)..(8)
<223> OTHER INFORMATION: X=S, T, R, K, D, E, N, or Q
<220> FEATURE:
<221> NAME/KEY: MISC_FEATURE
<222> LOCATION: (10)..(11)
<223> OTHER INFORMATION: X=S, T, R, K, D, E, N, or Q
<220> FEATURE:
<221> NAME/KEY: MISC_FEATURE
<222> LOCATION: (13)..(14)
<223> OTHER INFORMATION: X=S, T, R, K, D, E, N, or Q

<400> SEQUENCE: 208

Xaa Xaa Pro Xaa Xaa Pro Xaa Xaa Pro Xaa Xaa Pro Xaa Xaa Pro
1               5                   10                  15


<210> SEQ ID NO 209
<211> LENGTH: 20
<212> TYPE: PRT
<213> ORGANISM: Artificial sequence
<220> FEATURE:
<223> OTHER INFORMATION: Synthetic construct

<400> SEQUENCE: 209

Thr Pro Thr Pro Thr Pro Thr Pro Thr Pro Thr Pro Thr Pro Thr Pro
1               5                   10                  15

Thr Pro Thr Pro
            20


<210> SEQ ID NO 210
<211> LENGTH: 33
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(33)
<223> OTHER INFORMATION: X=S, T, or P

<400> SEQUENCE: 210

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa
```

STABILIZED GLYCOSIDE HYDROLASE VARIANTS

CROSS-REFERENCE TO RELATED APPLICATIONS

This application is a 35 U.S.C. 371 national application of international application no. PCT/EP2020/059965 filed Apr. 8, 2020 and published as WO 2020/20856 on Oct. 10, 2020, which claims priority or the benefit under 35 U.S.C. 119 of European application no. 19168931.4 filed Apr. 12, 2019 and European application no. 19209169.2 filed Nov. 14, 2019, the contents of which are fully incorporated herein by reference.

REFERENCE TO SEQUENCE LISTING

This application contains a Sequence Listing in computer readable form. The computer readable form, created on Feb. 13, 2025, is named SQ.txt and 71.6 KB in size, and is hereby incorporated herein by reference.

FIELD OF THE INVENTION

The present invention relates to variants of a glycoside hydrolase. The variants may have improved stability, in particular, stability in the presence of detergent and/or protease. Further, the invention relates to liquid detergent compositions comprising a stabilized glycoside hydrolase variant.

BACKGROUND OF THE INVENTION

Glycoside hydrolases such as cellulases generally contain a catalytic domain and one or more carbohydrate binding modules (CBM), which are joined by a linker region. Linkers are generally flexible connectors that provide connectivity between structured domains, but their functional role is largely unknown.

Cellulases have for many years been used in detergents due to their observed benefits in the laundry process, such as color clarification, prevent redeposition, anti-pilling/pill removal and improved whiteness, and are characterized by their ability to cleave the 1,4-beta-glycosidic linkages in cellulose molecules into smaller molecules.

In some applications a complex cellulase enzyme composition is used, where the composition comprises more than one cellulose degrading enzyme, selected among endoglucanases, cellobiohydrolases and beta-glucosidases are used, whereas other applications uses enzyme compositions mainly comprising one or more endoglucanases.

WO 1996/029397 discloses family 45 endoglucanases for detergent use. Most commercial detergent compositions comprise proteases that improve the removal of many common stains. However, proteases also degrade other proteins available in the washing solution, including other enzymes such as cellulases and other glycoside hydrolases. It is therefore desirable to provide glycoside hydrolases, such as cellulases and variants thereof having increased stability in the presence of proteases.

SUMMARY OF THE INVENTION

The invention provides variants of a parent polypeptide having glycoside hydrolase or (EC 3.2.1.-) activity, wherein the variant comprises a catalytic domain, an engineered linker region, such as a proline-rich linker region, and a carbohydrate binding module (CBM). Preferably, the variant has improved linker stability and/or improved CBM stability in comparison with the parent glycoside hydrolase in an aqueous composition comprising a protease, and wherein the variant has glycoside hydrolase activity.

The invention further relates to polynucleotides and expression constructs comprising the polynucleotide; host cells comprising the polynucleotides or expression constructs and the use of such host cells for producing the variants of the invention.

Compositions, in particular detergent compositions, such as liquid detergent compositions, comprising the variants, and the use of such compositions for laundering textiles are also disclosed.

Definitions

Detergent component: the term "detergent component" is defined herein to mean the types of chemicals which can be used in detergent compositions. Examples of detergent components are surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers. The detergent composition may comprise of one or more of any type of detergent component.

Detergent composition: the term "detergent composition" refers to compositions that find use in the removal of undesired compounds from items to be cleaned, such as textiles, dishes, and hard surfaces. The detergent composition may be used to e.g. clean textiles, dishes and hard surfaces for both household cleaning and industrial cleaning and/or for fabric care. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; hard surface cleaning formulations, such as for glass, wood, plastic, ceramic and metal counter tops and windows; carpet cleaners; oven cleaners; fabric fresheners; fabric softeners; and textile and laundry pre-spotters, as well as dish wash detergents). In addition to containing an enzyme of the invention, the detergent formulation may contain one or more additional enzymes (such as amylases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases (GH5 and/or GH26), licheninases, phosphodiesterases, pectin methylesterases, cellobiohydrolases, transglutaminases, nucleases, and combinations thereof, or any mixture thereof), and/or components such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti corrosion agents, enzyme inhibitors or stabilizers, enzyme activators, transferase(s), hydrolytic enzymes, oxido reductases, bluing agents and fluorescent dyes, antioxidants, and solubilizers.

Dish wash: The term "dish wash" refers to all forms of washing dishes, e.g. by hand dish wash (HDW) or automatic dish wash (ADW). Washing dishes includes, but is not limited to, the cleaning of all forms of crockery such as plates, cups, glasses, bowls, all forms of cutlery such as spoons, knives, forks and serving utensils as well as ceramics, plastics, metals, china, glass and acrylics.

Dish washing composition: The term "dish washing composition" refers to compositions intended for cleaning dishes, table ware, pots, pans, cutlery and all forms of compositions for cleaning hard surfaces areas in kitchens. The present invention is not restricted to any particular type of dish wash composition or any particular detergent.

Wash liquor: The term "wash liquor" refers to an aqueous solution containing a detergent composition in dilute form, such as but not limited to a detergent solution containing a laundry detergent composition in dilute form such as the wash liquor in a laundry process.

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fiber (e.g. polyamide fiber, acrylic fiber, polyester fiber, polyvinyl chloride fiber, polyurethane fiber, polyurea fiber, aramid fiber), and/or cellulose-containing fiber (e.g. rayon/viscose, ramie, flax/linen, jute, cellulose acetate fiber, lyocell). Fabric may be conventional washable laundry, for example stained household laundry. When the term fabric or garment is used, it is intended to include the broader term textiles as well.

Hard surface cleaning: The term "Hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, cutlery such as spoons, knives, forks, serving utensils, ceramics, plastics, metals, china, glass and acrylics.

Whiteness: The term "Whiteness" is defined herein as a broad term with different meanings in different regions and for different consumers. Loss of whiteness can e.g. be due to greying, yellowing, or removal of optical brighteners/hueing agents. Greying and yellowing can be due to soil redeposition, body soils, coloring from e.g. iron and copper ions or dye transfer. Whiteness might include one or several issues from the list below: colorant or dye effects; incomplete stain removal (e.g. body soils, sebum etc.); redeposition (greying, yellowing or other discolorations of the object) (removed soils re-associate with other parts of textile, soiled or unsoiled); chemical changes in textile during application; and clarification or brightening of colors.

Color clarification: During washing and wearing loose or broken fibers can accumulate on the surface of the fabrics. One consequence can be that the colors of the fabric appear less bright or less intense because of the surface contaminations. Removal of the loose or broken fibers from the textile will partly restore the original colors and looks of the textile. By the term "color clarification", as used herein, is meant the partial restoration of the initial colors of textile.

Anti-pilling: The term "anti-pilling" denotes removal of pills from the textile surface and/or prevention of formation of pills on the textile surface.

Fabric care: The term fabric care, also referred to as textile care, refers to treatments that retains or partly or fully restores the properties of the textile, e.g. by color clarification, anti-pilling or prevention of formation of pills on the textile surface.

Cellulolytic enzyme or cellulase: The term "cellulolytic enzyme" or "cellulase" means one or more (e.g., several) enzymes that hydrolyze a cellulosic material. Such enzymes include endoglucanase(s) (e.g. EC 3.2.1.4), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, Biotechnology Advances 24:452-481. Total cellulolytic enzyme activity can be measured using insoluble substrates, including Whatman N°1 filter paper, microcrystalline cellulose, bacterial cellulose, algal cellulose, cotton, pretreated lignocellulose, etc. The most common total cellulolytic activity assay is the filter paper assay using Whatman N°1 filter paper as the substrate. The assay was established by the International Union of Pure and Applied Chemistry (IUPAC) (Ghose, 1987, Pure Appl. Chem. 59:257-68).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Endoglucanase: The term "endoglucanase" means an enzyme that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-beta-1,4 glucans such as cereal beta-D-glucans or xyloglucans, and other plant material containing cellulosic components. For purposes of the present invention, endoglucanase activity is determined using carboxymethyl cellulose (CMC) hydrolysis according to the procedure of Ghose, 1987, Pure and Appl. Chem. 59:257-268. One unit of endoglucanase activity is defined as 1.0 μmole of reducing sugars produced per minute at 50° C., pH 4.8.

One particularly preferred class of endoglucanase are those of "family GH45," which are classified as glycoside hydrolase Family 45 according to the terminology of Henrissat et al., "Biochem. J. 280:309-316 (1991), as well as the Carbohydrate Active enZYmes database available at cazy.org. GH45 enzymes are endoglucanases of EC 3.2.1.4.

Glycoside hydrolase: The term "glycoside hydrolase" (GH) means an enzyme that catalyzes the hydrolysis of a glycosidic bond between two or more carbohydrates or between a carbohydrate and a non-carbohydrate moiety. For more details, see, for example, Henrissat B., "A classification of glycosyl hydrolases based on amino-acid sequence similarities." Biochem. J. 280:309-316 (1991), as well as the Carbohydrate Active enZYmes database available at cazy-.org.

Exemplary glycoside hydrolase families with reported cellulase activities useful according to the present invention include those of families GH5, GH6, GH7, GH8, GH9, GH12, GH44, GH45, GH48, GH51, GH124, with family GH45 being particularly preferred.

Carbohydrate binding module: The term "carbohydrate binding module" means the region within a carbohydrate-active enzyme that provides carbohydrate-binding affinity (Boraston et al., 2004, *Biochem. J.* 383:769-781). A majority of known carbohydrate binding modules (CBMs) are contiguous amino acid sequences with a discrete fold. The carbohydrate binding module (CBM) is typically found either at the N-terminal or at the C-terminal extremity of an enzyme. Some CBMs are known to have specificity for cellulose.

Exemplary CBM families useful according to the invention are those of CBM family 1, 4, 17, 28, 30, 44, 72 and 79. Again, with reference to cazy.org/Carbohydrate-Binding-Modules, CBM Family 1 includes modules of approximately 40 residues found almost exclusively in fungi. The cellulose-binding function has been demonstrated in many cases, and appears to be mediated by three aromatic residues separated by about 10.4 angstrom and which form a flat surface. CBM family 4 includes modules of approximately 150 residues found in bacterial enzymes. Binding of these modules has been demonstrated with xylan, beta-1,3-glucan, beta-1,3-1,4-glucan, beta-1,6-glucan and amorphous cellulose but not with crystalline cellulose. CBM family 17 includes modules of approximately 200 residues. Binding to amorphous cellulose, cellooligosaccharides and derivatized cellulose has been demonstrated. Regarding CBM family 28, the module from the endo-1,4-glucanase of *Bacillus* sp. 1139 binds to non-crystalline cellulose, cellooligosaccharides, and β-(1,3) (1,4)-glucans. For CBM Family 30, binding to cellulose has been demonstrated for the N-terminal module of Fibrobacter *succinogenes* CelF. The C-terminal CBM44 module of the *Clostridium thermocellum* enzyme has been demonstrated to bind equally well cellulose and xyloglucan. CBM Family 72 includes modules of 130-180 residues found at the C-terminus glycoside hydrolases from various families, sometimes as tandem repeats. The CBM72 found on an endoglucanase from an uncultivated microorganism was found to bind a broad spectrum of polysaccharides including soluble and insoluble cellulose, beta-1,3/1,4-mixed linked glucans, xylan, and beta-mannan. CBM Family 79 includes modules of approx. 130 residues found so far only in ruminococcal proteins. Binding to various beta-glucans was shown for the *R. flavefaciens* GH9 enzyme. Most preferred are CBM family 1 also referred to as "CBM1."

Catalytic domain: The term "catalytic domain" means the region of an enzyme containing the catalytic machinery of the enzyme.

Engineered: The term "engineered" means a synthetic construct.

Proline-rich linker: The term "proline-rich linker" means a sequence comprising one or more Pro-Pro, Pro-Xaa (or Xaa-Pro), Xaa-Pro-Xaa or Xaa-Xaa-Pro (or Pro-Xaa-Xaa) units, where Pro is the three-letter representation for the amino acid proline and Xaa is the three-letter representation for any amino acid. Preferably, the proline-rich linker comprises the above-noted units in repetition, e.g., PP, PPP, PPPP (SEQ ID NO: 27), PX, PXP, PS, PSP, PXPX (SEQ ID NO: 98), XP, XPX, SP, SPS, XPXP (SEQ ID NO: 99), XPXXPX (SEQ ID NO: 100), XXPXXP (SEQ ID NO: 101) and so forth, in combination and/or in succession.

In one aspect, the proline-rich linker comprises one or more of the following optionally repeating motifs: [P/S/T/R/K/D/E]P and P[S/T/R/K/D/E/N/Q]P[S/T/R/K/D/E] (SEQ ID NO: 102). In one aspect, the proline-rich linker comprises the following optionally repeating motifs: [S/T/R/K/D/E]P[S/T/R/K/D/E/N/Q], [P/S/T/R/K/D/E][P/S/T/R/K/D/E]P, and/or P[P/S/T/R/K/D/E][P/S/T/R/K/D/E]. In one aspect, the proline-rich linker comprises optionally repeating motifs of the same, or different, amino acids within the brackets as indicated: [P/S/T]P and P[S/E]PT (SEQ ID NO: 109).

In one aspect, the proline-rich linker comprises (a) (SP)a, a=2-10 (SEQ ID NO: 202); (b) (PS)a, a=2-10 (SEQ ID NO: 203); (c) Pb, b=4-20, preferably 4-15 (SEQ ID NO: 204); (d) (PEPT (SEQ ID NO: 125))c, c=2-5 (SEQ ID NO: 79); (e) (PSPT (SEQ ID NO: 104))d, d=2-5 (SEQ ID NO: 150); (f) (P[S/T/R/K/D/E/N/Q]P[S/T/R/K/D/E] (SEQ ID NO: 102))e, e=2-5 (SEQ ID NO: 205); (g) ([S/T/R/K/D/E]P)f, f=2-10, preferably 2-5 (SEQ ID NO: 206); (h) ([S/T/R/K/D/E/N/Q]P[S/T/R/K/D/E])g, g=2-6 (SEQ ID NO: 207); (i) ([S/T/R/K/D/E/N/Q][S/T/R/K/D/E/N/Q]P)h, h=2-5 (SEQ ID NO: 208); (j) (TP)i, i=2-10 (SEQ ID NO: 209); (k) ([S/T/P][S/T/P][S/T/P])j, j=2-11 (SEQ ID NO: 210); (l) and/or combinations thereof, wherein combinations of the respective monomeric units are contemplated.

In one aspect, the proline-rich linker comprises a linker in Table A., below, such as PPPPPPP (SEQ ID NO: 31), PPPPPPPG (SEQ ID NO: 30), SPSPSPSPSP (SEQ ID NO: 58) or SPSPSPSPSPG (SEQ ID NO: 25).

Preferably, the proline-rich linker comprises at least 25% proline, e.g., at least 28% proline, at least 30% proline, at least 35% proline, at least 40% proline, at least 50% proline, such as at least 60%, at least 66%, at least 70%, at least 75%, at least 80%, at least 85%, at least 90% proline. Preferably, the proline-rich linker includes at least 4 amino acids and not more than 30 amino acids, such as 4-28 amino acids, preferably 4-20 amino acids, or even 4-10 amino acids, such as 4 amino acids, 5 amino acids, 6 amino acids, 7 amino acids, 8 amino acids, 9 amino acids or 10 amino acids.

Moreover, the linker region as defined herein can include an interface of an additional 1-2 amino acids at the connection to the catalytic domain and/or carbohydrate binding module.

Allelic variant: The term "allelic variant" means any of two or more alternative forms of a gene occupying the same chromosomal locus. Allelic variation arises naturally through mutation and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has cellulolytic activity. In one aspect, a fragment contains at least 260 amino acid residues (e.g., amino acids 1 to 260 of SEQ ID NO: 1, SEQ ID NO: 2, SEQ ID NO: 3, or SEQ ID NO: 4), at least 240 amino acid residues (e.g., amino acids 1 to 240 of SEQ ID NO: 1, SEQ ID NO: 2, SEQ ID NO: 3, or SEQ ID NO: 4), or at least the residues corresponding to the catalytic domain, e.g. 210, 211, 212, or 216 amino acid residues (e.g., amino acids 1 to 212 of SEQ ID NO: 1 or amino acids 1 to 216 of SEQ ID NO: 1, amino acids 1 to 211 of SEQ ID NO: 2 or amino acids 1 to 212 of SEQ ID NO: 2, amino acids 1 to 211 of SEQ ID NO: 3 or amino acids 1 to 210 of SEQ ID NO: 3, amino acids 1 to 211 of SEQ ID NO: 4).

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Hybrid polypeptide: The term "hybrid polypeptide" means a polypeptide comprising domains from two or more polypeptides from different sources (origins), e.g., a binding module from one polypeptide and a catalytic domain from another polypeptide. The domains may be fused at the N-terminus or the C-terminus. Of particular interest herein are polypeptides comprising a binding module from one polypeptide (which may be naturally occurring or further modified), an engineered linker region, such as a proline-rich linker region, which is a synthetic construct, and a catalytic domain from another polypeptide (which may be naturally occurring or further modified).

Hybridization: The term "hybridization" means the pairing of substantially complementary strands of nucleic acids, using standard Southern blotting procedures. Hybridization may be performed under medium, medium-high, high or very high stringency conditions. Medium stringency conditions means prehybridization and hybridization at 42° C. in 5×SSPE, 0.3% SDS, 200 micrograms/ml sheared and denatured salmon sperm DNA, and 35% formamide for 12 to 24 hours, followed by washing three times each for 15 minutes using 0.2×SSC, 0.2% SDS at 55° C. Medium-high stringency conditions means prehybridization and hybridization at 42° C. in 5×SSPE, 0.3% SDS, 200 micrograms/ml sheared and denatured salmon sperm DNA, and 35% formamide for 12 to 24 hours, followed by washing three times each for 15 minutes using 0.2×SSC, 0.2% SDS at 60° C. High stringency conditions means prehybridization and hybridization at 42° C. in 5×SSPE, 0.3% SDS, 200 micrograms/ml sheared and denatured salmon sperm DNA, and 50% formamide for 12 to 24 hours, followed by washing three times each for 15 minutes using 0.2×SSC, 0.2% SDS at 65° C. Very high stringency conditions means prehybridization and hybridization at 42° C. in 5×SSPE, 0.3% SDS, 200 micrograms/ml sheared and denatured salmon sperm DNA, and 50% formamide for 12 to 24 hours, followed by washing three times each for 15 minutes using 0.2×SSC, 0.2% SDS at 70° C.

Improved property: The term "improved property" means a characteristic associated with a variant that is improved compared to the reference enzyme/parent enzyme. Some aspects of the invention relate to variants having an improvement factor above 1 when the variant is tested for a property of interest in a relevant assay, wherein the property of the reference enzyme/parent enzyme is given a value of 1.

Improved stability: The term "improved stability" means an enzyme having better stability in the presence of protease relative to the stability of a reference enzyme/parent enzyme, and includes, for example, proteolytic stability, in-detergent storage stability, improved stability during production of the detergent composition, as well as in-wash stability. The improvement in stability can be quantified by determining stability according to the assay described in Example 2 (linker stability assay—in the presence of protease), and/or Example 7 (In-wash Linker Stability Assay with proteases) herein.

Improved wash performance: The term "improved wash performance" is defined herein as an enzyme displaying an increased wash performance in a detergent composition relative to the wash performance of a reference enzyme/parent enzyme, e.g., by increased color clarification and/or anti-pilling effect, when evaluating the fresh samples and/or after the samples have been stored under the same conditions. The term "improved wash performance" includes wash performance in laundry but also in, e.g., hard surface cleaning such as automated dish wash (ADW).

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its mature form following N-terminal processing (e.g., removal of signal peptide).

Mature polypeptide coding sequence: The term "mature polypeptide coding sequence" means a polynucleotide that encodes a mature polypeptide having cellulase, such as endoglucanase activity.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent cellulase: The term "parent" or "parent cellulase" means any polypeptide with glycoside hydrolase activity, in particular cellulolytic or even endoglucanase activity, to which an alteration is made to produce the enzyme variants of the present invention.

Purified: The term "purified" means a nucleic acid or polypeptide that is substantially free from other components as determined by analytical techniques well known in the art (e.g., a purified polypeptide or nucleic acid may form a discrete band in an electrophoretic gel, chromatographic eluate, and/or a media subjected to density gradient centrifugation). A purified nucleic acid or polypeptide is at least about 50% pure, usually at least about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, a composition is enriched for a molecule when there is a substantial increase in the concentration of the molecule after application of a purification or enrichment technique. The term "enriched" refers to a compound, polypeptide, cell, nucleic acid, amino acid, or other specified material or component that is present in a composition at a relative or absolute concentration that is higher than a starting composition.

Recombinant: The term "recombinant," when used in reference to a cell, nucleic acid, protein or vector, means that it has been modified from its native state. Thus, for example, recombinant cells express genes that are not found within the native (non-recombinant) form of the cell, or express native genes at different levels or under different conditions than found in nature. Recombinant nucleic acids differ from a native sequence by one or more nucleotides and/or are operably linked to heterologous sequences, e.g., a heterologous promoter in an expression vector. Recombinant proteins may differ from a native sequence by one or more amino acids and/or are fused with heterologous sequences. A vector comprising a nucleic acid encoding a polypeptide is a recombinant vector. The term "recombinant" is synonymous with "genetically modified" and "transgenic".

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48:443-453) as implemented in the Needle program of the EMBOSS package (EMBOSS: The European Molecular Biology Open Software Suite, Rice et al., 2000, *Trends Genet.* 16:276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Variant: The term "variant" means a polypeptide having cellulolytic activity comprising a substitution at one or more (e.g., several) positions. A substitution means replacement of the amino acid occupying a position with a different amino acid. The variants of the present invention have at least 20%, e.g., at least 40%, at least 50%, at least 60%, at least 70%, at least 80%, at least 90%, at least 95%, or at least 100% of the cellulolytic activity of the parent, such as the mature polypeptide of SEQ ID NO: 1, SEQ ID NO: 2, SEQ ID NO: 3, or SEQ ID NO: 4. A "variant" as used herein may also include a hybrid polypeptide.

Wild-type: The term "wild-type" in reference to an amino acid sequence or nucleic acid sequence means that the amino acid sequence or nucleic acid sequence is a native or naturally-occurring sequence. As used herein, the term "naturally-occurring" refers to anything (e.g., proteins, amino acids, or nucleic acid sequences) that is found in nature. Conversely, the term "non-naturally occurring" refers to anything that is not found in nature (e.g., recombinant nucleic acids and protein sequences produced in the laboratory or modification of the wild-type sequence).

Conventions for Designation of Variants

For purposes of the present invention, the mature polypeptide disclosed in SEQ ID NO: 1 is used to determine the corresponding amino acid residue in another cellulase. The amino acid sequence of another cellulase is aligned with the mature polypeptide disclosed in SEQ ID NO: 1, and based on the alignment, the amino acid position number corresponding to any amino acid residue in the mature polypeptide disclosed in SEQ ID NO: 1 is determined using the Needleman-Wunsch algorithm (Needleman and Wunsch, 1970, *J. Mol. Biol.* 48:443-453) as implemented in the Needle program of the EMBOSS package (EMBOSS: The European Molecular Biology Open Software Suite, Rice et al., 2000, *Trends Genet.* 16:276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another cellulase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32:1792-1797), MAFFT (version 6.857 or later; Katoh and Kuma, 2002, *Nucleic Acids Research* 30:3059-3066; Katoh et al., 2005, *Nucleic Acids Research* 33:511-518; Katoh and Toh, 2007, *Bioinformatics* 23:372-374; Katoh et al., 2009, *Methods in Molecular Biology* 537:39-64; Katoh and Toh, 2010, *Bioinformatics* 26:1899-1900), and EMBOSS EMMA employing ClustalW (1.83 or later; Thompson et al., 1994, *Nucleic Acids Research* 22:4673-4680), using their respective default parameters.

When the other enzyme has diverged from the mature polypeptide of SEQ ID NO: 1 such that traditional sequence-based comparison fails to detect their relationship (Lindahl and Elofsson, 2000, *J. Mol. Biol.* 295:613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25:3389-3402). Even greater sensitivity can be achieved if the family or superfamily for the polypeptide has one or more representatives in the protein structure databases. Programs such as GenTHREADER (Jones, 1999, *J. Mol. Biol.* 287:797-815; McGuffin and Jones, 2003, *Bioinformatics* 19:874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313:903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example, the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33:88-96) or combinatorial extension (Shindyalov and Bourne, 1998, *Protein Engineering* 11:739-747), and implementation of these algorithms can additionally be utilized to query structure databases with a structure of interest in order to discover possible structural homologs (e.g., Holm and Park, 2000, *Bioinformatics* 16:566-567).

For example, the parent polypeptide may comprise any of SEQ ID NO: 2, SEQ ID NO: 3, SEQ ID NO: 4, or the mature polypeptide thereof.

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine(S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195<br>G | 195 195a 195b<br>G-K-A |

Multiple alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively. Different alterations. Where different alterations can be introduced at a position, the different alterations are separated by a comma, e.g., "Arg170Tyr, Glu" represents a substitution of arginine at position 170 with tyrosine or glutamic acid. Thus, "Tyr167Gly, Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

Nomenclature

For purposes of the present invention, brackets are used to indicate alternative amino acids (using their one letter codes) at a particular position in a sequence. For example, the nomenclature [S/E] means that the amino acid at this position may be a serine (Ser, S) or a glutamic acid (Glu, E). Likewise, the nomenclature [P/S/T] means that the amino acid at this position may be a proline (Pro, P), a serine (Ser, S), or a threonine (Thr, T), and so forth for other combinations as described herein. Amino acids indicated within brackets using this nomenclature may be separated by a vertical line or in some instances no line e.g. [P/S/T] can also be designated as [PST].

In some instance, a sequence motif includes more than one set of brackets, each of which independently represents a position in a sequence. Thus, P[S/T/R/K/D/E/N/Q]P[S/T/R/K/D/E] (SEQ ID NO: 102) means that P, conservative amino acid, is in the first position; any of S, T, R, K, D, E, N, or Q are in the second position; P, conservative amino acid, is in the third position; and any of S, T, R, K, D, or E are in the fourth position. The motif represented by this designation may then be any of PSPS (SEQ ID NO: 103), PSPT (SEQ ID NO: 104), PSPR (SEQ ID NO: 105), PSPK (SEQ ID NO: 106), PSPD (SEQ ID NO: 107), PSPE (SEQ ID NO: 108) and so on.

Unless otherwise limited further, the amino acid X (or Xaa) is used herein to represent any of the 20 natural amino acids.

DETAILED DESCRIPTION OF THE INVENTION

Many proteins are comprised of structured domains connected by linkers. For example, cellulases and other glycoside hydrolases (GH) are often found as modular enzymes having one or more catalytic domains, which may be connected to one or more CBMs via a peptide known as a linker, which is sometimes partially glycosylated. The catalytic domain is responsible for the hydrolytic degradation of cellulose, while the CBM, when present, works by increasing the effective concentration of enzyme near the substrate surface. In contrast, linkers are generally flexible connectors that provide connectivity between structured domains, but their functional role is largely unknown.

The invention is directed to variants of a glycoside hydrolase having a three-domain structure with the catalytic domain connected to one or more carbohydrate binding modules via a linker. The invention is directed to variants having peptide stretches that make the native linker more stable, i.e., less susceptible to proteolytic cleavage.

Cellulases in particular, are often cleaved (nicked) in exposed regions or partially or fully degraded by proteases in liquid detergents. Most commonly, the protease cleaves in the unstructured linker region of the cellulase and thereby reduces the ability of the cellulase to remove fuzz and pill and maintaining or restoring the colors of the textile by reducing its ability to bind to the insoluble cellulose substrate. The loss in binding affinity strongly impacts the performance of cellulases which is why a protease stable linker is highly valuable in the liquid laundry/dish detergent segment, as well as in softeners.

Variants

The present invention provides a variant of a parent polypeptide having glycoside hydrolase (EC 3.2.1.-) activity, wherein the variant comprises a catalytic domain, an engineered linker region, which can be for example a proline-rich linker region, such as a non-naturally-occurring proline-rich linker region, and a carbohydrate binding module (CBM), wherein the variant has improved linker stability and/or improved CBM stability in comparison with the parent glycoside hydrolase in an aqueous detergent composition comprising a protease, and wherein the variant has glycoside hydrolase activity.

In an embodiment, the parent polypeptide is a cellulase, and even more preferably an endoglucanase, and even more preferably a GH45 endoglucanase.

Polypeptides having N- and/or C-terminal CBMs are contemplated.

Linker

The variants according to the invention comprise a proline-rich amino acid sequence connecting the catalytic core with the CBM (linker region), such as a proline-rich linker region.

The proline-rich linkers as described herein comprise one or more Pro-Pro, Pro-Xaa (or Xaa-Pro), Xaa-Pro-Xaa or Xaa-Xaa-Pro (or Pro-Xaa-Xaa) units, e.g., PPPP (SEQ ID NO: 27), PXPX (SEQ ID NO: 98), XPXP (SEQ ID NO: 99), XPXXPX (SEQ ID NO: 100), XXPXXP (SEQ ID NO: 101) and so forth, optionally further combined and/or repeating.

For example, the linker region may comprise at least 25% proline, e.g. at least 28% proline, at least 30% proline, at least 40% proline, at least 50% proline, such as at least 60%, at least 66%, at least 70%, at least 75%, at least 80%, at least 85%, at least 90% proline. In other embodiments, the linker comprises at least 50% proline, such as at least 60%, at least 66%, at least 70%, at least 75%, at least 80%, at least 85%, at least 90% and has an overall negative charge. For example, the linker region comprises amino acids of an acidic nature.

Preferred linker regions have a length of at least 4 amino acids and not more than 30 amino acids, such as 4-28 amino acids, preferably 4-20 amino acids, or even 4-10 amino acids, such as 4 amino acids, 5 amino acids, 6 amino acids, 7 amino acids, 8 amino acids, 9 amino acids or 10 amino acids.

Exemplary linker regions comprise one or more of the following optionally repeating motifs:

```
                                  (SEQ ID NO: 102)
[P/S/T/R/K/D/E]P
and

P[S/T/R/K/D/E/N/Q]P[S/T/R/K/D/E]
```

Other preferred linker regions include the following optionally repeating motifs:

```
[S/T/R/K/D/E]P[S/T/R/K/D/E/N/Q]

[P/S/T/R/K/D/E][P/S/T/R/K/D/E]P,
and/or

P[P/S/T/R/K/D/E][P/S/T/R/K/D/E].
```

Particularly preferred linkers include the optionally repeating motifs of the same, or different, amino acids within the brackets as indicated:

```
                                  (SEQ ID NO: 109)
[P/S/T]P
and

P[S/E]PT.
```

Or more particularly, the optionally repeating motif represented by [P/S/T]P includes PPPPPP (SEQ ID NO: 29), as well as PPSPTP (SEQ ID NO: 110), PPTPTP (SEQ ID NO: 111), PPSPSP (SEQ ID NO: 112), SPPPTP (SEQ ID NO:

113), SPTPPP (SEQ ID NO: 114), SPPPPP (SEQ ID NO: 115), SPTPTP (SEQ ID NO: 116), TPPPSP (SEQ ID NO: 117), TPSPPP (SEQ ID NO: 118), TPPPPP (SEQ ID NO: 119), TPSPSP (SEQ ID NO: 120), and the optionally repeating motif represented by P[S/E]PT (SEQ ID NO: 109) would include PSPTPEPT (SEQ ID NO: 121), PSPTPEPTPSPTPEPT (SEQ ID NO: 122), PEPTPSPT (SEQ ID NO: 123), PEPTPSPTPSPT (SEQ ID NO: 124) and so forth.

Exemplary linkers further comprise (a) $(SP)_a$, a=2-10 (SEQ ID NO: 202);
(b) $(PS)_a$, a=2-10 (SEQ ID NO: 203);
(c) $P_b$, b=4-20, preferably 4-15 (SEQ ID NO: 204);
(d) (PEPT (SEQ ID NO: 125))c, c=2-5 (SEQ ID NO: 79);
(e) (PSPT (SEQ ID NO: $104))_d$, d=2-5 (SEQ ID NO: 150);
(f) (P[S/T/R/K/D/E/N/Q]P[S/T/R/K/D/E] (SEQ ID NO: $102))_e$, e=2-5 (SEQ ID NO: 205);
(g) $([S/T/R/K/D/E]P)_f$, f=2-10, preferably 2-5 (SEQ ID NO: 206);
(h) $([S/T/R/K/D/E/N/Q]P[S/T/R/K/D/E])_g$, g=2-6 (SEQ ID NO: 207);
(i) $([S/T/R/K/D/E/N/Q][S/T/R/K/D/E/N/Q]P)_h$, h=2-5 (SEQ ID NO: 208);
(j) $(TP)_i$, i=2-10 (SEQ ID NO: 209);
(k) $([S/T/P][S/T/P][S/T/P])_j$, j=2-11 (SEQ ID NO: 210);
(l) and/or combinations thereof, wherein combinations of the respective monomeric units are contemplated.

When combinations of these motifs are included, the minimal repeating unit is a monomeric unit. For example, linkers including SPPEPT (SEQ ID NO: 126), SPPSPT (SEQ ID NO: 127), PSPEPT (SEQ ID NO: 128), PSPSPT (SEQ ID NO: 129).

Additional exemplary linkers include: SPSP (SEQ ID NO: 130), SPSPSP (SEQ ID NO: 131), SPSPSPSP (SEQ ID NO: 132), SPSPSPSPSP (SEQ ID NO: 58), SPSPSPSPSPSP (SEQ ID NO: 133), SPSPSPSPSPSPSP (SEQ ID NO: 134), SPSPSPSPSPSPSPSP (SEQ ID NO: 135), PPPP (SEQ ID NO: 27), PPPPP (SEQ ID NO: 28), PPPPPP (SEQ ID NO: 29), PPPPPPP (SEQ ID NO: 31), PPPPPPPP (SEQ ID NO: 136), PPPPPPPPP (SEQS ID NO: 137), PPPPPPPPPP (SEQ ID NO: 138), PPPPPPPPPPP (SEQ ID NO: 139), PPPPPPPPPPPPPPPPPPPPPPPPP (SEQ ID NO: 141), PPPPPPPPPPPPPPPPPPPPPPPPPPPPPPPPPPPEPTPEPT (SEQ ID NO: 144), PEPTPEPTPEPT (SEQ ID NO: 145), PEPTPEPTPEPTPEPT (SEQ ID NO: 146), PEPTPEPTPEPTPEPTPEPT (SEQ ID NO: 79), PSPTPSPT (SEQ ID NO: 147), PSPTPSPTPSPT (SEQ ID NO: 148), PSPTPSPTPSPTPSPT (SEQ ID NO: 149), PSPTPSPTPSPTPSPTPSPT (SEQ ID NO: 150), SPSSPS (SEQ ID NO: 151), SPSSPSSPS (SEQ ID NO: 152), SPSSPSSPSSPS (SEQ ID NO: 153), SPSSPSSPSSPSSPS (SEQ ID NO: 154), TPTTPT (SEQ ID NO: 155), TPTTPTTPT (SEQ ID NO: 156), TPTTPTTPTTPT (SEQ ID NO: 157), TPTTPTTPTTPTTPT (SEQ ID NO: 158), PEPTPRPTPEPTPRPT (SEQ ID NO: 159), PEPTPKPTPEPTPKPT (SEQ ID NO: 160), PEPTPQPTPEPTPQPT (SEQ ID NO: 161), PRPTPEPTPRPT (SEQ ID NO: 162), PKPTPEPTPKPT (SEQ ID NO: 163), PEPTPQPT (SEQ ID NO: 164), PEPTPQPTPEPT (SEQ ID NO: 165), PEPTPRPTPEPTPRPTG (SEQ ID NO: 85), PEPTPKPTPEPTPKPTG (SEQ ID NO: 87), PEPTPQPTPEPTPQPTG (SEQ ID NO: 88), PRPTPEPTPRPTG (SEQ ID NO: 89), PKPTPEPTPKPTG (SEQ ID NO: 90), PEPTPQPTG (SEQ ID NO: 91), PEPTPQPTPEPTG (SEQ ID NO: 92), PPPGGPGGPGTPTSTAPGSGPTSPGGGSG (SEQ ID NO: 82), TTPPTPTPTPTP (SEQ ID NO: 166); TTPTPPTPTPTPTP (SEQ ID NO: 167), TTPTPTPPTPTPTPTP (SEQ ID NO: 168), TPPTPPTPPTPPTPPTPPTPPTPPTPPTPPTPP (SEQ ID NO: 169).

Additional exemplary linkers comprise the above-mentioned linkers, as well as a C-terminal glycine, for example, SPSPG (SEQ ID NO: 24), SPSPSPG, SPSPSPSPG, SPSPSPSPSPG (SEQ ID NO: 25), SPSPSPSPSPSPG, SPSPSPSPSPSPSPG, SPSPSPSPSPSPSPSPG, PPPPG, PPPPPG, PPPPPPG, PPPPPPPG (SEQ ID NO: 30), PPPPPPPPG (SEQ ID NO: 32), PPPPPPPPPG (SEQ ID NO: 33), PPPPPPPPPPG (SEQ ID NO: 34), PPPPPPPPPPPG (SEQ ID NO: 35), PPPPPPPPPPPPP PPPPPPPPPPPPPPPPPPPPPPPPPPPPG (SEQ ID NO: 171), PPPPPPPPPPPPPPPP ID NO: 172), PEPTPEPTG (SEQ ID NO: 37), PEPTPEPTPEPTG (SEQ ID NO: 38), PEPTPEPTPEPTPEPTG (SEQ ID NO: 39), PEPTPEPTPEPTPEPTPEPTG (SEQ ID NO: 40), PSPTPSPTG, PSPTPSPTPSPTG, PSPTPSPTPSPTPSPTG (SEQ ID NO: 41), PSPTPSPTPSPTPSPTPSPTG (SEQ ID NO: 42), SPSSPSG (SEQ ID NO: 94), SPSSPSSPSG (SEQ ID NO: 95), SPSSPSSPSSPSG (SEQ ID NO: 19), SPSSPSSPSSPSSPSG (SEQ ID NO: 20), TPTTPTG (SEQ ID NO: 96), TPTTPTTPTG (SEQ ID NO: 97), TPTTPTTPTTPTG (SEQ ID NO: 17), TPTTPTTPTTPTTPTG, PEPTPRPTPEPTPRPTG (SEQ ID NO: 85), PEPTPKPTPEPTPKPTG (SEQ ID NO: 87), PEPTPQPTPEPTPQPTG (SEQ ID NO: 88), PRPTPEPTPRPTG (SEQ ID NO: 89), PKPTPEPTPKPTG (SEQ ID NO: 90), PEPTPQPTG (SEQ ID NO: 91), PEPTPQPTPEPTG (SEQ ID NO: 92), PPPGGPGGPGTPTSTAPGSGPTSPGGGSG (SEQ ID NO: 82), TTPPTPTPTPTPG (SEQ ID NO: 12); TTPTPPTPTPTPTPG (SEQ ID NO: 13), TTPTPTPPTPTPTPTPG (SEQ ID NO: 14), TTPTPTPTPPTPTPTPTPG (SEQ ID NO: 15), TPPTPPTPPTPPTPPTPPTPPTPPTPPTPPTPPG (SEQ ID NO: 16).

Particularly preferred linkers are those comprising primarily or exclusively proline, e.g., PPPP (SEQ ID NO: 27), PPPPP (SEQ ID NO: 28), PPPPPP (SEQ ID NO: 29), PPPPPPP (SEQ ID NO: 31), PPPPPPPP (SEQ ID NO: 136), PPPPPPPPP (SEQ ID NO: 137), PPPPPPPPPP (SEQ ID NO: 138), PPPPPPPPPPP (SEQ ID NO: 139), PPPPPPPPPPPPP PPPPPPPPPPPPPPPPPPPPPPPPPPPP (SEQ ID NO: 142), PPPPPPPPPPPPPPPPEQ ID NO: 143), PPPPG, PPPPPG, PPPPPPG, PPPPPPPG (SEQ ID NO: 30), PPPPPPPPG (SEQ ID NO: 32), PPPPPPPPPG (SEQ ID NO: 33), PPPPPPPPPPG (SEQ ID NO: 34), PPPPPPPPPPPG (SEQ ID NO: 35), PPPPPPPPPPPPP PPPPPPPPPPPPPPPPPPPPPPPPPPPPP PPPPPPPPPPPPPPPP ID NO: 172).

For the above-contemplated embodiments, one of skill in the art will appreciate that the objective is to replace the linker of the parent of interest, with the proline-rich linkers herein to provide additional stability.

In an alternative embodiment, the linker can be considered as a variant of the linker of the parent molecule, having stabilizing point mutations, including mutations to proline.

Accordingly, the linker may, in some embodiments, comprise an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence as shown in positions 213-241 of SEQ ID NO: 1.

17

18

In an embodiment, the linker comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence as shown in positions 211-246 of SEQ ID NO: 2.

In an embodiment, the linker comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence as shown in positions 211-258 of SEQ ID NO: 3.

In an embodiment, the linker comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence as shown in positions 211-240 of SEQ ID NO: 4.

In a particularly preferred embodiment, the linker is selected from any of the following in Table A:

TABLE A

| Preferred Linkers |
| --- |
| TTPPTPTPTPTPG (SEQ ID NO: 12) |
| TTPTPPTPTPTPTPG (SEQ ID NO: 13) |
| TTPTPTPPTPTPTPTPG (SEQ ID NO: 14) |
| TTPTPTPTPPTPTPTPTPG (SEQ ID NO: 15) |
| TPPTPPTPPTPPTPPTPPTPPTPPTPPTPPTPPG (SEQ ID NO: 16) |
| TPTTPTTPTTPTG (SEQ ID NO: 17) |
| TPTTPTTPTTPTTPTTPTG (SEQ ID NO: 18) |
| SPSSPSSPSSPSG (SEQ ID NO: 19) |
| SPSSPSSPSSPSSPSG (SEQ ID NO: 20) |
| SPPSPPSPPSPPSPPG (SEQ ID NO: 21) |
| SPPSPPSPPSPPSPPSPPSPPSPPSPPSPPG (SEQ ID NO: 22) |
| PPSSPSSPSSPSSPSSPSSPSG (SEQ ID NO: 23) |
| SPSPG (SEQ ID NO: 24) |
| SPSPSPSPSPG (SEQ ID NO: 25) |
| TPTPTPTPTPG (SEQ ID NO: 26) |
| PPPP (SEQ ID NO: 27) |
| PPPPP (SEQ ID NO: 28) |
| PPPPPP (SEQ ID NO: 29) |
| PPPPPPPG (SEQ ID NO: 30) |
| PPPPPPP (SEQ ID NO: 31) |

TABLE A-continued

| Preferred Linkers |
| --- |
| PPPPPPPPG (SEQ ID NO: 32) |
| PPPPPPPPPG (SEQ ID NO: 33) |
| PPPPPPPPPPG (SEQ ID NO: 34) |
| PPPPPPPPPPPG (SEQ ID NO: 35) |
| PPPPPPPPPPPPPG (SEQ ID NO: 36) |
| PEPTPEPTG (SEQ ID NO: 37) |
| PEPTPEPTPEPTG (SEQ ID NO: 38) |
| PEPTPEPTPEPTPEPTG (SEQ ID NO: 39) |
| PEPTPEPTPEPTPEPTPEPTG (SEQ ID NO: 40) |
| PSPTPSPTPSPTPSPTG (SEQ ID NO: 41) |
| PSPTPSPTPSPTPSPTPSPTG (SEQ ID NO: 42) |
| PQPTPQPTG (SEQ ID NO: 43) |
| PDPTPDPTG (SEQ ID NO: 44) |
| PRPTPEPTG (SEQ ID NO: 45) |
| PQPTPEPTG (SEQ ID NO: 46) |
| PSPNSPNSPNG (SEQ ID NO: 47) |
| PEPTPRPTG (SEQ ID NO: 48) |
| PQPTPEPTPQPTPEPTPQPTPEPTPQPTG (SEQ ID NO: 49) |
| PDPTPDPTPDPTG (SEQ ID NO: 50) |
| PQPTPQPTPQPTPQPTG (SEQ ID NO: 51) |
| PQPTPEPTPQPTPEPTG (SEQ ID NO: 52) |
| SPSPSPSPPPG (SEQ ID NO: 53) |
| SPSPSPSPDPG (SEQ ID NO: 54) |
| SPSPSPSPKPG (SEQ ID NO: 55) |
| SPSPSPSPAPG (SEQ ID NO: 56) |
| SPSPSPSPSPSG (SEQ ID NO: 57) |
| SPSPSPSPSP (SEQ ID NO: 58) |
| SPSPSPSPSPS (SEQ ID NO: 59) |
| SPSPSPSPSPP (SEQ ID NO: 60) |
| SPSPSPSPSPE (SEQ ID NO: 61) |
| SPSPSPSPSPN (SEQ ID NO: 62) |
| SPSPSPSPSPGG (SEQ ID NO: 63) |
| SPSPSPSPSPK (SEQ ID NO: 64) |
| PEPTPEPTP (SEQ ID NO: 65) |
| PEPTPEPTR (SEQ ID NO: 66) |
| PEPTPEPTPEPTP (SEQ ID NO: 67) |
| PEPTPEPTPEPTPEPTPSPTG (SEQ ID NO: 68) |
| PEPTPEPTPEPTPEPTPTPTG (SEQ ID NO: 69) |
| PEPTPEPTPEPTPEPTPGPTG (SEQ ID NO: 70) |

TABLE A-continued

| Preferred Linkers |
|---|
| PEPTPEPTPEPTPEPTPDPTG (SEQ ID NO: 71) |
| PEPTPEPTPEPTPEPTPETG (SEQ ID NO: 72) |
| PEPTPEPTPEPTPEPTPEPTD (SEQ ID NO: 73) |
| PEPTPEPTE (SEQ ID NO: 74) |
| PEPTPEPTPEPTPEPTPEP (SEQ ID NO: 75) |
| PEPTPEPTPEPTPEPTPSPT (SEQ ID NO: 76) |
| PEPTPEPTPEPTPEPTPRPTT (SEQ ID NO: 77) |
| PEPTPEPTPEPTPEPTPEPTT (SEQ ID NO: 78) |
| PEPTPEPTPEPTPEPTPEPT (SEQ ID NO: 79) |
| PEPTPEPTPEPTPEPTPEPTS (SEQ ID NO: 80) |
| PEPTPEPTPEPTPEPTPEPTR (SEQ ID NO: 81) |
| PPPGGPGGPGTPTSTAPGSGPTSPGGGSG (SEQ ID NO: 82) |
| PPPGGPGGTGTPTSTAPGSGPTSPGGGSG (SEQ ID NO: 83) |
| PPSGGPGGPGTPTSTAPGSGPTSPGGGSG (SEQ ID NO: 84) |
| PEPTPRPTPEPTPRPTG (SEQ ID NO: 85) |
| PKPTPEPTPKPTPEPTG (SEQ ID NO: 86) |
| PEPTPKPTPEPTPKPTG (SEQ ID NO: 87) |
| PEPTPQPTPEPTPQPTG (SEQ ID NO: 88) |
| PRPTPEPTPRPTG (SEQ ID NO: 89) |
| PKPTPEPTPKPTG (SEQ ID NO: 90) |
| PEPTPQPTG (SEQ ID NO: 91) |
| PEPTPQPTPEPTG (SEQ ID NO: 92) |
| TPPTPPG (SEQ ID NO: 93) |
| SPSSPSG (SEQ ID NO: 94) |
| SPSSPSSPSG (SEQ ID NO: 95) |
| TPTTPTG (SEQ ID NO: 96) |
| TPTTPTTPTG (SEQ ID NO: 97) |

In a particular embodiment, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25).

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 6.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 7.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 8.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 9.

In an embodiment, the variant comprises a catalytic domain having an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 173.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 174.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 175.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 176.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 177.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 178.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 179.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 180.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 181.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 182.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 183.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 184.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 185.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 186.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 187.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 188.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 189.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 190.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 191.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 192.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 193.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 194.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 195.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 196.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 197.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 198.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 199.

In an embodiment, the variant comprises a catalytic domain having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 200.

In some aspects, a variant of the invention has an improved property relative to a reference enzyme/parent enzyme.

In one aspect, the improved property is increased stability e.g. improved proteolytic stability, improved detergent stability, improved in-wash stability or improved thermostability. In another aspect, the improved property is increased stability during production of the detergent composition or increased performance after storage in the detergent composition relative to the performance of the parent molecule stored at similar conditions. Some aspects of the invention relate to cellulase variants having an improvement factor above 1 when the cellulase variant is tested for a property of interest in a relevant assay, wherein the property of the reference enzyme/parent enzyme is given a value of 1. In some aspects, the property is stability, such as improved proteolytic stability. Some aspects of the invention relate to cellulase variants having an improvement factor above 1 when the cellulase variant is tested for a property of interest in the assay described in Example 2, wherein the property of the reference enzyme/parent enzyme is given a value of 1. In some aspects, the property is stability, such as proteolytic stability.

In some aspects, the improved property is increased stability e.g. improved detergent stability, improved in-wash stability and improved thermostability. Some aspects of the invention relate to cellulase variants having an improvement factor above 1 when the cellulase variant is tested for a property of interest in a relevant assay, wherein the property of the reference enzyme/parent enzyme is given a value of 1, such as when the cellulase variant is tested for a property of interest in the assay described in Example 7.

In some aspects, the improved property is improved thermostability.

In some aspects, the improved property is improved stability in detergent.

In some aspects, the improved property is improved proteolytic stability.

In some aspects, the improved property is one or more or even all of improved thermostability, improved detergent stability, improved proteolytic stability.

A variant according to the invention is improved under the measured conditions when the residual activity ratio, defined as:

Residual Activity Ratio (RAR)=(RA, variant)/(RA, reference) is above 1.0 compared to the reference cellulase.

In a particularly preferred aspect, a variant according to the invention results in improved stability (e.g., thermostability, detergent stability, proteolytic stability, or more than one or even all of these), where RAR>1.0. In some aspects, the variants according to the invention have a Residual Activity Ratio (RAR) which is at least 1.1; 1.2; 1.3; 1.4; 1.5; 1.6; 1.7; 1.8; 1.9; 2.0; 2.1; 2.2; 2.3; 2.4; 2.5; 2.6; 2.7, 2.8; 2.9; 3.0, 3.1; 3.2; 3.3; 3.4; 3.5, 3.6, 3.7, 3.8, 3.9; 4.0, 4.1; 4.2; 4.3; 4.4; 4.5, 4.6, 4.7, 4.8, 4.9, 5.0, 5.1; 5.2; 5.3; 5.4; 5.5, 5.6, 5.7, 5.8, 5.9; 3.0, 6.1; 6.2; 6.3; 6.4; 6.5, 6.6, 6.7, 6.8, 6.9; 7.0, 7.1; 7.2; 7.3; 7.4; 7.5, 7.6, 7.7, 7.8, 7.9; 8.0, 8.1; 8.2; 8.3; 8.4; 8.5, 8.6, 8.7, 8.8, 8.9; 9.0, 9.1; 9.2; 9.3; 9.4; 9.5, 9.6, 9.7, 9.8, 9.9; 10.0, 10.1; 10.2; 10.3; 10.4; 10.5, 10.6, 10.7, 10.8, 10.9; 12, 15, 16, 20, 25 or 30 compared to a parent or reference enzyme, and in particular compared to a cellulase of SEQ ID NO: 1, SEQ ID NO: 2, SEQ ID NO: 3, or SEQ ID NO: 4.

One preferred embodiment relates to a cellulase variant having improved stability, wherein RAR>1.0, compared to SEQ ID NO: 1. One preferred embodiment relates to a cellulase variant having improved stability, wherein the residual activity ratio (RAR) is at least 1.5, compared to SEQ ID NO: 1, when measured as described in Example 2.

Catalytic Domain

Particularly preferred enzymes are those having cellulase, such as endoglucanase activity. In particular, relevant catalytic domains are from enzymes of the glycoside hydrolase family 45 (GH45), using the nomenclature of Henrissat et al. outlined on the CAZY database available at cazy.org The catalytic domain can comprise a wild type or variant thereof.

In an embodiment, the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence as shown in positions 1-212 of SEQ ID NO: 1.

In an embodiment, the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence as shown in positions 1-211 of SEQ ID NO: 2.

In an embodiment, the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence as shown in positions 1-210 of SEQ ID NO: 3.

In an embodiment, the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence as shown in positions 1-210 of SEQ ID NO: 4.

In one aspect, the catalytic domain further comprises a number of substitutions in the variants of the present invention is 2-20, e.g., 2-10 and 2-5, such as 2, 3, 4, 5, 6, 7, 8, 9 or 10 substitutions.

In another aspect, the variant comprises or consists of two substitution at positions selected among the positions corresponding to: 25, 32, 41, 44, 56, 77, 104, 132, 146, 147, 156, 162, 169, 183, 186, 194, or 201 in SEQ ID NO: 1. In another aspect, the amino acid at this position is substituted with Ala, Arg, Asn, Asp, Cys, Gln, Glu, Gly, His, Ile, Leu, Lys, Met, Phe, Pro, Ser, Thr, Trp, Tyr, or Val.

In an aspect, the variant comprises or consists of substitutions of one or more of the following X25G; X32S; X41T; X44D; X56A; X77N; X851; X103A; X104K; X114W or X114F; X134D; X137K or X137R; X146D or X146S; X147R; X152K; X156E; X159D or X159E; X162E; X169Y; X179T); X183V; X186R; X194L or X194S; and/or X201K.

In some embodiments, the variants comprise a substitution X32S and one or more substitutions corresponding to the substitutions A25G; S41T; S56A; S77N; T104K; N134D; A146D or A146S; Q147R; Q156E; A162E; Q169Y; F183V; Q186R; 1194L; K201R and G219W of the polypeptide having the sequence of SEQ ID NO: 1 or SEQ ID NO: 5, wherein the variant has cellulolytic activity.

In some embodiments, the variants comprise a substitution X56A and one or more substitutions corresponding to the substitutions A25G; A32S; S41T; S77N; T104K; N134D; A146D or A146S; Q147R; Q156E; A162E; Q169Y; F183V; Q186R; 1194L; K201R and G219W of the polypeptide having the sequence of SEQ ID NO: 1 or SEQ ID NO: 5, wherein the variant has cellulolytic activity.

In some embodiments, the variants comprise a substitution X134D and one or more substitutions corresponding to the substitutions A25G; A32S; S41T; S56A; S77N; S851; T104K; G114F; G114W; S137E; S137R; S137D; S137K; A146D or A146S; Q147R; S152K; Q156E; S159E; S159D; A162E; Q169Y; D179T; F183V; Q186R; 1194L; 1194S; K201R and G219W of the polypeptide having the sequence of SEQ ID NO: 1 or SEQ ID NO: 5, wherein the variant has cellulolytic activity.

In some embodiments, the variants comprise a substitution A146D and further a substitution selected among substitutions corresponding the following substitutions in SEQ ID NO: 1: A25G; A32S; S41T; S56A; S77N; K103A; T104K; G114F; G114W; N134D; S137R; S152K; Q156E; S159D; S159E; A162E; Q169Y; D179T; F183V; Q186R; 1194L; K201R and G219W of the polypeptide having the sequence of SEQ ID NO: 1 or SEQ ID NO: 5, wherein the variant has cellulolytic activity.

In some embodiments, the variants comprise a substitution X147R and one or more substitutions corresponding to the substitutions A25G; A32S; S41T; S56A; S77N; T104K; N134D; A146D or A146S; Q156E; A162E; Q169Y; F183V; Q186R; 1194L; K201R and G219W of the polypeptide having the sequence of SEQ ID NO: 1 or SEQ ID NO: 5, wherein the variant has cellulolytic activity.

In some embodiments, the variants comprise a substitution S159D and further a substitution selected among substitutions corresponding the following substitutions in SEQ ID NO: 1: A25G; A32S; S41T; S56A; S77N; K103A; T104K; G114F; G114W; N134D; S137R; A146D; S152K; Q156E; A162E; Q169Y; D179T; F183V; Q186R; 1194L; K201R and G219W, of the polypeptide having the sequence of SEQ ID NO:1 or SEQ ID NO: 5 wherein the variant has cellulytic activity.

In some embodiments, the variants comprise a substitution X169Y and one or more substitutions corresponding to the substitutions A25G; A32S; S41T; S56A; S77N; T104K; N134D; A146D or A146S; Q147R; Q156E; A162E; F183V; Q186R; 1194L; K201R and G219W of the polypeptide having the sequence of SEQ ID NO: 1 or SEQ ID NO: 5, wherein the variant has cellulolytic activity.

In an embodiment, the variant comprises one or more of the combinations 25G+56A, 25G+114W, 25G+134D, 25G+146D, 25G+147R, 25G+156E, 25G+162E, 25G+169Y, 25G+183V, 56A+114W, 56A+134D, 56A+146D, 56A+147R, 56A+156E, 56A+162E, 56A+169Y, 56A+183V, 114W+134D, 114W+146D, 114W+147R, 114W+156E, 114W+162E, 114W+169Y, 114W+183V, 134D+146D, 134D+147R, 134D+156E, 134D+162E, 134D+169Y, 134D+183V, 146D+147R, 146D+156E, 146D+162E, 146D+169Y, 146D+183V, 147R+156E, 147R+162E, 147R+169Y, 147R+183V, 156E+162E, 156E+169Y, 156E+183V, 162E+169Y, 162E+183V, 169Y+183V wherein SEQ ID NO: 1 or SEQ ID NO: 5 is used for numbering.

In an embodiment, the variant comprises one or more of the combinations 25G+56A+114W, 25G+56A+134D, 25G+56A+146D, 25G+56A+147R, 25G+56A+156E, 25G+56A+162E, 25G+56A+169Y, 25G+56A+183V, 25G+114W+134D, 25G+114W+146D, 25G+114W+147R, 25G+114W+156E, 25G+114W+162E, 25G+114W+169Y, 25G+114W+183V, 25G+134D+146D, 25G+134D+147R, 25G+134D+156E, 25G+134D+162E, 25G+134D+169Y, 25G+134D+183V, 25G+146D+147R, 25G+146D+156E, 25G+146D+162E, 25G+146D+169Y, 25G+146D+183V, 25G+147R+156E, 25G+147R+162E, 25G+147R+169Y, 25G+147R+183V, 25G+156E+162E, 25G+156E+169Y, 25G+156E+183V, 25G+162E+169Y, 25G+162E+183V, 25G+169Y+183V, 56A+114W+134D, 56A+114W+146D, 56A+114W+147R, 56A+114W+156E, 56A+114W+162E, 56A+114W+169Y, 56A+114W+183V, 56A+134D+146D, 56A+134D+147R, 56A+134D+156E, 56A+134D+162E, 56A+134D+169Y, 56A+134D+183V, 56A+146D+147R, 56A+146D+156E, 56A+146D+162E, 56A+146D+169Y, 56A+146D+183V, 56A+147R+156E, 56A+147R+162E, 56A+147R+169Y, 56A+147R+183V, 56A+156E+162E, 56A+156E+169Y, 56A+156E+183V, 56A+162E+169Y, 56A+162E+183V, 56A+169Y+183V, 114W+134D+146D, 114W+134D+147R, 114W+134D+156E, 114W+134D+162E, 114W+134D+169Y, 114W+134D+183V, 114W+146D+147R, 114W+146D+156E, 114W+146D+162E, 114W+146D+169Y, 114W+146D+183V, 114W+147R+156E, 114W+147R+162E, 114W+147R+169Y, 114W+147R+183V, 114W+156E+162E, 114W+156E+169Y, 114W+156E+183V, 114W+162E+169Y, 114W+162E+183V, 114W+169Y+183V, 134D+146D+147R, 134D+146D+156E, 134D+146D+162E, 134D+146D+169Y, 134D+146D+183V, 134D+147R+156E, 134D+147R+162E, 134D+147R+169Y, 134D+147R+183V, 134D+156E+162E, 134D+156E+169Y, 134D+156E+183V, 134D+162E+169Y, 134D+162E+183V, 134D+169Y+183V, 146D+147R+156E, 146D+147R+162E, 146D+147R+169Y, 146D+147R+183V, 146D+156E+162E, 146D+156E+169Y, 146D+156E+183V, 146D+162E+169Y, 146D+162E+183V, 146D+169Y+183V, 147R+156E+162E, 147R+156E+169Y, 147R+156E+183V, 147R+162E+169Y, 147R+162E+183V, 147R+169Y+183V, 156E+162E+169Y, 156E+162E+183V, 156E+169Y+183V, 162E+169Y+183V, wherein SEQ ID NO: 1 or SEQ ID NO: 5 is used for numbering.

In an embodiment, the variant comprises one or more of the combinations 25G+56A+114W+146D, 25G+56A+114W+147R, 25G+56A+114W+134D, 25G+56A+114W+156E, 25G+56A+114W+162E, 25G+56A+114W+169Y, 25G+56A+114W+183V, 25G+56A+134D+146D, 25G+56A+134D+147R, 25G+56A+134D+156E, 25G+56A+134D+162E, 25G+56A+134D+169Y, 25G+56A+134D+183V, 25G+56A+146D+147R, 25G+56A+146D+156E, 25G+56A+146D+162E, 25G+56A+146D+169Y, 25G+56A+146D+183V, 25G+56A+147R+156E, 25G+56A+147R+162E, 25G+56A+147R+169Y, 25G+56A+147R+183V, 25G+56A+156E+162E, 25G+56A+156E+169Y, 25G+56A+156E+183V, 25G+56A+162E+169Y, 25G+56A+162E+183V, 25G+56A+169Y+183V, 25G+114W+134D+146D, 25G+114W+134D+147R, 25G+114W+134D+156E, 25G+114W+134D+162E, 25G+114W+134D+169Y, 25G+114W+134D+183V, 25G+114W+146D+147R, 25G+114W+146D+156E, 25G+114W+146D+162E, 25G+114W+146D+169Y, 25G+114W+146D+183V, 25G+114W+147R+156E, 25G+114W+147R+162E, 25G+114W+147R+169Y, 25G+114W+147R+183V, 25G+114W+156E+162E, 25G+114W+156E+169Y, 25G+114W+156E+183V, 25G+114W+162E+169Y, 25G+114W+162E+183V, 25G+

114W+169Y+183V, 25G+134D+146D+147R, 25G+134D+146D+156E, 25G+134D+146D+162E, 25G+134D+146D+169Y, 25G+134D+146D+183V, 25G+134D+147R+156E, 25G+134D+147R+162E, 25G+134D+147R+169Y, 25G+134D+147R+183V, 25G+134D+156E+162E, 25G+134D+156E+169Y, 25G+134D+156E+183V, 25G+134D+162E+169Y, 25G+134D+162E+183V, 25G+134D+169Y+183V, 25G+146D+147R+156E, 25G+146D+147R+162E, 25G+146D+147R+169Y, 25G+146D+147R+183V, 25G+146D+156E+162E, 25G+146D+156E+169Y, 25G+146D+156E+183V, 25G+146D+162E+169Y, 25G+146D+162E+183V, 25G+146D+169Y+183V, 25G+147R+156E+162E, 25G+147R+156E+169Y, 25G+147R+156E+183V, 25G+147R+162E+169Y, 25G+147R+162E+183V, 25G+147R+169Y+183V, 25G+156E+162E+169Y, 25G+156E+162E+183V, 25G+156E+169Y+183V, 25G+162E+169Y+183V, 56A+114W+134D+146D, 56A+114W+134D+147R, 56A+114W+134D+156E, 56A+114W+134D+162E, 56A+114W+134D+169Y, 56A+114W+134D+183V, 56A+114W+146D+147R, 56A+114W+146D+156E, 56A+114W+146D+162E, 56A+114W+146D+169Y, 56A+114W+146D+183V, 56A+114W+147R+156E, 56A+114W+147R+162E, 56A+114W+147R+169Y, 56A+114W+147R+183V, 56A+114W+156E+162E, 56A+114W+156E+169Y, 56A+114W+156E+183V, 56A+114W+162E+169Y, 56A+114W+162E+183V, 56A+134D+146D+156E, 56A+114W+169Y+183V, 56A+134D+146D+147R, 56A+134D+146D+162E, 56A+134D+146D+169Y, 56A+134D+146D+183V, 56A+134D+147R+156E, 56A+134D+147R+162E, 56A+134D+147R+183V, 56A+134D+156E+162E, 56A+134D+147R+169Y, 56A+134D+156E+169Y, 56A+134D+156E+183V, 56A+134D+162E+169Y, 56A+134D+162E+183V, 56A+134D+169Y+183V, 56A+146D+147R+162E, 56A+146D+147R+169Y, 56A+146D+156E+162E, 56A+146D+156E+169Y, 56A+146D+162E+169Y, 56A+146D+162E+183V, 56A+146D+147R+156E, 56A+146D+147R+183V, 56A+146D+156E+183V, 56A+146D+169Y+183V, 56A+147R+156E+162E, 56A+147R+156E+169Y, 56A+147R+156E+183V, 56A+147R+169Y+183V, 56A+147R+162E+169Y, 56A+147R+162E+183V, 56A+156E+162E+183V, 56A+156E+169Y+183V, 56A+156E+162E+169Y, 56A+162E+169Y+183V, 114W+134D+146D+147R, 114W+134D+146D+156E, 114W+134D+146D+162E, 114W+134D+146D+169Y, 114W+134D+146D+183V, 114W+134D+147R+156E, 114W+134D+147R+162E, 114W+134D+147R+169Y, 114W+134D+147R+183V, 114W+134D+156E+162E, 114W+134D+156E+169Y, 114W+134D+156E+183V, 114W+134D+162E+169Y, 114W+134D+162E+183V, 114W+134D+169Y+183V, 114W+146D+147R+156E, 114W+146D+147R+162E, 114W+146D+147R+169Y, 114W+146D+147R+183V, 114W+146D+156E+162E, 114W+146D+156E+169Y, 114W+146D+156E+183V, 114W+146D+162E+169Y, 114W+146D+162E+183V, 114W+146D+169Y+183V, 114W+147R+156E+162E, 114W+147R+156E+169Y, 114W+147R+156E+183V, 114W+147R+162E+169Y, 114W+147R+162E+183V, 114W+147R+169Y+183V, 114W+156E+162E+169Y, 114W+156E+162E+183V, 114W+156E+169Y+183V, 114W+162E+169Y+183V, 134D+146D+147R+156E, 134D+146D+147R+162E, 134D+146D+147R+169Y, 134D+146D+147R+183V, 134D+146D+156E+162E, 134D+146D+156E+169Y, 134D+146D+156E+183V, 134D+146D+162E+169Y, 134D+146D+162E+183V, 134D+146D+169Y+183V, 134D+147R+156E+162E, 134D+147R+156E+169Y, 134D+147R+156E+183V, 134D+147R+162E+169Y, 134D+147R+162E+183V, 134D+147R+169Y+183V, 134D+156E+162E+169Y, 134D+156E+162E+183V, 134D+156E+169Y+183V, 134D+162E+169Y+183V, 146D+147R+156E+162E, 146D+147R+156E+169Y, 146D+147R+156E+183V, 146D+147R+162E+169Y, 146D+147R+162E+183V, 146D+147R+169Y+183V, 146D+156E+162E+169Y, 146D+156E+162E+183V, 146D+156E+169Y+183V, 146D+162E+169Y+183V, 147R+156E+162E+169Y, 147R+156E+162E+183V, 147R+156E+169Y+183V, 147R+162E+169Y+183V, 156E+162E+169Y+183V wherein SEQ ID NO: 1 or SEQ ID NO: 5 is used for numbering.

Particularly preferred variants in the catalytic domain includes variants comprising substitutions selected from the group consisting of:

X147R+X156E;
X147R+X169Y;
X56A+X147R;
X147R+X162E;
X147R+X156E+X162E;
X25G+X56A+X147R;
X134D+X156E+X162E;
X56A+X134D+X156E+X162E;
X25G+X56A+X156E+X162E;
X25G+X134D+X156E+X162E;
X25G+X56A+X134D+X169Y;
X56A+X134D+X162E;
X56A+X147R+X169Y;
X134D+X147R;
X156E+X169Y;
X56A+X134D+X147R;
X56A+X134D+X156E+X169Y;
X56A+X146D+X147R+X169Y;
X56A+X134D+X147R+X169Y;
X56A+X147R+X162E+X169Y;
X2*+X56A+X147R+X169Y;
X41T+X56A+X147R+X169Y;
X56A+X77N+X147R+X169Y;
X56A+X104K+X147R+X169Y;
X56A+X147R+X165Q+X169Y;
X56A+X147R+X169Y+X194L;
X56A+X147R+X169Y+X201R;
X56A+X147R+X169Y+X219W;
X44D+X56A+X147R+X169Y;
X50E+X56A+X147R+X169Y;
X32S+X56A+X147R+X169Y;
X44D+X56A+X147R+X169Y;
X56A+X147R+X169Y+X186R;
X56A+X147R+X169Y+X183V;
X56A+X146S+X147R+X162E+X169Y;
X56A+X134D+X147R;
X56A+X134D+X147R+X162E;
X32S+X56A+X134D+X147R+X169Y+X183V;
X56A+X134D+X147R+X162E+X169Y+X183V;
X32S+X56A+X77N+X134D+X147R+X162E+X169Y;
X32S+X56A+X134D+X146D+X147R+X169Y+X183V;
X32S+X56A+X134D+X147R+X169Y;
X56A+X134D+X147R+X162E+X169Y;
X32S+X56A+X134D+X146S+X147R+X169Y;
X32S+X56A+X134D+X146D+X147R+X169Y;
X32S+X56A+X134D+X147R+X169Y+X183V;
X32S+X56A+X134D+X147R+X169Y+X201R;
X56A+X134D+X146D+X147R+X169Y+X183V;
X56A+X134D+X146D+X147R+X162E+X169Y;
X56A+X134D+X146D+X147R+X169Y+X201R;
X56A+X134D+X147R+X162E+X169Y+X183V;
X56A+X134D+X147R+X169Y+X183V+X201R;
X32S+X56A+X77N+X134D+X147R+X169Y+X183V;

X32S+X56A+X77N+X134D+X147R+X162E+X169Y;
X32S+X56A+X134D+X146S+X147R+X169Y+X183V;
X32S+X56A+X134D+X146D+X147R+X169Y+X183V; or
X32S+X56A+X134D+X146D+X147R+X162E+X169Y;
wherein SEQ ID NO: 1 or SEQ ID NO: 5 is used for numbering.

In a particularly preferred embodiment, the catalytic domain comprises variants of SEQ ID NO: 5 comprising or consisting of one or more of the following: A25G; A32S; S41T; N44D; S56A; S77N; S851; K103A; T104K; G114W or G114F; N134D; S137K or S137R; A146D or A146S; Q147R; S152K; Q156E; S159D or S159E; A162E; Q169Y; D179T; F183V; Q186R; 1194L; K201R; and combinations thereof.

In an embodiment, the parent cellulase is the cellulase having the SEQ ID NO: 1 or SEQ ID NO: 5 and the variant comprises one or more of the combinations: A25G+S56A, A25G+G114W, A25G+N134D, A25G+A146D, A25G+Q147R, A25G+Q156E, A25G+A162E, A25G+Q169Y, A25G+F183V, S56A+G114W, S56A+N134D, S56A+A146D, S56A+Q147R, S56A+Q156E, S56A+A162E, S56A+Q169Y, S56A+F183V, G114W+N134D, G114W+A146D, G114W+Q147R, G114W+Q156E, G114W+A162E, G114W+Q169Y, G114W+F183V, N134D+A146D, N134D+Q147R, N134D+Q156E, N134D+A162E, N134D+Q169Y, N134D+F183V, A146D+Q147R, A146D+Q156E, A146D+A162E, A146D+Q169Y, A146D+F183V, Q147R+Q156E, Q147R+A162E, Q147R+Q169Y, Q147R+F183V, Q156E+A162E, Q156E+Q169Y, Q156E+F183V, A162E+Q169Y, A162E+F183V, Q169Y+F183V.

In an embodiment, the parent cellulase is the cellulase having the SEQ ID NO: 1 or SEQ ID NO: 5 and the variant comprises one or more of the combinations: A25G+S56A+G114W, A25G+S56A+N134D, A25G+S56A+A146D, A25G+S56A+Q147R, A25G+S56A+Q156E, A25G+S56A+A162E, A25G+S56A+Q169Y, A25G+S56A+F183V, A25G+G114W+N134D, A25G+G114W+A146D, A25G+G114W+Q147R, A25G+G114W+Q156E, A25G+G114W+A162E, A25G+G114W+Q169Y, A25G+G114W+F183V, A25G+N134D+A146D, A25G+N134D+Q147R, A25G+N134D+Q156E, A25G+N134D+A162E, A25G+N134D+Q169Y, A25G+N134D+F183V, A25G+A146D+Q147R, A25G+A146D+Q156E, A25G+A146D+A162E, A25G+A146D+Q169Y, A25G+A146D+F183V, A25G+Q147R+Q156E, A25G+Q147R+A162E, A25G+Q147R+Q169Y, A25G+Q147R+F183V, A25G+Q156E+A162E, A25G+Q156E+Q169Y, A25G+Q156E+F183V, A25G+A162E+Q169Y, A25G+A162E+F183V, A25G+Q169Y+F183V, S56A+G114W+N134D, S56A+G114W+A146D, S56A+G114W+Q147R, S56A+G114W+Q156E, S56A+G114W+A162E, S56A+G114W+Q169Y, S56A+G114W+F183V, S56A+N134D+A146D, S56A+N134D+Q147R, S56A+N134D+Q156E, S56A+N134D+A162E, S56A+N134D+Q169Y, S56A+N134D+F183V, S56A+A146D+Q147R, S56A+A146D+Q156E, S56A+A146D+A162E, S56A+A146D+Q169Y, S56A+A146D+F183V, S56A+Q147R+Q156E, S56A+Q147R+A162E, S56A+Q147R+Q169Y, S56A+Q147R+F183V, S56A+Q156E+A162E, S56A+Q156E+Q169Y, S56A+Q156E+F183V, S56A+A162E+Q169Y, S56A+A162E+F183V, S56A+Q169Y+F183V, G114W+N134D+A146D, G114W+N134D+Q147R, G114W+N134D+Q156E, G114W+N134D+A162E, G114W+N134D+Q169Y, G114W+N134D+F183V, G114W+A146D+Q147R, G114W+A146D+Q156E, G114W+A146D+A162E, G114W+A146D+Q169Y, G114W+A146D+F183V, G114W+Q147R+Q156E, G114W+Q147R+A162E, G114W+Q147R+Q169Y, G114W+Q147R+F183V, G114W+Q156E+A162E, G114W+Q156E+Q169Y, G114W+Q156E+F183V, G114W+A162E+Q169Y, G114W+A162E+F183V, G114W+Q169Y+F183V, N134D+A146D+Q147R, N134D+A146D+Q156E, N134D+A146D+A162E, N134D+A146D+Q169Y, N134D+Q147R+A162E, N134D+A146D+F183V, N134D+Q147R+Q156E, N134D+Q147R+Q169Y, N134D+Q147R+F183V, N134D+Q156E+A162E, N134D+Q156E+Q169Y, N134D+Q156E+F183V, N134D+A162E+Q169Y, N134D+A162E+F183V, N134D+Q169Y+F183V, A146D+Q147R+Q156E, A146D+Q147R+A162E, A146D+Q147R+Q169Y, A146D+Q147R+F183V, A146D+Q156E+A162E, A146D+Q156E+Q169Y, A146D+Q156E+F183V, A146D+A162E+Q169Y, A146D+A162E+F183V, A146D+Q169Y+F183V, Q147R+Q156E+A162E, Q147R+Q156E+Q169Y, Q147R+Q156E+F183V, Q147R+A162E+Q169Y, Q147R+A162E+F183V, Q147R+Q169Y+F183V, Q156E+A162E+Q169Y, Q156E+A162E+F183V, Q156E+Q169Y+F183V, A162E+Q169Y+F183V.

In an embodiment, the parent cellulase is the cellulase having the SEQ ID NO: 1 or SEQ ID NO: 5 and the variant comprises one or more of the combinations: A25G+S56A+G114W+N134D, A25G+S56A+G114W+A146D, A25G+S56A+G114W+Q147R, A25G+S56A+G114W+Q156E, A25G+S56A+G114W+A162E, A25G+S56A+G114W+Q169Y, A25G+S56A+G114W+F183V, A25G+S56A+N134D+A146D, A25G+S56A+N134D+Q147R, A25G+S56A+N134D+Q156E, A25G+S56A+N134D+A162E, A25G+S56A+N134D+Q169Y, A25G+S56A+N134D+F183V, A25G+S56A+A146D+Q147R, A25G+S56A+A146D+Q156E, A25G+S56A+A146D+F183V, A25G+S56A+A146D+A162E, A25G+S56A+A146D+Q169Y, A25G+S56A+Q147R+Q169Y, A25G+S56A+Q147R+A162E, A25G+S56A+Q147R+Q156E, A25G+S56A+Q156E+Q169Y, A25G+S56A+Q147R+F183V, A25G+S56A+Q156E+A162E, A25G+S56A+A162E+F183V, A25G+S56A+Q156E+F183V, A25G+S56A+A162E+Q169Y, A25G+S56A+Q169Y+F183V, A25G+G114W+N134D+A146D, A25G+G114W+N134D+Q147R, A25G+G114W+N134D+Q156E, A25G+G114W+N134D+Q169Y, A25G+G114W+A146D+Q147R, A25G+G114W+N134D+A162E, A25G+G114W+N134D+F183V, A25G+G114W+A146D+Q156E, A25G+G114W+A146D+A162E, A25G+G114W+A146D+Q169Y, A25G+G114W+A146D+F183V, A25G+G114W+Q147R+Q156E, A25G+G114W+Q147R+A162E, A25G+G114W+Q147R+Q169Y, A25G+G114W+Q147R+F183V, A25G+G114W+Q156E+A162E, A25G+G114W+Q156E+F183V, A25G+G114W+Q156E+Q169Y, A25G+G114W+A162E+Q169Y, A25G+G114W+A162E+F183V, A25G+G114W+Q169Y+F183V, A25G+N134D+A146D+Q147R, A25G+N134D+A146D+Q156E, A25G+N134D+A146D+A162E, A25G+N134D+A146D+Q169Y, A25G+N134D+A146D+F183V, A25G+N134D+Q147R+Q156E, A25G+N134D+Q147R+A162E, A25G+N134D+Q147R+Q169Y, A25G+N134D+Q147R+F183V, A25G+N134D+Q156E+A162E, A25G+N134D+Q156E+Q169Y, A25G+N134D+Q156E+F183V, A25G+N134D+A162E+Q169Y, A25G+N134D+A162E+F183V, A25G+N134D+Q169Y+F183V, A25G+A146D+Q147R+Q156E, A25G+A146D+Q147R+A162E, A25G+A146D+Q147R+Q169Y, A25G+A146D+Q147R+F183V, A25G+A146D+Q156E+A162E, A25G+A146D+Q156E+Q169Y, A25G+A146D+Q156E+F183V, A25G+A146D+A162E+Q169Y, A25G+A146D+A162E+F183V, A25G+A146D+Q169Y+F183V, A25G+Q147R+Q156E+A162E, A25G+Q147R+Q156E+Q169Y, A25G+Q147R+Q156E+F183V, A25G+Q147R+

A162E+Q169Y, A25G+Q147R+A162E+F183V, A25G+Q147R+Q169Y+F183V, A25G+Q156E+A162E+Q169Y, A25G+Q156E+A162E+F183V, A25G+Q156E+Q169Y+F183V, A25G+A162E+Q169Y+F183V, S56A+G114W+N134D+A146D, S56A+G114W+N134D+Q147R, S56A+G114W+N134D+Q156E, S56A+G114W+N134D+A162E, S56A+G114W+N134D+Q169Y, S56A+G114W+N134D+F183V, S56A+G114W+A146D+Q156E, S56A+G114W+A146D+Q147R, S56A+G114W+A146D+A162E, S56A+G114W+A146D+Q169Y, S56A+G114W+A146D+F183V, S56A+G114W+Q147R+Q156E, S56A+G114W+Q147R+A162E, S56A+G114W+Q147R+F183V, S56A+G114W+Q147R+Q169Y, S56A+G114W+Q156E+Q169Y, S56A+G114W+Q156E+A162E, S56A+G114W+Q156E+F183V, S56A+G114W+A162E+Q169Y, S56A+G114W+A162E+F183V, S56A+G114W+Q169Y+F183V, S56A+N134D+A146D+Q147R, S56A+N134D+A146D+Q156E, S56A+N134D+A146D+A162E, S56A+N134D+A146D+Q169Y, S56A+N134D+A146D+F183V, S56A+N134D+Q147R+Q156E, S56A+N134D+Q147R+A162E, S56A+N134D+Q147R+Q169Y, S56A+N134D+Q147R+F183V, S56A+N134D+Q156E+A162E, S56A+N134D+Q156E+Q169Y, S56A+N134D+Q156E+F183V, S56A+N134D+A162E+Q169Y, S56A+N134D+A162E+F183V, S56A+N134D+Q169Y+F183V, S56A+A146D+Q147R+Q156E, S56A+A146D+Q147R+A162E, S56A+A146D+Q147R+Q169Y, S56A+A146D+Q147R+F183V, S56A+A146D+Q156E+A162E, S56A+A146D+Q156E+Q169Y, S56A+A146D+Q156E+F183V, S56A+A146D+A162E+Q169Y, S56A+A146D+A162E+F183V, S56A+A146D+Q169Y+F183V, S56A+Q147R+Q156E+A162E, S56A+Q147R+Q156E+Q169Y, S56A+Q147R+Q156E+F183V, S56A+Q147R+A162E+Q169Y, S56A+Q147R+A162E+F183V, S56A+Q147R+Q169Y+F183V, S56A+Q156E+A162E+Q169Y, S56A+Q156E+A162E+F183V, S56A+Q156E+Q169Y+F183V, S56A+A162E+Q169Y+F183V, G114W+N134D+A146D+Q147R, G114W+N134D+A146D+Q156E, G114W+N134D+A146D+A162E, G114W+N134D+A146D+Q169Y, G114W+N134D+A146D+F183V, G114W+N134D+Q147R+Q156E, G114W+N134D+Q147R+Q169Y, G114W+N134D+Q147R+A162E, G114W+N134D+Q147R+F183V, G114W+N134D+Q156E+Q169Y, G114W+N134D+A162E+Q169Y, G114W+N134D+Q156E+A162E, G114W+N134D+Q156E+F183V, G114W+N134D+A162E+F183V, G114W+N134D+Q169Y+F183V, G114W+A146D+Q147R+Q156E, G114W+A146D+Q147R+A162E, G114W+A146D+Q147R+Q169Y, G114W+A146D+Q147R+F183V, G114W+A146D+Q156E+A162E, G114W+A146D+Q156E+Q169Y, G114W+A146D+Q156E+F183V, G114W+A146D+A162E+Q169Y, G114W+A146D+A162E+F183V, G114W+A146D+Q169Y+F183V, G114W+Q147R+Q156E+A162E, G114W+Q147R+Q156E+Q169Y, G114W+Q147R+Q156E+F183V, G114W+Q147R+A162E+Q169Y, G114W+Q147R+A162E+F183V, G114W+Q147R+Q169Y+F183V, G114W+Q156E+A162E+Q169Y, G114W+Q156E+A162E+F183V, G114W+Q156E+Q169Y+F183V, G114W+A162E+Q169Y+F183V, N134D+A146D+Q147R+Q156E, N134D+A146D+Q147R+A162E, N134D+A146D+Q147R+Q169Y, N134D+A146D+Q147R+F183V, N134D+A146D+Q156E+A162E, N134D+A146D+Q156E+Q169Y, N134D+A146D+Q156E+F183V, N134D+A146D+A162E+Q169Y, N134D+A146D+A162E+F183V, N134D+A146D+Q169Y+F183V, N134D+Q147R+Q156E+A162E, N134D+Q147R+Q156E+Q169Y, N134D+Q147R+Q156E+F183V, N134D+Q147R+A162E+Q169Y, N134D+Q147R+A162E+F183V, N134D+Q147R+Q169Y+F183V, N134D+Q156E+A162E+Q169Y, N134D+Q156E+A162E+F183V, N134D+Q156E+Q169Y+F183V, N134D+A162E+Q169Y+F183V, A146D+Q147R+Q156E+A162E, A146D+Q147R+Q156E+Q169Y, A146D+Q147R+Q156E+F183V, A146D+Q147R+A162E+Q169Y, A146D+Q147R+A162E+F183V, A146D+Q147R+Q169Y+F183V, A146D+Q156E+A162E+Q169Y, A146D+Q156E+A162E+F183V, A146D+Q156E+Q169Y+F183V, Q147R+Q156E+A162E+Q169Y, A146D+A162E+Q169Y+F183V, Q147R+Q156E+Q169Y+F183V, Q147R+Q156E+A162E+F183V, Q147R+A162E+Q169Y+F183V, Q156E+A162E+Q169Y+F183V.

Further preferred variants comprises substitutions in the catalytic domain, e.g., SEQ ID NO: 5, selected from the group consisting of:

Q147R+Q156E;
Q147R+Q169Y;
S56A+Q147R;
Q147R+A162E;
Q147R+Q156E+A162E;
A25G+S56A+Q147R;
N134D+Q156E+A162E;
S56A+N134D+Q156E+A162E;
A25G+S56A+Q156E+A162E;
A25G+N134D+Q156E+A162E;
A25G+S56A+N134D+Q169Y;
S56A+N134D+A162E;
S56A+Q147R+Q169Y;
N134D+Q147R;
Q156E+Q169Y;
S56A+N134D+Q147R;
S56A+N134D+Q156E+Q169Y;
S56A+A146D+Q147R+Q169Y;
S56A+N134D+Q147R+Q169Y;
S56A+Q147R+A162E+Q169Y;
S2*+S56A+Q147R+Q169Y;
S41T+S56A+Q147R+Q169Y;
S56A+S77N+Q147R+Q169Y;
S56A+T104K+Q147R+Q169Y;
S56A+Q147R+K165Q+Q169Y;
S56A+Q147R+Q169Y+1194L;
S56A+Q147R+Q169Y+K201R;
S56A+Q147R+Q169Y+G219W;
N44D+S56A+Q147R+Q169Y;
N50E+S56A+Q147R+Q169Y;
A32S+S56A+Q147R+Q169Y;
N44D+S56A+Q147R+Q169Y;
S56A+Q147R+Q169Y+Q186R;
S56A+Q147R+Q169Y+F183V;
S56A+A146S+Q147R+A162E+Q169Y;
S56A+N134D+Q147R;
S56A+N134D+Q147R+A162E;
A32S+S56A+N134D+Q147R+Q169Y+F183V;
S56A+N134D+Q147R+A162E+Q169Y+F183V;
A32S+S56A+S77N+N134D+Q147R+A162E+Q169Y;
A32S+S56A+N134D+A146D+Q147R+Q169Y+F183V;
A32S+S56A+N134D+Q147R+Q169Y;
S56A+N134D+Q147R+A162E+Q169Y;
A32S+S56A+N134D+A146S+Q147R+Q169Y;
A32S+S56A+N134D+A146D+Q147R+Q169Y;
A32S+S56A+N134D+Q147R+Q169Y+F183V;
A32S+S56A+N134D+Q147R+Q169Y+K201R;
S56A+N134D+A146D+Q147R+Q169Y+F183V;
S56A+N134D+A146D+Q147R+A162E+Q169Y;
S56A+N134D+A146D+Q147R+Q169Y+K201R;
S56A+N134D+Q147R+A162E+Q169Y+F183V;
S56A+N134D+Q147R+Q169Y+F183V+K201R;
A32S+S56A+S77N+N134D+Q147R+A162E+Q169Y;

A32S+S56A+N134D+A146S+Q147R+Q169Y+F183V;
A32S+S56A+N134D+A146D+Q147R+Q169Y+F183V;
or
A32S+S56A+N134D+A146D+Q147R+A162E+Q169Y.

Further preferred variants comprise substitutions in the catalytic domain, e.g. SEQ ID NO: 5, selected from the group consisting of:

| |
|---|
| G114W + N134D |
| G114W + S137R |
| G114W + A146D |
| G114W + Q147R |
| G114W + S152K |
| G114W + S159D |
| G114W + S159E |
| N134D + S137E |
| S85I + N134D |
| N134D + S137R |
| N134D + S137D |
| S85I + S137E |
| S85I + Q147R |
| N134D + S137K |
| N134D + A146D |
| S85I + D179T |
| N134D + S152K |
| K103A + S159E |
| N134D + S159E |
| G114F + S137E |
| N134D + D179T |
| G114F + S137R |
| S137E + Q147R |
| S137E + S152K |
| G114F + Q147R |
| G114F + S159D |
| S137E + D179T |
| S137E + I194S |
| G114F + S159E |
| G114F + D179T |
| S137R + A146D |
| F37W + G114F |
| S137R + Q147R |
| S137R + S159D |
| S137R + D179T |
| S137D + Q147R |
| N134D + Q147R |
| N134D + S159D |
| S137K + D179T |
| A146D + S152K |
| A146D + S159D |
| Q147R + D179T |
| S85I + I194S |
| K103A + G114F |
| G114W + S137D |
| K103A + G114W |
| G114W + S137K |
| K103A + S152K |
| S137R + S152K |
| S137D + S152K |
| G114F + S137K |
| G114F + S152K |
| S137D + I194S |
| N134D + I194S |
| A146D + S159E |
| A146D + D179T |
| S137K + Q147R |
| Q147R + S152K |
| S137K + S152K |
| S137K + S159E |
| S137K + I194S |
| S159D + I194S |
| S159E + I194S |
| G114W + S137E |
| S137E + S159D |
| S85I + S159E |
| S137E + S159E |
| S137R + S159E |
| G114F + S137D |
| S137D + S159D |
| S137D + D179T |

-continued

| |
|---|
| A146D + Q147R |
| Q147R + S159D |
| S137K + S159E |
| S137K + I194S |
| Q147R + S159E |
| S159D + D179T |
| S159E + D179T |
| S85I + S159D |
| K103A + A146D |
| K103A + Q147R |
| K103A + D179T |
| G114F + N134D; |
| and |
| G114F + A146D. |

The variants may further comprise one or more additional alterations at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244:1081-1085). In the latter technique, single alanine mutations are introduced at every residue in the molecule, and the resultant mutant molecules are tested for cellulolytic activity to identify amino acid residues that are critical to the activity of the molecule. See also, Hilton et al., 1996, *J. Biol. Chem.* 271:4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255:306-312; Smith et al., 1992, *J. Mol. Biol.* 224:899-904; Wlodaver et al., 1992, *FEBS Lett.* 309:59-64. The identity of essential amino acids can also be inferred from an alignment with a related polypeptide.

For example, the catalytic residues of the cellulase having the amino acid sequence of SEQ ID NO: 1 have been identified as Asp 12 and Asp 122.

Carbohydrate Binding Module (CBM)

The carbohydrate binding module (CBM) can comprise a wild type or variant thereof, and it is also contemplated that the variants herein may comprise the wild type catalytic domain of a first microbe, which is wild type or variant thereof, and a carbohydrate binding module that is a wild type or variant thereof from a second microbe joined by a linker region.

For example, the variant may include the catalytic domain of SEQ ID NO: 1, or a variant thereof, as well as the carbohydrate binding module from SEQ ID NO: 2, joined by a linker region.

Preferably, the CBM is a CBM1.

In an embodiment, the carbohydrate binding module/domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 6.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 7.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 8.

In an embodiment, the carbohydrate binding module comprises an amino acid sequence having at least 70% sequence identity, e.g., at least 75% sequence identity, at least 80% sequence identity, at least 99% or 100% sequence identity to the amino acid sequence as shown in SEQ ID NO: 9.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 173.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 174.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 175.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 176.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 177.

In an embodiment, the carbohydrate binding module comprises an amino acid sequence having at least 70% sequence identity, e.g., at least 75% sequence identity, at least 80% sequence identity, at least 99% or 100% sequence identity to the amino acid sequence as shown in SEQ ID NO: 178.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 179.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 180.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 181.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 182.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 183.

In an embodiment, the carbohydrate binding module comprises an amino acid sequence having at least 70% sequence identity, e.g., at least 75% sequence identity, at least 80% sequence identity, at least 99% or 100% sequence identity to the amino acid sequence as shown in SEQ ID NO: 184.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 185.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 186.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 187.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 188.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 189.

In an embodiment, the carbohydrate binding module comprises an amino acid sequence having at least 70% sequence identity, e.g., at least 75% sequence identity, at least 80% sequence identity, at least 99% or 100% sequence identity to the amino acid sequence as shown in SEQ ID NO: 190.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 191.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 192.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 193.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 194.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 195.

In an embodiment, the carbohydrate binding module comprises an amino acid sequence having at least 70% sequence identity, e.g., at least 75% sequence identity, at least 80% sequence identity, at least 99% or 100% sequence identity to the amino acid sequence as shown in SEQ ID NO: 196.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 197.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 198.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 199.

In an embodiment, the carbohydrate binding module comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% or 100% sequence identity to the amino acid sequence as shown in SEQ ID NO: 200.

In an embodiment, the variant comprises SEQ ID NO: 5, or a variant thereof, and SEQ ID NO: 6. In a further embodiment, the variant comprises, in order from N-terminal to C-terminal, SEQ ID NO: 5 or a variant thereof, a linker, and SEQ ID NO: 6.

In an embodiment, the variant comprises SEQ ID NO: 5, or a variant thereof, and SEQ ID NO: 7. In a further embodiment, the variant comprises, in order from N-terminal to C-terminal, SEQ ID NO: 5 or a variant thereof, a linker, and SEQ ID NO: 7.

In an embodiment, the variant comprises SEQ ID NO: 5, or a variant thereof, and SEQ ID NO: 8. In a further embodiment, the variant comprises, in order from N-terminal to C-terminal, SEQ ID NO: 5 or a variant thereof, a linker, and SEQ ID NO: 8.

In an embodiment, the variant comprises SEQ ID NO: 5, or a variant thereof, and SEQ ID NO: 9. In a further embodiment, the variant comprises, in order from N-terminal to C-terminal, SEQ ID NO: 5 or a variant thereof, a linker, and SEQ ID NO: 9.

In an embodiment, the variant comprises SEQ ID NO: 5, or a variant thereof, and SEQ ID NO: 173. In a further embodiment, the variant comprises, in order from N-terminal to C-terminal, SEQ ID NO: 5 or a variant thereof, a linker, and SEQ ID NO: 173.

In an embodiment, the variant comprises SEQ ID NO: 5, or a variant thereof, and SEQ ID NO: 174. In a further embodiment, the variant comprises, in order from N-terminal to C-terminal, SEQ ID NO: 5 or a variant thereof, a linker, and SEQ ID NO: 174.

Tables B1-B2., C1-C2., and Table D. provide exemplary preferred variants according to the invention, which are provided in Table form for ease of comparative reference. As used in the Tables herein, the variants are represented in their entirety, in order from N- to C-terminus, with no additional linker or further modification between sequences designated in the respective columns. Thus, Variant 1 represented in the Table as

| Variant Concept | | |
|---|---|---|
| Catalytic domain (N-terminal) | Linker | CBM (C-terminal) |
| SEQ ID NO: 5 | TTPPTPTPTPTPG (SEQ ID NO: 12) | SEQ ID NO: 6 |

could be equally represented as:

(SEQ ID NO: 201)
ASGSGQSTRYWDCCKPSCAWPGKAAVSQPVYACDANFQRLSDFNVQSGCN
GGSAYSCADQTPWAVNDNLAYGFAATSIAGGSESSWCCACYALTFTSGPV
AGKTMVVQSTSTGGDLGSNHFDIAMPGGGVGIFNGCSSQFGGLPGAQYGG
ISSRDQCDSFPAPLKPGCQWRFDVVFQNADNPTFTFQQVQCPAEIVARSG
CKRNDDSSFPVFTTTPPTPTPTPTPGCTSQKWAQCGGIGFSGCTTCVSGT
TCQKLNDYYSQCL

TABLE B1

| | Variant Concept | | |
|---|---|---|---|
| Variant ID | Catalytic domain (N-terminal) | Linker | CBM (C-terminal) |
| Variant 1 | SEQ ID NO: 5 | TTPPTPTPTPTPG (SEQ ID NO: 12) | SEQ ID NO: 6 |
| Variant 2 | SEQ ID NO: 5 | TTPTPPTPTPTPTPG (SEQ ID NO: 13) | SEQ ID NO: 6 |
| Variant 3 | SEQ ID NO: 5 | TTPTPTPPTPTPTPTPG (SEQ ID NO: 14) | SEQ ID NO: 6 |
| Variant 4 | SEQ ID NO: 5 | TTPTPTPTPPTPTPTPTPG (SEQ ID NO: 15) | SEQ ID NO: 6 |

TABLE B1-continued

| | Variant Concept | | |
|---|---|---|---|
| Variant ID | Catalytic domain (N-terminal) | Linker | CBM (C-terminal) |
| Variant 5 | SEQ ID NO: 5 having mutations S56A N134D Q147R | TPPTPPTPPTPPTPPTPPTPPTPPTPPTPPTPPG (SEQ ID NO: 16) | SEQ ID NO: 6 |
| Variant 6 | SEQ ID NO: 5 having mutations S56A N134D Q147R | TPTTPTTPTTPTG (SEQ ID NO: 17) | SEQ ID NO: 6 |
| Variant 7 | SEQ ID NO: 5 having mutations S56A N134D Q147R | TPTTPTTPTTPTTPTTPTG (SEQ ID NO: 18) | SEQ ID NO: 6 |
| Variant 8 | SEQ ID NO: 5 having mutations S56A N134D Q147R | SPSSPSSPSSPSG (SEQ ID NO: 19) | SEQ ID NO: 6 |
| Variant 9 | SEQ ID NO: 5 having mutations S56A N134D Q147R | SPSSPSSPSSPSSPSG (SEQ ID NO: 20) | SEQ ID NO: 6 |
| Variant 10 | SEQ ID NO: 5 having mutations S56A N134D Q147R | SPPSPPSPPSPPSPPG (SEQ ID NO: 21) | SEQ ID NO: 6 |
| Variant 11 | SEQ ID NO: 5 having mutations S56A N134D Q147R | SPPSPPSPPSPPSPPSPPSPPSPPSPPSPPG (SEQ ID NO: 22) | SEQ ID NO: 6 |
| Variant 12 | SEQ ID NO: 5 having mutations S56A N134D Q147R | PPSSPSSPSSPSSPSSPSSPSG (SEQ ID NO: 23) | SEQ ID NO: 6 |
| Variant 13 | SEQ ID NO: 5 having mutations N134D Q147R | SPSPG (SEQ ID NO: 24) | SEQ ID NO: 6 |
| Variant 14 | SEQ ID NO: 5 having mutations S56A N134D Q156E A162E | SPSPG (SEQ ID NO: 24) | SEQ ID NO: 6 |
| Variant 15 | SEQ ID NO: 5 having mutations S56A N134D Q156E Q169Y | SPSPG (SEQ ID NO: 24) | SEQ ID NO: 6 |
| Variant 16 | SEQ ID NO: 5 | SPSPSPSPSPG (SEQ ID NO: 25) | SEQ ID NO: 6 |
| Variant 17 | SEQ ID NO: 5 having mutations S56A N134D Q156E A162E | SPSPSPSPSPG (SEQ ID NO: 25) | SEQ ID NO: 6 |
| Variant 18 | SEQ ID NO: 5 having mutations S56A Q147R Q169Y | SPSPSPSPSPG (SEQ ID NO: 25) | SEQ ID NO: 6 |
| Variant 19 | SEQ ID NO: 5 having mutations S56A N134D Q147R | SPSPSPSPSPG (SEQ ID NO: 25) | SEQ ID NO: 6 |
| Variant 20 | SEQ ID NO: 5 | TPTPTPTPTPG (SEQ ID NO: 26) | SEQ ID NO: 6 |
| Variant 21 | SEQ ID NO: 5 having mutations S56A N134D Q156E A162E | TPTPTPTPTPG (SEQ ID NO: 26) | SEQ ID NO: 6 |
| Variant 22 | SEQ ID NO: 5 having mutations S56A N134D Q156E Q169Y | TPTPTPTPTPG (SEQ ID NO: 26) | SEQ ID NO: 6 |
| Variant 23 | SEQ ID NO: 5 having mutations S56A N134D Q147R | TPTPTPTPTPG (SEQ ID NO: 26) | SEQ ID NO: 6 |

TABLE B1-continued

| | Variant Concept | | |
|---|---|---|---|
| Variant ID | Catalytic domain (N-terminal) | Linker | CBM (C-terminal) |
| Variant 24 | SEQ ID NO: 5 having mutations S56A N134D Q147R Q169Y | PPPP (SEQ ID NO: 27) | SEQ ID NO: 6 |
| Variant 25 | SEQ ID NO: 5 having mutations S56A N134D Q147R Q169Y | PPPPP (SEQ ID NO: 28) | SEQ ID NO: 6 |
| Variant 26 | SEQ ID NO: 5 having mutations S56A N134D Q147R Q169Y | PPPPPP (SEQ ID NO: 29) | SEQ ID NO: 6 |
| Variant 27 | SEQ ID NO: 5 | PPPPPPPG (SEQ ID NO: 30) | SEQ ID NO: 6 |
| Variant 28 | SEQ ID NO: 5 having mutations S56A N134D Q147R Q169Y | PPPPPPPG (SEQ ID NO: 30) | SEQ ID NO: 6 |
| Variant 29 | SEQ ID NO: 5 having mutations S56A N134D Q147R Q169Y | PPPPPPP (SEQ ID NO: 31) | SEQ ID NO: 6 |
| Variant 30 | SEQ ID NO: 5 | PPPPPPPPG (SEQ ID NO: 32) | SEQ ID NO: 6 |
| Variant 31 | SEQ ID NO: 5 | PPPPPPPPPG (SEQ ID NO: 33) | SEQ ID NO: 6 |
| Variant 32 | SEQ ID NO: 5 having mutations S56A N134D Q147R | PPPPPPPPPG (SEQ ID NO: 33) | SEQ ID NO: 6 |
| Variant 33 | SEQ ID NO: 5 | PPPPPPPPPPG (SEQ ID NO: 34) | SEQ ID NO: 6 |
| Variant 34 | SEQ ID NO: 5 | PPPPPPPPPPPG (SEQ ID NO: 35) | SEQ ID NO: 6 |
| Variant 35 | SEQ ID NO: 5 | PPPPPPPPPPPPPG (SEQ ID NO: 36) | SEQ ID NO: 6 |
| Variant 36 | SEQ ID NO: 5 | PEPTPEPTG (SEQ ID NO: 37) | SEQ ID NO: 6 |
| Variant 37 | SEQ ID NO: 5 having mutations S56A N134D Q147R | PEPTPEPTG (SEQ ID NO: 37) | SEQ ID NO: 6 |
| Variant 38 | SEQ ID NO: 5 | PEPTPEPTPEPTG (SEQ ID NO: 38) | SEQ ID NO: 6 |
| Variant 39 | SEQ ID NO: 5 having mutations S56A N134D Q147R | PEPTPEPTPEPTG (SEQ ID NO: 38) | SEQ ID NO: 6 |
| Variant 40 | SEQ ID NO: 5 | PEPTPEPTPEPTPEPTG (SEQ ID NO: 39) | SEQ ID NO: 6 |
| Variant 41 | SEQ ID NO: 5 having mutations S56A N134D Q156E A162E | PEPTPEPTPEPTPEPTG (SEQ ID NO: 39) | SEQ ID NO: 6 |
| Variant 42 | SEQ ID NO: 5 having mutations S56A N134D Q156E Q169Y | PEPTPEPTPEPTPEPTG (SEQ ID NO: 39) | SEQ ID NO: 6 |
| Variant 43 | SEQ ID NO: 5 having mutations S56A N134D Q147R | PEPTPEPTPEPTPEPTG (SEQ ID NO: 39) | SEQ ID NO: 6 |
| Variant 44 | SEQ ID NO: 5 | PEPTPEPTPEPTPEPTPEPTG (SEQ ID NO: 40) | SEQ ID NO: 6 |
| Variant 45 | SEQ ID NO: 5 having mutations S56A N134D Q156E Q169Y | PEPTPEPTPEPTPEPTPEPTG (SEQ ID NO: 40) | SEQ ID NO: 6 |

TABLE B1-continued

| Variant ID | Variant Concept: Catalytic domain (N-terminal) | Linker | CBM (C-terminal) |
|---|---|---|---|
| Variant 46 | SEQ ID NO: 5 having mutations S56A N134D Q147R | PEPTPEPTPEPTPEPTPEPT (SEQ ID NO: 40) | SEQ ID NO: 6 |
| Variant 47 | SEQ ID NO: 5 | PSPTPSPTPSPTPSPTG (SEQ ID NO: 41) | SEQ ID NO: 6 |
| Variant 48 | SEQ ID NO: 5 having mutations S56A N134D Q147R | PSPTPSPTPSPTPSPTG (SEQ ID NO: 41) | SEQ ID NO: 6 |
| Variant 49 | SEQ ID NO: 5 having mutations S56A N134D Q147R | PSPTPSPTPSPTPSPTPSPTG (SEQ ID NO: 42) | SEQ ID NO: 6 |
| Variant 50 | SEQ ID NO: 5 having mutations S56A N134D Q147R | PQPTPQPTG (SEQ ID NO: 43) | SEQ ID NO: 6 |
| Variant 51 | SEQ ID NO: 5 having mutations S56A N134D Q147R | PDPTPDPTG (SEQ ID NO: 44) | SEQ ID NO: 6 |
| Variant 52 | SEQ ID NO: 5 having mutations S56A N134D Q147R | PRPTPEPTG (SEQ ID NO: 45) | SEQ ID NO: 6 |
| Variant 53 | SEQ ID NO: 5 having mutations S56A N134D Q147R | PQPTPEPTG (SEQ ID NO: 46) | SEQ ID NO: 6 |
| Variant 54 | SEQ ID NO: 5 having mutations S56A N134D Q147R | PSPNSPNSPNG (SEQ ID NO: 47) | SEQ ID NO: 6 |
| Variant 55 | SEQ ID NO: 5 having mutations S56A N134D Q147R | PEPTPRPTG (SEQ ID NO: 48) | SEQ ID NO: 6 |
| Variant 56 | SEQ ID NO: 5 having mutations S56A N134D Q147R | PQPTPEPTPQPTPEPTPQPTPEPTPQPTG (SEQ ID NO: 49) | SEQ ID NO: 6 |
| Variant 57 | SEQ ID NO: 5 having mutations S56A N134D Q147R | PDPTPDPTPDPTG (SEQ ID NO: 50) | SEQ ID NO: 6 |
| Variant 58 | SEQ ID NO: 5 having mutations S56A N134D Q147R | PQPTPQPTPQPTPQPTG (SEQ ID NO: 51) | SEQ ID NO: 6 |
| Variant 59 | SEQ ID NO: 5 having mutations S56A N134D Q147R | PQPTPEPTPQPTPEPTG (SEQ ID NO: 52) | SEQ ID NO: 6 |

TABLE B2

| Variant ID | Variant Concept: Catalytic domain (N-terminal) | Linker | CBM (C-terminal) |
|---|---|---|---|
| Variant 60 | SEQ ID NO: 5 | PPPPPPPG (SEQ ID NO: 30) | SEQ ID NO: 6 |
| Variant 61 | SEQ ID NO: 5 | PPPPPPPPG (SEQ ID NO: 32) | SEQ ID NO: 6 |
| Variant 62 | SEQ ID NO: 5 | PPPPPPPPPG (SEQ ID NO: 33) | SEQ ID NO: 6 |
| Variant 63 | SEQ ID NO: 5 having mutations S56A N134D Q147R | PPPPPPPPPG (SEQ ID NO: 33) | SEQ ID NO: 6 |
| Variant 64 | SEQ ID NO: 5 | PPPPPPPPPPPPPG (SEQ ID NO: 36) | SEQ ID NO: 6 |

TABLE B2-continued

| Variant ID | Variant Concept Catalytic domain (N-terminal) | Linker | CBM (C-terminal) |
|---|---|---|---|
| Variant 65 | SEQ ID NO: 5 having mutations N134D Q147R | SPSPG (SEQ ID NO: 24) | SEQ ID NO: 6 |
| Variant 66 | SEQ ID NO: 5 having mutations S56A Q147R | SPSPSPSPSPG (SEQ ID NO: 25) | SEQ ID NO: 6 |
| Variant 67 | SEQ ID NO: 5 having mutations S56A N134D Q147R | SPSPSPSPSPG (SEQ ID NO: 25) | SEQ ID NO: 6 |
| Variant 68 | SEQ ID NO: 5 having mutations S56A N134D Q147R | SPSPSPSPPPG (SEQ ID NO: 53) | SEQ ID NO: 6 |
| Variant 69 | SEQ ID NO: 5 having mutations S56A N134D Q147R | SPSPSPSPDPG (SEQ ID NO: 54) | SEQ ID NO: 6 |
| Variant 70 | SEQ ID NO: 5 having mutations S56A N134D Q147R | SPSPSPSPKPG (SEQ ID NO: 55) | SEQ ID NO: 6 |
| Variant 71 | SEQ ID NO: 5 having mutations S56A N134D Q147R | SPSPSPSPAPG (SEQ ID NO: 56) | SEQ ID NO: 6 |
| Variant 72 | SEQ ID NO: 5 having mutations S56A N134D Q147R | SPSPSPSPSPSG (SEQ ID NO: 57) | SEQ ID NO: 6 |
| Variant 73 | SEQ ID NO: 5 having mutations S56A N134D Q147R | SPSPSPSPSP (SEQ ID NO: 58) | SEQ ID NO: 6 |
| Variant 74 | SEQ ID NO: 5 having mutations S56A N134D Q147R | SPSPSPSPSPS (SEQ ID NO: 59) | SEQ ID NO: 6 |
| Variant 75 | SEQ ID NO: 5 having mutations S56A N134D Q147R | SPSPSPSPSPP (SEQ ID NO: 60) | SEQ ID NO: 6 |
| Variant 76 | SEQ ID NO: 5 having mutations S56A N134D Q147R | SPSPSPSPSPE (SEQ ID NO: 61) | SEQ ID NO: 6 |
| Variant 77 | SEQ ID NO: 5 having mutations S56A N134D Q147R | SPSPSPSPSPN (SEQ ID NO: 62) | SEQ ID NO: 6 |
| Variant 78 | SEQ ID NO: 5 having mutations S56A N134D Q147R | SPSPSPSPSPGG (SEQ ID NO: 63) | SEQ ID NO: 6 |
| Variant 79 | SEQ ID NO: 5 having mutations S56A N134D Q147R | SPSPSPSPSPK (SEQ ID NO: 64) | SEQ ID NO: 6 |
| Variant 80 | SEQ ID NO: 5 having mutations N134D Q147R | TPTPTPTPTPG (SEQ ID NO: 26) | SEQ ID NO: 6 |
| Variant 81 | SEQ ID NO: 5 having mutations S56A N134D Q147R | TPTPTPTPTPG (SEQ ID NO: 26) | SEQ ID NO: 6 |
| Variant 82 | SEQ ID NO: 5 having mutations S56A N134D Q147R | TTPTPTPTPPTPTPTPTPG (SEQ ID NO: 15) | SEQ ID NO: 6 |

TABLE B2-continued

| | Variant Concept | | |
|---|---|---|---|
| Variant ID | Catalytic domain (N-terminal) | Linker | CBM (C-terminal) |
| Variant 83 | SEQ ID NO: 5 having mutations N134D Q147R | PEPTPEPTG (SEQ ID NO: 37) | SEQ ID NO: 6 |
| Variant 84 | SEQ ID NO: 5 having mutations S56A N134D Q147R | PEPTPEPTG (SEQ ID NO: 37) | SEQ ID NO: 6 |
| Variant 85 | SEQ ID NO: 5 having mutations S56A Q147R | PEPTPEPTPEPTG (SEQ ID NO: 38) | SEQ ID NO: 6 |
| Variant 86 | SEQ ID NO: 5 having mutations N134D Q147R | PEPTPEPTPEPTG (SEQ ID NO: 38) | SEQ ID NO: 6 |
| Variant 87 | SEQ ID NO: 5 having mutations S56A N134D Q147R | PEPTPEPTPEPTG (SEQ ID NO: 38) | SEQ ID NO: 6 |
| Variant 88 | SEQ ID NO: 5 | PEPTPEPTPEPTPEPTG (SEQ ID NO: 39) | SEQ ID NO: 6 |
| Variant 89 | SEQ ID NO: 5 having mutations S56A Q147R | PEPTPEPTPEPTPEPTG (SEQ ID NO: 39) | SEQ ID NO: 6 |
| Variant 90 | SEQ ID NO: 5 having mutations N134D Q147R | PEPTPEPTPEPTPEPTG (SEQ ID NO: 39) | SEQ ID NO: 6 |
| Variant 91 | SEQ ID NO: 5 having mutations S56A N134D Q147R | PEPTPEPTPEPTPEPTG (SEQ ID NO: 39) | SEQ ID NO: 6 |
| Variant 92 | SEQ ID NO: 5 having mutations S56A Q147R | PEPTPEPTPEPTPEPTPEPTG (SEQ ID NO: 40) | SEQ ID NO: 6 |
| Variant 93 | SEQ ID NO: 5 having mutations N134D Q147R | PEPTPEPTPEPTPEPTPEPTG (SEQ ID NO: 40) | SEQ ID NO: 6 |
| Variant 94 | SEQ ID NO: 5 having mutations S56A N134D Q147R | PEPTPEPTPEPTPEPTPEPTG (SEQ ID NO: 40) | SEQ ID NO: 6 |
| Variant 95 | SEQ ID NO: 5 having mutations S56A N134D Q147R | PEPTPEPTP (SEQ ID NO: 65) | SEQ ID NO: 6 |
| Variant 96 | SEQ ID NO: 5 having mutations S56A N134D Q147R | PEPTPEPTR (SEQ ID NO: 66) | SEQ ID NO: 6 |
| Variant 97 | SEQ ID NO: 5 having mutations S56A N134D Q147R | PEPTPEPTPEPTP (SEQ ID NO: 67) | SEQ ID NO: 6 |
| Variant 98 | SEQ ID NO: 5 having mutations S56A N134D Q147R | PEPTPEPTPEPTPEPTPSPTG (SEQ ID NO: 68) | SEQ ID NO: 6 |
| Variant 99 | SEQ ID NO: 5 having mutations S56A N134D Q147R | PEPTPEPTPEPTPEPTPTPTG (SEQ ID NO: 69) | SEQ ID NO: 6 |
| Variant 100 | SEQ ID NO: 5 having mutations S56A N134D Q147R | PEPTPEPTPEPTPEPTPGPTG (SEQ ID NO: 70) | SEQ ID NO: 6 |
| Variant 101 | SEQ ID NO: 5 having mutations S56A N134D Q147R | PEPTPEPTPEPTPEPTPDPTG (SEQ ID NO: 71) | SEQ ID NO: 6 |

TABLE B2-continued

| | Variant Concept | | |
|---|---|---|---|
| Variant ID | Catalytic domain (N-terminal) | Linker | CBM (C-terminal) |
| Variant 102 | SEQ ID NO: 5 having mutations S56A N134D Q147R | PEPTPEPTPEPTPEPTPETG (SEQ ID NO: 72) | SEQ ID NO: 6 |
| Variant 103 | SEQ ID NO: 5 having mutations S56A N134D Q147R | PEPTPEPTPEPTPEPTPEPTD (SEQ ID NO: 73) | SEQ ID NO: 6 |
| Variant 104 | SEQ ID NO: 5 having mutations S56A N134D Q147R | PEPTPEPTE (SEQ ID NO: 74) | SEQ ID NO: 6 |
| Variant 105 | SEQ ID NO: 5 having mutations S56A N134D Q147R | PEPTPEPTPEPTPEPTPEP (SEQ ID NO: 75) | SEQ ID NO: 6 |
| Variant 106 | SEQ ID NO: 5 having mutations S56A N134D Q147R | PEPTPEPTPEPTPEPTPSPT (SEQ ID NO: 76) | SEQ ID NO: 6 |
| Variant 107 | SEQ ID NO: 5 having mutations S56A N134D Q147R | PEPTPEPTPEPTPEPTPRPTT (SEQ ID NO: 77) | SEQ ID NO: 6 |
| Variant 108 | SEQ ID NO: 5 having mutations S56A N134D Q147R | PEPTPEPTPEPTPEPTPEPTT (SEQ ID NO: 78) | SEQ ID NO: 6 |
| Variant 109 | SEQ ID NO: 5 having mutations S56A N134D Q147R | PEPTPEPTPEPTPEPTPEPT (SEQ ID NO: 79) | SEQ ID NO: 6 |
| Variant 110 | SEQ ID NO: 5 having mutations S56A N134D Q147R | PEPTPEPTPEPTPEPTPEPTS (SEQ ID NO: 80) | SEQ ID NO: 6 |
| Variant 111 | SEQ ID NO: 5 having mutations S56A N134D Q147R | PEPTPEPTPEPTPEPTPEPTR (SEQ ID NO: 81) | SEQ ID NO: 6 |
| Variant 112 | SEQ ID NO: 5 having mutations A32S S56A N134D A146D Q147R Q169Y F183V | PEPTPEPTPEPTPEPTPEPTG (SEQ ID NO: 40) | SEQ ID NO: 6 |
| Variant 113 | SEQ ID NO: 5 | PSPTPSPTPSPTPSPTG (SEQ ID NO: 41) | SEQ ID NO: 6 |
| Variant 114 | SEQ ID NO: 5 having mutations S56A N134D Q147R | PSPTPSPTPSPTPSPTPSPTG (SEQ ID NO: 42) | SEQ ID NO: 6 |
| Variant 115 | SEQ ID NO: 5 having mutations A32S S56A N134D A146D Q147R Q169Y F183V | PSPTPSPTPSPTPSPTPSPTG (SEQ ID NO: 42) | SEQ ID NO: 6 |
| Variant 116 | SEQ ID NO: 5 having mutations S56A N134D Q147R | PPPGGPGGPGTPTSTAPGSGPTSPGGGSG (SEQ ID NO: 82) | SEQ ID NO: 6 |
| Variant 117 | SEQ ID NO: 5 having mutations S56A N134D Q147R | PPPGGPGGTGTPTSTAPGSGPTSPGGGSG (SEQ ID NO: 83) | SEQ ID NO: 6 |
| Variant 118 | SEQ ID NO: 5 having mutations S56A N134D Q147R | PPSGGPGGPGTPTSTAPGSGPTSPGGGSG (SEQ ID NO: 84) | SEQ ID NO: 6 |
| Variant 119 | SEQ ID NO: 5 having mutations S56A N134D Q147R | PEPTPRPTPEPTPRPTG (SEQ ID NO: 85) | SEQ ID NO: 6 |
| Variant 120 | SEQ ID NO: 5 having mutations S56A N134D Q147R | PKPTPEPTPKPTPEPTG (SEQ ID NO: 86) | SEQ ID NO: 6 |

TABLE B2-continued

| Variant ID | Variant Concept<br>Catalytic domain (N-terminal) | Linker | CBM (C-terminal) |
|---|---|---|---|
| Variant 121 | SEQ ID NO: 5 having mutations S56A N134D Q147R | PEPTPKPTPEPTPKPTG (SEQ ID NO: 87) | SEQ ID NO: 6 |
| Variant 122 | SEQ ID NO: 5 having mutations S56A N134D Q147R | PEPTPQPTPEPTPQPTG (SEQ ID NO: 88) | SEQ ID NO: 6 |
| Variant 123 | SEQ ID NO: 5 having mutations S56A N134D Q147R | PRPTPEPTPRPTG (SEQ ID NO: 89) | SEQ ID NO: 6 |
| Variant 124 | SEQ ID NO: 5 having mutations S56A N134D Q147R | PKPTPEPTPKPTG (SEQ ID NO: 90) | SEQ ID NO: 6 |
| Variant 125 | SEQ ID NO: 5 having mutations S56A N134D Q147R | PEPTPQPTG (SEQ ID NO: 91) | SEQ ID NO: 6 |
| Variant 126 | SEQ ID NO: 5 having mutations S56A N134D Q147R | PEPTPQPTPEPTG (SEQ ID NO: 92) | SEQ ID NO: 6 |
| Variant 127 | SEQ ID NO: 5 having mutations S56A N134D Q147R | TPPTPPG (SEQ ID NO: 93) | SEQ ID NO: 6 |
| Variant 128 | SEQ ID NO: 5 having mutations S56A N134D Q147R | SPSSPSG (SEQ ID NO: 94) | SEQ ID NO: 6 |
| Variant 129 | SEQ ID NO: 5 having mutations S56A N134D Q147R | SPSSPSSPSG (SEQ ID NO: 95) | SEQ ID NO: 6 |
| Variant 130 | SEQ ID NO: 5 having mutations S56A N134D Q147R | TPTTPTG (SEQ ID NO: 96) | SEQ ID NO: 6 |
| Variant 131 | SEQ ID NO: 5 having mutations S56A N134D Q147R | TPTTPTTPTG (SEQ ID NO: 97) | SEQ ID NO: 6 |

TABLE C1

| Variant ID | Variant Concept<br>Catalytic domain (N-terminal) | Linker | CBM (C-terminal) |
|---|---|---|---|
| Variant 201 | SEQ ID NO: 5 | TTPPTPTPTPTPG (SEQ ID NO: 12) | SEQ ID NO: 7 |
| Variant 202 | SEQ ID NO: 5 | TTPTPPTPTPTPTPG (SEQ ID NO: 13) | SEQ ID NO: 7 |
| Variant 203 | SEQ ID NO: 5 | TTPTPTPPTPTPTPTPG (SEQ ID NO: 14) | SEQ ID NO: 7 |
| Variant 204 | SEQ ID NO: 5 | TTPTPTPTPPTPTPTPTPG (SEQ ID NO: 15) | SEQ ID NO: 7 |
| Variant 205 | SEQ ID NO: 5 having mutations S56A N134D Q147R | TPPTPPTPPTPPTPPTPPTPPTPPTPPTPPTPPG (SEQ ID NO: 16) | SEQ ID NO: 7 |
| Variant 206 | SEQ ID NO: 5 having mutations S56A N134D Q147R | TPTTPTTPTTPTG (SEQ ID NO: 17) | SEQ ID NO: 7 |

TABLE C1-continued

| Variant ID | Variant Concept<br>Catalytic domain (N-terminal) | Linker | CBM (C-terminal) |
|---|---|---|---|
| Variant 207 | SEQ ID NO: 5 having mutations S56A N134D Q147R | TPTTPTTPTTPTTPTTPTG (SEQ ID NO: 18) | SEQ ID NO: 7 |
| Variant 208 | SEQ ID NO: 5 having mutations S56A N134D Q147R | SPSSPSSPSSPSG (SEQ ID NO: 19) | SEQ ID NO: 7 |
| Variant 209 | SEQ ID NO: 5 having mutations S56A N134D Q147R | SPSSPSSPSSPSSPSG (SEQ ID NO: 20) | SEQ ID NO: 7 |
| Variant 210 | SEQ ID NO: 5 having mutations S56A N134D Q147R | SPPSPPSPPSPPSPPG (SEQ ID NO: 21) | SEQ ID NO: 7 |
| Variant 211 | SEQ ID NO: 5 having mutations S56A N134D Q147R | SPPSPPSPPSPPSPPSPPSPPSPPSPPSPPG (SEQ ID NO: 22) | SEQ ID NO: 7 |
| Variant 212 | SEQ ID NO: 5 having mutations S56A N134D Q147R | PPSSPSSPSSPSSPSSPSSPS (SEQ ID NO: 23) | SEQ ID NO: 7 |
| Variant 213 | SEQ ID NO: 5 having mutations N134D Q147R | SPSPG (SEQ ID NO: 24) | SEQ ID NO: 7 |
| Variant 214 | SEQ ID NO: 5 having mutations S56A N134D Q156E A162E | SPSPG (SEQ ID NO: 24) | SEQ ID NO: 7 |
| Variant 215 | SEQ ID NO: 5 having mutations S56A N134D Q156E Q169Y | SPSPG (SEQ ID NO: 24) | SEQ ID NO: 7 |
| Variant 216 | SEQ ID NO: 5 | SPSPSPSPSPG (SEQ ID NO: 25) | SEQ ID NO: 7 |
| Variant 217 | SEQ ID NO: 5 having mutations S56A N134D Q156E A162E | SPSPSPSPSPG (SEQ ID NO: 25) | SEQ ID NO: 7 |
| Variant 218 | SEQ ID NO: 5 having mutations S56A Q147R Q169Y | SPSPSPSPSPG (SEQ ID NO: 25) | SEQ ID NO: 7 |
| Variant 219 | SEQ ID NO: 5 having mutations S56A N134D Q147R | SPSPSPSPSPG (SEQ ID NO: 25) | SEQ ID NO: 7 |
| Variant 220 | SEQ ID NO: 5 | TPTPTPTPTPG (SEQ ID NO: 26) | SEQ ID NO: 7 |
| Variant 221 | SEQ ID NO: 5 having mutations S56A N134D Q156E A162E | TPTPTPTPTPG (SEQ ID NO: 26) | SEQ ID NO: 7 |
| Variant 222 | SEQ ID NO: 5 having mutations S56A N134D Q156E Q169Y | TPTPTPTPTPG (SEQ ID NO: 26) | SEQ ID NO: 7 |
| Variant 223 | SEQ ID NO: 5 having mutations S56A N134D Q147R | TPTPTPTPTPG (SEQ ID NO: 26) | SEQ ID NO: 7 |
| Variant 224 | SEQ ID NO: 5 having mutations S56A N134D Q147R Q169Y | PPPP (SEQ ID NO: 27) | SEQ ID NO: 7 |
| Variant 225 | SEQ ID NO: 5 having mutations S56A N134D Q147R Q169Y | PPPPP (SEQ ID NO: 28) | SEQ ID NO: 7 |

TABLE C1-continued

| | Variant Concept | | |
|---|---|---|---|
| Variant ID | Catalytic domain (N-terminal) | Linker | CBM (C-terminal) |
| Variant 226 | SEQ ID NO: 5 having mutations S56A N134D Q147R Q169Y | PPPPPP (SEQ ID NO: 29) | SEQ ID NO: 7 |
| Variant 227 | SEQ ID NO: 5 | PPPPPPPG (SEQ ID NO: 30) | SEQ ID NO: 7 |
| Variant 228 | SEQ ID NO: 5 having mutations S56A N134D Q147R Q169Y | PPPPPPPG (SEQ ID NO: 30) | SEQ ID NO: 7 |
| Variant 229 | SEQ ID NO: 5 having mutations S56A N134D Q147R Q169Y | PPPPPPP (SEQ ID NO: 31) | SEQ ID NO: 7 |
| Variant 230 | SEQ ID NO: 5 | PPPPPPPPG (SEQ ID NO: 32) | SEQ ID NO: 7 |
| Variant 231 | SEQ ID NO: 5 | PPPPPPPPPG (SEQ ID NO: 33) | SEQ ID NO: 7 |
| Variant 232 | SEQ ID NO: 5 having mutations S56A N134D Q147R | PPPPPPPPPG (SEQ ID NO: 33) | SEQ ID NO: 7 |
| Variant 233 | SEQ ID NO: 5 | PPPPPPPPPPG (SEQ ID NO: 34) | SEQ ID NO: 7 |
| Variant 234 | SEQ ID NO: 5 | PPPPPPPPPPPG (SEQ ID NO: 35) | SEQ ID NO: 7 |
| Variant 235 | SEQ ID NO: 5 | PPPPPPPPPPPPPG (SEQ ID NO: 36) | SEQ ID NO: 7 |
| Variant 236 | SEQ ID NO: 5 | PEPTPEPTG (SEQ ID NO: 37) | SEQ ID NO: 7 |
| Variant 237 | SEQ ID NO: 5 having mutations S56A N134D Q147R | PEPTPEPTG (SEQ ID NO: 37) | SEQ ID NO: 7 |
| Variant 238 | SEQ ID NO: 5 | PEPTPEPTPEPTG (SEQ ID NO: 38) | SEQ ID NO: 7 |
| Variant 239 | SEQ ID NO: 5 having mutations S56A N134D Q147R | PEPTPEPTPEPTG (SEQ ID NO: 38) | SEQ ID NO: 7 |
| Variant 240 | SEQ ID NO: 5 | PEPTPEPTPEPTPEPTG (SEQ ID NO: 39) | SEQ ID NO: 7 |
| Variant 241 | SEQ ID NO: 5 having mutations S56A N134D Q156E A162E | PEPTPEPTPEPTPEPTG (SEQ ID NO: 39) | SEQ ID NO: 7 |
| Variant 242 | SEQ ID NO: 5 having mutations S56A N134D Q156E Q169Y | PEPTPEPTPEPTPEPTG (SEQ ID NO: 39) | SEQ ID NO: 7 |
| Variant 243 | SEQ ID NO: 5 having mutations S56A N134D Q147R | PEPTPEPTPEPTPEPTG (SEQ ID NO: 39) | SEQ ID NO: 7 |
| Variant 244 | SEQ ID NO: 5 | PEPTPEPTPEPTPEPTPEPTG (SEQ ID NO: 40) | SEQ ID NO: 7 |
| Variant 245 | SEQ ID NO: 5 having mutations S56A N134D Q156E Q169Y | PEPTPEPTPEPTPEPTPEPTG (SEQ ID NO: 40) | SEQ ID NO: 7 |
| Variant 246 | SEQ ID NO: 5 having mutations S56A N134D Q147R | PEPTPEPTPEPTPEPTPEPTG (SEQ ID NO: 40) | SEQ ID NO: 7 |

TABLE C1-continued

| Variant ID | Variant Concept: Catalytic domain (N-terminal) | Linker | CBM (C-terminal) |
|---|---|---|---|
| Variant 247 | SEQ ID NO: 5 | PSPTPSPTPSPTPSPTG (SEQ ID NO: 41) | SEQ ID NO: 7 |
| Variant 248 | SEQ ID NO: 5 having mutations S56A N134D Q147R | PSPTPSPTPSPTPSPTG (SEQ ID NO: 41) | SEQ ID NO: 7 |
| Variant 249 | SEQ ID NO: 5 having mutations S56A N134D Q147R | PSPTPSPTPSPTPSPTPSPTG (SEQ ID NO: 42) | SEQ ID NO: 7 |
| Variant 250 | SEQ ID NO: 5 having mutations S56A N134D Q147R | PQPTPQPTG (SEQ ID NO: 43) | SEQ ID NO: 7 |
| Variant 251 | SEQ ID NO: 5 having mutations S56A N134D Q147R | PDPTPDPTG (SEQ ID NO: 44) | SEQ ID NO: 7 |
| Variant 252 | SEQ ID NO: 5 having mutations S56A N134D Q147R | PRPTPEPTG (SEQ ID NO: 45) | SEQ ID NO: 7 |
| Variant 253 | SEQ ID NO: 5 having mutations S56A N134D Q147R | PQPTPEPTG (SEQ ID NO: 46) | SEQ ID NO: 7 |
| Variant 254 | SEQ ID NO: 5 having mutations S56A N134D Q147R | PSPNSPNSPNG (SEQ ID NO: 47) | SEQ ID NO: 7 |
| Variant 255 | SEQ ID NO: 5 having mutations S56A N134D Q147R | PEPTPRPTG (SEQ ID NO: 48) | SEQ ID NO: 7 |
| Variant 256 | SEQ ID NO: 5 having mutations S56A N134D Q147R | PQPTPEPTPQPTPEPTPQPTPEPTPQPTG (SEQ ID NO: 49) | SEQ ID NO: 7 |
| Variant 257 | SEQ ID NO: 5 having mutations S56A N134D Q147R | PDPTPDPTPDPTG (SEQ ID NO: 50) | SEQ ID NO: 7 |
| Variant 258 | SEQ ID NO: 5 having mutations S56A N134D Q147R | PQPTPQPTPQPTPQPTG (SEQ ID NO: 51) | SEQ ID NO: 7 |
| Variant 259 | SEQ ID NO: 5 having mutations S56A N134D Q147R | PQPTPEPTPQPTPEPTG (SEQ ID NO: 52) | SEQ ID NO: 7 |

TABLE C2

| Variant ID | Variant Concept: Catalytic domain (N-terminal) | Linker | CBM (C-terminal) |
|---|---|---|---|
| Variant 260 | SEQ ID NO: 5 | PPPPPPPG (SEQ ID NO: 30) | SEQ ID NO: 7 |
| Variant 261 | SEQ ID NO: 5 | PPPPPPPPG (SEQ ID NO: 32) | SEQ ID NO: 7 |
| Variant 262 | SEQ ID NO: 5 | PPPPPPPPPG (SEQ ID NO: 33) | SEQ ID NO: 7 |
| Variant 263 | SEQ ID NO: 5 having mutations S56A N134D Q147R | PPPPPPPPPG (SEQ ID NO: 33) | SEQ ID NO: 7 |
| Variant 264 | SEQ ID NO: 5 | PPPPPPPPPPPPPG (SEQ ID NO: 36) | SEQ ID NO: 7 |

TABLE C2-continued

| | Variant Concept | | |
|---|---|---|---|
| Variant ID | Catalytic domain (N-terminal) | Linker | CBM (C-terminal) |
| Variant 265 | SEQ ID NO: 5 having mutations N134D Q147R | SPSPG (SEQ ID NO: 24) | SEQ ID NO: 7 |
| Variant 266 | SEQ ID NO: 5 having mutations S56A Q147R | SPSPSPSPSPG (SEQ ID NO: 25) | SEQ ID NO: 7 |
| Variant 267 | SEQ ID NO: 5 having mutations S56A N134D Q147R | SPSPSPSPSPG (SEQ ID NO: 25) | SEQ ID NO: 7 |
| Variant 268 | SEQ ID NO: 5 having mutations S56A N134D Q147R | SPSPSPSPPPG (SEQ ID NO: 53) | SEQ ID NO: 7 |
| Variant 269 | SEQ ID NO: 5 having mutations S56A N134D Q147R | SPSPSPSPDPG (SEQ ID NO: 54) | SEQ ID NO: 7 |
| Variant 270 | SEQ ID NO: 5 having mutations S56A N134D Q147R | SPSPSPSPKPG (SEQ ID NO: 55) | SEQ ID NO: 7 |
| Variant 271 | SEQ ID NO: 5 having mutations S56A N134D Q147R | SPSPSPSPAPG (SEQ ID NO: 56) | SEQ ID NO: 7 |
| Variant 272 | SEQ ID NO: 5 having mutations S56A N134D Q147R | SPSPSPSPSPSG (SEQ ID NO: 57) | SEQ ID NO: 7 |
| Variant 273 | SEQ ID NO: 5 having mutations S56A N134D Q147R | SPSPSPSPSP (SEQ ID NO: 58) | SEQ ID NO: 7 |
| Variant 274 | SEQ ID NO: 5 having mutations S56A N134D Q147R | SPSPSPSPSPS (SEQ ID NO: 59) | SEQ ID NO: 7 |
| Variant 275 | SEQ ID NO: 5 having mutations S56A N134D Q147R | SPSPSPSPSPP (SEQ ID NO: 60) | SEQ ID NO: 7 |
| Variant 276 | SEQ ID NO: 5 having mutations S56A N134D Q147R | SPSPSPSPSPE (SEQ ID NO: 61) | SEQ ID NO: 7 |
| Variant 277 | SEQ ID NO: 5 having mutations S56A N134D Q147R | SPSPSPSPSPN (SEQ ID NO: 62) | SEQ ID NO: 7 |
| Variant 278 | SEQ ID NO: 5 having mutations S56A N134D Q147R | SPSPSPSPSPGG (SEQ ID NO: 63) | SEQ ID NO: 7 |
| Variant 279 | SEQ ID NO: 5 having mutations S56A N134D Q147R | SPSPSPSPSPK (SEQ ID NO: 64) | SEQ ID NO: 7 |
| Variant 280 | SEQ ID NO: 5 having mutations N134D Q147R | TPTPTPTPTPG (SEQ ID NO: 26) | SEQ ID NO: 7 |
| Variant 281 | SEQ ID NO: 5 having mutations S56A N134D Q147R | TPTPTPTPTPG (SEQ ID NO: 26) | SEQ ID NO: 7 |
| Variant 282 | SEQ ID NO: 5 having mutations S56A N134D Q147R | TTPTPTPTPPTPTPTPTPG (SEQ ID NO: 15) | SEQ ID NO: 7 |
| Variant 283 | SEQ ID NO: 5 having mutations N134D Q147R | PEPTPEPTG (SEQ ID NO: 37) | SEQ ID NO: 7 |
| Variant 284 | SEQ ID NO: 5 having mutations S56A N134D Q147R | PEPTPEPTG (SEQ ID NO: 37) | SEQ ID NO: 7 |
| Variant 285 | SEQ ID NO: 5 having mutations S56A Q147R | PEPTPEPTPEPTG (SEQ ID NO: 38) | SEQ ID NO: 7 |
| Variant 286 | SEQ ID NO: 5 having mutations N134D Q147R | PEPTPEPTPEPTG (SEQ ID NO: 38) | SEQ ID NO: 7 |
| Variant 287 | SEQ ID NO: 5 having mutations S56A N134D Q147R | PEPTPEPTPEPTG (SEQ ID NO: 38) | SEQ ID NO: 7 |
| Variant 288 | SEQ ID NO: 5 | PEPTPEPTPEPTPEPTG (SEQ ID NO: 39) | SEQ ID NO: 7 |
| Variant 289 | SEQ ID NO: 5 having mutations S56A Q147R | PEPTPEPTPEPTPEPTG (SEQ ID NO: 39) | SEQ ID NO: 7 |

TABLE C2-continued

| | Variant Concept | | |
|---|---|---|---|
| Variant ID | Catalytic domain (N-terminal) | Linker | CBM (C-terminal) |
| Variant 290 | SEQ ID NO: 5 having mutations N134D Q147R | PEPTPEPTPEPTPEPTG (SEQ ID NO: 39) | SEQ ID NO: 7 |
| Variant 291 | SEQ ID NO: 5 having mutations S56A N134D Q147R | PEPTPEPTPEPTPEPTG (SEQ ID NO: 39) | SEQ ID NO: 7 |
| Variant 292 | SEQ ID NO: 5 having mutations S56A Q147R | PEPTPEPTPEPTPEPTPEPTG (SEQ ID NO: 40) | SEQ ID NO: 7 |
| Variant 293 | SEQ ID NO: 5 having mutations N134D Q147R | PEPTPEPTPEPTPEPTPEPTG (SEQ ID NO: 40) | SEQ ID NO: 7 |
| Variant 294 | SEQ ID NO: 5 having mutations S56A N134D Q147R | PEPTPEPTPEPTPEPTPEPTG (SEQ ID NO: 40) | SEQ ID NO: 7 |
| Variant 295 | SEQ ID NO: 5 having mutations S56A N134D Q147R | PEPTPEPTP (SEQ ID NO: 65) | SEQ ID NO: 7 |
| Variant 296 | SEQ ID NO: 5 having mutations S56A N134D Q147R | PEPTPEPTR (SEQ ID NO: 66) | SEQ ID NO: 7 |
| Variant 297 | SEQ ID NO: 5 having mutations S56A N134D Q147R | PEPTPEPTPEPTP (SEQ ID NO: 67) | SEQ ID NO: 7 |
| Variant 298 | SEQ ID NO: 5 having mutations S56A N134D Q147R | PEPTPEPTPEPTPEPTPSPTG (SEQ ID NO: 68) | SEQ ID NO: 7 |
| Variant 299 | SEQ ID NO: 5 having mutations S56A N134D Q147R | PEPTPEPTPEPTPEPTPTPTG (SEQ ID NO: 69) | SEQ ID NO: 7 |
| Variant 300 | SEQ ID NO: 5 having mutations S56A N134D Q147R | PEPTPEPTPEPTPEPTPGPTG (SEQ ID NO: 70) | SEQ ID NO: 7 |
| Variant 301 | SEQ ID NO: 5 having mutations S56A N134D Q147R | PEPTPEPTPEPTPEPTPDPTG (SEQ ID NO: 71) | SEQ ID NO: 7 |
| Variant 302 | SEQ ID NO: 5 having mutations S56A N134D Q147R | PEPTPEPTPEPTPEPTPETG (SEQ ID NO: 72) | SEQ ID NO: 7 |
| Variant 303 | SEQ ID NO: 5 having mutations S56A N134D Q147R | PEPTPEPTPEPTPEPTPEPTD (SEQ ID NO: 73) | SEQ ID NO: 7 |
| Variant 304 | SEQ ID NO: 5 having mutations S56A N134D Q147R | PEPTPEPTE (SEQ ID NO: 74) | SEQ ID NO: 7 |
| Variant 305 | SEQ ID NO: 5 having mutations S56A N134D Q147R | PEPTPEPTPEPTPEPTPEP (SEQ ID NO: 75) | SEQ ID NO: 7 |
| Variant 306 | SEQ ID NO: 5 having mutations S56A N134D Q147R | PEPTPEPTPEPTPEPTPSPT (SEQ ID NO: 76) | SEQ ID NO: 7 |
| Variant 307 | SEQ ID NO: 5 having mutations S56A N134D Q147R | PEPTPEPTPEPTPEPTPRPTT (SEQ ID NO: 77) | SEQ ID NO: 7 |
| Variant 308 | SEQ ID NO: 5 having mutations S56A N134D Q147R | PEPTPEPTPEPTPEPTPEPTT (SEQ ID NO: 78) | SEQ ID NO: 7 |
| Variant 309 | SEQ ID NO: 5 having mutations S56A N134D Q147R | PEPTPEPTPEPTPEPTPEPT (SEQ ID NO: 79) | SEQ ID NO: 7 |
| Variant 310 | SEQ ID NO: 5 having mutations S56A N134D Q147R | PEPTPEPTPEPTPEPTPEPTS (SEQ ID NO: 80) | SEQ ID NO: 7 |
| Variant 311 | SEQ ID NO: 5 having mutations S56A N134D Q147R | PEPTPEPTPEPTPEPTPEPTR (SEQ ID NO: 81) | SEQ ID NO: 7 |
| Variant 312 | SEQ ID NO: 5 having mutations A32S S56A N134D A146D Q147R Q169Y F183V | PEPTPEPTPEPTPEPTPEPTG (SEQ ID NO: 40) | SEQ ID NO: 7 |
| Variant 313 | SEQ ID NO: 5 | PSPTPSPTPSPTPSPTG (SEQ ID NO: 41) | SEQ ID NO: 7 |

TABLE C2-continued

| Variant ID | Variant Concept: Catalytic domain (N-terminal) | Linker | CBM (C-terminal) |
|---|---|---|---|
| Variant 314 | SEQ ID NO: 5 having mutations S56A N134D Q147R | PSPTPSPTPSPTPSPTPSPTG (SEQ ID NO: 42) | SEQ ID NO: 7 |
| Variant 315 | SEQ ID NO: 5 having mutations A32S S56A N134D A146D Q147R Q169Y F183V | PSPTPSPTPSPTPSPTPSPTG (SEQ ID NO: 42) | SEQ ID NO: 7 |
| Variant 316 | SEQ ID NO: 5 having mutations S56A N134D Q147R | PPPGGPGGPGTPTSTAPGSGPTSPGGGSG (SEQ ID NO: 82) | SEQ ID NO: 7 |
| Variant 317 | SEQ ID NO: 5 having mutations S56A N134D Q147R | PPPGGPGGTGTPTSTAPGSGPTSPGGGSG (SEQ ID NO: 83) | SEQ ID NO: 7 |
| Variant 318 | SEQ ID NO: 5 having mutations S56A N134D Q147R | PPSGGPGGPGTPTSTAPGSGPTSPGGGSG (SEQ ID NO: 84) | SEQ ID NO: 7 |
| Variant 319 | SEQ ID NO: 5 having mutations S56A N134D Q147R | PEPTPRPTPEPTPRPTG (SEQ ID NO: 85) | SEQ ID NO: 7 |
| Variant 320 | SEQ ID NO: 5 having mutations S56A N134D Q147R | PKPTPEPTPKPTPEPTG (SEQ ID NO: 86) | SEQ ID NO: 7 |
| Variant 321 | SEQ ID NO: 5 having mutations S56A N134D Q147R | PEPTPKPTPEPTPKPTG (SEQ ID NO: 87) | SEQ ID NO: 7 |
| Variant 322 | SEQ ID NO: 5 having mutations S56A N134D Q147R | PEPTPQPTPEPTPQPTG (SEQ ID NO: 88) | SEQ ID NO: 7 |
| Variant 323 | SEQ ID NO: 5 having mutations S56A N134D Q147R | PRPTPEPTPRPTG (SEQ ID NO: 89) | SEQ ID NO: 7 |
| Variant 324 | SEQ ID NO: 5 having mutations S56A N134D Q147R | PKPTPEPTPKPTG (SEQ ID NO: 90) | SEQ ID NO: 7 |
| Variant 325 | SEQ ID NO: 5 having mutations S56A N134D Q147R | PEPTPQPTG (SEQ ID NO: 91) | SEQ ID NO: 7 |
| Variant 326 | SEQ ID NO: 5 having mutations S56A N134D Q147R | PEPTPQPTPEPTG (SEQ ID NO: 92) | SEQ ID NO: 7 |
| Variant 327 | SEQ ID NO: 5 having mutations S56A N134D Q147R | TPPTPPG (SEQ ID NO: 93) | SEQ ID NO: 7 |
| Variant 328 | SEQ ID NO: 5 having mutations S56A N134D Q147R | SPSSPSG (SEQ ID NO: 94) | SEQ ID NO: 7 |
| Variant 329 | SEQ ID NO: 5 having mutations S56A N134D Q147R | SPSSPSSPSG (SEQ ID NO: 95) | SEQ ID NO: 7 |
| Variant 330 | SEQ ID NO: 5 having mutations S56A N134D Q147R | TPTTPTG (SEQ ID NO: 96) | SEQ ID NO: 7 |
| Variant 331 | SEQ ID NO: 5 having mutations S56A N134D Q147R | TPTTPTTPTG (SEQ ID NO: 97) | SEQ ID NO: 7 |

TABLE D

| Variant ID | Variant Concept: Catalytic domain (N-terminal) | Linker | CBM (C-terminal) |
|---|---|---|---|
| Variant 401 | SEQ ID NO: 5 having mutations A32S S56A N134D A146D Q147R Q169Y F183V | SPSPSPSPSP (SEQ ID NO: 58) | SEQ ID NO: 173 |
| Variant 402 | SEQ ID NO: 5 having mutations A32S S56A N134D A146D Q147R Q169Y F183V | PPPPPPPG (SEQ ID NO: 30) | SEQ ID NO: 173 |

TABLE D-continued

| | Variant Concept | | |
|---|---|---|---|
| Variant ID | Catalytic domain (N-terminal) | Linker | CBM (C-terminal) |
| Variant 403 | SEQ ID NO: 5 having mutations A32S S56A N134D A146D Q147R Q169Y F183V | SPSPSPSPSP (SEQ ID NO: 58) | SEQ ID NO: 174 |
| Variant 404 | SEQ ID NO: Shaving mutations A32S S56A N134D A146D Q147R Q169Y F183V | PPPPPPPG (SEQ ID NO: 30) | SEQ ID NO: 174 |
| Variant 405 | SEQ ID NO: Shaving mutations A32S S56A N134D A146D Q147R Q169Y F183V | PPPPPPPG (SEQ ID NO: 30) | SEQ ID NO: 175 |
| Variant 406 | SEQ ID NO: Shaving mutations A32S S56A N134D A146D Q147R Q169Y F183V | PPPPPPPG (SEQ ID NO: 30) | SEQ ID NO: 176 |
| Variant 407 | SEQ ID NO: Shaving mutations A32S S56A N134D A146D Q147R Q169Y F183V | PPPPPPPG (SEQ ID NO: 30) | SEQ ID NO: 177 |
| Variant 408 | SEQ ID NO: Shaving mutations A32S S56A N134D A146D Q147R Q169Y F183V | PPPPPPPG (SEQ ID NO: 30) | SEQ ID NO: 178 |
| Variant 409 | SEQ ID NO: Shaving mutations A32S S56A N134D A146D Q147R Q169Y F183V | PPPPPPPG (SEQ ID NO: 30) | SEQ ID NO: 179 |
| Variant 410 | SEQ ID NO: Shaving mutations A32S S56A N134D A146D Q147R Q169Y F183V | PPPPPPPG (SEQ ID NO: 30) | SEQ ID NO: 180 |
| Variant 411 | SEQ ID NO: Shaving mutations A32S S56A N134D A146D Q147R Q169Y F183V | PPPPPPPG (SEQ ID NO: 30) | SEQ ID NO: 181 |
| Variant 412 | SEQ ID NO: Shaving mutations A32S S56A N134D A146D Q147R Q169Y F183V | PPPPPPPG (SEQ ID NO: 30) | SEQ ID NO: 182 |
| Variant 413 | SEQ ID NO: Shaving mutations A32S S56A N134D A146D Q147R Q169Y F183V | PPPPPPPG (SEQ ID NO: 30) | SEQ ID NO: 183 |
| Variant 414 | SEQ ID NO: Shaving mutations A32S S56A N134D A146D Q147R Q169Y F183V | PPPPPPPG (SEQ ID NO: 30) | SEQ ID NO: 184 |
| Variant 415 | SEQ ID NO: Shaving mutations A32S S56A N134D A146D Q147R Q169Y F183V | PPPPPPPG (SEQ ID NO: 30) | SEQ ID NO: 185 |
| Variant 416 | SEQ ID NO: Shaving mutations A32S S56A N134D A146D Q147R Q169Y F183V | PPPPPPPG (SEQ ID NO: 30) | SEQ ID NO: 186 |
| Variant 417 | SEQ ID NO: Shaving mutations A32S S56A N134D A146D Q147R Q169Y F183V | PPPPPPPG (SEQ ID NO: 30) | SEQ ID NO: 187 |
| Variant 418 | SEQ ID NO: 5 having mutations A32S S56A N134D A146D Q147R Q169Y F183V | PPPPPPPG (SEQ ID NO: 30) | SEQ ID NO: 188 |
| Variant 419 | SEQ ID NO: 5 having mutations A32S S56A N134D A146D Q147R Q169Y F183V | PPPPPPPG (SEQ ID NO: 30) | SEQ ID NO: 189 |
| Variant 420 | SEQ ID NO: 5 having mutations A32S S56A N134D A146D Q147R Q169Y F183V | PPPPPPPG (SEQ ID NO: 30) | SEQ ID NO: 190 |
| Variant 421 | SEQ ID NO: Shaving mutations A32S S56A N134D A146D Q147R Q169Y F183V | PPPPPPPG (SEQ ID NO: 30) | SEQ ID NO: 191 |

TABLE D-continued

| | Variant Concept | | |
|---|---|---|---|
| Variant ID | Catalytic domain (N-terminal) | Linker | CBM (C-terminal) |
| Variant 422 | SEQ ID NO: Shaving mutations A32S S56A N134D A146D Q147R Q169Y F183V | PPPPPPPG (SEQ ID NO: 30) | SEQ ID NO: 192 |
| Variant 423 | SEQ ID NO: Shaving mutations A32S S56A N134D A146D Q147R Q169Y F183V | PPPPPPPG (SEQ ID NO: 30) | SEQ ID NO: 193 |
| Variant 424 | SEQ ID NO: 5 having mutations A32S S56A N134D A146D Q147R Q169Y F183V | PPPPPPPG (SEQ ID NO: 30) | SEQ ID NO: 194 |
| Variant 425 | SEQ ID NO: Shaving mutations A32S S56A N134D A146D Q147R Q169Y F183V | PPPPPPPG (SEQ ID NO: 30) | SEQ ID NO: 195 |
| Variant 426 | SEQ ID NO: Shaving mutations A32S S56A N134D A146D Q147R Q169Y F183V | PPPPPPPG (SEQ ID NO: 30) | SEQ ID NO: 196 |
| Variant 427 | SEQ ID NO: Shaving mutations A32S S56A N134D A146D Q147R Q169Y F183V | PPPPPPPG (SEQ ID NO: 30) | SEQ ID NO: 197 |
| Variant 428 | SEQ ID NO: 5 having mutations A32S S56A N134D A146D Q147R Q169Y F183V | PPPPPPPG (SEQ ID NO: 30) | SEQ ID NO: 198 |
| Variant 429 | SEQ ID NO: Shaving mutations A32S S56A N134D A146D Q147R Q169Y F183V | PPPPPPPG (SEQ ID NO: 30) | SEQ ID NO: 199 |
| Variant 430 | SEQ ID NO: 5 having mutations A32S S56A N134D A146D Q147R Q169Y F183V | PPPPPPPG (SEQ ID NO: 30) | SEQ ID NO: 200 |

Stability in the Presence of Protease

In an embodiment, the variant has improved stability in the presence of a protease compared to the parent enzyme. Preferably the variant has improved stability in the presence of a protease and a surfactant, such as a detergent composition; in comparison with the parent cellulase.

Stability in the presence of protease is beneficial for, e.g. cellulases used under conditions where protease is present, because it extends the time where the cellulases are functional and active and can exert the function they were intended to do.

One preferred use of the variants of the invention is in detergents, where proteases typically are included to improve the detergency. The improved stability of the variants of the invention means that the variants can exert the cellulolytic activity for a longer time during the laundry process compared with the parent cellulase, and thereby provide an improved wash performance benefit compared with the parent cellulase.

For liquid detergent compositions, the variants of the invention further have the benefit that improved stability in the presence of protease means that the liquid detergent composition comprising a protease and further comprising a variant of the invention have a longer shelf life in comparison with the same liquid detergent composition comprising the parent cellulase.

Stability in presence of protease may be determined by incubating a given cellulase under defined conditions in the presence of a protease, measuring the cellulolytic activity after the incubation and comparing it with a sample of the cellulase that has not been incubated with protease.

Another method for determining the stability in presence of protease is to prepare two identical test tubes comprising the given cellulase to be tested in a defined solution comprising a protease, incubating one test tube under elevated temperature e.g. in the range of 30-90° C. (stress) whereas the other tube is incubated at low temperature e.g. in the range of 0-5° C. (non-stress). The tubes are incubated for a predetermined time e.g. between 1 and 24 hours, typically 16 hours. After the incubation both samples are analysed for cellulolytic activity and the residual activity is determined as Residual activity (%)=(Activity, stress/Activity, non-stress)*100.

For example, it is possible to determine the residual activity in 50% liquid detergent A containing 0.166 v/v-% protease, where the samples are incubated for 16 hours at elevated temperature (stress) and 5° C. (non-stress) before the activity is determined. The temperature should be selected so the residual activity of the parent molecule is in the range of 10-50%.

This core stability method is illustrated in more details in Example 1.

The variants of the invention have higher residual activities than the parent cellulases. In one embodiment, the variants of the invention have at least 10% higher Residual activity compared with the parent cellulase, e.g. at least 20% higher Residual activity, e.g. at least 30% higher Residual activity, e.g. at least 40% higher Residual activity, e.g. at least 50% higher Residual activity, e.g. at least 60% higher Residual activity, e.g. at least 70% higher Residual activity, e.g. at least 80% higher Residual activity, e.g. at least 90% higher Residual activity or at least 100% higher Residual activity, compared with the parent.

However, in the traditional enzyme stability assays used for testing thermostability, activity measures of the stressed and unstressed sample typically focused on measuring changes affecting the catalytic site of the enzyme molecule, e.g. by using a small synthetic substrate such as 4-Methyl-umbelliferyl-B-cellopentaoside or soluble carboxymethyl cellulose (CMC).

Importantly, however, changes in other properties of the enzyme of interest due to the stress, properties important for the function of the enzyme in the application but not directly affecting the active site of the enzyme, is not necessarily detected in these assays. One such example is the glycosyl hydrolases having a separate catalytic domain and a CBM joined by a linker as e.g. in cellulases used for removing fuzz and pills in laundry detergents and textile care products. If the stress affects only the linker and/or CBM part of the molecule but not the catalytic domain part, these changes will not be detected by the traditional assays as described above and/or in Example 1. The activity, when using a simple substrate such as CMC or 4-methylumbelliferyl-B-cellopentaoside, will appear to be maintained during the stress but the performance is significantly affected, as the CBM part of the enzyme molecule plays an important role in directing the enzyme to the proper location on the textile to be treated.

As an alternative, the importance of the CBM for the performance can be tested by comparing the performance of the catalytic domain with that of the catalytic domain with intact linker and CBM.

To detect changes in the linker and/or CBM after storage under stressed conditions special measures must be taken when testing if the stress has affected the performance of the enzyme. This can be done by comparing the performance of the enzymes before and after stress. Alternatively, it can be tested by ensuring that binding of the enzyme to its natural, insoluble substrate, such as cotton linters, is included as part of the assay used for testing the stability, and/or first probing the binding of the enzyme to microcrystalline cellulose or cotton linters and then measure the activity of the enzymes having lost their binding ability to the cellulose compared to the total activity.

Thus, linker and/or CBM stability is measured by incubating the cellulase in detergent containing protease, followed by determining the ability of the incubated cellulase to bind to cellulose fibers. If the linker or the cellulose binding domain is affected by the protease the binding affinity of the cellulase to cellulose fibers will be reduced.

This linker and CBM specific assay are illustrated by the conditions described in Example 2.

Parent Cellulases

The parent cellulase may be a polypeptide having cellulolytic activity and having at least 80%, at least 85%, at least 90%, at least 91%, at least 92%, at least 93%, at least 94%, at least 95%, at least 96%, at least 97%, at least 98%, at least 99%, or 100%, sequence identity to the polypeptide having the sequence of SEQ ID NO: 1, SEQ ID NO: 2, SEQ ID NO: 3, or SEQ ID NO: 4. In one aspect, the amino acid sequence of the parent differs by up to 10 amino acids, e.g., 1, 2, 3, 4, 5, 6, 7, 8, 9, or 10, from the mature polypeptide of SEQ ID NO: 1, SEQ ID NO: 2, SEQ ID NO: 3, or SEQ ID NO: 4.

In another aspect, the parent comprises or consists of the amino acid sequence of SEQ ID NO: 1, SEQ ID NO: 2, SEQ ID NO: 3, or SEQ ID NO: 4.

The parent cellulase may be a polypeptide having cellulolytic activity and having at least 80%, at least 85%, at least 90%, at least 91%, at least 92%, at least 93%, at least 94%, at least 95%, at least 96%, at least 97%, at least 98%, at least 99%, or 100%, sequence identity to the catalytic domain of the mature polypeptide having the sequence of SEQ ID NO: 1, SEQ ID NO: 2, SEQ ID NO: 3, or SEQ ID NO: 4. In one aspect, the amino acid sequence of the parent differs by up to 10 amino acids, e.g., 1, 2, 3, 4, 5, 6, 7, 8, 9, or 10, from the catalytic domain of the mature polypeptide of SEQ ID NO: 1, SEQ ID NO: 2, SEQ ID NO: 3, or SEQ ID NO: 4.

In another aspect, the parent comprises the catalytic domain of SEQ ID NO: 1, e.g., amino acids 1 to 212, or amino acids 1 to 216 of SEQ ID NO: 1. In another aspect the parent comprises SEQ ID NO: 5.

In another aspect, the parent comprises the catalytic domain of SEQ ID NO: 2, e.g., amino acids 1 to 211, or amino acids 1 to 213 of SEQ ID NO: 2.

In another aspect, the parent comprises the catalytic domain of SEQ ID NO: 3, e.g., amino acids 1 to 210 of SEQ ID NO: 3.

In another aspect, the parent comprises the catalytic domain of SEQ ID NO: 4, e.g., amino acids 1 to 211 of SEQ ID NO: 4.

In another embodiment, the parent is an allelic variant of the mature polypeptide, or the catalytic domain, of SEQ ID NO: 1, SEQ ID NO: 2, SEQ ID NO: 3, or SEQ ID NO: 4.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12:2575-2583; Dawson et al., 1994, *Science* 266:776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3:568-576; Svetina et al., 2000, *J. Biotechnol.* 76:245-251; Rasmussen-Wilson et al., 1997, *Appl. Environ. Microbiol.* 63:3488-3493; Ward et al., 1995, *Biotechnology* 13:498-503; and Contreras et al., 1991, *Biotechnology* 9:378-381; Eaton et al., 1986, *Biochemistry* 25:505-512; Collins-Racie et al., 1995, *Biotechnology* 13:982-987; Carter et al., 1989, Proteins: Structure, *Function, and Genetics* 6:240-248; and Stevens, 2003, *Drug Discovery World* 4:35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly. The parent may be a bacterial cellulase. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* cellulase, or a Gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* cellulase.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* cellulase.

In another aspect, the parent is a *Streptococcus equisimilis, Streptococcus pyogenes, Streptococcus uberis*, or *Streptococcus equi* subsp. *Zooepidemicus* cellulase.

In another aspect, the parent is a *Streptomyces achromogenes, Streptomyces avermitilis, Streptomyces coelicolor, Streptomyces griseus*, or *Streptomyces lividans* cellulase.

The parent may be a fungal cellulase. For example, the parent may be a yeast cellulase such as a *Candida, Kluyveromyces, Pichia, Saccharomyces, Schizosaccharomyces*, or *Yarrowia* cellulase; or a filamentous fungal cellulase such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* cellulase.

In another aspect, the parent is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cellulase.

In another aspect, the parent is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei*, or *Trichoderma viride* cellulase.

In another aspect, the parent is a *Thielavia terrestris* cellulase, e.g., the cellulase of SEQ ID NO: 1 or the mature polypeptide thereof.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a variant having glycoside hydrolase activity, comprising: (a) introducing into a parent glycoside hydrolase one or more substitutions of the mature polypeptide of the parent polypeptide; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76:4949-4955; and Barton et al., 1990, *Nucleic Acids Res.* 18:7349-4966.

Site-directed mutagenesis can also be accomplished in vivo by methods known in the art. See, e.g., U.S. Patent Application Publication No. 2004/0171154; Storici et al., 2001, *Nature Biotechnol.* 19:773-776; Kren et al., 1998, *Nat. Med.* 4:285-290; and Calissano and Macino, 1996, *Fungal Genet. Newslett.* 43:15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432:1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86:2152-2156; WO 95/17413; or WO 95/22625. Other methods that can be used include error-prone PCR, phage display (e.g., Lowman et al., 1991, *Biochemistry* 30:10832-10837; U.S. Pat. No. 5,223,409; WO 92/06204) and region-directed mutagenesis (Derbyshire et al., 1986, *Gene* 46:145; Ner et al., 1988, *DNA* 7:127).

Mutagenesis/shuffling methods can be combined with high-throughput, automated screening methods to detect activity of cloned, mutagenized polypeptides expressed by host cells (Ness et al., 1999, *Nature Biotechnology* 17:893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13:97-107), *E. coli* lac operon, *E. coli* trc promoter (Egon et al., 1988, *Gene* 69:301-315), *Streptomyces coelicolor* agarase gene (dagA), and prokaryotic beta-lactamase gene (Villa-Kamaroff et al., 1978, *Proc. Natl. Acad. Sci. USA* 75:3727-3731), as well as the tac promoter (DeBoer et al., 1983, *Proc. Natl. Acad. Sci. USA* 80:21-25). Further promoters are described in "Useful proteins from recombinant bacteria" in Gilbert et al., 1980, *Scientific American* 242:74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8:423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, Journal of Bacteriology 177:3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15:5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57:109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT),

*Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, Gene 98:61-67; Cullen et al., 1987, Nucleic Acids Res. 15:9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168:111-115), competent cell transformation (see, e.g., Young and Spizizen, 1961, *J. Bacteriol.* 81:823-829, or Dubnau and Davidoff-Abelson, 1971, *J. Mol. Biol.* 56:209-221), electroporation (see, e.g., Shigekawa and Dower, 1988, *Biotechniques* 6:742-751), or conjugation (see, e.g., Koehler and Thorne, 1987, *J. Bacteriol.* 169:5271-5278). The introduction of DNA into an *E. coli* cell may be effected by protoplast transformation (see, e.g., Hanahan, 1983, *J. Mol. Biol.* 166:557-580) or electroporation (see, e.g., Dower et al., 1988, *Nucleic Acids Res.* 16:6127-6145). The introduction of DNA into a *Streptomyces* cell may be effected by protoplast transformation, electroporation (see, e.g., Gong et al., 2004, *Folia Microbiol.* (Praha) 49:399-405), conjugation (see, e.g., Mazodier et al., 1989, *J. Bacteriol.* 171:3583-3585), or transduction (see, e.g., Burke et al., 2001, *Proc. Natl. Acad. Sci. USA* 98:6289-6294). The introduction of DNA into a *Pseudomonas* cell may be effected by electroporation (see, e.g., Choi et al., 2006, *J. Microbiol. Methods* 64:391-397), or conjugation (see, e.g., Pinedo and Smets, 2005, *Appl. Environ. Microbiol.* 71:51-57). The introduction of DNA into a *Streptococcus* cell may be effected by natural competence (see, e.g., Perry and Kuramitsu, 1981, *Infect. Immun.* 32:1295-1297), protoplast transformation (see, e.g., Catt and Jollick, 1991, *Microbios* 68:189-207), electroporation (see, e.g., Buckley et al., 1999, *Appl. Environ. Microbiol.* 65:3800-3804) or conjugation (see, e.g., Clewell, 1981, *Microbiol. Rev.* 45:409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In, Ainsworth and Bisby's Dictionary of The Fungi,* 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolismis obligately aerobic. In contrast, vegetative growth by yeasts such as *Saccharomyces cerevisiae* is by budding of a unicellular thallus and carbon catabolismmay be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Chrysosporium inops, Chrysosporium keratinophilum, Ceriporiopsis subvermispora, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81:1470-1474, and Christensen et al., 1988, *Bio/Technology* 6:1419-1422. Suitable methods for transforming *Fusarium* species are described by Malardier et al., 1989, *Gene* 78:147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153:163; and Hinnen et al., 1978, *Proc. Natl. Acad. Sci. USA* 75:1920.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid-state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Detergent Compositions

In one embodiment, the invention is directed to detergent compositions comprising an enzyme of the present invention in combination with one or more additional cleaning composition components. The choice of additional components is within the skill of the artisan and includes conventional ingredients, including the exemplary non-limiting components set forth below.

The choice of components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

In one embodiment, the invention is directed to a liquid laundry detergent composition comprising an enzyme of the present invention in combination with one or more additional laundry detergent composition components, specifically a protease. In another embodiment, the invention comprises an ancillary product used in laundry, such as a prespotter or stain removal booster. The present invention also relates to an ADW (Automatic Dish Wash) compositions comprising an enzyme of the present invention in combination with one or more additional ADW composition components. The choice of additional components is within the skill of the artisan and includes conventional ingredients, including the exemplary non-limiting components set forth below.

Enzyme of the Present Invention

In one embodiment of the present invention, the polypeptide of the present invention may be added to a detergent composition in an amount corresponding to 0.001-200 mg of protein, such as 0.005-100 mg of protein, preferably 0.01-50 mg of protein, more preferably 0.05-20 mg of protein, even more preferably 0.1-10 mg of protein per liter of wash liquor.

The enzyme(s) of the detergent composition of the invention may be stabilized using conventional stabilizing agents, e.g. a polyol such as propylene glycol or glycerol, a sugar or sugar alcohol, lactic acid, boric acid, or a boric acid derivative, e.g. an aromatic borate ester, or a phenyl boronic acid derivative such as 4-formylphenyl boronic acid, and the composition may be formulated as described in, for example, WO92/19709 and WO92/19708.

A polypeptide of the present invention may also be incorporated in the detergent formulations disclosed in WO97/07202, which is hereby incorporated by reference.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 5% to 60% by weight, such as about 5% to about 50%, or about 10% to about 50%, or about 20% to about 50%. The surfactant(s) is chosen based on the desired cleaning application, and may include any conventional surfactant(s) known in the art.

When included therein the detergent will usually contain from about 5% to about 60% by weight of one or more anionic surfactants, such as from about 5% to about 40%, including from about 10% to about 25%, Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diyl-bis (sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salts of fatty acids (soap) or fatty acids, and combinations thereof.

When included therein the detergent will usually contain from about from about 0.1% to about 10% by weigh of a cationic surfactant, for example from about 0.1% to about 5%, Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 60% by weight of a nonionic surfactant, for example from about 1% to about 40%, in particular from about 5% to about 20%, from about 3% to about 15%, Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), methylester ethoxylates (MEE), as well as products available under the trade names SPAN and TWEEN, and combinations thereof.

When included therein the detergent will usually contain from about 0.1% to about 10% by weight of a semipolar surfactant. Non-limiting examples of semipolar surfactants include amine oxides (AO) such as alkyldimethylamineoxide, N-(coco alkyl)-N, N-dimethylamine oxide and N-(tallow-alkyl)-N,N-bis (2-hydroxyethyl)amine oxide, and combinations thereof.

When included therein the detergent will usually contain from about 0.1% to about 10% by weight of a zwitterionic surfactant. Non-limiting examples of zwitterionic surfactants include betaines such as alkyldimethylbetaines, sulfobetaines, and combinations thereof.

Solvent system: For dissolution of the surfactant and other detergent ingredients, a solvent system is needed. Solvents are typically water, alcohols, polyols, sugars and/or mixtures thereof. Preferred solvents are water, glycerol, sorbitol, propylene glycol (MPG, 1,2-propanediol or 1,3-propane diol), dipropylene glycol (DPG), polyethylene glycol family (PEG300-600), hexylene glycol, inositol, mannitol, Ethanol, isopropanol, n-butoxy propoxy propanol, ethanolamines (monoethanol amine, diethanol amines and triethanol amines), sucrose, dextrose, glucose, ribose, xylose, and related mono and di pyranosides and furanosides.

The solvent system is present in typically totally 5-90%, 5-60%, 5-40%, 10-30% by weight.

The water content for unit doses wrapped in PVA film is typically in the range 1-15%, 2-12%, 3-10%, 5-10%.

The polyol content for unit doses wrapped in PVA film is typically in the range 5-50%, 10-40% or 20-30%.

In an embodiment, the surfactant is a non-naturally occurring surfactant.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants), however the molecular structure of hydrotropes generally do not favor spontaneous self-aggregation, see e.g. review by Hodgdon and Kaler (2007), Current Opinion in Colloid & Interface Science 12:121-128. Hydrotropes do not display a critical concentration above which self-aggregation occurs as found for surfactants and lipids forming micellar, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65%, 0-20%; or 0.5-5% of a detergent builder or co-builder, or a mixture thereof. In a dish wash detergent, the level of builder is typically 10--65%, particularly 20-40%. The builder and/or co-builder may particularly be a chelating agent that forms water-soluble complexes with Ca and Mg. Any builder and/or co-builder known in the art for use in laundry detergents may be utilized. Nonlimiting examples are citrate, sodium carbonate, sodium bicarbonate and sodium citrate, Examples of phosphonates include 1-Hydroxy Ethylidene-1,1-Diphosphonic Acid (HEDP, etidronic acid), Diethylenetriamine Penta (Methylene Phosphonic acid) (DTPMP), Ethylene diamine tetra (methylene phosphonic acid) (EDTMPA), amino tris (methylenephosphonic acid) (ATMP), Nitrilo trimethylene phosphonic acid (NTMP), 2-Amino ethyl phosphonic acid (AEPn), Dimethyl methylphosphonate (DMPP), Tetramethylene diamine tetra (methylene phosphonic acid) (TDTMP), Hexamethylene diamine tetra (methylene phosphonic acid) (HDTMP), Phosphonobutane-tricarboxylic acid (PBTC), N-(phosphonomethyl) iminodiacetic acid (PMIDA), 2-carboxyethyl phosphonic acid (CEPA), 2-Hydroxy phosphonocarboxylic acid (HPAA) and Amino-tris-(methylene-phosphonic acid) (AMP). L-glutamic acid N,N-diacetic acid tetra sodium salt (GLDA)., methylglycinediacetic acid (MGDA). Non-limiting examples of builders include homopolymers of polyacrylates or copolymers thereof, such as poly (acrylic acid) (PAA) or copoly (acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra (methylenephosphonic acid) (EDTMPA), diethylenetriaminepentakis (methylenephosphonic acid) (DTMPA or DTPMPA), N-(2-hydroxyethyl) iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylenetriamine penta (methylenephosphonic acid) d) (DTPMP), aminotris(methylenephosphonic acid) (ATMP), and combinations and salts thereof. Further exemplary builders and/or co-builders are described in, e.g., WO 09/102854, U.S. Pat. No. 5,977,053

In an embodiment, the builder or co-builder is a non-naturally occurring builder or co-builder.

Bleaching Systems

The detergent may contain 0-30% by weight, such as about 1% to about 20%, of a bleaching system. Any bleaching system known in the art for use in laundry detergents may be utilized. Suitable bleaching system components include bleaching catalysts, photobleaches, bleach activators, sources of hydrogen peroxide such as sodium percarbonate, sodium perborates and hydrogen peroxide—urea (1:1), preformed peracids and mixtures thereof. Suitable preformed peracids include, but are not limited to, peroxycarboxylic acids and salts, diperoxydicarboxylic acids, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with hydrogen peroxide to form a peracid via perhydrolysis. The peracid thus formed constitutes the activated bleach. Suitable bleach activators to be used herein include those belonging to the class of esters, amides, imides or anhydrides. Suitable examples are tetraacetylethylenediamine (TAED), sodium 4-[(3,5,5-trimethylhexanoyl)oxy] benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), and/or those disclosed in WO98/17767. A particular family of bleach activators of interest was disclosed in EP624154 and particulary preferred in that family is acetyl triethyl citrate (ATC). ATC or a short chain triglyceride like triacetin has the advantage that it is environmentally friendly Furthermore acetyl triethyl citrate and triacetin have good hydrolytical stability in the product upon storage and are efficient bleach activators. Finally, ATC is multifunctional, as the citrate released in the perhydrolysis reaction may function as a builder. Alternatively, the bleaching system may comprise peroxyacids of, for example, the amide, imide, or sulfone type. The bleaching system may also comprise peracids such as 6-(phthalimido) peroxyhexanoic acid (PAP). The bleaching system may also include a bleach catalyst. In some embodiments the bleach component may be an organic catalyst selected from the group consisting of organic catalysts having the following formulae:

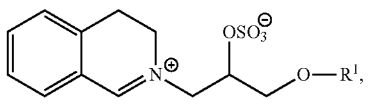

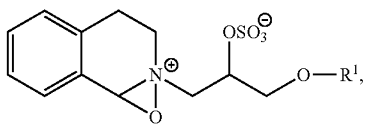

(iii) and mixtures thereof, wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl. Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Preferably the bleach component comprises a source of peracid in addition to bleach catalyst, particularly organic bleach catalyst. The source of peracid may be selected from (a) pre-formed peracid; (b) percarbonate, perborate or persulfate salt (hydrogen peroxide source) preferably in combination with a bleach activator; and (c) perhydrolase enzyme and an ester for forming peracid in situ in the presence of water in a textile or hard surface treatment step.

In an embodiment, the bleaching system is a non-naturally occurring bleaching system.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl) cellulose (CMC), poly (vinyl alcohol) (PVA), poly(vinylpyrrolidone) (PVP), poly (ethyleneglycol) or poly (ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly (vinylimidazole) (PVI), poly (vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

In an embodiment, the polymer is a non-naturally occurring polymer.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Color Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Additional Enzymes

The detergent additive as well as the detergent composition may comprise one or more [additional] enzymes such as hydrolases (EC 3.-.-.-) such as hydrolases acting on ester bonds (EC 3.1.-.-), glycosidases (EC 3.2.-.-), and hydrolases acting on peptide bonds (EC 3.4.-.-), oxidoreductases (EC 1.-.-.-) such as laccases (EC 1.10.-.-) or peroxidases (EC 1.11.-.-) or lyases (EC 4.-.-.-) such as carbon-oxygen lyases (EC 4.2.-.-). In a specific embodiment the detergent composition may comprise one or more [additional] enzymes such as a protease, lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases providing or maintaining whiteness and preventing redeposition or having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500 (B)™ (Kao Corporation).

Mannanases

Suitable mannanases include those of bacterial or fungal origin. Chemically or genetically modified mutants are included. The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. Suitable mannanases are described in WO 1999/064619. A commercially available mannanase is Mannaway (Novozymes A/S).

Proteases

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Eng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and subtilisin *lentus*, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from Cellumonas described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the subtilase variants may comprise the mutations: S3T, V41, S9R, A15T, K27R, *36D, V68A, N76D, N87S,R, *97E, A98S, S99G,D,A, S99AD, S101G,M,R S103A, V1041, Y,N, S106A, G118V,R, H120D,N, N123S, S128L, P129Q, S130A, G160D, Y167A, R170S, A194P, G195E, V199M, V2051, L217D, N218D, M222S, A232V, K235L, Q236H, Q245R, N252K, T274A (using BPN' numbering).

Suitable commercially available protease enzymes include those sold under the trade names Alcalase®, Blaze®, Blaze® Evity®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® Esperase®, Progress Excel®, and Progress UnoR (Novozymes A/S), those sold under the tradename Maxatase®, Maxacal®, Maxapem®, Purafect®, Purafect Prime®, Preferenz™, Purafect MAR, Purafect Ox®, Purafect OxPR, Puramax®, Properase®, Effectenz™, FN2®, FN3®, FN4®, Excellase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases and Cutinases:

Suitable lipases and cutinases include those of bacterial or fungal origin. Chemically modified or protein engineered mutant enzymes are included. Examples include lipase from *Thermomyces*, e.g. from T. *lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), P. sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases:

Suitable amylases which can be used together with the variants of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, 1201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, 1206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T1311, T1651, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;

N128C+K178L+T182G+F202Y+Y305R+D319T+G475K;

S125A+N128C+K178L+T182G+Y305R+G475K; or

S125A+N128C+T1311+T165I+K178L+T182G+Y305R+G475K wherein the variants are C-terminally truncated and optionally further comprises a substitution at position 243 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™ Stainzyme™, Stainzyme Plus™, Natalase™ and BAN™ (from Novozymes A/S), and Rapidase™, Purastar™/Effectenz™, Powerase™, Preferenz S1000™ Preferenz S110™ and Preferenz S100™ (from Genencor International Inc./DuPont).

Peroxidases/Oxidases:

A peroxidase is a peroxidase enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A peroxidase may also include a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an embodiment, the haloperoxidase is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as *Caldariomyces*, e.g., *C. fumago, Alternaria, Curvularia*, e.g., *C. verruculosa* and *C. inaequalis, Drechslera, Ulocladium* and *Botrytis.*

Haloperoxidases have also been isolated from bacteria such as *Pseudomonas*, e.g., *P. pyrrocinia* and *Streptomyces*, e.g., *S. aureofaciens.*

In an preferred embodiment, the haloperoxidase is derivable from *Curvularia* sp., in particular *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendryphiella salina* as described in WO 01/79458, *Phaeotrichoconis crotalarie* as described in WO 01/79461, or *Geniculosporium* sp. as described in WO 01/79460.

An oxidase can include, in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5).

Preferred laccase enzymes are enzymes of microbial origin. The enzymes may be derived from plants, bacteria or fungi (including filamentous fungi and yeasts).

Suitable examples from fungi include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata* (WO 92/01046), or *Coriolus*, e.g., *C. hirsutus* (JP 2238885).

Suitable examples from bacteria include a laccase derivable from a strain of *Bacillus*.

A laccase derived from *Coprinopsis* or *Myceliophthora* is preferred; in particular a laccase derived from *Coprinopsis cinerea*, as disclosed in WO 97/08325; or from *Myceliophthora thermophila*, as disclosed in WO 95/33836.

Nucleases

Suitable nucleases include deoxyribonucleases (DNases) and ribonucleases (RNases) which are any enzyme that catalyzes the hydrolytic cleavage of phosphodiester linkages in the DNA or RNA backbone respectively, thus degrading DNA and RNA. There are two primary classifications based on the locus of activity. Exonucleases digest nucleic acids from the ends. Endonucleases act on regions in the middle of target molecules. The nuclease is preferably a DNase, which is preferable is obtainable from a microorganism, preferably a fungi or bacterium. In particular, a DNase which is obtainable from a species of *Bacillus* is preferred; in particular a DNase which is obtainable from *Bacillus cibi, Bacillus subtilis* or *Bacillus licheniformis* is preferred. Examples of such DNases are described in WO 2011/098579, WO2014/087011 and WO2017/060475. Particularly preferred is also a DNase obtainable from a species of *Aspergillus*; in particular a DNase which is obtainable from *Aspergillus oryzae*, such as a DNase described in WO 2015/155350.

Licheninases

Suitable licheninases (lichenases) include enzymes that catalyse the hydrolysis of the beta-1,4-glucosidic bonds to give beta-glucans. Licheninases (or lichenases) (e.g. EC 3.2.1.73) hydrolyse (1,4)-beta-D-glucosidic linkages in beta-D-glucans containing (1,3)- and (1,4)-bonds and can act on lichenin and cereal beta-D-glucans, but not on beta-D-glucans containing only 1,3- or 1,4-bonds. Examples of such licheninases are described in patent application WO 2017/097866 and in WO 2017/129754.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g. as disclosed in U.S. Pat. Nos. 4,106,991 and 4,661,452 and may optionally be coated by methods known in the art. Examples of waxy coating materials are poly (ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

Dispersants—The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents—The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent whitening agent—The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl) stilbene-2,2'-disulfonate and sodium 5-(2H-naphtho[1,2-d][1,2,3]triazol-2-yl)-2-[(E)-2-phenylvinyl]benzenesulfonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil release polymers—The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-redeposition agents—The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers—are structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, and solvents.

Protease Inhibitor

The protease inhibitor maybe any compound which stabilises or inhibits the protease so that the protease or other enzyme(s) in the laundry soap bar are not degraded. Examples of protease inhibitors are aprotinin, bestatin, calpain inhibitor I and II, chymostatin, leupeptin, pepstatin, phenylmethanesulfonyl fluoride (PMSF), boric acid, borate, borax, boronic acids, phenylboronic acids such as 4-formylphenylboronic acid (4-FPBA), peptide aldehydes or hydrosulfite adducts or hemiacetal adducts thereof and peptide trifluromethyl ketones. There may be one or more protease inhibitors, such as 5,4,3,2 or 1 inhibitor(s) of which at least one is a peptide aldehyde, a hydrosulfite adduct or a hemiacetal adduct thereof.

Peptide Aldehyde Inhibitor

The peptide aldehyde may have the formula P-$(A)_y$-L-$(B)_x$-$B^0$-H or a hydrosulfite adduct or hemiacetal adduct thereof, wherein:

i. H is hydrogen;
ii. $B^0$ is a single amino acid residue with L- or D-configuration of the formula —NH—CH(R)—C(═O)—;
iii. x is 1, 2 or 3 for $(B)_x$, and B is independently a single amino acid connected to $B^0$ via the C-terminal of the B amino acid
iv. L is absent or L is independently a linker group of the formula —C(═O)—, —C(═O)—C(═O)—, —C(═S)—, —C(═S)—C(═S)— or —C(═S)—C(═O)—;
v. y is 0, 1 or 2 for $(A)_y$, and A is independently a single amino acid residue connected to L via the N-terminal of the A amino acid, with the proviso that if L is absent then A is absent;
vi. P is selected from the group consisting of hydrogen and an N-terminal protection group, with the proviso that if L is absent then P is an N-terminal protection group;
vii. R is independently selected from the group consisting of $C_{1-6}$ alkyl, $C_{6-10}$ aryl or $C_{7-10}$ arylalkyl optionally substituted with one or more, identical or different, substituent's R';
viii. R' is independently selected from the group consisting of halogen, —OH, —OR", —SH, —SR", —$NH_2$, —NHR", —$NR"_2$, —$CO_2H$, —$CONH_2$, —CONHR", —$CONR"_2$, —NHC(═N) $NH_2$; and
ix. R" is a $C_{1-6}$ alkyl group.

x may be 1, 2 or 3 and therefore B may be 1, 2 or 3 amino acid residues respectively. Thus, B may represent $B^1$, $B^2$-$B^1$ or $B^3$-$B^2$-$B^1$, where $B^3$, $B^2$ and $B^1$ each represent one amino acid residue. y may be 0, 1 or 2 and therefore A may be absent, or 1 or 2 amino acid residues respectively having the formula $A^1$ or $A^2$-$A^1$ wherein $A^2$ and $A^1$ each represent one amino acid residue.

$B^0$ may be a single amino acid residue with L- or D-configuration, which is connected to H via the C-terminal of the amino acid, wherein R is a $C_{1-6}$ alkyl, $C_{6-10}$ aryl or $C_{7-10}$ arylalkyl side chain, such as methyl, ethyl, propyl, isopropyl, butyl, isobutyl, phenyl or benzyl, and wherein R may be optionally substituted with one or more, identical or different, substituent's R'. Particular examples are the D- or L-form of arginine (Arg), 3,4-dihydroxyphenylalanine, isoleucine (Ile), leucine (Leu), methionine (Met), norleucine (Nle), norvaline (Nva), phenylalanine (Phe), m-tyrosine, p-tyrosine (Tyr) and valine (Val). A particular embodiment is when $B^0$ is leucine, methionine, phenylalanine, p-tyrosine and valine.

$B^1$, which is connected to $B^0$ via the C-terminal of the $B^1$ amino acid, may be an aliphatic, hydrophobic and/or neutral amino acid. Examples of $B^1$ are alanine (Ala), cysteine (Cys), glycine (Gly), isoleucine (Ile), leucine (Leu), norleucine (Nle), norvaline (Nva), proline (Pro), serine (Ser), threonine (Thr) and valine (Val). Particular examples of $B^1$ are alanine, glycine, isoleucine, leucine and valine. A particular embodiment is when $B^1$ is alanine, glycine or valine.

If present, $B^2$, which is connected to $B^1$ via the C-terminal of the $B^2$ amino acid, may be an aliphatic, hydrophobic, neutral and/or polar amino acid. Examples of $B^2$ are alanine (Ala), arginine (Arg), capreomycidine (Cpd), cysteine (Cys), glycine (Gly), isoleucine (Ile), leucine (Leu), norleucine (Nle), norvaline (Nva), phenylalanine (Phe), proline (Pro), serine (Ser), threonine (Thr), and valine (Val). Particular examples of $B^2$ are alanine, arginine, capreomycidine, glycine, isoleucine, leucine, phenylalanine and valine. A particular embodiment is when $B^2$ is arginine, glycine, leucine, phenylalanine or valine.

$B^3$, which if present is connected to $B^2$ via the C-terminal of the $B^3$ amino acid, may be a large, aliphatic, aromatic, hydrophobic and/or neutral amino acid. Examples of $B^3$ are isoleucine (Ile), leucine (Leu), norleucine (Nle), norvaline (Nva), phenylalanine (Phe), phenylglycine, tyrosine (Tyr), tryptophan (Trp) and valine (Val). Particular examples of $B^3$ are leucine, phenylalanine, tyrosine and tryptophan.

The linker group L may be absent or selected from the group consisting of —C(═O)—, —C(═O)—C(═O)—, —C(═S)—, —C(═S)—C(═S)— or —C(═S)—C(═O)—. Particular embodiments include when L is absent or L is a carbonyl group-C(═O)—.

$A^1$, which if present is connected to L via the N-terminal of the amino acid, may be an aliphatic, aromatic, hydrophobic, neutral and/or polar amino acid. Examples of $A^1$ are alanine (Ala), arginine (Arg), capreomycidine (Cpd), glycine (Gly), isoleucine (Ile), leucine (Leu), norleucine (Nle), norvaline (Nva), phenylalanine (Phe), threonine (Thr), tyrosine (Tyr), tryptophan (Trp) and valine (Val). Particular examples of $A^1$ are alanine, arginine, glycine, leucine, phenylalanine, tyrosine, tryptophan and valine. A particular embodiment is when $B^2$ is leucine, phenylalanine, tyrosine or tryptophan.

The $A^2$ residue, which if present is connected to $A^1$ via the N-terminal of the amino acid, may be a large, aliphatic, aromatic, hydrophobic and/or neutral amino acid. Examples of $A^2$ are arginine (Arg), isoleucine (Ile), leucine (Leu), norleucine (Nle), norvaline (Nva), phenylalanine (Phe), phenylglycine, Tyrosine (Tyr), tryptophan (Trp) and valine (Val). Particular examples of $A^2$ are phenylalanine and tyrosine.

The N-terminal protection group P (if present) may be selected from formyl, acetyl (Ac), benzoyl (Bz), trifluoroacetyl, methoxysuccinyl, aromatic and aliphatic urethane protecting groups such as fluorenylmethyloxycarbonyl (Fmoc), methoxycarbonyl, (fluoromethoxy)carbonyl, benzyloxycarbonyl (Cbz), t-butyloxycarbonyl (Boc) and adamantyloxycarbonyl; p-methoxybenzyl carbonyl (Moz), benzyl (Bn), p-methoxybenzyl (PMB), p-methoxyphenyl (PMP), methoxyacetyl, methylamino carbonyl, methylsulfonyl, ethylsulfonyl, benzylsulfonyl, methylphosphoramidyl (MeOP(OH)(═O)) and benzylphosphoramidyl ($PhCH_2OP(OH)(═O)$).

The general formula of the peptide aldehyde may also be written: P-$A^2$-$A^1$-L-$B^3$-$B^2$ $B^1$-$B^0$-H, where P, $A^2$, $A^1$,L, $B^3$, $B^2$, $B^1$ and $B^0$ are as defined above.

In the case of a tripeptide aldehyde with a protection group (i.e. x=2, L is absent and A is absent), P is preferably acetyl, methoxycarbonyl, benzyloxycarbonyl, methylamino carbonyl, methylsulfonyl, benzylsulfonyl and benzylphosphoramidyl. In the case of a tetrapeptide aldehyde with a protection group (i.e. x=3, L is absent and A is absent), P is preferably acetyl, methoxycarbonyl, methylsulfonyl, ethylsulfonyl and methylphosphoramidyl.

Suitable peptide aldehydes are described in WO94/04651, WO95/25791, WO98/13458, WO98/13459, WO98/13460, WO98/13461, WO98/13462, WO07/141736, WO07/145963, WO09/118375, WO10/055052 and WO11/036153.

More particularly, the peptide aldehyde may be

Cbz-Arg-Ala-Tyr-H (L-Alaninamide, N2-[(phenylmethoxy)carbonyl]-L-arginyl-N-[(1S)-1-formyl-2-(4-hydroxyphenyl)ethyl]-), Ac-Gly-Ala-Tyr-H (L-Alaninamide, N-acetylglycyl-N-[(1S)-1-formyl-2-(4-hydroxyphenyl)ethyl]-)

Cbz-Gly-Ala-Tyr-H (L-Alaninamide, N-[(phenylmethoxy)carbonyl]glycyl-N-[(1S)-1-formyl-2-(4-hydroxyphenyl)ethyl]-), Cbz-Gly-Ala-Leu-H (L-Alaninamide, N-[(phenylmethoxy)carbonyl]glycyl-N-[(1S)-1-formyl-3-methylbutyl]-), Cbz-Val-Ala-Leu-H (L-Alaninamide, N-[(phenylmethoxy)carbonyl]-L-valyl-N-[(1S)-1-formyl-3-methylbutyl]-), Cbz-Gly-Ala-Phe-H (L-Alaninamide, N-[(phenylmethoxy)carbonyl]glycyl-N-[(1S)-1-formyl-2-phenylethyl]-), Cbz-Gly-Ala-Val-H (L-Alaninamide, N-[(phenylmethoxy)carbonyl]glycyl-N-[(1S)-1-formyl-2-methylpropyl]-), Cbz-Gly-Gly-Tyr-H (Glycinamide, N-[(phenylmethoxy)carbonyl]glycyl-N-[(1S)-1-formyl-2-(4-hydroxyphenyl)ethyl]-), Cbz-Gly-Gly-Phe-H (Glycinamide, N-[(phenylmethoxy)carbonyl]glycyl-N-[(1S)-1-formyl-2-phenylethyl]-), Cbz-Arg-Val-Tyr-H (L-Valinamide, N2-[(phenylmethoxy)carbonyl]-L-arginyl-N-[(1S)-1-formyl-2-(4-hydroxyphenyl)ethyl]-), Cbz-Leu-Val-Tyr-H (L-Valinamide, N-[(phenylmethoxy)carbonyl]-L-leucyl-N-[(1S)-1-formyl-2-(4-hydroxyphenyl)ethyl]-)

Ac-Leu-Gly-Ala-Tyr-H (L-Alaninamide, N-acetyl-L-leucylglycyl-N-[(1S)-1-formyl-2-(4-hydroxyphenyl)ethyl]-), Ac-Phe-Gly-Ala-Tyr-H (L-Alaninamide, N-acetyl-L-phenylalanylglycyl-N-[(1S)-1-formyl-2-(4-hydroxyphenyl)ethyl]-), Ac-Tyr-Gly-Ala-Tyr-H (L-Alaninamide, N-acetyl-L-tyrosylglycyl-N-[(1S)-1-formyl-2-(4-hydroxyphenyl)ethyl]-), Ac-Phe-Gly-Ala-Leu-H (L-Alaninamide, N-acetyl-L-phenylalanylglycyl-N-[(1S)-1-formyl-3-methylbutyl]-), Ac-Phe-Gly-Ala-Phe-H (L-Alaninamide, N-acetyl-L-phenylalanylglycyl-N-[(1S)-1-formyl-2-phenylethyl]-)

Ac-Phe-Gly-Val-Tyr-H (L-Valinamide, N-acetyl-L-phenylalanylglycyl-N-[(1S)-1-formyl-2-(4-hydroxyphenyl)ethyl]-), Ac-Phe-Gly-Ala-Met-H (L-Alaninamide, N-acetyl-L-phenylalanylglycyl-N-[(1S)-1-formyl-3-(methylthio)propyl]-), Ac-Trp-Leu-Val-Tyr-H (L-Valinamide, N-acetyl-L-tryptophyl-L-leucyl-N-[(1S)-1-formyl-2-(4-hydroxyphenyl)ethyl]-), MeO-CO-Val-Ala-Leu-H (L-Alaninamide, N-(methoxycarbonyl)-L-valyl-N-[(1S)-1-formyl-3-methylbutyl]-)

MeNHCO-Val-Ala-Leu-H (L-Alaninamide, N-(aminomethylcarbonyl)-L-valyl-N-[(1S)-1-formyl-3-methylbutyl]-), MeO-CO-Phe-Gly-Ala-Leu-H (L-Alaninamide, N-(methoxycarbonyl)-L-phenylalanylglycyl-N-[(1S)-1-formyl-3-methylbutyl]-), MeO-CO-Phe-Gly-Ala-Phe-H (L-Alaninamide, N-(methoxycarbonyl)-L-phenylalanylglycyl-N-[(1S)-1-formyl-2-phenylethyl]-), MeSO2-Phe-Gly-Ala-Leu-H (L-Alaninamide, N-(methylsulfonyl)-L-phenylalanylglycyl-N-[(1S)-1-formyl-3-methylbutyl]-),
MeSO2-Val-Ala-Leu-H (L-Alaninamide, N-(methylsulfonyl)-L-valyl-N-[(1S)-1-formyl-3-methylbutyl]-),
PhCH2O-P(OH)(O)-Val-Ala-Leu-H (L-Alaninamide, N-[hydroxy (phenylmethoxy) phosphinyl]-L-valyl-N-[(1S)-1-formyl-3-methylbutyl]-),
EtSO2-Phe-Gly-Ala-Leu-H (L-Alaninamide, N-(ethylsulfonyl)-L-phenylalanylglycyl-N-[(1S)-1-formyl-3-methylbutyl]-),
PhCH2SO2-Val-Ala-Leu-H (L-Alaninamide, N-[(phenylmethyl) sulfonyl]-L-valyl-N-[(1S)-1-formyl-3-methylbutyl]-),
PhCH2O-P(OH)(O)-Leu-Ala-Leu-H (L-Alaninamide, N-[hydroxy (phenylmethoxy) phosphinyl]-L-leucyl-N-[(1S)-1-formyl-3-methylbutyl]-),
PhCH2O-P(OH)(O)-Phe-Ala-Leu-H (L-Alaninamide, N-[hydroxy (phenylmethoxy) phosphinyl]-L-phenylalanyl-N-[(1S)-1-formyl-3-methylbutyl]-), or
MeO-P(OH)(O)-Leu-Gly-Ala-Leu-H; (L-Alaninamide, N-(hydroxymethoxyphosphinyl)-L-leucylglycyl-N-[(1S)-1-formyl-3-methylbutyl]-).

A preferred example is Cbz-Gly-Ala-Tyr-H.

Further examples of such peptide aldehydes include

α-MAPI (3,5,8,11-Tetraazatridecanoic acid, 6-[3-[(aminoiminomethyl)amino]propyl]-12-formyl-9-(1-methylethyl)-4,7,10-trioxo-13-phenyl-2-(phenylmethyl)-, (2S,6S,9S,12S)-
L-Valinamide, N2-[[(1-carboxy-2-phenylethyl)amino]carbonyl]-L-arginyl-N-(1-formyl-2-phenylethyl)-, [1(S), 2(S)]-; L-Valinamide, N2-[[[(1S)-1-carboxy-2-phenylethyl]amino]carbonyl]-L-arginyl-N-[(1S)-1-formyl-2-phenylethyl]-(9CI); SP-Chymostatin B),
β-MAPI (L-Valinamide, N2-[[[(1S)-1-carboxy-2-phenylethyl]amino]carbonyl]-L-arginyl-N-[(1R)-1-formyl-2-phenylethyl]-L-Valinamide, N2-[[(1-carboxy-2-phenylethyl)amino]carbonyl]-L-arginyl-N-(1-formyl-2-phenylethyl)-, [1(S),2(R)]-),
Phe-C(═O)-Arg-Val-Tyr-H (L-Valinamide, N2-[[[(1S)-1-carboxy-2-phenylethyl]amino]carbonyl]-L-arginyl-N-[(1S)-1-formyl-2-(4-hydroxyphenyl)ethyl]-(9CI)),
Phe-C(═O)-Gly-Gly-Tyr-H, (3,5,8,11-Tetraazatridecanoic acid, 12-formyl-13-(4-hydroxyphenyl)-4,7,10-trioxo-2-(phenylmethyl)-, (2S, 12S)-),
Phe-C(═O)-Gly-Ala-Phe-H, (3,5,8,11-Tetraazatridecanoic acid, 12-formyl-9-methyl-4,7,10-trioxo-13-phenyl-2-(phenylmethyl)-, (2S,9S, 12S)-),
Phe-C(═O)-Gly-Ala-Tyr-H (3,5,8,11-Tetraazatridecanoic acid, 12-formyl-13-(4-hydroxyphenyl)-9-methyl-4,7,10-trioxo-2-(phenylmethyl)-, (2S,9S, 12S)-),
Phe-C(═O)-Gly-Ala-Leu-H, (3,5,8,11-Tetraazapentadecanoic acid, 12-formyl-9,14-dimethyl-4,7,10-trioxo-2-(phenylmethyl)-, (2S,9S, 12S)-),
Phe-C(═O)-Gly-Ala-Nva-H, (3,5,8,11-Tetraazapentadecanoic acid, 12-formyl-9-methyl-4,7,10-trioxo-2-(phenylmethyl)-, (2S,9S,12S)-),
Phe-C(═O)-Gly-Ala-Nle-H (3,5,8,11-Tetraazahexadecanoic acid, 12-formyl-9-methyl-4,7,10-trioxo-2-(phenylmethyl)-, (2S,9S,12S)-),
Tyr-C(═O)-Arg-Val-Tyr-H (L-Valinamide, N2-[[[(1S)-1-carboxy-2-(4-hydroxyphenyl)ethyl]amino]carbonyl]-L-arginyl-N-[(1S)-1-formyl-2-(4-hydroxyphenyl)ethyl]-(9CI))
Tyr-C(═O)-Gly-Ala-Tyr-H (3,5,8,11-Tetraazatridecanoic acid, 12-formyl-13-(4-hydroxyphenyl)-2-[(4-hydroxyphenyl)methyl]-9-methyl-4,7,10-trioxo-, (2S,9S, 12S)-)
Phe-C(═S)-Arg-Val-Phe-H, (3,5,8,11-Tetraazatridecanoic acid, 6-[3-[(aminoiminomethyl)amino]propyl]-12-formyl-9-(1-methylethyl)-7,10-dioxo-13-phenyl-2-(phenylmethyl)-4-thioxo-, (2S,6S,9S,12S)-),
Phe-C(═S)-Arg-Val-Tyr-H, (3,5,8,11-Tetraazatridecanoic acid, 6-[3-[(aminoiminomethyl)amino]propyl]-12-formyl-13-(4-hydroxyphenyl)-9-(1-methylethyl)-7,10-dioxo-2-(phenylmethyl)-4-thioxo-, (2S,6S,9S, 12S)-),
Phe-C(═S)-Gly-Ala-Tyr-H, (3,5,8,11-Tetraazatridecanoic acid, 12-formyl-13-(4-hydroxyphenyl)-9-methyl-7,10-dioxo-2-(phenylmethyl)-4-thioxo-, (2S, 9S, 12S)-),
Antipain (L-Valinamide, N2-[[(1-carboxy-2-phenylethyl)amino]carbonyl]-L-arginyl-N-[4-[(aminoiminomethyl)amino]-1-formylbutyl]-),
GE20372A (L-Valinamide, N2-[[[(1S)-1-carboxy-2-(4-hydroxyphenyl)ethyl]amino]carbonyl]-L-arginyl-N-[(1S)-1-formyl-2-phenylethyl]-
L-Valinamide, N2-[[[1-carboxy-2-(4-hydroxyphenyl)ethyl]amino]carbonyl]-L-arginyl-N-(1-formyl-2-phenylethyl)-, [1(S),2(S)]-),
GE20372B (L-Valinamide, N2-[[[(1S)-1-carboxy-2-(4-hydroxyphenyl)ethyl]amino]carbonyl]-L-arginyl-N-[(1R)-1-formyl-2-phenylethyl]-
L-Valinamide, N2-[[[1-carboxy-2-(4-hydroxyphenyl)ethyl]amino]carbonyl]-L-arginyl-N-(1-formyl-2-phenylethyl)-, [1(S),2(R)]-),
Chymostatin A (L-Leucinamide, (2S)-2-[(4S)-2-amino-3,4,5,6-tetrahydro-4-pyrimidinyl]-N-[[[(1S)-1-carboxy-2-phenylethyl]amino]carbonyl]glycyl-N-(1-formyl-2-phenylethyl)-
L-Leucinamide, (2S)-2-[(4S)-2-amino-1,4,5,6-tetrahydro-4-pyrimidinyl]-N-[[[(1S)-1-carboxy-2-phenylethyl]amino]carbonyl]glycyl-N-(1-formyl-2-phenylethyl)-(9CI); L-Leucinamide,
L-2-(2-amino-1,4,5,6-tetrahydro-4-pyrimidinyl)-N-[[(1-carboxy-2-phenylethyl)amino]carbonyl]glycyl-N-(1-formyl-2-phenylethyl)-, stereoisomer),
Chymostatin B (L-Valinamide, (2S)-2-[(4S)-2-amino-3,4,5,6-tetrahydro-4-pyrimidinyl]-N-[[[(1S)-1-carboxy-2-phenylethyl]amino]carbonyl]glycyl-N-(1-formyl-2-phenylethyl)-
L-Valinamide, (2S)-2-[(4S)-2-amino-1,4,5,6-tetrahydro-4-pyrimidinyl]-N-[[[(1S)-1-carboxy-2-phenylethyl]amino]carbonyl]glycyl-N-(1-formyl-2-phenylethyl)-(9CI); L-Valinamide, L-2-(2-amino-1,4,5,6-tetrahydro-4-pyrimidinyl)-N-[[(1-carboxy-2-phenylethyl)amino]carbonyl]glycyl-N-(1-formyl-2-phenylethyl)-, stereoisomer), and
Chymostatin C (L-Isoleucinamide, (2S)-2-[(4S)-2-amino-3,4,5,6-tetrahydro-4-pyrimidinyl]-N-[[[(1S)-1-carboxy-2-phenylethyl]amino]carbonyl]glycyl-N-(1-formyl-2-phenylethyl)-
L-Isoleucinamide, (2S)-2-[(4S)-2-amino-1,4,5,6-tetrahydro-4-pyrimidinyl]-N-[[[(1S)-1-carboxy-2-phenylethyl]amino]carbonyl]glycyl-N-(1-formyl-2-phenylethyl)-(9CI); L-Isoleucinamide, L-2-(2-amino-1,4,5,6-tetrahydro-4-pyrimidinyl)-N-[[(1-carboxy-2-phenylethyl)amino]carbonyl]glycyl-N-(1-formyl-2-phenylethyl)-, stereoisomer).

Peptide Aldehyde Adducts

Instead of a peptide aldehyde, the protease inhibitor may be an adduct of a peptide aldehyde. The adduct maybe a hydrosulfite adduct having the formula P-$(A)_y$-L-$(B)_x$-N(H)—CHR—CH(OH)—$SO_3M$, wherein P, A, y, L, B, x and R are defined as above, and M is H or an alkali metal, preferably Na or K. Alternatively, the adduct may be a hemiacetal having the formula P-$(A)_y$-L-$(B)_x$-N(H)—CHR—CH(OH)—OR, wherein P, A, y, L, B, x and R are defined as above. A preferred embodiment is a hydrosulfite adduct wherein P=Cbz, $B^2$=Gly; $B^1$=Ala; $B^0$=Tyr (so R=$PhCH_2$, R'=OH), x=2, y=0, L=A=absent and M=Na (Cbz-Gly-Ala-N(H)—$CH(CH_2$-p-$C_6H_4OH)$—CH(OH)—$SO_3Na$, L-Alaninamide, N-[(phenylmethoxy)carbonyl] glycyl-N-[2-hydroxy-1-[(4-hydroxyphenyl)methyl]-2-sulfoethyl]-, sodium salt (1:1)).

The general formula of the hydrosulfite adduct of a peptide aldehyde may also be written: P-$A^2$-$A^1$-L-$B^3$-$B^2$-$B^1$-N(H)—CHR—CH(OH)—$SO_3M$, where P, $A^2$, $A^1$,L, $B^3$, $B^2$, $B^1$, R and M are as defined above.

Alternatively, the adduct of a peptide aldehyde can be Cbz-Gly-Ala-N(H)—$CH(CH_2$-p-$C_6H_4OH)$—CH(OH)—$SO_3Na$ (Sodium (2S)—[(N—{N-[(benzyloxy)carbonyl] glycyl}-L-alaninyl)amino]-1-hydroxy-3-(4-hydroxyphenyl) propane-1-sulfonate) or Cbz-Gly-Ala-N(H)—$CH(CH_2Ph)$-CH(OH)—$SO_3Na$ (Sodium (2S)—[(N—{N-[(benzyloxy) carbonyl]glycyl}-L-alaninyl)amino]-1-hydroxy-3-(phenyl) propane-1-sulfonate) or "MeO-CO_Val-Ala-N(H)—CH $(CH_2CH(CH_3)_2)$—CH(OH)—$SO_3Na$ (Sodium (2S)—[(N—{N-[(benzyloxy)carbonyl]glycyl}-L-alaninyl)amino]-1-hydroxy-3-(2-propanyl)propane-1-sulfonate).

Other preferred peptide aldehyde bisulfites are

- Cbz-Arg-Ala-$NHCH(CH_2C_6H_4OH)C(OH)(SO_3M)$-H where M=Na,
- Ac-Gly-Ala-$NHCH(CH_2C_6H_4OH)C(OH)(SO_3M)$-H, where M=Na,
- Cbz-Gly-Ala-$NHCH(CH_2C_6H_4OH)C(OH)(SO_3M)$-H, where M=Na (L-Alaninamide, N-[(phenylmethoxy) carbonyl]glycyl-N-[2-hydroxy-1-[(4-hydroxyphenyl) methyl]-2-sulfoethyl]-, sodium salt (1:1)),
- Cbz-Gly-Ala-$NHCH(CH_2CH(CH_3)_2))C(OH)(SO_3M)$-H, where M=Na,
- Cbz-Val-Ala-$NHCH(CH_2CH(CH_3)_2))C(OH)(SO_3M)$-H, where M=Na,
- Cbz-Gly-Ala-$NHCH(CH_2Ph)C(OH)(SO_3M)$-H, where M=Na,
- Cbz-Gly-Ala-$NHCH(CH(CH_3)_2)C(OH)(SO_3M)$-H, where M=Na,
- Cbz-Gly-Gly-$NHCH(CH_2C_6H_4OH)C(OH)(SO_3M)$-H, where M=Na,
- Cbz-Gly-Gly-$NHCH(CH_2Ph)C(OH)(SO_3M)$-H, where M=Na,
- Cbz-Arg-Val-$NHCH(CH_2C_6H_4OH)C(OH)(SO_3M)$-H, where M=Na,
- Cbz-Leu-Val-$NHCH(CH_2C_6H_4OH)C(OH)(SO_3M)$-H, where M=Na,
- Ac-Leu-Gly-Ala-$NHCH(CH_2C_6H_4OH)C(OH)(SO_3M)$-H, where M=Na,
- Ac-Phe-Gly-Ala-$NHCH(CH_2C_6H_4OH)C(OH)(SO_3M)$-H, where M=Na,
- Ac-Tyr-Gly-Ala-$NHCH(CH_2C_6H_4OH)C(OH)(SO_3M)$-H, where M=Na,
- Ac-Phe-Gly-Ala-$NHCH(CH_2CH(CH_3)_2))C(OH)(SO_3M)$-H, where M=Na,
- Ac-Phe-Gly-Ala-$NHCH(CH_2Ph)C(OH)(SO_3M)$-H, where M=Na,
- Ac-Phe-Gly-Val-$NHCH(CH_2C_6H_4OH)C(OH)(SO_3M)$-H, where M=Na,
- Ac-Phe-Gly-Ala-$NHCH(CH_2CH_2SCH_3)(SO_3M)$-H, where M=Na,
- Ac-Trp-Leu-Val-$NHCH(CH_2C_6H_4OH)C(OH)(SO_3M)$-H, where M=Na,
- MeO-CO-Val-Ala-$NHCH(CH_2CH(CH_3)_2))C(OH)(SO_3M)$-H, where M=Na,
- MeNCO-Val-Ala-$NHCH(CH_2CH(CH_3)_2))C(OH)(SO_3M)$-H, where M=Na,
- MeO-CO-Phe-Gly-Ala-$NHCH(CH_2CH(CH_3)_2))C(OH)(SO_3M)$-H, where M=Na,
- MeO-CO-Phe-Gly-Ala-$NHCH(CH_2Ph)C(OH)(SO_3M)$-H, where M=Na,
- $MeSO_2$-Phe-Gly-Ala-$NHCH(CH_2CH(CH_3)_2)C(OH)(SO_3M)$-H, where M=Na,
- $MeSO_2$-Val-Ala-$NHCH(CH_2CH(CH_3)_2))C(OH)(SO_3M)$-H, where M=Na,
- $PhCH_2O(OH)(O)$ P-Val-Ala-$NHCH(CH_2CH(CH_3)_2))C(OH)(SO_3M)$-H, where M=Na,
- $EtSO_2$-Phe-Gly-Ala-$NHCH(CH_2CH(CH_3)_2))C(OH)(SO_3M)$-H, where M=Na,
- $PhCH_2SO_2$-Val-Ala-$NHCH(CH_2CH(CH_3)_2))C(OH)(SO_3M)$-H, where M=Na,
- $PhCH_2O(OH)(O)$ P-Leu-Ala-$NHCH(CH_2CH(CH_3)_2))C(OH)(SO_3M)$-H, where M=Na,
- $PhCH_2O(OH)(O)$ P-Phe-Ala-$NHCH(CH_2CH(CH_3)_2))C(OH)(SO_3M)$-H, where M=Na,
- MeO(OH)(O) P-Leu-Gly-Ala-$NHCH(CH_2CH(CH_3)_2))C(OH)(SO_3M)$-H, where M=Na, and
- Phe-urea-Arg-Val-$NHCH(CH_2C_6H_4OH)C(OH)(SO_3M)$-H where M=Na.

Salt

The salt used in the bar is a salt of a monovalent cation and an organic anion. The monovalent cation may be for example $Na^+$, $K^+$ or $NH_4^+$. The organic anion may be for example formate, acetate, citrate or lactate. Thus, a salt of a monovalent cation and an organic anion may be, for example, sodium formate, potassium formate, ammonium formate, sodium acetate, potassium acetate, ammonium acetate, sodium lactate, potassium lactate, ammonium lactate, mono-sodium citrate, di-sodium citrate, tri-sodium citrate, sodium potassium citrate, potassium citrate, ammonium citrate or the like. A particular embodiment is sodium formate.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water-soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water-soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water-soluble film. The compartment for liquid components can be different in composition than compartments containing solids. Ref: (US2009/0011970 A1).

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may be non-aqueous.

Method of Producing the Composition

The present invention also relates to methods of producing the composition.

Uses

The present invention is also directed to methods for using the compositions thereof.

Use in Detergents.

The polypeptides of the present invention may be added to and thus become a component of a detergent composition.

The detergent composition of the present invention may be formulated, for example, as a hand or machine laundry detergent composition including a laundry additive composition suitable for pre-treatment of stained fabrics or for rejuvenating textile (e.g. by fuzz or pill removal) to restore some of the visual and feel properties of fabrics after extended use to match that of a new textile, and a rinse added fabric softener composition, or be formulated as a detergent composition for use in general household hard surface cleaning operations, or be formulated for hand or machine dishwashing operations.

In a specific aspect, the present invention provides a detergent additive comprising a polypeptide of the present invention as described herein.

Paragraphs

Paragraph 1. A variant of a parent polypeptide having glycoside hydrolase (EC 3.2.1.-) activity, wherein the variant comprises a catalytic domain, a proline-rich linker region, and a carbohydrate binding module (CBM), and wherein the variant has glycoside hydrolase activity.

Paragraph 2. A variant of a parent polypeptide having cellulase activity, wherein the variant comprises a catalytic domain, a proline-rich linker region, and a carbohydrate binding module (CBM), and wherein the variant has cellulase activity.

Paragraph 3. A variant of a parent polypeptide having endoglucanase activity, wherein the variant comprises a catalytic domain, a proline-rich linker region, and a carbohydrate binding module (CBM), and wherein the variant has endoglucanase activity.

Paragraph 4. The variant of any of paragraphs 1-3, wherein the variant has improved stability in comparison with the parent in an aqueous composition comprising a protease.

Paragraph 5. A variant of a parent polypeptide having glycoside hydrolase (EC 3.2.1.-) activity, wherein the variant comprises a catalytic domain, an engineered linker region, and a carbohydrate binding module (CBM), and wherein the variant has glycoside hydrolase activity, wherein the variant has improved stability in comparison with the parent in an aqueous composition comprising a protease.

Paragraph 6. A variant of a parent polypeptide having cellulase activity, wherein the variant comprises a catalytic domain, an engineered linker region, and a carbohydrate binding module (CBM), and wherein the variant has cellulase activity, wherein the variant has improved stability in comparison with the parent in an aqueous composition comprising a protease.

Paragraph 7. A variant of a parent polypeptide having endoglucanase activity, wherein the variant comprises a catalytic domain, an engineered linker region, and a carbohydrate binding module (CBM), and wherein the variant has endoglucanase activity, wherein the variant has improved stability in comparison with the parent in an aqueous composition comprising a protease.

Paragraph 8. A variant which is a hybrid polypeptide having glycoside hydrolase activity, such as endoglucanase activity, preferably GH45 endoglucanase activity, comprising (a) a catalytic domain from a polypeptide having glycoside hydrolase activity, such as endoglucanase activity, preferably GH45 endoglucanase activity, (b) a linker selected from the group consisting of PPPPPPP (SEQ ID NO: 31), PPPPPPPG (SEQ ID NO: 30), SPSPSPSPSP (SEQ ID NO: 58) and SPSPSPSPSPG (SEQ ID NO: 25), and (c) a carbohydrate binding module (CBM), preferably a CBM1.

Paragraph 9. The hybrid polypeptide of paragraph 8, which has improved stability in comparison with the parent in an aqueous composition comprising a protease.

Paragraph 10. The variant of any of the preceding paragraphs, wherein improved stability is determined according to the assay described in Example 2 and/or Example 7.

Paragraph 11. The variant of any of the preceding claims, which is a family GH45 endoglucanase.

Paragraph 12. The variant of any of the preceding paragraphs, wherein the CBM is a CBM1.

Paragraph 13. The variant of any of the preceding paragraphs, wherein the variant comprises an N-terminal catalytic domain and a C-terminal CBM.

Paragraph 14. The variant of any of the preceding paragraphs, wherein the variant comprises a C-terminal catalytic domain and an N-terminal CBM.

Paragraph 15. The variant of any of the preceding paragraphs, wherein the variant demonstrates improved fabric or textile care and/or improved wash performance relative to the parent, e.g., after storage in the presence of protease.

Paragraph 16. The variant of any of the preceding paragraphs, wherein the linker comprises at least 25% proline, e.g., at least 28% proline, at least 30% proline, at least 35% proline, at least 40% proline, at least 50% proline, such as at least 60%, at least 66%, at least 70%, at least 75%, at least 80%, at least 85%, at least 90% proline.

Paragraph 17. The variant of any of the preceding paragraphs, wherein the linker has a length of at least four amino acids, and comprises one or more of the following optionally repeating motifs:

a. [P/S/T/R/K/D/E]P, preferably [P/S/T]P; most preferably $(SP)_a$, a=2-10 or $P_b$, b=4-20, preferably 4-15 (SEQ ID NO: 202);
b. P[S/T/R/K/D/E/N/Q]P[S/T/R/K/D/E] (SEQ ID NO: 102), preferably P[S/E]PT (SEQ ID NO: 109).

Paragraph 18. The variant of any of the preceding paragraphs, wherein the linker has a length of at least four amino acids, and comprises the following optionally repeating motifs: [S/T/R/K/D/E]P[S/T/R/K/D/E/N/Q][P/S/T/R/K/D/E][P/S/T/R/K/D/E]P and/or P[P/S/T/R/K/D/E][P/S/T/R/K/D/E].

Paragraph 19. The variant of any of the preceding paragraphs, wherein the linker comprises:

a. $(SP)_a$, a=2-10 (SEQ ID NO: 202);
b. $(PS)_a$, a=2-10 (SEQ ID NO: 203);
c. $P_b$, b=4-20, preferably 4-15 (SEQ ID NO: 204);
d. (PEPT (SEQ ID NO: $125)_c$, c=2-5 (SEQ ID NO: 79);
e. (PSPT (SEQ ID NO: $104))_d$, d=2-5 (SEQ ID NO: 150);
f. (P[S/T/R/K/D/E/N/Q]P[S/T/R/K/D/E] (SEQ ID NO: $102))_e$, e=2-5 (SEQ ID NO: 205);
g. $([S/T/R/K/D/E]P)_f$, f=2-10, preferably 2-5 (SEQ ID NO: 206);
h. $([S/T/R/K/D/E/N/Q]P[S/T/R/K/D/E])_g$, g=2-6 (SEQ ID NO: 207);
i. $([S/T/R/K/D/E/N/Q][S/T/R/K/D/E/N/Q]P)_h$, h=2-5 (SEQ ID NO: 208);
j. $(TP)_i$, i=2-10 (SEQ ID NO: 209);
k. $([S/T/P][S/T/P][S/T/P]))_j$, j=2-11 (SEQ ID NO: 210); and/or combinations thereof, wherein combinations of the respective monomeric units are contemplated.

Paragraph 20. The variant of any of the preceding claims, wherein the linker comprises:

a. $(SP)_a$, a=2-10 (SEQ ID NO: 202);
b. $(PS)_a$, a=2-10 (SEQ ID NO: 203);
c. $P_b$, b=4-20, preferably 4-15 (SEQ ID NO: 204); or
d. (PEPT (SEQ ID NO: $125))_c$, c=2-5 (SEQ ID NO: 79).

Paragraph 21. The variant of any of the preceding paragraphs, wherein the linker has a length of at least 4 amino acids and not more than 30 amino acids, such as 4-28 amino acids, preferably 4-20 amino acids, or even 4-10 amino acids, such as 4 amino acids, 5 amino acids, 6 amino acids, 7 amino acids, 8 amino acids, 9 amino acids or 10 amino acids.

Paragraph 22. The variant of any of the preceding paragraphs, wherein the linker comprises one or more of SPSP (SEQ ID NO: 130), SPSPSP (SEQ ID NO: 131), SPSPSPSP (SEQ ID NO: 132), SPSPSPSPSP (SEQ ID NO: 58), SPSPSPSPSPSP (SEQ ID NO: 133), SPSPSPSPSPSPSP (SEQ ID NO: 134), SPSPSPSPSPSPSPSP (SEQ ID NO: 135), PPPP (SEQ ID NO: 27), PPPPP (SEQ ID NO: 28), PPPPPP (SEQ ID NO: 29), PPPPPPP (SEQ ID NO: 31), PPPPPPPP (SEQ ID NO: 136), PPPPPPPPP (SEQ ID NO: 137), PPPPPPPPPP (SEQ ID NO: 138), PPPPPPPPPPP (SEQ ID NO: 139), PPPPPPPPPPPP PPPPPPPPPPPPPPPPPPPPPPPPPPP (SEQ ID NO: 142), PPPPPPPPPPPPPPPPPEQ ID NO: 143), PEPTPEPT (SEQ ID NO: 144), PEPTPEPTPEPT (SEQ ID NO: 145), PEPTPEPTPEPTPEPT (SEQ ID NO: 146), PEPTPEPTPEPTPEPTPEPT (SEQ ID NO: 79), PSPTPSPT (SEQ ID NO: 147), PSPTPSPTPSPT (SEQ ID NO: 148), PSPTPSPTPSPTPSPT (SEQ ID NO: 149), PSPTPSPTPSPTPSPTPSPT (SEQ ID NO: 150), SPSSPS (SEQ ID NO: 151), SPSSPSSPS (SEQ ID NO: 152), SPSSPSSPSSPS (SEQ ID NO: 153), SPSSPSSPSSPSSPS (SEQ ID NO: 154), TPTTPT (SEQ ID NO: 155), TPTTPTG (SEQ ID NO: 96), TPTTPTTPT (SEQ ID NO: 156), TPTTPTTPTTPT (SEQ ID NO: 157), TPTTPTTPTTPTTPT (SEQ ID NO: 158), PEPTPRPTPEPTPRPT (SEQ ID NO: 159), PEPTPKPTPEPTPKPT (SEQ ID NO: 160), PEPTPQPTPEPTPQPT (SEQ ID NO: 161), PRPTPEPTPRPT (SEQ ID NO: 162), PKPTPEPTPKPT (SEQ ID NO: 163), PEPTPQPT (SEQ ID NO: 164), PEPTPQPTPEPT (SEQ ID NO: 165), PEPTPRPTPEPTPRPTG (SEQ ID NO: 85), PEPTPKPTPEPTPKPTG (SEQ ID NO: 87), PEPTPQPTPEPTPQPTG (SEQ ID NO: 88), PRPTPEPTPRPTG (SEQ ID NO: 89), PKPTPEPTPKPTG (SEQ ID NO: 90), PEPTPQPTG (SEQ ID NO: 91), PEPTPQPTPEPTG (SEQ ID NO: 92), PPPGGPGGPGTPTSTAPGSGPTSPGGGSG (SEQ ID NO: 82).

Paragraph 23. The variant of any of the preceding paragraphs, wherein the linker further comprises a glycine in the C-terminal position.

Paragraph 24. The variant of any of the preceding paragraphs, wherein the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25).

Paragraph 25. The variant of any of the preceding paragraphs, wherein the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is a CBM1.

Paragraph 26. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence as shown in positions 1-212 of SEQ ID NO: 1, positions 1-211 of SEQ ID NO: 2, positions 1-210 of SEQ ID NO: 3, positions 1-211 of SEQ ID NO: 4. Paragraph 27. The variant of any of the preceding paragraphs, wherein the CBM comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence as shown in SEQ ID NO: 6, SEQ ID NO: 7, SEQ ID NO: 8, SEQ ID NO: 9, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200.

Paragraph 28. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is a CBM1.

Paragraph 29. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 6.

Paragraph 30. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 7.

Paragraph 31. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 8.

Paragraph 32. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 9.

Paragraph 33. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 173.

Paragraph 34. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 174.

Paragraph 35. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 175.

Paragraph 36. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 176.

Paragraph 37. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 177.

Paragraph 38. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 178.

Paragraph 39. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 179.

Paragraph 40. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 180.

Paragraph 41. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 181.

Paragraph 42. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 182.

Paragraph 43. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 183.

Paragraph 44. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 184.

Paragraph 45. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 185.

Paragraph 46. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 186.

Paragraph 47. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 187.

Paragraph 48. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 188.

Paragraph 49. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 189.

Paragraph 50. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 190.

Paragraph 51. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 191.

Paragraph 52. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 192.

Paragraph 53. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 193.

Paragraph 54. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 194.

Paragraph 55. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 195.

Paragraph 56. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 196.

Paragraph 57. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 197.

Paragraph 58. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 198.

Paragraph 59. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 199.

Paragraph 60. The variant of any of the preceding paragraphs, wherein the catalytic domain comprises an amino acid sequence having at least 70% sequence identity, e.g., at least 75% sequence identity, at least 80% sequence identity, at least 85% sequence identity, at least 90% sequence identity, at least 95% sequence identity, at least 96% sequence identity, at least 97% sequence identity, at least 98% sequence identity, at least 99% sequence identity to the amino acid sequence of SEQ ID NO: 5, the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25) and the CBM is SEQ ID NO: 200.

Paragraph 61. The variant of any of the preceding paragraphs, further comprising a substitution selected from the group consisting of:

Q147R+Q156E;
Q147R+Q169Y;
S56A+Q147R;
Q147R+A162E;
Q147R+Q156E+A162E;
A25G+S56A+Q147R;
N134D+Q156E+A162E;
S56A+N134D+Q156E+A162E;
A25G+S56A+Q156E+A162E;
A25G+N134D+Q156E+A162E;
A25G+S56A+N134D+Q169Y;

S56A+N134D+A162E;
S56A+Q147R+Q169Y;
N134D+Q147R;
Q156E+Q169Y;
S56A+N134D+Q147R;
S56A+N134D+Q156E+Q169Y;
S56A+A146D+Q147R+Q169Y;
S56A+N134D+Q147R+Q169Y;
S56A+Q147R+A162E+Q169Y;
S2*+S56A+Q147R+Q169Y;
S41T+S56A+Q147R+Q169Y;
S56A+S77N+Q147R+Q169Y;
S56A+T104K+Q147R+Q169Y;
S56A+Q147R+K165Q+Q169Y;
S56A+Q147R+Q169Y+1194L;
S56A+Q147R+Q169Y+K201R;
S56A+Q147R+Q169Y+G219W;
N44D+S56A+Q147R+Q169Y;
N50E+S56A+Q147R+Q169Y;
A32S+S56A+Q147R+Q169Y;
N44D+S56A+Q147R+Q169Y;
S56A+Q147R+Q169Y+Q186R;
S56A+Q147R+Q169Y+F183V;
S56A+A146S+Q147R+A162E+Q169Y;
S56A+N134D+Q147R;
S56A+N134D+Q147R+A162E;
A32S+S56A+N134D+Q147R+Q169Y+F183V;
S56A+N134D+Q147R+A162E+Q169Y+F183V;
A32S+S56A+S77N+N134D+Q147R+A162E+Q169Y;
A32S+S56A+N134D+Q147R+Q169Y;
S56A+N134D+Q147R+A162E+Q169Y;
A32S+S56A+N134D+A146S+Q147R+Q169Y;
A32S+S56A+N134D+A146D+Q147R+Q169Y;
A32S+S56A+N134D+Q147R+Q169Y+F183V;
A32S+S56A+N134D+Q147R+Q169Y+K201R;
S56A+N134D+A146D+Q147R+Q169Y+F183V;
S56A+N134D+A146D+Q147R+A162E+Q169Y;
S56A+N134D+A146D+Q147R+Q169Y+K201R;
S56A+N134D+Q147R+A162E+Q169Y+F183V;
S56A+N134D+Q147R+Q169Y+F183V+K201R;
A32S+S56A+S77N+N134D+Q147R+Q169Y+F183V;
A32S+S56A+S77N+N134D+Q147R+A162E+Q169Y;
A32S+S56A+N134D+A146S+Q147R+Q169Y+F183V;
A32S+S56A+N134D+A146D+Q147R+Q169Y+F183V; or
A32S+S56A+N134D+A146D+Q147R+A162E+Q169Y.

Paragraph 62. The variant of any of the preceding paragraphs, wherein the linker is as set forth in Table A.

Paragraph 63. The variant of any of the preceding paragraphs, wherein the variant is as set forth in Table B1, Table B2, Table C1, Table C2, Table D.

Paragraph 64. An isolated polynucleotide encoding the variant of any of paragraphs 1-63.

Paragraph 65. A nucleic acid construct comprising the polynucleotide of paragraph 64.

Paragraph 66. An expression vector comprising the polynucleotide of paragraph 64.

Paragraph 67. A host cell comprising the polynucleotide of paragraph 64.

Paragraph 68. A method of producing variant having glycoside hydrolase (EC 3.2.1.-), cellulase, or endoglucanase activity, comprising:

a. cultivating the host cell of paragraph 67 under conditions suitable for expression of the variant; and
b. recovering the variant.

Paragraph 69. A method for obtaining a variant having glycoside hydrolase (EC 3.2.1.-), cellulase, or endoglucanase activity, comprising introducing into a parent glycoside hydrolase a proline-rich linker region; and recovering the variant.

Paragraph 70. A whole broth formulation or cell culture composition comprising the variant of any of paragraphs 1-63.

Paragraph 71. A composition comprising a variant according to any of the paragraphs 1-63.

Paragraph 72. The composition of paragraph 71, further comprising a protease.

Paragraph 73. The composition of any of paragraphs 71-72, further comprising one or more additional enzymes selected from the group consisting of (additional) protease, lipase, cutinase, amylase, (additional) carbohydrase, (additional) cellulase, pectinase, mannanase, arabinase, galactanase, xylanase, nuclease, licheninase, oxidase, e.g., a laccase, and/or peroxidase, and combinations thereof.

Paragraph 74. The composition of any of paragraphs 71-73, further comprising an amylase.

Paragraph 75. The composition of any of paragraphs 71-74, further comprising another carbohydrase.

Paragraph 76. The composition of any of paragraphs 71-75, further comprising a licheninase.

Paragraph 77. The composition according to any of paragraphs 71-76, which is a detergent composition.

Paragraph 78. The composition according to any of paragraphs 71-77, further comprising one or more compounds selected among surfactants, builders and co-builders and polymers.

Paragraph 79. The composition according to any one of paragraphs 71-78, being a liquid detergent composition.

Paragraph 80. Use of a variant according to any of the paragraphs 1-63 for cleaning fabric, textiles or hard surfaces.

Paragraph 81. Use of a variant according to any one of paragraphs 1-63 or a composition of any one of paragraphs 71-78 for fabric or textile care, such as for pre-treatment of stained fabrics or for rejuvenating textile (e.g. by fuzz or pill removal), to restore the visual and feel properties of fabrics after extended use to match that of a new textile.

Paragraph 82. The use of paragraph 80-81 comprising the use of a variant according to any of the paragraphs 1-63 or a composition according to any of the paragraphs 71-79 for laundry.

Paragraph 83. The use of paragraph 82 comprising use of a variant according to any of paragraphs 1-63 or a composition according to any of paragraphs 71-79 as a rinse added fabric softener composition.

Paragraph 84. A method for reducing or preventing soil redeposition comprising contacting a polypeptide or composition or detergent composition of any of the preceding paragraphs.

Paragraph 85. A method for fabric or textile care using a polypeptide or composition or detergent composition of any of the preceding paragraphs.

Paragraph 86. A method for washing an object, such as a fabric or textile, comprising (a) providing a wash liquor by dissolving/mixing the variant according to any of paragraphs 1-63 or the composition according to any of paragraphs 71-79 in water to provide a wash liquor;
(b) washing the object in the wash liquor;
(c) draining the wash liquor and optionally repeating the wash cycle; and
(d) rinsing and optionally drying the object.

Paragraph 87. A method for washing an object, such as a fabric or textile, comprising (a) providing water and rinsing the object;

(b) optionally, draining the water and providing fresh water;

(c) dosing the variant according to any of paragraphs 1-63 or the composition according to any of paragraphs 71-79 to form a wash liquor;

(d) agitating the wash liquor, thereby washing the object, optionally heating the wash liquor; and (e) draining the wash liquor.

EXAMPLES

Materials and Methods

General methods of PCR, cloning, ligation nucleotides etc. are well-known to a person skilled in the art and may for example be found in in "Molecular cloning: A laboratory manual", Sambrook et al. (1989), Cold Spring Harbor lab., Cold Spring Harbor, NY; Ausubel, F. M. et al. (eds.); "Current protocols in Molecular Biology", John Wiley and Sons, (1995); Harwood, C. R., and Cutting, S. M. (eds.); "DNA Cloning: A Practical Approach, Volumes I and II", D.N. Glover ed. (1985); "Oligonucleotide Synthesis", M.J. Gait ed. (1984); "Nucleic Acid Hybridization", B.D. Hames & S. J. Higgins eds (1985); "A Practical Guide To Molecular Cloning", B. Perbal, (1984).

Assay for Cellulolytic Activity

Cellulolytic activity is determined using the Cellulase Assay Kit (CellG5 Method) provided from Megazyme, (Wicklow, Ireland; Product-code: K-CellG5-4V), following the manufacturer's instructions.

The CellG5 assay reagent for the measurement of endo-cellulase (endo-1,4-B-glucanase) contains two components;

1) 4,6-O-(3-Ketobutylidene)-4-nitrophenyl-β-D-cello-pentaoside (BPNPG5) and 2) thermostable B-glucosidase. The ketone blocking group prevents any hydrolytic action by the β-glucosidase on BPNPG5. Incubation with an endo-cellulase generates a non-blocked colourimetric oligosaccharide that is rapidly hydrolysed by the ancillary B-glucosidase. The rate of formation of 4-nitrophenol is therefore directly related to the hydrolysis of BPNPG5 by the endo-cellulase.

Composition of Model Detergent A (Liquid)

Composition of detergent A (liquid): Ingredients: 12% LAS, 11% AEO Biosoft N25-7 (NI), 7% AEOS (SLES), 6% MPG (monopropylene glycol), 3% ethanol, 3% TEA, 2.75% cocoa soap, 2.75% soya soap, 2% glycerol, 2% sodium hydroxide, 2% sodium citrate, 1% sodium formiate, 0.2% DTMPA and 0.2% PCA (all percentages are w/w).

Protease

The proteases used for the examples is of SEQ ID NO: 10. Other proteases include those of SEQ ID NO: 11, or SEQ ID NO: 11 having mutations

S9E+N42R+N74D+V199I+Q200L+Y203W+S253D+N255W+L256E.

Wash Assays

Launder-O-Meter (LOM) Model Wash System

The Launder-O-Meter (LOM) is a medium scale model wash system that can be applied to test up to 20 different wash conditions simultaneously. A LOM is basically a large temperature-controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker.

The LOM model wash system is mainly used in medium scale testing of detergents and enzymes at European wash conditions. In a LOM experiment, factors such as the ballast to soil ratio and the fabric to wash liquor ratio can be varied. Therefore, the LOM provides the link between small scale experiments, such as AMSA and mini-wash, and the more time-consuming full-scale experiments in front loader washing machines.

Mini Launder-O-Meter (MiniLOM) Model Wash System

MiniLOM is a modified mini wash system of the Launder-O-Meter (LOM), which is a medium scale model wash system that can be applied to test up to 20 different wash conditions simultaneously. A LOM is basically a large temperature-controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker.

The LOM model wash system is mainly used in medium scale testing of detergents and enzymes at European wash conditions. In a LOM experiment, factors such as the ballast to soil ratio and the fabric to wash liquor ratio can be varied. Therefore, the LOM provides the link between small scale experiments, such as AMSA and mini-wash, and the more time-consuming full-scale experiments in front loader washing machines.

In miniLOM, washes are performed in 50 ml test tubes placed in Stuart rotator.

Terg-O-Tometer (TOM) Wash Assay

The Terg-O-tometer (TOM) is a medium scale model wash system that can be applied to test 12 different wash conditions simultaneously. A TOM is basically a large temperature-controlled water bath with up to 12 open metal beakers submerged into it. Each beaker constitutes one small top loader style washing machine and during an experiment, each of them will contain a solution of a specific detergent/enzyme system and the soiled and unsoiled fabrics its performance is tested on. Mechanical stress is achieved by a rotating stirring arm, which stirs the liquid within each beaker. Because the TOM beakers have no lid, it is possible to withdraw samples during a TOM experiment and assay for information on-line during wash.

The TOM model wash system is mainly used in medium scale testing of detergents and enzymes at US or LA/AP wash conditions. In a TOM experiment, factors such as the ballast to soil ratio and the fabric to wash liquor ratio can be varied. Therefore, the TOM provides the link between small scale experiments and the more time-consuming full-scale experiments in top loader washing machines.

Example 1: Determining the Stability of Cellulase Variants (Core Stability Method)

The stability of cellulase variants is measured in 90% liquid detergent A containing protease. The in-detergent stability is assessed by measuring the activity of the variants by the CellG5 kit after incubation of the enzyme-detergent mixture containing protease.

Temperature/Protease Stress Conditions in 90% Detergent A:

In a 96well microplate (polystyrene), 20 μL of a 1000 ppm purified endo-cellulase diluted in buffer (100 mM HEPES; 0.01% Tween-20; pH 7.5)) is mixed with 180 μL of detergent A containing 0.3 mg/mL active enzyme protease protein 15 μL of the enzyme/detergent mix is transferred into two new 384 well microplates and sealed. One of the two identical plates was stored at 5° C. (reference) while the other was incubated at elevated temperature (stress) for 16 or 17 hours. See result-tables for stress-temperature used. After incubation, 60 μL of assay buffer (100 mM HEPES; 0.01% Tween-20; pH 7.5) is added to the samples in both plates and mixed vigorously for the subsequent activity measurement.

Assaying Samples for Cellulolytic Activity (CellG5 Kit);

The enzymatic activity is measured by mixing 20 μL of the diluted enzyme-detergent mixture with 10 UL assay buffer (100 mM HEPES; 0.01% Tween-20; pH 7.5) and 10 μL freshly prepared substrate solution in a UV-transparent 384well microplate. Substrate solution of the CellG5 assay kit is prepared by mixing 10 μL of bottle #2 with 300 ML bottle #1.

The UV-absorbance (405 nm) is measured kinetically (every 2nd minute for 44 minutes) using a microplate reader (Tecan; Infinite, M1000, pro). The part of the curve displaying a constant absorbance increase was used to calculate the enzymatic activity of the sample (mOD/min). Thereafter the residual activity is calculated as the enzymatic activity of the sample incubated at elevated temperature for 16 or 17 hours relative to the enzymatic activity in the corresponding sample stored at 5° C.

Residual activity (%)=(Activity, sample incubated at elevated temperature/Activity, sample incubated at 5° C.)*100

Example 2: Linker Stability Assay

Principle

The linker stability is measured by (A) incubating the cellulase in detergent containing protease, then (B) determining the ability of the incubated cellulase to bind to cellulose fibers. If the linker or the cellulose binding domain is affected by the protease the binding affinity of the cellulase to cellulose fibers will be reduced.

The binding is determined by adding a dilution of the incubated cellulase to a suspension of cellulose fibers. After incubation at 5° C., the cellulase bound to cellulose is removed by centrifugation, and the amount of cellulase not bound to the cellulose is determined by measuring (C) the activity of cellulase in the supernatant. The activity of the cellulase not bound to the cellulose relative to the activity of a parallel sample incubated at similar conditions but in the absence of cellulose is a measure of the linker stability.

The activity is based on hydrolysis of the soluble carboxymethyl cellulose (CMC) followed by (D) detection of the number of reducing ends formed. CMC is a substrate both for the intact cellulase and cellulases having no cellulose binding domain.

A. Incubation in Detergent Containing Protease

Chemicals

Detergent: Model Detergent A

Protease: SEQ ID NO: 10

HEPES: 4-(2-hydroxyethyl)-1-piperazineethanesulfonic acid, Sigma H3375

Reagents

Dilution Buffer: 50 mM HEPES, pH 8

Protease stock solution, e.g., protease of SEQ ID NO: 10

Detergent with 0.3 mg/mL Protease: 300 ppm in Model Detergent A

Model Detergent A as above

Procedure

1) Detergent with 0.3 mg/mL protease is prepared by adding Protease stock solution to 100 mL Detergent to a final protease concentration of 300 ppm active protease protein in the detergent and mix for 1 hour by magnetic stirring at room temperature.

2) The cellulases are diluted to 300 ppm in Dilution Buffer.

3)$_{270}$ μL of Detergent with Protease from (1) is pipetted into 96-well polypropylene microplates (Thermo Scientific™ 249944) in well positions A1 to D12.

4) 30 μL of diluted cellulase from (2) is added to each well (positions A1 to D12). Each cellulase is tested in triplicates and positions D4 to D6 are used for blanks, where 30 μL Milli Q water is added instead of cellulase.

5) Small magnets are added to each well (position A1 to D12) and the plate is sealed with heat seal (Thermo Scientific™ Adhesive PCR Plate Seals AB0558) followed by mixing by magnetic stirring for 30 minutes.

6) After mixing, the plate is incubated at the time and temperature indicated in the examples.

B. Binding to Cellulose Fibers

Chemicals

Cellulose fibers: Avicel®, PH-101, (Sigma 11365)

HEPES: 4-(2-hydroxyethyl)-1-piperazineethanesulfonic acid, Sigma H3375

Reagents:

Binding Buffer: 50 mM HEPES, pH 8

Avicel suspension: 1.25 g/100 mL Avicel in Binding Buffer, mixed 1 hour before use Procedure:

1) 180 μL Avicel suspension is added to position A1→D12 in new 96-well microplates (Thermo Scientific™ cat. No. 269620) and 180 μL Binding Buffer was added to position E1→H12

2) 20 μL sample aliquots from each well in the incubated plate from step A is then added to the wells in position A1→D12 and in position E1→H12, respectively.

3) The plate is shaken at a speed sufficient for keeping the cellulose fibers in suspension for 1 hour at 5° C. to allow the cellulase to bind to cellulose 4) After binding, the plate is centrifuged for 10 sec. at 1500 rpm and the supernatant diluted 2.5-fold in Binding Buffer (40 μL sample+60 μL buffer). Both supernatants from Avicel and corresponding wells without Avicel are diluted.

C. CMC Activity Assay

Chemicals:

CMC: Sodium carboxymethyl cellulose (Sigma C5678)

K-Na-Tartrate: Merck 8087

β-glucosidase Megazyme (*Thermotoga maritima*; accession number Q08638, Megazyme Cat. No. E-BGOS™) diluted to 0.1 mg/ml (specific activity 70 U/mg and activity in product ~460 U/mL→6.57 mg/mL)

PAHBAH 4-Hydroxybenzhydrazide (Sigma H9882)

NaOH sodium hydroxide (J.T. Baker 0402.1000)

HEPES: 4-(2-hydroxyethyl)-1-piperazineethanesulfonic acid, Sigma H3375

Reagents:

Assay Buffer: 50 mM HEPES, pH 8

CMC Substrate: 1.25 g CMC/100 mL Assay Buffer, mixed 1 hr before use

PAHBAH Buffer: 50 g/L K-Na-tartrate+20 g/L NaOH

PAHBAH Reagent: 15 mg/mL PAHBAH in PAHBAH Buffer

B-glucosidase Solution: 0.1 mg/ml B-glucosidase in Assay Buffer

Procedure:

1) 160 μL CMC Substrate is pipetted into new 96-well microplates (Thermo Scientific™ cat. No. 269620)

2)$_{20}$ μL diluted supernatant from step B is added together with 20 UL B-glucosidase Solution 3) The plate was sealed with heat seal (Thermo Scientific™ Adhesive PCR Plate Seals AB0558), and incubated for 45 minutes at 40° C.

4) After reaction, 100 μL from each well is transferred to ThermoFast 96 Non-Skirted® PCR plate (Thermo Scientific™ cat. No. AB-0600) followed by 75 μL PAHBAH Reagent 5) The plate from (4) is then sealed with sealing foil (Greiner bio-one platesealer, Cat. No. 676001) and incubated at 95° C. for 10 minutes followed by cooling at 10° C. for 5 minutes in BioRad T100™ Thermal cycler PCR machine 6) After cooling, 100 μL aliquots are transferred to new 96-well microplates (Thermo Scientific™ cat. No. 269620) and the absorbance is read at 405 nm (A405 nm). The absorbance is an expression of the activity of the cellulase in the supernatant.

D. Data-Treatment

1) From the absorbance readings from step C, the average of the 3 blanks from the wells without Avicel, A405 nm (blank_ref), is calculated (position H4→H6), and the average of the 3 blanks from the wells with Avicel, A405 nm (blank_Avicel) is calculated (position D4→D6).

2) The absorbance readings from the cellulase containing wells are then corrected for their respective blanks (i.e. those from (1)).

3) The linker stability is calculated as $$1-[Act_{405nm}(+Avicel)/Act_{405nm}(-Avicel)],$$

where $Act_{405nm}$(+Avicel) and $Act_{405nm}$(−Avicel) is the activity (i.e. absorbance corrected for blank) in the well with supernatant from incubation with Avicel and without Avicel, respectively.

4) The linker stabilities reported in the examples are the averages of the triplicates analyzed.

This assay clearly distinguishes over binding with and without the core present, as further demonstrated by Example 3 below.

Example 3: Cellulose Binding Assay-without Protease

Principle

The cellulase is (A) allowed to bind to cellulose by incubation with Avicel at 5° C. for 60 minutes in a dilute detergent solution. After incubation, the activity of the cellulase not bound to the cellulose is determined in the supernatant (B) and compared relative to a parallel cellulase sample incubated in the absence of cellulase. The temperature during incubation with Avicel is kept low to ensure that the catalytic activity of the cellulase during the binding step has an insignificant effect on the binding assay.

A. Binding to Cellulose

Chemicals

Detergent: Model Detergent A

HEPES: 4-(2-hydroxyethyl)-1-piperazineethanesulfonic acid, Sigma H3375

Cellulose fibers: Avicel®, PH-101, (Sigma 11365)

Reagents

Binding Buffer: 50 mM HEPES, pH 8

Avicel Suspension: 1.25 g/100 mL Avicel in Binding Buffer, mixed 1 hour before use Model Detergent A as above Procedure 1) The cellulases are diluted to 300 ppm in Binding Buffer.

2)$_{270}$ μL of Detergent is pipetted into 96-well polypropylene microplates (Thermo Scientific™ 249944) in well positions A1 to D12.

3) 30 μL of diluted cellulase from (1) is added to each well (positions A1 to D12). Each cellulase is tested in triplicates and positions D4 to D6 are used for blanks, where 30 UL Milli Q water is added instead of cellulase.

4) Small magnets are added to each well (position A1 to D12) and the plate is sealed with heat seal (Thermo Scientific Adhesive PCR Plate Seals AB0558) followed by mixing by magnetic stirring for 30 minutes.

5) 160 μL Binding buffer is pipetted into new 96-well microplate (Thermo Scientific™ Nunc™ 96-well Polypropylene DeepWell™ Storage Plates (position A1 to D12 and 160 μL Avicel suspension is pipetted into position E1 to H12.

6) 20 μL Milli Q water is added to all wells (A1 to H12) 6)

7) Aliquots of 20 μL cellulase-detergent sample from ((4) is added to wells with (A1 to D12) and without Avicel (E1 to H12).

8) The plate is then incubated for 60 minutes in 5° C. cold room to allow binding of the cellulase to the cellulose in a Heidolph Titramax 101 shaker. Shaking speed is adjusted to ensure cellulose is kept suspended during incubation.

9) After binding, the plate is centrifuged for 10 sec. at 1500 rpm and the supernatant diluted 2.5-fold in Binding Buffer (40 μL sample+60 μL buffer). Both supernatants from Avicel and corresponding wells without Avicel are diluted.

B. CMC Activity Assay

Chemicals:

CMC: Sodium carboxymethyl cellulose (Sigma C5678)

K—Na-Tartrate: Merck 8087

β-glucosidase Megazyme (*Thermotoga maritima*; accession number Q08638, Megazyme Cat. No. E-BGOS™) diluted to 0.1 mg/ml (specific activity 70 U/mg and activity in product ~460 U/mL→6.57 mg/mL)

PAHBAH 4-Hydroxybenzhydrazide (Sigma H9882)

NaOH sodium hydroxide (J.T. Baker 0402.1000)

HEPES: 4-(2-hydroxyethyl)-1-piperazineethanesulfonic acid, Sigma H3375

Reagents:

Assay Buffer: 50 mM HEPES, pH 8

CMC Substrate: 1.25 g CMC/100 mL Assay Buffer, mixed 1 hr before use

PAHBAH Buffer: 50 g/L K-Na-tartrate+20 g/L NaOH

PAHBAH Reagent: 15 mg/mL PAHBAH in PAHBAH Buffer

β-glucosidase Solution: 0.1 mg/ml β-glucosidase in Assay Buffer

Procedure:

1) 160 μL CMC Substrate is pipetted into new 96-well microplates (Thermo Scientific cat. No. 269620)
2) 20 μL diluted supernatant from step A is added together with 20 μL B-glucosidase Solution
3) The plate was sealed with heat seal (Thermo Scientific Adhesive PCR Plate Seals AB0558), and incubated for 45 minutes at 40° C.
4) After reaction, 100 μL from each well is transferred to ThermoFast 96 Non-Skirted® PCR plate (Thermo Scientific cat. No. AB-0600) followed by 75 μL PAHBAH Reagent
5) The plate from (4) is then sealed with sealing foil (Greiner bio-one platesealer, Cat. No. 676001) and incubated at 95° C. for 10 minutes followed by cooling at 10° C. for 5 minutes in BioRad T100™ Thermal cycler PCR machine
6) After cooling, 100 μL aliquots are transferred to new 96-well microplates (Thermo Scientific cat. No. 269620) and the absorbance is read at 405 nm (A405 nm). The absorbance is an expression of the activity of the cellulase in the supernatant.

C. Data-Treatment

1) From the absorbance readings from step B, the average of the 3 blanks from the wells without Avicel, A405 nm (blank_ref), is calculated (position H4→H6), and the average of the 3 blanks from the wells with Avicel, A405 nm (blank_Avicel) is calculated (position D4→D6).
2) The absorbance readings from the cellulase containing wells are then corrected for their respective blanks (i.e. those from (1)).
3) The binding is calculated as 3)

$$1-[Act_{405nm}(+Avicel)/Act_{405nm}(-Avicel)],$$

where $Act_{405nm}$(+Avicel) and $Act_{405nm}$(−Avicel) is the activity (i.e. absorbance corrected for blank) in the well with supernatant from incubation with Avicel and without Avicel, respectively. The linker stabilities reported in the examples are the averages of the triplicates analyzed.

To demonstrate this, samples of cellulases with and without CBM were tested for binding to cellulose as described in this Example. The ratio is calculated as the binding of the intact cellulase, i.e. cellulase with catalytic domain, linker and CBM to that of the catalytic domain alone.

| Variant | Binding | Ratio |
|---|---|---|
| SEQ ID NO: 2 | 0.79 | 4.6 |
| Amino acids 1-213 of SEQ ID NO: 2* | 0.17 | |
| SEQ ID NO: 1 | 0.58 | 5.2 |
| Amino acids 1-216 of SEQ ID NO: 1* | 0.11 | |

*Sequence length reflects catalytic domain as annotated by bioinformatics processing The data clearly demonstrates that in the absence of the CBM, the binding to cellulose is significantly reduced.

Example 4: Construction of Variants

Cellulase variants were constructed of the *Thielavia terrestris* cellulase (SEQ ID NO: 1). The variants were made by traditional cloning of DNA fragments (Sambrook et al., Molecular Cloning: A Laboratory Manual, 2nd Ed., Cold Spring Harbor, 1989) using PCR together with properly designed oligonucleotides that introduced the desired mutations in the resulting sequence. Alternatively, synthetic gene fragments purchased from vendors such IDTDNA were used to replace the native DNA sequence with the new, desired DNA sequence.

The oligos are designed corresponding to the DNA sequence flanking the desired site(s) of mutation or stretch of DNA to be replaced, separated by the DNA base pairs defining the insertions/deletions/substitution/synthetic DNA sequence, and purchased from an oligo vendor such as IDTDNA. In order to test the variants of the invention, the mutated DNA comprising a variant of the invention are integrated into a competent *A. oryzae* strain by homologous recombination, fermented using standard protocols (yeast extract based media, 4-5 days, 30° C.), and purified as follows.

Culture broth is filtered through a Nalgene 0.2 μm filtration unit to remove the *Aspergillus* host cells. The pH in the filtrate is adjusted to pH 4.0 with 20% $CH_3COOH$ and the pH adjusted filtrate was applied to a Capto MMC column (from GE Healthcare) equilibrated in 20 mM $CH_3COOH$/NaOH, 1 mM $CaCl_2$), pH 4.0. After washing the column extensively with the equilibration buffer, the cellulase is eluted with 50 mM Tris-base, 1 mM $CaCl_2$), unbuffered. Fractions from the column are analysed for cellulase activity. The cellulase peak is pooled and applied to a Q-sepharose FF column (from GE Healthcare) equilibrated in 50 mM Tris/HCl, pH 9.0. After washing the column extensively with the equilibration buffer, the cellulase is eluted with a linear NaCl gradient over three column volumes between the equilibration buffer and 50 mM Tris/HCl, 5 mM $CaCl_2$), 500 mM NaCl, pH 9.0. Fractions from the column are analysed for cellulase activity and the cellulase peak is pooled as the purified product. The purified variants are analysed by SDS-PAGE. As the cellulase variants are glycosylated they gave diffuse bands on coomassie stained SDS-PAGE gels. The purified products are used for further characterization.

Example 5: Stability of Variants

Variants were prepared as described in Example 4. The stability was determined using the assay described in Example 2 (linker stability assay—in the presence of protease), where the stress condition was incubation at 20° C. for 21 hours with Protease (SEQ ID NO: 10) before analyzing the residual activity. Results are shown in Table 1.

TABLE 1

| linker stability after incubation 20° C., 21 hours | | | |
|---|---|---|---|
| Variant | | | |
| Catalytic domain (N-terminal) | Linker | CBM (C-terminal) | Linker stability |
| SEQ ID NO: 1 (control) | | | 0.12 |
| SEQ ID NO: 5 | TTPPTPTPTPTPG (SEQ ID NO: 12) | SEQ ID NO: 6 | 0.60 |
| SEQ ID NO: 5 | TTPTPPTPTPTPTPG (SEQ ID NO: 13) | SEQ ID NO: 6 | 0.65 |

TABLE 1-continued

| linker stability after incubation 20° C., 21 hours | | | |
|---|---|---|---|
| Variant | | | |
| Catalytic domain (N-terminal) | Linker | CBM (C-terminal) | Linker stability |
| SEQ ID NO: 5 | TTPTPTPPTPTPTPTPG (SEQ ID NO: 14) | SEQ ID NO: 6 | 0.81 |
| SEQ ID NO: 5 | TTPTPTPTPPTPTPTPTPG (SEQ ID NO: 15) | SEQ ID NO: 6 | 0.67 |
| SEQ ID NO: 5 having mutations S56A N134D Q147R | TPPTPPTPPTPPTPPTPPTPPTPPTPPTPPTPPG (SEQ ID NO: 16) | SEQ ID NO: 6 | 0.29 |
| SEQ ID NO: 5 having mutations S56A N134D Q147R | TPTTPTTPTTPTG (SEQ ID NO: 17) | SEQ ID NO: 6 | 0.56 |
| SEQ ID NO: 5 having mutations S56A N134D Q147R | TPTTPTTPTTPTTPTTPTG (SEQ ID NO: 18) | SEQ ID NO: 6 | 0.96 |
| SEQ ID NO: 5 having mutations S56A N134D Q147R | SPSSPSSPSSPSG (SEQ ID NO: 19) | SEQ ID NO: 6 | 0.27 |
| SEQ ID NO: 5 having mutations S56A N134D Q147R | SPSSPSSPSSPSSPSG (SEQ ID NO: 20) | SEQ ID NO: 6 | 0.74 |
| SEQ ID NO: 5 having mutations S56A N134D Q147R | SPPSPPSPPSPPSPPG (SEQ ID NO: 21) | SEQ ID NO: 6 | 0.47 |
| SEQ ID NO: 5 having mutations S56A N134D Q147R | SPPSPPSPPSPPSPPSPPSPPSPPSPPSPPG (SEQ ID NO: 22) | SEQ ID NO: 6 | 0.90 |
| SEQ ID NO: 5 having mutations S56A N134D Q147R | PPSSPSSPSSPSSPSSPSSPSG (SEQ ID NO: 23) | SEQ ID NO: 6 | 0.52 |
| SEQ ID NO: 5 having mutations N134D Q147R | SPSPG (SEQ ID NO: 24) | SEQ ID NO: 6 | 0.57 |
| SEQ ID NO: 5 having mutations S56A N134D Q156E A162E | SPSPG (SEQ ID NO: 24) | SEQ ID NO: 6 | 0.34 |
| SEQ ID NO: 5 having mutations S56A N134D Q156E Q169Y | SPSPG (SEQ ID NO: 24) | SEQ ID NO: 6 | 0.71 |
| SEQ ID NO: 5 | SPSPSPSPSPG (SEQ ID NO: 25) | SEQ ID NO: 6 | 0.58 |
| SEQ ID NO: 5 having mutations S56A N134D Q156E A162E | SPSPSPSPSPG (SEQ ID NO: 25) | SEQ ID NO: 6 | 0.66 |
| SEQ ID NO: 5 having mutations S56A Q147R Q169Y | SPSPSPSPSPG (SEQ ID NO: 25) | SEQ ID NO: 6 | 0.79 |
| SEQ ID NO: 5 having mutations S56A N134D Q147R | SPSPSPSPSPG (SEQ ID NO: 25) | SEQ ID NO: 6 | 0.65 |
| SEQ ID NO: 5 | TPTPTPTPTPG (SEQ ID NO: 26) | SEQ ID NO: 6 | 0.68 |
| SEQ ID NO: 5 having mutations S56A N134D Q156E A162E | TPTPTPTPTPG (SEQ ID NO: 26) | SEQ ID NO: 6 | 0.79 |
| SEQ ID NO: 5 having mutations S56A N134D Q156E Q169Y | TPTPTPTPTPG (SEQ ID NO: 26) | SEQ ID NO: 6 | 0.76 |

TABLE 1-continued

| linker stability after incubation 20° C., 21 hours | | | |
|---|---|---|---|
| Variant | | | |
| Catalytic domain (N-terminal) | Linker | CBM (C-terminal) | Linker stability |
| SEQ ID NO: 5 having mutations S56A N134D Q147R | TPTPTPTPTPG (SEQ ID NO: 26) | SEQ ID NO: 6 | 0.62 |
| SEQ ID NO: 5 having mutations S56A N134D Q147R Q169Y | PPPP (SEQ ID NO: 27) | SEQ ID NO: 6 | 0.89 |
| SEQ ID NO: 5 having mutations S56A N134D Q147R Q169Y | PPPPP (SEQ ID NO: 28) | SEQ ID NO: 6 | 0.83 |
| SEQ ID NO: 5 having mutations S56A N134D Q147R Q169Y | PPPPPP (SEQ ID NO: 29) | SEQ ID NO: 6 | 0.85 |
| SEQ ID NO: 5 | PPPPPPPG (SEQ ID NO: 30) | SEQ ID NO: 6 | 0.94 |
| SEQ ID NO: 5 having mutations S56A N134D Q147R Q169Y | PPPPPPPG (SEQ ID NO: 30) | SEQ ID NO: 6 | 0.89 |
| SEQ ID NO: 5 having mutations S56A N134D Q147R Q169Y | PPPPPPP (SEQ ID NO: 31) | SEQ ID NO: 6 | 0.77 |
| SEQ ID NO: 5 | PPPPPPPPG (SEQ ID NO: 32) | SEQ ID NO: 6 | 0.87 |
| SEQ ID NO: 5 | PPPPPPPPPG (SEQ ID NO: 33) | SEQ ID NO: 6 | 0.82 |
| SEQ ID NO: 5 having mutations S56A N134D Q147R | PPPPPPPPPG (SEQ ID NO: 33) | SEQ ID NO: 6 | 0.83 |
| SEQ ID NO: 5 | PPPPPPPPPPG (SEQ ID NO: 34) | SEQ ID NO: 6 | 0.80 |
| SEQ ID NO: 5 | PPPPPPPPPPPG (SEQ ID NO: 35) | SEQ ID NO: 6 | 0.95 |
| SEQ ID NO: 5 | PPPPPPPPPPPPPG (SEQ ID NO: 36) | SEQ ID NO: 6 | 0.90 |
| SEQ ID NO: 5 | PEPTPEPTG (SEQ ID NO: 37) | SEQ ID NO: 6 | 0.68 |
| SEQ ID NO: 5 having mutations S56A N134D Q147R | PEPTPEPTG (SEQ ID NO: 37) | SEQ ID NO: 6 | 0.71 |
| SEQ ID NO: 5 | PEPTPEPTPEPTG (SEQ ID NO: 38) | SEQ ID NO: 6 | 0.73 |
| SEQ ID NO: 5 having mutations S56A N134D Q147R | PEPTPEPTPEPTG (SEQ ID NO: 38) | SEQ ID NO: 6 | 0.84 |
| SEQ ID NO: 5 | PEPTPEPTPEPTPEPTG (SEQ ID NO: 39) | SEQ ID NO: 6 | 0.81 |
| SEQ ID NO: 5 having mutations S56A N134D Q156E A162E | PEPTPEPTPEPTPEPTG (SEQ ID NO: 39) | SEQ ID NO: 6 | 0.81 |
| SEQ ID NO: 5 having mutations S56A N134D Q156E Q169Y | PEPTPEPTPEPTPEPTG (SEQ ID NO: 39) | SEQ ID NO: 6 | 0.94 |
| SEQ ID NO: 5 having mutations S56A N134D Q147R | PEPTPEPTPEPTPEPTG (SEQ ID NO: 39) | SEQ ID NO: 6 | 0.89 |

TABLE 1-continued

| linker stability after incubation 20° C., 21 hours | | | |
|---|---|---|---|
| Variant | | | |
| Catalytic domain (N-terminal) | Linker | CBM (C-terminal) | Linker stability |
| SEQ ID NO: 5 | PEPTPEPTPEPTPEPTPEPTG (SEQ ID NO: 40) | SEQ ID NO: 6 | 0.88 |
| SEQ ID NO: 5 having mutations S56A N134D Q156E Q169Y | PEPTPEPTPEPTPEPTPEPTG (SEQ ID NO: 40) | SEQ ID NO: 6 | 0.93 |
| SEQ ID NO: 5 having mutations S56A N134D Q147R | PEPTPEPTPEPTPEPTPEPTG (SEQ ID NO: 40) | SEQ ID NO: 6 | 0.84 |
| SEQ ID NO: 5 | PSPTPSPTPSPTPSPTG (SEQ ID NO: 41) | SEQ ID NO: 6 | 1.05 |
| SEQ ID NO: 5 having mutations S56A N134D Q147R | PSPTPSPTPSPTPSPTG (SEQ ID NO: 41) | SEQ ID NO: 6 | 0.90 |
| SEQ ID NO: 5 having mutations S56A N134D Q147R | PSPTPSPTPSPTPSPTPSPTG (SEQ ID NO: 42) | SEQ ID NO: 6 | 0.88 |
| SEQ ID NO: 5 having mutations S56A N134D Q147R | PQPTPQPTG (SEQ ID NO: 43) | SEQ ID NO: 6 | 0.92 |
| SEQ ID NO: 5 having mutations S56A N134D Q147R | PDPTPDPTG (SEQ ID NO: 44) | SEQ ID NO: 6 | 0.32 |
| SEQ ID NO: 5 having mutations S56A N134D Q147R | PRPTPEPTG (SEQ ID NO: 45) | SEQ ID NO: 6 | 0.76 |
| SEQ ID NO: 5 having mutations S56A N134D Q147R | PQPTPEPTG (SEQ ID NO: 46) | SEQ ID NO: 6 | 0.94 |
| SEQ ID NO: 5 having mutations S56A N134D Q147R | PSPNSPNSPNG (SEQ ID NO: 47) | SEQ ID NO: 6 | 0.40 |
| SEQ ID NO: 5 having mutations S56A N134D Q147R | PEPTPRPTG (SEQ ID NO: 48) | SEQ ID NO: 6 | 0.85 |
| SEQ ID NO: 5 having mutations S56A N134D Q147R | PQPTPEPTPQPTPEPTPQPTPEPTPQPTG (SEQ ID NO: 49) | SEQ ID NO: 6 | 0.92 |
| SEQ ID NO: 5 having mutations S56A N134D Q147R | PDPTPDPTPDPTG (SEQ ID NO: 50) | SEQ ID NO: 6 | 0.38 |
| SEQ ID NO: 5 having mutations S56A N134D Q147R | PQPTPQPTPQPTPQPTG (SEQ ID NO: 51) | SEQ ID NO: 6 | 0.97 |
| SEQ ID NO: 5 having mutations S56A N134D Q147R | PQPTPEPTPQPTPEPTG (SEQ ID NO: 52) | SEQ ID NO: 6 | 0.94 |

Example 6: Stability of Variants

Variants were prepared as described in Example 4. The stability was determined using the assay described in Example 2, where the stress condition was incubation at 37° C. for 21 hours with Protease (SEQ ID NO: 10) before analyzing the residual activity. Results are shown in Table 2.

TABLE 2 linker stability after incubation 37° C., 21 hours

| Variant | | | |
|---|---|---|---|
| Catalytic domain (N-terminal) | Linker | CBM (C-terminal) | Linker stability |
| SEQ ID NO: 1 (control) | | | 0.17 |
| SEQ ID NO: 5 | PPPPPPPG (SEQ ID NO: 30) | SEQ ID NO: 6 | 0.34 |
| SEQ ID NO: 5 | PPPPPPPPG (SEQ ID NO: 32) | SEQ ID NO: 6 | 0.26 |
| SEQ ID NO: 5 | PPPPPPPPPG (SEQ ID NO: 33) | SEQ ID NO: 6 | 0.23 |
| SEQ ID NO: 5 having mutations S56A N134D Q147R | PPPPPPPPPG (SEQ ID NO: 33) | SEQ ID NO: 6 | 0.47 |
| SEQ ID NO: 5 | PPPPPPPPPPPPPG (SEQ ID NO: 36) | SEQ ID NO: 6 | 0.17 |
| SEQ ID NO: 5 having mutations N134D Q147R | SPSPG (SEQ ID NO: 24) | SEQ ID NO: 6 | 0.22 |
| SEQ ID NO: 5 having mutations S56A Q147R | SPSPSPSPSPG (SEQ ID NO: 25) | SEQ ID NO: 6 | 0.18 |
| SEQ ID NO: 5 having mutations S56A N134D Q147R | SPSPSPSPSPG (SEQ ID NO: 25) | SEQ ID NO: 6 | 0.33 |
| SEQ ID NO: 5 having mutations S56A N134D Q147R | SPSPSPSPPPG (SEQ ID NO: 53) | SEQ ID NO: 6 | 0.34 |
| SEQ ID NO: 5 having mutations S56A N134D Q147R | SPSPSPSPDPG (SEQ ID NO: 54) | SEQ ID NO: 6 | 0.37 |
| SEQ ID NO: 5 having mutations S56A N134D Q147R | SPSPSPSPKPG (SEQ ID NO: 55) | SEQ ID NO: 6 | 0.32 |
| SEQ ID NO: 5 having mutations S56A N134D Q147R | SPSPSPSPAPG (SEQ ID NO: 56) | SEQ ID NO: 6 | 0.34 |
| SEQ ID NO: 5 having mutations S56A N134D Q147R | SPSPSPSPSPSG (SEQ ID NO: 57) | SEQ ID NO: 6 | 0.43 |
| SEQ ID NO: 5 having mutations S56A N134D Q147R | SPSPSPSPSP (SEQ ID NO: 58) | SEQ ID NO: 6 | 0.32 |
| SEQ ID NO: 5 having mutations S56A N134D Q147R | SPSPSPSPSPS (SEQ ID NO: 59) | SEQ ID NO: 6 | 0.32 |
| SEQ ID NO: 5 having mutations S56A N134D Q147R | SPSPSPSPSPP (SEQ ID NO: 60) | SEQ ID NO: 6 | 0.33 |
| SEQ ID NO: 5 having mutations S56A N134D Q147R | SPSPSPSPSPE (SEQ ID NO: 61) | SEQ ID NO: 6 | 0.29 |

TABLE 2-continued

| linker stability after incubation 37° C., 21 hours | | | |
|---|---|---|---|
| Variant | | | |
| Catalytic domain (N-terminal) | Linker | CBM (C-terminal) | Linker stability |
| SEQ ID NO: 5 having mutations S56A N134D Q147R | SPSPSPSPSPN (SEQ ID NO: 62) | SEQ ID NO: 6 | 0.31 |
| SEQ ID NO: 5 having mutations S56A N134D Q147R | SPSPSPSPSPGG (SEQ ID NO: 63) | SEQ ID NO: 6 | 0.30 |
| SEQ ID NO: 5 having mutations S56A N134D Q147R | SPSPSPSPSPK (SEQ ID NO: 64) | SEQ ID NO: 6 | 0.24 |
| SEQ ID NO: 5 having mutations N134D Q147R | TPTPTPTPTPG (SEQ ID NO: 26) | SEQ ID NO: 6 | 0.30 |
| SEQ ID NO: 5 having mutations S56A N134D Q147R | TPTPTPTPTPG (SEQ ID NO: 26) | SEQ ID NO: 6 | 0.31 |
| SEQ ID NO: 5 having mutations S56A N134D Q147R | TTPTPTPTPPTPTPTPTPG (SEQ ID NO: 15) | SEQ ID NO: 6 | 0.21 |
| SEQ ID NO: 5 having mutations N134D Q147R | PEPTPEPTG (SEQ ID NO: 37) | SEQ ID NO: 6 | 0.30 |
| SEQ ID NO: 5 having mutations S56A N134D Q147R | PEPTPEPTG (SEQ ID NO: 37) | SEQ ID NO: 6 | 0.43 |
| SEQ ID NO: 5 having mutations S56A Q147R | PEPTPEPTPEPTG (SEQ ID NO: 38) | SEQ ID NO: 6 | 0.34 |
| SEQ ID NO: 5 having mutations N134D Q147R | PEPTPEPTPEPTG (SEQ ID NO: 38) | SEQ ID NO: 6 | 0.46 |
| SEQ ID NO: 5 having mutations S56A N134D Q147R | PEPTPEPTPEPTG (SEQ ID NO: 38) | SEQ ID NO: 6 | 0.46 |
| SEQ ID NO: 5 | PEPTPEPTPEPTPEPTG (SEQ ID NO: 39) | SEQ ID NO: 6 | 0.17 |
| SEQ ID NO: 5 having mutations S56A Q147R | PEPTPEPTPEPTPEPTG (SEQ ID NO: 39) | SEQ ID NO: 6 | 0.32 |
| SEQ ID NO: 5 having mutations N134D Q147R | PEPTPEPTPEPTPEPTG (SEQ ID NO: 39) | SEQ ID NO: 6 | 0.36 |
| SEQ ID NO: 5 having mutations S56A N134D Q147R | PEPTPEPTPEPTPEPTG (SEQ ID NO: 39) | SEQ ID NO: 6 | 0.41 |
| SEQ ID NO: 5 having mutations S56A Q147R | PEPTPEPTPEPTPEPTPEPTG (SEQ ID NO: 40) | SEQ ID NO: 6 | 0.42 |
| SEQ ID NO: 5 having mutations N134D Q147R | PEPTPEPTPEPTPEPTPEPTG (SEQ ID NO: 40) | SEQ ID NO: 6 | 0.52 |
| SEQ ID NO: 5 having mutations S56A N134D Q147R | PEPTPEPTPEPTPEPTPEPTG (SEQ ID NO: 40) | SEQ ID NO: 6 | 0.37 |
| SEQ ID NO: 5 having mutations S56A N134D Q147R | PEPTPEPTP (SEQ ID NO: 65) | SEQ ID NO: 6 | 0.24 |

TABLE 2-continued

| linker stability after incubation 37° C., 21 hours | | | |
|---|---|---|---|
| Variant | | | |
| Catalytic domain (N-terminal) | Linker | CBM (C-terminal) | Linker stability |
| SEQ ID NO: 5 having mutations S56A N134D Q147R | PEPTPEPTR (SEQ ID NO: 66) | SEQ ID NO: 6 | 0.30 |
| SEQ ID NO: 5 having mutations S56A N134D Q147R | PEPTPEPTPEPTP (SEQ ID NO: 67) | SEQ ID NO: 6 | 0.26 |
| SEQ ID NO: 5 having mutations S56A N134D Q147R | PEPTPEPTPEPTPEPTPSPTG (SEQ ID NO: 68) | SEQ ID NO: 6 | 0.45 |
| SEQ ID NO: 5 having mutations S56A N134D Q147R | PEPTPEPTPEPTPEPTPTPTG (SEQ ID NO: 69) | SEQ ID NO: 6 | 0.27 |
| SEQ ID NO: 5 having mutations S56A N134D Q147R | PEPTPEPTPEPTPEPTPGPTG (SEQ ID NO: 70) | SEQ ID NO: 6 | 0.17 |
| SEQ ID NO: 5 having mutations S56A N134D Q147R | PEPTPEPTPEPTPEPTPDPTG (SEQ ID NO: 71) | SEQ ID NO: 6 | 0.25 |
| SEQ ID NO: 5 having mutations S56A N134D Q147R | PEPTPEPTPEPTPEPTPETG (SEQ ID NO: 72) | SEQ ID NO: 6 | 0.21 |
| SEQ ID NO: 5 having mutations S56A N134D Q147R | PEPTPEPTPEPTPEPTPEPTD (SEQ ID NO: 73) | SEQ ID NO: 6 | 0.36 |
| SEQ ID NO: 5 having mutations S56A N134D Q147R | PEPTPEPTE (SEQ ID NO: 74) | SEQ ID NO: 6 | 0.26 |
| SEQ ID NO: 5 having mutations S56A N134D Q147R | PEPTPEPTPEPTPEPTPEP (SEQ ID NO: 75) | SEQ ID NO: 6 | 0.21 |
| SEQ ID NO: 5 having mutations S56A N134D Q147R | PEPTPEPTPEPTPEPTPSPT (SEQ ID NO: 76) | SEQ ID NO: 6 | 0.20 |
| SEQ ID NO: 5 having mutations S56A N134D Q147R | PEPTPEPTPEPTPEPTPRPTT (SEQ ID NO: 77) | SEQ ID NO: 6 | 0.26 |
| SEQ ID NO: 5 having mutations S56A N134D Q147R | PEPTPEPTPEPTPEPTPEPTT (SEQ ID NO: 78) | SEQ ID NO: 6 | 0.30 |
| SEQ ID NO: 5 having mutations S56A N134D Q147R | PEPTPEPTPEPTPEPTPEPT (SEQ ID NO: 79) | SEQ ID NO: 6 | 0.21 |
| SEQ ID NO: 5 having mutations S56A N134D Q147R | PEPTPEPTPEPTPEPTPEPTS (SEQ ID NO: 80) | SEQ ID NO: 6 | 0.30 |
| SEQ ID NO: 5 having mutations S56A N134D Q147R | PEPTPEPTPEPTPEPTPEPTR (SEQ ID NO: 81) | SEQ ID NO: 6 | 0.36 |
| SEQ ID NO: 5 having mutations A32S S56A N134D A146D Q147R Q169Y F183V | PEPTPEPTPEPTPEPTPEPTG (SEQ ID NO: 40) | SEQ ID NO: 6 | 0.35 |
| SEQ ID NO: 5 | PSPTPSPTPSPTPSPTG (SEQ ID NO: 41) | SEQ ID NO: 6 | 0.36 |

TABLE 2-continued

| linker stability after incubation 37° C., 21 hours | | | |
|---|---|---|---|
| Variant | | | |
| Catalytic domain (N-terminal) | Linker | CBM (C-terminal) | Linker stability |
| SEQ ID NO: 5 having mutations S56A N134D Q147R | PSPTPSPTPSPTPSPTPSPTG (SEQ ID NO: 42) | SEQ ID NO: 6 | 0.49 |
| SEQ ID NO: 5 having mutations A32S S56A N134D A146D Q147R Q169Y F183V | PSPTPSPTPSPTPSPTPSPTG (SEQ ID NO: 42) | SEQ ID NO: 6 | 0.38 |
| SEQ ID NO: 5 having mutations S56A N134D Q147R | PPPGGPGGPGTPTSTAPGSGPTSPGGGSG (SEQ ID NO: 82) | SEQ ID NO: 6 | 0.38 |
| SEQ ID NO: 5 having mutations S56A N134D Q147R | PPPGGPGGTGTPTSTAPGSGPTSPGGGSG (SEQ ID NO: 83) | SEQ ID NO: 6 | 0.36 |
| SEQ ID NO: 5 having mutations S56A | PPSGGPGGPGTPTSTAPGSGPTSPGGGSG (SEQ ID NO: 84) | SEQ ID NO: 6 | 0.34 |
| N134D Q147R SEQ ID NO: 5 having mutations S56A N134D Q147R | PEPTPRPTPEPTPRPTG (SEQ ID NO: 85) | SEQ ID NO: 6 | 0.42 |
| SEQ ID NO: 5 having mutations S56A N134D Q147R | PKPTPEPTPKPTPEPTG (SEQ ID NO: 86) | SEQ ID NO: 6 | 0.47 |
| SEQ ID NO: 5 having mutations S56A N134D Q147R | PEPTPKPTPEPTPKPTG (SEQ ID NO: 87) | SEQ ID NO: 6 | 0.42 |
| SEQ ID NO: 5 having mutations S56A N134D Q147R | PEPTPQPTPEPTPQPTG (SEQ ID NO: 88) | SEQ ID NO: 6 | 0.44 |
| SEQ ID NO: 5 having mutations S56A N134D Q147R | PRPTPEPTPRPTG (SEQ ID NO: 89) | SEQ ID NO: 6 | 0.46 |
| SEQ ID NO: 5 having mutations S56A N134D Q147R | PKPTPEPTPKPTG (SEQ ID NO: 90) | SEQ ID NO: 6 | 0.42 |
| SEQ ID NO: 5 having mutations S56A N134D Q147R | PEPTPQPTG (SEQ ID NO: 91) | SEQ ID NO: 6 | 0.49 |
| SEQ ID NO: 5 having mutations S56A N134D Q147R | PEPTPQPTPEPTG (SEQ ID NO: 92) | SEQ ID NO: 6 | 0.42 |
| SEQ ID NO: 5 having mutations S56A N134D Q147R | TPPTPPG (SEQ ID NO: 93) | SEQ ID NO: 6 | 0.37 |
| SEQ ID NO: 5 having mutations S56A N134D Q147R | SPSSPSG (SEQ ID NO: 94) | SEQ ID NO: 6 | 0.35 |
| SEQ ID NO: 5 having mutations S56A N134D Q147R | SPSSPSSPSG (SEQ ID NO: 95) | SEQ ID NO: 6 | 0.27 |
| SEQ ID NO: 5 having mutations S56A N134D Q147R | TPTTPTG (SEQ ID NO: 96) | SEQ ID NO: 6 | 0.34 |
| SEQ ID NO: 5 having mutations S56A N134D Q147R | TPTTPTTPTG (SEQ ID NO: 97) | SEQ ID NO: 6 | 0.37 |

Example 7: In-Wash Linker Stability Assay with Proteases

Principle

The linker stability is measured by (A) incubating the cellulase in detergent wash-solution containing protease, then (B) determining the ability of the incubated cellulase to bind to cellulose fibers. If the linker or the cellulose binding domain is affected by the protease the binding affinity of the cellulase to cellulose fibers will be reduced.

The binding is determined by adding a dilution of the incubated cellulase to a suspension of cellulose fibers. After incubation at 5° C., the cellulase bound to cellulose is removed by centrifugation, and the amount of cellulase not bound to the cellulose is determined by measuring (C) the activity of cellulase in the supernatant. The activity of the cellulase not bound to the cellulose relative to the activity of a parallel sample incubated at similar conditions but in the absence of cellulose is a measure of the linker stability.

The activity is based on hydrolysis of the soluble carboxymethyl cellulose (CMC) followed by (D) detection of the number of reducing ends formed. CMC is a substrate both for the intact cellulase and cellulases having no cellulose binding domain.

E. Incubation in Detergent Containing Protease

Chemicals

- Detergent: Model Detergent A
- Protease: Protease with SEQ ID NO: 10
- HEPES: 4-(2-hydroxyethyl)-1-piperazineethanesulfonic acid, Sigma H3375

Reagents

- Dilution Buffer: 50 mM HEPES, pH 8
- Detergent with Protease: 0.3 ug/mL active protease protein in Model Detergent A
- Detergent wash-solution: 3.3 g/L Detergent with Protease in water with 15° dH water hardness.

Procedure

7) Detergent wash-solution is prepared
8) The cellulases are diluted to 300 ppm in Dilution Buffer.
9) 270 μL of Detergent wash-solution from (1) is pipetted into 96-well polypropylene microplates (Thermo Scientific™ 249944) in well positions A1 to D12.
10) 30 μL of diluted cellulase from (2) is added to each well (positions A1 to D12). Each cellulase is tested in triplicates and positions D4 to D6 are used for blanks, where 30 μL Milli Q water is added instead of cellulase.
11) Small magnets are added to each well (position A1 to D12) and the plate is sealed with heat seal (Thermo Scientific™ Adhesive PCR Plate Seals AB0558) followed by mixing by magnetic stirring for 30 minutes.
12) After mixing, the plate is incubated at the time and temperature indicated in the examples, e.g. 2 hours at 40° C.

F. Binding to Cellulose Fibers

Chemicals

- Cellulose fibers: Avicel®, PH-101, (Sigma 11365)
- HEPES: 4-(2-hydroxyethyl)-1-piperazineethanesulfonic acid, Sigma H3375

Reagents:

- Binding Buffer: 50 mM HEPES, pH 8
- Avicel suspension: 1.25 g/100 mL Avicel in Binding Buffer, mixed 1 hour before use Procedure:

5) 180 μL Avicel suspension is added to position A1→D12 in new 96-well microplates (Thermo Scientific™ cat. No. 269620) and 180 μL Binding Buffer was added to position E1→H12
6) 20 μL sample aliquots from each well in the incubated plate from step A is then added to the wells in position A1→D12 and in position E1→H12, respectively.
7) The plate is shaken at a speed sufficient for keeping the cellulose fibers in suspension for 1 hour at 5° C. to allow the cellulase to bind to cellulose
8) After binding, the plate is centrifuged for 10 sec. at 1500 rpm and the supernatant diluted 2.5-fold in Binding Buffer (40 μL sample+60 μL buffer). Both supernatants from Avicel and corresponding wells without Avicel are diluted.

G. CMC Activity Assay

Chemicals:

- CMC: Sodium carboxymethyl cellulose (Sigma C5678)
- K-Na-Tartrate: Merck 8087
- β-glucosidase Megazyme (*Thermotoga maritima*; accession number Q08638, Megazyme Cat. No. E-BGOS™) diluted to 0.1 mg/ml (specific activity 70 U/mg and activity in product ~460 U/mL→6.57 mg/mL)
- PAHBAH 4-Hydroxybenzhydrazide (Sigma H9882)
- NaOH sodium hydroxide (J.T. Baker 0402.1000)
- HEPES: 4-(2-hydroxyethyl)-1-piperazineethanesulfonic acid, Sigma H3375

Reagents:

- Assay Buffer: 50 mM HEPES, pH 8
- CMC Substrate: 1.25 g CMC/100 mL Assay Buffer, mixed 1 hr before use
- PAHBAH Buffer: 50 g/L K-Na-tartrate+20 g/L NaOH
- PAHBAH Reagent: 15 mg/mL PAHBAH in PAHBAH Buffer
- B-glucosidase Solution: 0.1 mg/ml B-glucosidase in Assay Buffer Procedure:

7) 160 μL CMC Substrate is pipetted into new 96-well microplates (Thermo Scientific™ cat. No. 269620)
8) 20 μL diluted supernatant from step B is added together with 20 μL B-glucosidase Solution
9) The plate was sealed with heat seal (Thermo Scientific™ Adhesive PCR Plate Seals AB0558), and incubated for 45 minutes at 40° C.
10) After reaction, 100 μL from each well is transferred to ThermoFast 96 Non-Skirted® PCR plate (Thermo Scientific™ cat. No. AB-0600) followed by 75 μL PAHBAH Reagent
11) The plate from (4) is then sealed with sealing foil (Greiner bio-one platesealer, Cat. No. 676001) and incubated at 95° C. for 10 minutes followed by cooling at 10° C. for 5 minutes in BioRad T100™ Thermal cycler PCR machine
12) After cooling, 100 μL aliquots are transferred to new 96-well microplates (Thermo Scientific™ cat. No. 269620) and the absorbance is read at 405 nm (A405 nm). The absorbance is an expression of the activity of the cellulase in the supernatant.

H. Data-Treatment

5) From the absorbance readings from step C, the average of the 3 blanks from the wells without Avicel, $A_{405nm}$ (blank_ref), is calculated (position H4→H6), and the average of the 3 blanks from the wells with Avicel, $A_{405nm}$(blank_Avicel) is calculated (position D4→D6).
6) The absorbance readings from the cellulase containing wells are then corrected for their respective blanks (i.e. those from (1)).

7) The linker stability is calculated as $$1-[Act_{405nm}(+Avicel)/Act_{405nm}(-Avicel)],$$

where $Act_{405nm}$(+Avicel) and $Act_{405nm}$(−Avicel) is the activity (i.e. absorbance corrected for blank) in the well with supernatant from incubation with Avicel and without Avicel, respectively.

8) The linker stabilities reported in the examples are the averages of the triplicates analyzed.

Example 8: Stability of Variants

Variants were prepared as described in Example 4. The stability was determined using the assay described in Example 2, where the stress condition was incubation at 20° C. for 20 hours with Protease (SEQ ID NO: 10) before analyzing the residual activity.

Linker stabilities relative to the linker stability of the Control are shown in Table 3.

TABLE 3

| Sample | Relative Stability |
|---|---|
| SEQ ID NO: 1 (control) | 1.0 |
| Variant 405 | 7.7 |
| Variant 401 | 7.4 |
| Variant 416 | 3.6 |
| Variant 407 | 3.5 |
| Variant 406 | 7.3 |
| Variant 411 | 4.2 |
| Variant 409 | 4.5 |
| Variant 415 | 7.0 |
| Variant 410 | 3.4 |
| Variant 412 | 5.4 |
| Variant 414 | 5.4 |
| Variant 408 | 2.7 |
| Variant 413 | 3.0 |
| Variant 424 | 3.5 |
| Variant 423 | 5.2 |
| Variant 430 | 3.5 |
| Variant 428 | 4.1 |
| Variant 427 | 4.8 |
| Variant 429 | 1.7 |
| Variant 421 | 4.5 |
| Variant 419 | 4.8 |
| Variant 418 | 6.0 |
| Variant 417 | 4.1 |
| Variant 426 | 4.2 |

The invention claimed is:

1. A variant of a polypeptide having cellulase activity, wherein the variant comprises a catalytic domain, a linker region, and a carbohydrate binding module (CBM), wherein the variant has cellulase activity and wherein:

a) the catalytic domain comprises an amino acid sequence having at least 90% sequence identity to the amino acid sequence as shown in positions 1-212 of SEQ ID NO: 1, b) the CBM comprises an amino acid sequence having at least 90% sequence identity to the amino acid sequence as shown in SEQ ID NO: 6, SEQ ID NO: 7, SEQ ID NO: 8, SEQ ID NO: 9, SEQ ID NO: 173, SEQ ID NO:

174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, or SEQ ID NO: 200; and c) the linker is selected from the group consisting of:

(SEQ ID NO: 12)
TTPPTPTPTPTPG (SEQ ID NO: 13)
TTPTPPTPTPTPTPG (SEQ ID NO: 14)
TTPTPTPPTPTPTPTPG (SEQ ID NO: 15)
TTPTPTPTPPTPTPTPTPG (SEQ ID NO: 16)
TPPTPPTPPTPPTPPTPPTPPTPPTPPTPPTPPG (SEQ ID NO: 17)
TPTTPTTPTTPTG (SEQ ID NO: 18)
TPTTPTTPTTPTTPTTPTG (SEQ ID NO: 19)
SPSSPSSPSSPSG (SEQ ID NO: 20)
SPSSPSSPSSPSSPSG (SEQ ID NO: 21)
SPPSPPSPPSPPSPPG (SEQ ID NO: 22)
SPPSPPSPPSPPSPPSPPSPPSPPSPPSPPG (SEQ ID NO: 23)
PPSSPSSPSSPSSPSSPSSPSG (SEQ ID NO: 24)
SPSPG (SEQ ID NO: 25)
SPSPSPSPSPG (SEQ ID NO: 26)
TPTPTPTPTPG (SEQ ID NO: 27)
PPPP (SEQ ID NO: 28)
PPPPP (SEQ ID NO: 29)
PPPPPP (SEQ ID NO: 30)
PPPPPPG (SEQ ID NO: 31)
PPPPPPP (SEQ ID NO: 32)
PPPPPPPG (SEQ ID NO: 33)
PPPPPPPPG (SEQ ID NO: 34)

-continued

PPPPPPPPPPG (SEQ ID NO: 35)
PPPPPPPPPPPG (SEQ ID NO: 36)
PPPPPPPPPPPPPG (SEQ ID NO: 37)
PEPTPEPTG (SEQ ID NO: 38)
PEPTPEPTPEPTG (SEQ ID NO: 39)
PEPTPEPTPEPTPEPTG (SEQ ID NO: 40)
PEPTPEPTPEPTPEPTPEPTG (SEQ ID NO: 41)
PSPTPSPTPSPTPSPTG (SEQ ID NO: 42)
PSPTPSPTPSPTPSPTPSPTG (SEQ ID NO: 43)
PQPTPQPTG (SEQ ID NO: 44)
PDPTPDPTG (SEQ ID NO: 45)
PRPTPEPTG (SEQ ID NO: 46)
PQPTPEPTG (SEQ ID NO: 47)
PSPNSPNSPNG (SEQ ID NO: 48)
PEPTPRPTG (SEQ ID NO: 49)
PQPTPEPTPQPTPEPTPQPTPEPTPQPTG (SEQ ID NO: 50)
PDPTPDPTPDPTG (SEQ ID NO: 51)
PQPTPQPTPQPTPQPTG (SEQ ID NO: 52)
PQPTPEPTPQPTPEPTG (SEQ ID NO: 53)
SPSPSPSPPPG (SEQ ID NO: 54)
SPSPSPSPDPG (SEQ ID NO: 55)
SPSPSPSPKPG (SEQ ID NO: 56)
SPSPSPSPAPG (SEQ ID NO: 57)
SPSPSPSPSPSG (SEQ ID NO: 58)
SPSPSPSPSP (SEQ ID NO: 59)
SPSPSPSPSPS (SEQ ID NO: 60)
SPSPSPSPSPP (SEQ ID NO: 61)

-continued

SPSPSPSPSPE (SEQ ID NO: 62)
SPSPSPSPSPN (SEQ ID NO: 63)
SPSPSPSPSPGG (SEQ ID NO: 64)
SPSPSPSPSPK (SEQ ID NO: 65)
PEPTPEPTP (SEQ ID NO: 66)
PEPTPEPTR (SEQ ID NO: 67)
PEPTPEPTPEPTP (SEQ ID NO: 68)
PEPTPEPTPEPTPEPTPSPTG (SEQ ID NO: 69)
PEPTPEPTPEPTPEPTPTPTG (SEQ ID NO: 70)
PEPTPEPTPEPTPEPTPGPTG (SEQ ID NO: 71)
PEPTPEPTPEPTPEPTPDPTG (SEQ ID NO: 72)
PEPTPEPTPEPTPEPTPETG (SEQ ID NO: 73)
PEPTPEPTPEPTPEPTPEPTD (SEQ ID NO: 74)
PEPTPEPTE (SEQ ID NO: 75)
PEPTPEPTPEPTPEPTPEP (SEQ ID NO: 76)
PEPTPEPTPEPTPEPTPSPT (SEQ ID NO: 77)
PEPTPEPTPEPTPEPTPRPTT (SEQ ID NO: 78)
PEPTPEPTPEPTPEPTPEPTT (SEQ ID NO: 79)
PEPTPEPTPEPTPEPTPEPT (SEQ ID NO: 80)
PEPTPEPTPEPTPEPTPEPTS (SEQ ID NO: 81)
PEPTPEPTPEPTPEPTPEPTR (SEQ ID NO: 82)
PPPGGPGGPGTPTSTAPGSGPTSPGGGSG (SEQ ID NO: 83)
PPPGGPGGTGTPTSTAPGSGPTSPGGGSG (SEQ ID NO: 84)
PPSGGPGGPGTPTSTAPGSGPTSPGGGSG (SEQ ID NO: 85)
PEPTPRPTPEPTPRPTG (SEQ ID NO: 86)
PKPTPEPTPKPTPEPTG (SEQ ID NO: 87)
PEPTPKPTPEPTPKPTG (SEQ ID NO: 88)
PEPTPQPTPEPTPQPTG (SEQ ID NO: 89)
PRPTPEPTPRPTG (SEQ ID NO: 90)
PKPTPEPTPKPTG (SEQ ID NO: 91)
PEPTPQPTG (SEQ ID NO: 92)
PEPTPQPTPEPTG (SEQ ID NO: 93)
TPPTPPG (SEQ ID NO: 94)
SPSSPSG (SEQ ID NO: 95)
SPSSPSSPSG (SEQ ID NO: 96)
TPTTPTG;
and (SEQ ID NO: 97)
TPTTPTTPTG wherein the variant has improved stability in comparison with the polypeptide of SEQ ID NO: 1 in an aqueous composition comprising a protease.

2. The variant of claim 1, wherein the catalytic domain comprises an amino acid sequence having at least 95% sequence identity to the amino acid sequence as shown in positions 1-212 of SEQ ID NO: 1, and the CBM comprises an amino acid sequence having at least 95% sequence identity to the amino acid sequence as shown in SEQ ID NO: 6, SEQ ID NO: 7, SEQ ID NO: 8, SEQ ID NO: 9, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, or SEQ ID NO: 200.

3. The variant of claim 2, wherein the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25).

4. The variant of claim 3, which comprises S56A+N134D.

5. The variant of claim 2, which comprises S56A+N134D.

6. The variant of claim 1, wherein the catalytic domain comprises an amino acid sequence having at least 97% sequence identity to the amino acid sequence as shown in positions 1-212 of SEQ ID NO: 1, and the CBM comprises an amino acid sequence having at least 97% sequence identity to the amino acid sequence as shown in SEQ ID NO: 6, SEQ ID NO: 7, SEQ ID NO: 8, SEQ ID NO: 9, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO:

192, SEQ ID NO: 193, SEQ ID NO: 194, SEQ ID NO: 195, SEQ ID NO: 196, SEQ ID NO: 197, SEQ ID NO: 198, SEQ ID NO: 199, or SEQ ID NO: 200.

7. The variant of claim 6, wherein the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25).

8. The variant of claim 7, which comprises S56A+N134D.

9. The variant of claim 6, which comprises S56A+N134D.

10. The variant of claim 1, wherein the linker is PPPPPPP (SEQ ID NO: 31), PPPPPPPG (SEQ ID NO: 30), SPSPSPSPSP (SEQ ID NO: 58) or SPSPSPSPSPG (SEQ ID NO: 25).

11. The variant of claim 10, which comprises S56A+N134D.

12. The variant of claim 1, which comprises S56A+N134D.

13. The variant of claim 1, wherein the catalytic domain is an N-terminal catalytic domain and the CBM is a C-terminal CBM.

14. The variant of claim 1, wherein the catalytic domain is a C-terminal catalytic domain and the CBM is an N-terminal CBM.

15. The variant of claim 1, which has improved fabric or textile care and/or improved wash performance relative to the polypeptide of SEQ ID NO: 1 after storage in the presence of protease.

16. The variant of claim 1, which is selected from the group consisting of:

| Catalytic domain (N-terminal) | Linker | CBM (C-terminal) |
|---|---|---|
| SEQ ID NO: 5 with A32S S56A N134D A146D Q147R Q169Y F183V | SPSPSPSPSP (SEQ ID NO: 58) | SEQ ID NO: 173 |
| SEQ ID NO: 5 with A32S S56A N134D A146D Q147R Q169Y F183V | PPPPPPPG (SEQ ID NO: 30) | SEQ ID NO: 173 |
| SEQ ID NO: 5 with A32S S56A N134D A146D Q147R Q169Y F183V | SPSPSPSPSP (SEQ ID NO: 58) | SEQ ID NO: 174 |
| SEQ ID NO: 5 with A32S S56A N134D A146D Q147R Q169Y F183V | PPPPPPPG (SEQ ID NO: 30) | SEQ ID NO: 174 |
| SEQ ID NO: 5 with A32S S56A N134D A146D Q147R Q169Y F183V | PPPPPPPG (SEQ ID NO: 30) | SEQ ID NO: 175 |
| SEQ ID NO: 5 with A32S S56A N134D A146D Q147R Q169Y F183V | PPPPPPPG (SEQ ID NO: 30) | SEQ ID NO: 176 |
| SEQ ID NO: 5 with A32S S56A N134D A146D Q147R Q169Y F183V | PPPPPPPG (SEQ ID NO: 30) | SEQ ID NO: 177 |
| SEQ ID NO: 5 with A32S S56A N134D A146D Q147R Q169Y F183V | PPPPPPPG (SEQ ID NO: 30) | SEQ ID NO: 178 |
| SEQ ID NO: 5 with A32S S56A N134D A146D Q147R Q169Y F183V | PPPPPPPG (SEQ ID NO: 30) | SEQ ID NO: 179 |
| SEQ ID NO: 5 with A32S S56A N134D A146D Q147R Q169Y F183V | PPPPPPPG (SEQ ID NO: 30) | SEQ ID NO: 180 |
| SEQ ID NO: 5 with A32S S56A N134D A146D Q147R Q169Y F183V | PPPPPPPG (SEQ ID NO: 30) | SEQ ID NO: 181 |
| SEQ ID NO: 5 with A32S S56A N134D A146D Q147R Q169Y F183V | PPPPPPPG (SEQ ID NO: 30) | SEQ ID NO: 182 |
| SEQ ID NO: 5 with A32S S56A N134D A146D Q147R Q169Y F183V | PPPPPPPG (SEQ ID NO: 30) | SEQ ID NO: 183 |
| SEQ ID NO: 5 with A32S S56A N134D A146D Q147R Q169Y F183V | PPPPPPPG (SEQ ID NO: 30) | SEQ ID NO: 184 |
| SEQ ID NO: 5 with A32S S56A N134D A146D Q147R Q169Y F183V | PPPPPPPG (SEQ ID NO: 30) | SEQ ID NO: 185 |
| SEQ ID NO: 5 with A32S S56A N134D A146D Q147R Q169Y F183V | PPPPPPPG (SEQ ID NO: 30) | SEQ ID NO: 186 |
| SEQ ID NO: 5 with A32S S56A N134D A146D Q147R Q169Y F183V | PPPPPPPG (SEQ ID NO: 30) | SEQ ID NO: 187 |
| SEQ ID NO: 5 with A32S S56A N134D A146D Q147R Q169Y F183V | PPPPPPPG (SEQ ID NO: 30) | SEQ ID NO: 188 |
| SEQ ID NO: 5 with A32S S56A N134D A146D Q147R Q169Y F183V | PPPPPPPG (SEQ ID NO: 30) | SEQ ID NO: 189 |
| SEQ ID NO: 5 with A32S S56A N134D A146D Q147R Q169Y F183V | PPPPPPPG (SEQ ID NO: 30) | SEQ ID NO: 190 |

-continued

| Catalytic domain (N-terminal) | Linker | CBM (C-terminal) |
|---|---|---|
| SEQ ID NO: 5 with A32S S56A N134D A146D Q147R Q169Y F183V | PPPPPPPG (SEQ ID NO: 30) | SEQ ID NO: 191 |
| SEQ ID NO: 5 with A32S S56A N134D A146D Q147R Q169Y F183V | PPPPPPPG (SEQ ID NO: 30) | SEQ ID NO: 192 |
| SEQ ID NO: 5 with A32S S56A N134D A146D Q147R Q169Y F183V | PPPPPPPG (SEQ ID NO: 30) | SEQ ID NO: 193 |
| SEQ ID NO: 5 with A32S S56A N134D A146D Q147R Q169Y F183V | PPPPPPPG (SEQ ID NO: 30) | SEQ ID NO: 194 |
| SEQ ID NO: 5 with A32S S56A N134D A146D Q147R Q169Y F183V | PPPPPPPG (SEQ ID NO: 30) | SEQ ID NO: 195 |
| SEQ ID NO: 5 with A32S S56A N134D A146D Q147R Q169Y F183V | PPPPPPPG (SEQ ID NO: 30) | SEQ ID NO: 196 |
| SEQ ID NO: 5 with A32S S56A N134D A146D Q147R Q169Y F183V | PPPPPPPG (SEQ ID NO: 30) | SEQ ID NO: 197 |
| SEQ ID NO: 5 with A32S S56A N134D A146D Q147R Q169Y F183V | PPPPPPPG (SEQ ID NO: 30) | SEQ ID NO: 198 |
| SEQ ID NO: 5 with A32S S56A N134D A146D Q147R Q169Y F183V | PPPPPPPG (SEQ ID NO: 30) | SEQ ID NO: 199 and |
| SEQ ID NO: 5 with A32S S56A N134D A146D Q147R Q169Y F183V | PPPPPPPG (SEQ ID NO: 30) | SEQ ID NO: 200. |

17. A composition comprising a variant of claim 1.

18. The composition of claim 17, further comprising a protease.

19. The composition of claim 17, further comprising one or more additional enzymes selected from the group consisting of protease, lipase, cutinase, amylase, carbohydrase, additional cellulase, pectinase, mannanase, arabinase, galactanase, xylanase, nuclease, licheninase, oxidase, peroxidase, and any combination thereof.

20. The composition of claim 17, which is a liquid detergent composition.

21. A method of treatment of a fabric or textile, comprising applying a variant of claim 1 to the fabric or textile, wherein the treated fabric or textile has less staining or less pilling, as compared to a fabric or textile not treated with the variant.

22. An isolated polynucleotide encoding the variant of claim 1.

23. A nucleic acid construct comprising the polynucleotide of claim 22.

24. An expression vector comprising the polynucleotide of claim 22.

25. A host cell comprising the polynucleotide of claim 22.

26. A method of producing a variant having cellulase activity, comprising:
a. cultivating the host cell of claim 25 under conditions suitable for expression of the variant; and
b. recovering the variant.

27. A whole broth formulation or cell culture composition comprising the variant of claim 1.

* * * * *